US012655428B2

(12) United States Patent
Nicholas et al.

(10) Patent No.: US 12,655,428 B2
(45) Date of Patent: Jun. 16, 2026

(54) RNAi AGENTS FOR INHIBITING EXPRESSION OF Beta-ENaC, COMPOSITIONS THEREOF, AND METHODS OF USE

(71) Applicant: Arrowhead Pharmaceuticals, Inc., Pasadena, CA (US)

(72) Inventors: Anthony Nicholas, Oregon, WI (US); Casi M. Schienebeck, Deerfield, WI (US); Erik W. Bush, Verona, WI (US); Tao Pei, Middleton, WI (US); Zhao Xu, Brookfield, WI (US); Zhen Li, San Diego, CA (US); Rui Zhu, San Diego, CA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 981 days.

(21) Appl. No.: 17/731,766

(22) Filed: Apr. 28, 2022

(65) Prior Publication Data

US 2023/0013022 A1 Jan. 19, 2023

Related U.S. Application Data

(63) Continuation of application No. PCT/US2020/057778, filed on Oct. 28, 2020.

(Continued)

(51) Int. Cl.

*C12N 15/113* (2010.01)
*A61K 47/68* (2017.01)

(52) U.S. Cl.

CPC ........ *C12N 15/113* (2013.01); *A61K 47/6807* (2017.08); *C12N 2310/312* (2013.01);

(Continued)

(58) Field of Classification Search

CPC .............. C12N 15/113; C12N 15/1138; C12N 2310/14; C12N 2310/312;

(Continued)

(56) References Cited

U.S. PATENT DOCUMENTS 4,522,811 A 6/1985 Eppstein et al.
5,032,401 A 7/1991 Jamas et al.

(Continued)

FOREIGN PATENT DOCUMENTS

WO 2000053722 A2 9/2000
WO 2003057847 A2 7/2003

(Continued)

OTHER PUBLICATIONS

Smith et al. (European Journal of Pharmaceutical Sciences 11 (2000) 191-198).*

(Continued)

*Primary Examiner* — Terra C Gibbs
(74) *Attorney, Agent, or Firm* — Paul VanderVelde; Meibo Chen; Mitchell Porter

(57) ABSTRACT

Described are RNAi agents, compositions that include RNAi agents, and methods for inhibition of a beta-ENaC (SCNN1B) gene. The beta-ENaC RNAi agents and RNAi agent conjugates disclosed herein inhibit the expression of a beta-ENaC gene. Pharmaceutical compositions that include one or more beta-ENaC RNAi agents, optionally with one or more additional therapeutics, are also described. Delivery of the described beta-ENaC RNAi agents to epithelial cells, such as pulmonary epithelial cells, in vivo, provides for inhibition of beta-ENaC gene expression and a reduction in ENaC activity, which can provide a therapeutic benefit to subjects, including human subjects, for the treatment of (Continued)

(Tri-SM2)

various diseases including chronic obstructive pulmonary disease (COPD).

13 Claims, 45 Drawing Sheets

Specification includes a Sequence Listing.

Related U.S. Application Data

(60) Provisional application No. 63/024,722, filed on May 14, 2020, provisional application No. 62/927,637, filed on Oct. 29, 2019.

(52) U.S. Cl.
CPC .................. *C12N 2310/321* (2013.01); *C12N 2310/3233* (2013.01); *C12N 2310/332* (2013.01); *C12N 2310/351* (2013.01)

(58) Field of Classification Search
CPC ........ C12N 2310/315; C12N 2310/321; C12N 2310/322; C12N 2310/343; C12N 2310/351; C12N 2310/3515; A61K 31/7105; A61K 47/6807
See application file for complete search history.

(56) References Cited

U.S. PATENT DOCUMENTS

| | | | | |
|---|---|---|---|---|
| 5,998,203 | A | 12/1999 | Matulic-adamic et al. | |
| 7,691,997 | B2 | 4/2010 | Khvorova et al. | |
| 7,718,632 | B2 | 5/2010 | Van Heeke et al. | |
| 7,939,508 | B2 | 5/2011 | Van Heeke et al. | |
| 7,943,592 | B2 | 5/2011 | Van Heeke et al. | |
| 8,344,127 | B2 | 1/2013 | Fougerolles et al. | |
| 9,752,152 | B2 * | 9/2017 | De Fougerolles ...... | A61P 13/12 |
| 2005/0245475 | A1 | 11/2005 | Khvorova et al. | |
| 2005/0246794 | A1 | 11/2005 | Khvorova et al. | |
| 2007/0031844 | A1 * | 2/2007 | Khvorova ................. | A61P 3/10 435/6.13 |
| 2008/0113351 | A1 | 5/2008 | Naito et al. | |
| 2009/0306189 | A1 | 12/2009 | Raemaekers et al. | |
| 2011/0054005 | A1 | 3/2011 | Naito et al. | |
| 2011/0263681 | A1 * | 10/2011 | De Fougerolles ........ | A61P 1/00 530/394 |
| 2013/0012571 | A1 | 1/2013 | De Fougerolles et al. | |
| 2019/0010494 | A1 | 1/2019 | Li et al. | |

FOREIGN PATENT DOCUMENTS

| | | | |
|---|---|---|---|
| WO | 2003070910 | A2 | 8/2003 |
| WO | 2004045543 | A2 | 6/2004 |
| WO | 2008022309 | A2 | 2/2008 |
| WO | 2008152131 | A2 | 12/2008 |
| WO | 2011104169 | A1 | 9/2011 |
| WO | 2011131707 | A1 | 10/2011 |
| WO | 2012083185 | A2 | 6/2012 |
| WO | 2013032829 | A1 | 3/2013 |
| WO | 2013158141 | A1 | 10/2013 |
| WO | 2017214112 | A1 | 12/2017 |
| WO | 2018085415 | A1 | 5/2018 |
| WO | 2019010274 | A1 | 1/2019 |
| WO | 2019089765 | A1 | 5/2019 |
| WO | 2019161213 | A1 | 8/2019 |

OTHER PUBLICATIONS

Gianotti A, Melani R, Caci E, Sondo E, Ravazzolo R, Galietta LJ, Zegarra-Moran O. Epithelial sodium channel silencing as a strategy to correct the airway surface fluid deficit in cystic fibrosis. Am J Respir Cell Mol Biol. Sep. 2013;49(3):445-52. doi: 10.1165/rcmb.2012-0408OC. PMID: 23600628.

Kim EC, Ahn DS, Yeon SI, Lim M, Lee YH. Epithelial Na+ channel proteins are mechanotransducers of myogenic constriction in rat posterior cerebral arteries. Exp Physiol. Apr. 2012; 97(4):544-55. doi: 10.1113/expphysiol.2011.062232. Epub Nov. 16, 2011. PMID: 22090066.

Caci et al.; "Epithelial Sodium Channel Inhibition in Primary Human Bronchial Epithelia by Transfected siRNA"; Am J Respir Cell Mol Biol; 40(2):211-216 & Supplemental Data (2009).

Chan, JH et al.; "Antisense oligonucleotides: from design to therapeutic application." Clin Exp Pharmacol Physiol.; vol. 33(5-6): pp. 533-540; May to June of 2006.

Chu and Rana; "Potent RNAi by short RNA triggers"; RNA; 2008; 14: 1714-1719.

Czauderna et al.; "Structural variations and stabilizing modifications of synthetic siRNAs in mammalian cells"; Nucleic Acids Research; vol. 31, No. 11; 2705-2716; 2003.

Hyde et al., Pediatric Pulmonology, pp. 306-307 (2007).

Jernigan et al.; "Myogenic vasoconstriction in mouse renal interlobar arteries: role of endogenous Beta and yENaC"; Am J Physiol Renal Physiol; 291:F 1184-F1191 [XP-002649088] (2006).

O'Riordan et al., "Acute Hyperkalemia Associated with Inhalation of a Potent ENaC Antagonist: Phase 1 Trial of GS-9411"; J. Aerosol Med. & Pulmonary Drug Dev.; vol. 27, No. 3; 200-208 (2014).

Qian, et al.; "Sodium Channel Subunit SCNN1B Suppresses Gastric Cancer Growth and Metastasis via GRP78 Degradation"; Cancer Res.; 77(8); Apr. 15, 2017.

International Preliminary Report dated May 3, 2022, for corresponding PCT Application No. PCT/US20/57778.

GenBank NM_000336.2 (2018).

GenBank NM_000336.3 (2023).

* cited by examiner (Tri-SM2)

(Tri-SM1)

(Tri-SM6.1)

(Tri-SM9)

(Tri-SM6)

(Tri-SM8)

(Tri-SM10)

(Tri-SM11)

AD06495

Sense Strand (5' → 3') (AM08758-SS) (SEQ ID NO: 167)

Antisense Strand (3' ← 5') (AM08759-AS) (SEQ ID NO: 130)

AD06497

Sense Strand (5' → 3') (AM08762-SS) (SEQ ID NO: 169)

Antisense Strand (3' ← 5') (AM08761-AS) (SEQ ID NO: 131)

AD06501

Sense Strand (5' → 3') (AM08768-SS) (SEQ ID NO: 172)

Antisense Strand (3' ← 5') (AM08769-AS) (SEQ ID NO: 135)

SEQUENCE LISTING

```
<160> NUMBER OF SEQ ID NOS: 246

<210> SEQ ID NO 1
<211> LENGTH: 2597
<212> TYPE: DNA
<213> ORGANISM: Homo Sapiens
<220> FEATURE:
<223> OTHER INFORMATION: Homo sapiens sodium channel epithelial 1
      subunit beta (SCNN1B), gene transcript, version NM_000336.2

<400> SEQUENCE: 1

gtgcttcccc gcccctgaac ctgctccctc ccagtcggtc tcgccgcgct cgccgggtgt     60

cccagtgtca ccaacactcg gccgccgccg ccagcttggc gcgcaccgcc gcctccgcca    120

ccgccgacag cgcgcatcct ccgtgtcccc gctccgccgc ccgagcaggt gccactatgc    180

acgtgaagaa gtacctgctg aagggcctgc atcggctgca gaagggcccc ggctacacgt    240
```

-continued

```
acaaggagct gctggtgtgg tactgcgaca acaccaacac ccacggcccc aagcgcatca    300
tctgtgaggg gcccaagaag aaagccatgt ggttcctgct caccctgctc ttcgccgccc    360
tcgtctgctg gcagtggggc atcttcatca ggacctactt gagctgggag gtcagcgtct    420
ccctctccgt aggcttcaag accatggact tccctgccgt caccatctgc aatgctagcc    480
ccttcaagta ttccaaaatc aagcatttgc tgaaggacct ggatgagctg atggaagctg    540
tcctggagag aatcctggct cctgagctaa gccatgccaa tgccaccagg aacctgaact    600
tctccatctg gaaccacaca cccctggtcc ttattgatga acggaacccc caccacccca    660
tggtccttga tctctttgga gacaaccaca atggcttaac aagcagctca gcatcagaaa    720
agatctgtaa tgcccacggg tgcaaaatgg ccatgagact atgtagcctc aacaggaccc    780
agtgtacctt ccggaacttc accagtgcta cccaggcatt gacagagtgg tacatcctgc    840
aggccaccaa catctttgca caggtgccac agcaggagct agtagagatg agctaccccg    900
gcgagcagat gatcctggcc tgcctattcg gagctgagcc ctgcaactac cggaacttca    960
cgtccatctt ctaccctcac tatggcaact gttacatctt caactggggc atgacagaga   1020
aggcacttcc ttcggccaac cctggaactg aattcggcct gaagttgatc ctggacatag   1080
gccaggaaga ctacgtcccc ttccttgcgt ccacggccgg ggtcaggctg atgcttcacg   1140
agcagaggtc ataccccttc atcagagatg agggcatcta cgccatgtcg gggacagaga   1200
cgtccatcgg ggtactcgtg gacaagcttc agcgcatggg ggagccctac agcccgtgca   1260
ccgtgaatgg ttctgaggtc cccgtccaaa acttctacag tgactacaac acgacctact   1320
ccatccaggc ctgtcttcgc tcctgcttcc aagaccacat gatccgtaac tgcaactgtg   1380
gccactacct gtacccactg ccccgtgggg agaaatactg caacaaccgg gacttcccag   1440
actgggccca ttgctactca gatctacaga tgagcgtggc gcagagagag acctgcattg   1500
gcatgtgcaa ggagtcctgc aatgacaccc agtacaagat gaccatctcc atggctgact   1560
ggccttctga ggcctccgag gactggattt tccacgtctt gtctcaggag cgggaccaaa   1620
gcaccaatat caccctgagc aggaagggaa ttgtcaagct caacatctac ttccaagaat   1680
ttaactatcg caccattgaa gaatcagcag ccaataacat cgtctggctg ctctcgaatc   1740
tgggtggcca gtttggcttc tggatggggg gctctgtgct gtgcctcatc gagtttgggg   1800
agatcatcat cgactttgtg tggatcacca tcatcaagct ggtggccttg gccaagagcc   1860
tacggcagcg gcgagcccaa gccagctacg ctggcccacc gcccaccgtg gccgagctgg   1920
tggaggccca caccaacttt ggcttccagc ctgacacggc cccccgcagc cccaacactg   1980
ggccctaccc cagtgagcag gccctgccca tcccaggcac cccgcccccc aactatgact   2040
ccctgcgtct gcagccgctg gacgtcatcg agtctgacag tgagggtgat gccatctaac   2100
cctgccccctg cccaccccgg gcggctgaaa ctcactgagc agccaagact gttgcccgag   2160
gcctcactgt atggtgccct ctccaaaggg tcgggagggt agctctccag gccagagctt   2220
gtgtccttca acagagaggc cagcggcaac tggtccgtta ctggccaagg gctctgtaga   2280
atcacggtgc tggtacagga tgcaggaata aattgtatct tcacctggtt cctaccctcg   2340
tccctacctg tcctgatcct ggtcctgaag acccctcgga acaccctctc ctggtggcag   2400
gccacttccc tcccagtgcc agtctccatc caccccagag aggaacaggc gggtgggcca   2460
tgtggttttc tccttcctgg ccttggctgg cctctggggc aggggtggtg gagagatgga   2520
agggcatcag gtgtagggac cctgccaagt ggcacctgat ttactctaga aaataaaagt   2580
agaaaatact gagtcca                                                  2597
```

<210> SEQ ID NO 2
<211> LENGTH: 2560
<212> TYPE: DNA
<213> ORGANISM: Homo Sapiens
<220> FEATURE:
<223> OTHER INFORMATION: Homo sapiens sodium channel epithelial 1
subunit beta (SCNN1B), gene transcript, version NM_000336.3

<400> SEQUENCE: 2

```
agtcggtctc gccgcgctcg ccgggtgtcc cagtgtcacc aacactcggc cgccgccgcc     60
agcttggcgc gcaccgccgc ctccgccacc gccgacagcg cgcatcctcc gtgtccccgc    120
tccgccgccc gagcaggtgc cactatgcac gtgaagaagt acctgctgaa gggcctgcat    180
cggctgcaga agggccccgg ctacacgtac aaggagctgc tggtgtggta ctgcgacaac    240
accaacaccc acggccccaa gcgcatcatc tgtgaggggc ccaagaagaa agccatgtgg    300
ttcctgctca ccctgctctt cgccgccctc gtctgctggc agtggggcat cttcatcagg    360
acctacttga gctgggaggt cagcgtctcc ctctccgtag gcttcaagac catggacttc    420
cctgccgtca ccatctgcaa tgctagcccc ttcaagtatt ccaaaatcaa gcatttgctg    480
aaggacctgg atgagctgat ggaagctgtc ctggagagaa tcctggctcc tgagctaagc    540
catgccaatg ccaccaggaa cctgaacttc tccatctgga accacacacc cctggtcctt    600
attgatgaac ggaaccccca ccaccccatg gtccttgatc tctttggaga caaccacaat    660
ggcttaacaa gcagctcagc atcagaaaag atctgtaatg cccacgggtg caaaatggcc    720
atgagactat gtagcctcaa caggacccag tgtaccttcc ggaacttcac cagtgctacc    780
caggcattga cagagtggta catcctgcag gccaccaaca tctttgcaca ggtgccacag    840
caggagctag tagagatgag ctaccccggc gagcagatga tcctggcctg cctattcgga    900
gctgagccct gcaactaccg gaacttcacg tccatcttct accctcacta tggcaactgt    960
tacatcttca actggggcat gacagagaag gcacttcctt cggccaaccc tggaactgaa   1020
ttcggcctga agttgatcct ggacataggc caggaagact acgtcccctt ccttgcgtcc   1080
acggccgggg tcaggctgat gcttcacgag cagaggtcat accccttcat cagagatgag   1140
ggcatctacg ccatgtcggg gacagagacg tccatcgggg tactcgtgga caagcttcag   1200
cgcatggggg agccctacag cccgtgcacc gtgaatggtt ctgaggtccc cgtccaaaac   1260
ttctacagtg actacaacac gacctactcc atccaggcct gtcttcgctc ctgcttccaa   1320
gaccacatga tccgtaactg caactgtggc cactacctgt acccactgcc ccgtggggag   1380
aaatactgca acaaccggga cttcccagac tgggcccatt gctactcaga tctacagatg   1440
agcgtggcgc agagagagac ctgcattggc atgtgcaagg agtcctgcaa tgacacccag   1500
tacaagatga ccatctccat ggctgactgg ccttctgagg cctccgagga ctggattttc   1560
cacgtcttgt ctcaggagcg ggaccaaagc accaatatca ccctgagcag gaagggaatt   1620
gtcaagctca acatctactt ccaagaattt aactatcgca ccattgaaga atcagcagcc   1680
aataacatcg tctggctgct ctcgaatctg ggtggccagt ttggcttctg gatgggggc    1740
tctgtgctgt gcctcatcga gtttggggag atcatcatcg actttgtgtg gatcaccatc   1800
atcaagctgg tggccttggc caagagccta cggcagcggc gagcccaagc cagctacgct   1860
ggcccaccgc ccaccgtggc cgagctggtg gaggcccaca ccaactttgg cttccagcct   1920
gacacggccc cccgcagccc caacactggg ccctacccca gtgagcaggc cctgcccatc   1980
ccaggcaccc cgccccccaa ctatgactcc ctgcgtctgc agccgctgga cgtcatcgag   2040
```

-continued

```
tctgacagtg agggtgatgc catctaaccc tgcccctgcc caccccgggc ggctgaaact   2100

cactgagcag ccaagactgt tgcccgaggc ctcactgtat ggtgccctct ccaaagggtc   2160

gggagggtag ctctccaggc cagagcttgt gtccttcaac agagaggcca gcggcaactg   2220

gtccgttact ggccaagggc tctgtagaat cacggtgctg gtacaggatg caggaataaa   2280

ttgtatcttc acctggttcc taccctcgtc cctacctgtc ctgatcctgg tcctgaagac   2340

ccctcggaac accctctcct ggtggcaggc cacttccctc ccagtgccag tctccatcca   2400

ccccagagag gaacaggcgg gtgggccatg tggttttctc cttcctggcc ttggctggcc   2460

tctggggcag gggtggtgga gagatggaag ggcatcaggt gtagggaccc tgccaagtgg   2520

cacctgattt actctagaaa ataaaagtag aaaatactga                         2560


<210> SEQ ID NO 3
<211> LENGTH: 19
<212> TYPE: RNA
<213> ORGANISM: Artificial sequence
<220> FEATURE:
<223> OTHER INFORMATION: Beta-ENaC mRNA (gene transcript) target
      sequence

<400> SEQUENCE: 3

accccugguc cuuauugau                                                  19


<210> SEQ ID NO 4
<211> LENGTH: 19
<212> TYPE: RNA
<213> ORGANISM: Artificial sequence
<220> FEATURE:
<223> OTHER INFORMATION: Beta-ENaC mRNA (gene transcript) target
      sequence

<400> SEQUENCE: 4

cccugguccu uauugauga                                                  19


<210> SEQ ID NO 5
<211> LENGTH: 19
<212> TYPE: RNA
<213> ORGANISM: Artificial sequence
<220> FEATURE:
<223> OTHER INFORMATION: Beta-ENaC mRNA (gene transcript) target
      sequence

<400> SEQUENCE: 5

aacuguuaca ucuucaacu                                                  19


<210> SEQ ID NO 6
<211> LENGTH: 19
<212> TYPE: RNA
<213> ORGANISM: Artificial sequence
<220> FEATURE:
<223> OTHER INFORMATION: Beta-ENaC mRNA (gene transcript) target
      sequence

<400> SEQUENCE: 6

ucuacaguga cuacaacac                                                  19


<210> SEQ ID NO 7
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
```

-continued

<400> SEQUENCE: 7
uacagugacu acaacacga 19

<210> SEQ ID NO 8
<211> LENGTH: 19
<212> TYPE: RNA
<213> ORGANISM: Artificial sequence
<220> FEATURE:
<223> OTHER INFORMATION: Beta-ENaC mRNA (gene transcript) target sequence

<400> SEQUENCE: 8
uuccaagacc acaugaucc 19

<210> SEQ ID NO 9
<211> LENGTH: 19
<212> TYPE: RNA
<213> ORGANISM: Artificial sequence
<220> FEATURE:
<223> OTHER INFORMATION: Beta-ENaC mRNA (gene transcript) target sequence

<400> SEQUENCE: 9
uccaagacca caugauccg 19

<210> SEQ ID NO 10
<211> LENGTH: 19
<212> TYPE: RNA
<213> ORGANISM: Artificial sequence
<220> FEATURE:
<223> OTHER INFORMATION: Beta-ENaC mRNA (gene transcript) target sequence

<400> SEQUENCE: 10
guggggagaa auacugcaa 19

<210> SEQ ID NO 11
<211> LENGTH: 19
<212> TYPE: RNA
<213> ORGANISM: Artificial sequence
<220> FEATURE:
<223> OTHER INFORMATION: Beta-ENaC mRNA (gene transcript) target sequence

<400> SEQUENCE: 11
ggagaaauac ugcaacaac 19

<210> SEQ ID NO 12
<211> LENGTH: 19
<212> TYPE: RNA
<213> ORGANISM: Artificial sequence
<220> FEATURE:
<223> OTHER INFORMATION: Beta-ENaC mRNA (gene transcript) target sequence

<400> SEQUENCE: 12
gagaaauacu gcaacaacc 19

<210> SEQ ID NO 13
<211> LENGTH: 19
<212> TYPE: RNA
<213> ORGANISM: Artificial sequence
<220> FEATURE:
<223> OTHER INFORMATION: Beta-ENaC mRNA (gene transcript) target sequence -continued

<400> SEQUENCE: 13
aucacccuga gcaggaagg 19

<210> SEQ ID NO 14
<211> LENGTH: 19
<212> TYPE: RNA
<213> ORGANISM: Artificial sequence
<220> FEATURE:
<223> OTHER INFORMATION: Beta-ENaC mRNA (gene transcript) target
sequence

<400> SEQUENCE: 14
gggagaucau caucgacuu 19

<210> SEQ ID NO 15
<211> LENGTH: 19
<212> TYPE: RNA
<213> ORGANISM: Artificial sequence
<220> FEATURE:
<223> OTHER INFORMATION: RNAi agent antisense strand core 19-mer base
sequence

<400> SEQUENCE: 15
aguugaagau guaacaguu 19

<210> SEQ ID NO 16
<211> LENGTH: 19
<212> TYPE: RNA
<213> ORGANISM: Artificial sequence
<220> FEATURE:
<223> OTHER INFORMATION: RNAi agent antisense strand core 19-mer base
sequence

<400> SEQUENCE: 16
uguugaagau guaacaguu 19

<210> SEQ ID NO 17
<211> LENGTH: 19
<212> TYPE: RNA
<213> ORGANISM: Artificial sequence
<220> FEATURE:
<223> OTHER INFORMATION: RNAi agent antisense strand core 19-mer base
sequence
<220> FEATURE:
<221> NAME/KEY: modified_base
<222> LOCATION: 1
<223> OTHER INFORMATION: n = any nucleobase

<400> SEQUENCE: 17
nguugaagau guaacaguu 19

<210> SEQ ID NO 18
<211> LENGTH: 19
<212> TYPE: RNA
<213> ORGANISM: Artificial sequence
<220> FEATURE:
<223> OTHER INFORMATION: RNAi agent antisense strand core 19-mer base
sequence
<220> FEATURE:
<221> NAME/KEY: modified_base
<222> LOCATION: 1, 19
<223> OTHER INFORMATION: n = any nucleobase

<400> SEQUENCE: 18
nguugaagau guaacagun 19

<210> SEQ ID NO 19

-continued

<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 19
aucaauaagg accaggggu 19

<210> SEQ ID NO 20
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 20
uucaauaagg accaggggu 19

<210> SEQ ID NO 21
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 21
nucaauaagg accaggggu 19

<210> SEQ ID NO 22
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 22
nucaauaagg accaggggn 19

<210> SEQ ID NO 23
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 23
ucaucaauaa ggaccaggg 19

<210> SEQ ID NO 24
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 24
ncaucaauaa ggaccaggg 19

<210> SEQ ID NO 25
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 25
ncaucaauaa ggaccaggn 19

<210> SEQ ID NO 26
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 26
guguuguagu cacuguaga 19

<210> SEQ ID NO 27
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 27
uuguuguagu cacuguaga 19

<210> SEQ ID NO 28
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 28
nuguuguagu cacuguaga 19

<210> SEQ ID NO 29
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base -continued
<222> LOCATION: 1, 19
<223> OTHER INFORMATION: n = any nucleobase

<400> SEQUENCE: 29
nuguuguagu cacuguagn 19

<210> SEQ ID NO 30
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 30
ucguguugua gucacugua 19

<210> SEQ ID NO 31
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 31
ncguguugua gucacugua 19

<210> SEQ ID NO 32
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 32
ncguguugua gucacugun 19

<210> SEQ ID NO 33
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 33
ucguguugua gucacugua 19

<210> SEQ ID NO 34
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 34
ncguguugua gucacugua 19

<210> SEQ ID NO 35
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 35
ncguguugua gucacugun 19

<210> SEQ ID NO 36
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 36
ggaucaugug gucuuggaa 19

<210> SEQ ID NO 37
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 37
ugaucaugug gucuuggaa 19

<210> SEQ ID NO 38
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 38
ugaucaugug gucuuggaa 19

<210> SEQ ID NO 39
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 39
ngaucaugug gucuuggaa 19

<210> SEQ ID NO 40
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 40
ngaucaugug gucuuggan 19

<210> SEQ ID NO 41
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 41
cggaucaugu ggucuugga 19

<210> SEQ ID NO 42
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 42
uggaucaugu ggucuugga 19

<210> SEQ ID NO 43
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 43
nggaucaugu ggucuugga 19

<210> SEQ ID NO 44
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 44
nggaucaugu ggucuuggn 19

<210> SEQ ID NO 45
<211> LENGTH: 19

<212> TYPE: RNA
<213> ORGANISM: Artificial sequence
<220> FEATURE:
<223> OTHER INFORMATION: RNAi agent antisense strand core 19-mer base sequence

<400> SEQUENCE: 45
uugcaguauu ucuccccac 19

<210> SEQ ID NO 46
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 46
nugcaguauu ucuccccac 19

<210> SEQ ID NO 47
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 47
nugcaguauu ucuccccan 19

<210> SEQ ID NO 48
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 48
guuguugcag uauuucucc 19

<210> SEQ ID NO 49
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 49
uuuguugcag uauuucucc 19

<210> SEQ ID NO 50
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:

-continued

<221> NAME/KEY: modified_base
<222> LOCATION: 1
<223> OTHER INFORMATION: n = any nucleobase

<400> SEQUENCE: 50
nuuguugcag uauuucucc 19

<210> SEQ ID NO 51
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 51
nuuguugcag uauuucucn 19

<210> SEQ ID NO 52
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 52
gguuguugca guauuucuc 19

<210> SEQ ID NO 53
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 53
uguuguugca guauuucuc 19

<210> SEQ ID NO 54
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 54
nguuguugca guauuucuc 19

<210> SEQ ID NO 55
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19

<223> OTHER INFORMATION: n = any nucleobase

<400> SEQUENCE: 55
nguuguugca guauuucun 19

<210> SEQ ID NO 56
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 56
ccuuccugcu cagggugau 19

<210> SEQ ID NO 57
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 57
ucuuccugcu cagggugau 19

<210> SEQ ID NO 58
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 58
ncuuccugcu cagggugau 19

<210> SEQ ID NO 59
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 59
ncuuccugcu cagggugan 19

<210> SEQ ID NO 60
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 60
aagucgauga ugaucuccc 19

<210> SEQ ID NO 61
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 61
uagucgauga ugaucuccc 19

<210> SEQ ID NO 62
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 62
aagucgauga ugaucuccc 19

<210> SEQ ID NO 63
<211> LENGTH: 19
<212> TYPE: RNA
<213> ORGANISM: Artificial sequence
<220> FEATURE:
<223> OTHER INFORMATION: RNAi agent antisense strand core 19-mer base sequence

<400> SEQUENCE: 63
uagucgauga ugaucuccc 19

<210> SEQ ID NO 64
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 64
nagucgauga ugaucuccc 19

<210> SEQ ID NO 65
<211> LENGTH: 19
<212> TYPE: RNA
<213> ORGANISM: Artificial sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 65
nagucgauga ugaucuccc 19

<210> SEQ ID NO 66
<211> LENGTH: 19
<212> TYPE: RNA
<213> ORGANISM: Artificial sequence
<220> FEATURE:

-continued

<223> OTHER INFORMATION: RNAi agent antisense strand core 19-mer base
sequence
<220> FEATURE:
<221> NAME/KEY: modified_base
<222> LOCATION: 1, 19
<223> OTHER INFORMATION: n = any nucleobase

<400> SEQUENCE: 66
nagucgauga ugaucuccn 19

<210> SEQ ID NO 67
<211> LENGTH: 19
<212> TYPE: RNA
<213> ORGANISM: Artificial sequence
<220> FEATURE:
<223> OTHER INFORMATION: RNAi agent antisense strand core 19-mer base
sequence
<220> FEATURE:
<221> NAME/KEY: modified_base
<222> LOCATION: 1, 19
<223> OTHER INFORMATION: n = any nucleobase

<400> SEQUENCE: 67
nagucgauga ugaucuccn 19

<210> SEQ ID NO 68
<211> LENGTH: 19
<212> TYPE: RNA
<213> ORGANISM: Artificial sequence
<220> FEATURE:
<223> OTHER INFORMATION: RNAi agent sense strand core 19-mer base
sequence

<400> SEQUENCE: 68
aacuguuaca ucuucaacu 19

<210> SEQ ID NO 69
<211> LENGTH: 19
<212> TYPE: RNA
<213> ORGANISM: Artificial sequence
<220> FEATURE:
<223> OTHER INFORMATION: RNAi agent sense strand core 19-mer base
sequence

<400> SEQUENCE: 69
aacuguuaca ucuucaaca 19

<210> SEQ ID NO 70
<211> LENGTH: 19
<212> TYPE: RNA
<213> ORGANISM: Artificial sequence
<220> FEATURE:
<223> OTHER INFORMATION: RNAi agent sense strand core 19-mer base
sequence
<220> FEATURE:
<221> NAME/KEY: modified_base
<222> LOCATION: 19
<223> OTHER INFORMATION: n = any nucleobase

<400> SEQUENCE: 70
aacuguuaca ucuucaacn 19

<210> SEQ ID NO 71
<211> LENGTH: 19
<212> TYPE: RNA
<213> ORGANISM: Artificial sequence
<220> FEATURE:
<223> OTHER INFORMATION: RNAi agent sense strand core 19-mer base
sequence <220> FEATURE:
<221> NAME/KEY: modified_base
<222> LOCATION: 1, 19
<223> OTHER INFORMATION: n = any nucleobase

<400> SEQUENCE: 71
nacuguuaca ucuucaacn 19

<210> SEQ ID NO 72
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 72
accccugguc cuuauugau 19

<210> SEQ ID NO 73
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 73
accccugguc cuuauugaa 19

<210> SEQ ID NO 74
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 74
accccugguc cuuauugan 19

<210> SEQ ID NO 75
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 75
nccccugguc cuuauugan 19

<210> SEQ ID NO 76
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 76
cccugguccu uauugauga 19

<210> SEQ ID NO 77
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 77
cccugguccu uauugaugn 19

<210> SEQ ID NO 78
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 78
nccugguccu uauugaugn 19

<210> SEQ ID NO 79
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 79
ucuacaguga cuacaacac 19

<210> SEQ ID NO 80
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 80
ucuacaguga cuacaacaa 19

<210> SEQ ID NO 81
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 81
ucuacaguga cuacaacan 19

<210> SEQ ID NO 82
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 82
ncuacaguga cuacaacan 19

<210> SEQ ID NO 83
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 83
uacagugacu acaacacga 19

<210> SEQ ID NO 84
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 84
uacagugacu acaacacgn 19

<210> SEQ ID NO 85
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 85
nacagugacu acaacacgn 19

<210> SEQ ID NO 86
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 18
<223> OTHER INFORMATION: n = hypoxanthine (inosine)

<400> SEQUENCE: 86
uacagugacu acaacacna 19

<210> SEQ ID NO 87
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 87
uacagugacu acaacacnn 19

<210> SEQ ID NO 88
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = hypoxanthine (inosine)

<400> SEQUENCE: 88
nacagugacu acaacacnn 19

<210> SEQ ID NO 89
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 89
uuccaagacc acaugaucc 19

<210> SEQ ID NO 90
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 90
uuccaagacc acaugauca 19

<210> SEQ ID NO 91
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 15
<223> OTHER INFORMATION: n = hypoxanthine (inosine)

<400> SEQUENCE: 91
uuccaagacc acaunauca 19

<210> SEQ ID NO 92
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 92
uuccaagacc acaugaucn 19

<210> SEQ ID NO 93
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 93
nuccaagacc acaugaucn 19

<210> SEQ ID NO 94
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 94
uccaagacca caugauccg 19

<210> SEQ ID NO 95
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 95
uccaagacca caugaucca 19

<210> SEQ ID NO 96
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 96
uccaagacca caugauccn 19

<210> SEQ ID NO 97
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 97
nccaagacca caugauccn 19

<210> SEQ ID NO 98
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 98
guggggagaa auacugcaa 19

<210> SEQ ID NO 99
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 99
guggggagaa auacugcan 19

<210> SEQ ID NO 100
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 100
nuggggagaa auacugcan 19

<210> SEQ ID NO 101
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 101
ggagaaauac ugcaacaac 19

<210> SEQ ID NO 102
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 102
ggagaaauac ugcaacaaa 19

<210> SEQ ID NO 103
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 103
ggagaaauac ugcaacaan 19

<210> SEQ ID NO 104
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 104
ngagaaauac ugcaacaan 19

<210> SEQ ID NO 105
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 105
gagaaauacu gcaacaacc 19

<210> SEQ ID NO 106
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 106
gagaaauacu gcaacaaca 19

<210> SEQ ID NO 107
<211> LENGTH: 19
<212> TYPE: RNA
<213> ORGANISM: Artificial sequence
<220> FEATURE:
<223> OTHER INFORMATION: RNAi agent sense strand core 19-mer base
sequence
<220> FEATURE:
<221> NAME/KEY: modified_base
<222> LOCATION: 19
<223> OTHER INFORMATION: n = any nucleobase

<400> SEQUENCE: 107
gagaaauacu gcaacaacn 19

<210> SEQ ID NO 108
<211> LENGTH: 19
<212> TYPE: RNA
<213> ORGANISM: Artificial sequence
<220> FEATURE:
<223> OTHER INFORMATION: RNAi agent sense strand core 19-mer base
sequence
<220> FEATURE:
<221> NAME/KEY: modified_base
<222> LOCATION: 1, 19
<223> OTHER INFORMATION: n = any nucleobase

<400> SEQUENCE: 108
nagaaauacu gcaacaacn 19

<210> SEQ ID NO 109
<211> LENGTH: 19
<212> TYPE: RNA
<213> ORGANISM: Artificial sequence
<220> FEATURE:
<223> OTHER INFORMATION: RNAi agent sense strand core 19-mer base
sequence

<400> SEQUENCE: 109
aucacccuga gcaggaagg 19

<210> SEQ ID NO 110
<211> LENGTH: 19
<212> TYPE: RNA
<213> ORGANISM: Artificial sequence
<220> FEATURE:
<223> OTHER INFORMATION: RNAi agent sense strand core 19-mer base
sequence

<400> SEQUENCE: 110
aucacccuga gcaggaaga 19

<210> SEQ ID NO 111
<211> LENGTH: 19
<212> TYPE: RNA
<213> ORGANISM: Artificial sequence
<220> FEATURE:
<223> OTHER INFORMATION: RNAi agent sense strand core 19-mer base
sequence
<220> FEATURE:
<221> NAME/KEY: modified_base
<222> LOCATION: 19
<223> OTHER INFORMATION: n = any nucleobase

<400> SEQUENCE: 111
aucacccuga gcaggaagn 19

<210> SEQ ID NO 112
<211> LENGTH: 19

<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 112
nucacccuga gcaggaagn 19

<210> SEQ ID NO 113
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 113
gggagaucau caucgacuu 19

<210> SEQ ID NO 114
<211> LENGTH: 19
<212> TYPE: RNA
<213> ORGANISM: Artificial sequence
<220> FEATURE:
<223> OTHER INFORMATION: RNAi agent sense strand core 19-mer base sequence

<400> SEQUENCE: 114
gggagaucau caucgacua 19

<210> SEQ ID NO 115
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 15
<223> OTHER INFORMATION: n = hypoxanthine (inosine)

<400> SEQUENCE: 115
gggagaucau caucnacuu 19

<210> SEQ ID NO 116
<211> LENGTH: 19
<212> TYPE: RNA
<213> ORGANISM: Artificial sequence
<220> FEATURE:
<223> OTHER INFORMATION: RNAi agent sense strand core 19-mer base sequence
<220> FEATURE:
<221> NAME/KEY: modified_base
<222> LOCATION: 15
<223> OTHER INFORMATION: n = hypoxanthine (inosine)

<400> SEQUENCE: 116
gggagaucau caucnacua 19

<210> SEQ ID NO 117
<211> LENGTH: 19
<212> TYPE: RNA
<213> ORGANISM: Artificial sequence -continued
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 117
gggagaucau caucgacun 19

<210> SEQ ID NO 118
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 118
gggagaucau caucnacun 19

<210> SEQ ID NO 119
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 119
nggagaucau caucgacun 19

<210> SEQ ID NO 120
<211> LENGTH: 19
<212> TYPE: RNA
<213> ORGANISM: Artificial sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = hypoxanthine (inosine)

<400> SEQUENCE: 120
nggagaucau caucnacun 19

<210> SEQ ID NO 121
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 121
aucaauaagg accaggggug u 21

<210> SEQ ID NO 122
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 122
ugaucaugug gucuuggaag c 21

<210> SEQ ID NO 123
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 123
uggaucaugu ggucuuggaa g 21

<210> SEQ ID NO 124
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 124
uugcaguauu ucuccccacg g 21

<210> SEQ ID NO 125
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 125
ucuuccugcu cagggugauc c 21

<210> SEQ ID NO 126
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 126
aagucgauga ugaucucccc a 21

<210> SEQ ID NO 127
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 127
aguugaagau guaacaguug c 21

<210> SEQ ID NO 128
<211> LENGTH: 21

<212> TYPE: RNA
<213> ORGANISM: Artificial sequence
<220> FEATURE:
<223> OTHER INFORMATION: RNAi agent antisense strand modified sequence

<400> SEQUENCE: 128
aagucgauga ugaucucccu u 21

<210> SEQ ID NO 129
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 129
ucaucaauaa ggaccagggg u 21

<210> SEQ ID NO 130
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 130
uuguuguagu cacuguagac g 21

<210> SEQ ID NO 131
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 131
ucguguugua gucacuguag g 21

<210> SEQ ID NO 132
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 132
ucguguugua gucacuguag g 21

<210> SEQ ID NO 133
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 133
ugaucaugug gucuuggaag c 21

<210> SEQ ID NO 134
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 134
uuuguugcag uauuucuccc c 21

<210> SEQ ID NO 135
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 135
uguuguugca guauuucucc c 21

<210> SEQ ID NO 136
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 136
aguugaagau guagcaguug c 21

<210> SEQ ID NO 137
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 137
ucguguugua gucacuguag g 21

<210> SEQ ID NO 138
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 138
uguugaagau guaacaguug c 21

<210> SEQ ID NO 139
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 139
aguugaagau guaacaguug c 21

<210> SEQ ID NO 140
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 140
aguugaagau guaacaguug c 21

<210> SEQ ID NO 141
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 141
aguugaagau guaacaguug c 21

<210> SEQ ID NO 142
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 142
aguugaagau guaacaguug c 21

<210> SEQ ID NO 143
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 143
uguugaagau guaacaguug c 21

<210> SEQ ID NO 144
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 144
uagucgauga ugaucucccc a 21

<210> SEQ ID NO 145
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 145
uagucgauga ugaucucccc a 21

<210> SEQ ID NO 146
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 146
aagucgauga ugaucuuccc a 21

<210> SEQ ID NO 147
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 147
aaguugauga ugaucucccc a 21

<210> SEQ ID NO 148
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 148
aagucgauga ugaucucccc a 21

<210> SEQ ID NO 149
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 149
aagucgauga ugaucucccc a 21

<210> SEQ ID NO 150
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 150
uguugaagau guaacaguug c 21

<210> SEQ ID NO 151
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 151
uguugaagau guagcaguug c 21

<210> SEQ ID NO 152
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 152
uguugaagau guagcaguug c 21

<210> SEQ ID NO 153
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 153
aguugaagau guaacaguug c 21

<210> SEQ ID NO 154
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 154
aguugaagau guaacaguug c 21

<210> SEQ ID NO 155
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 155
uguugaagau guagcaguug c 21

<210> SEQ ID NO 156
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 156
aguugaagau guaacaguug c 21

<210> SEQ ID NO 157
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 157
aguugaagau guaacaguug c 21

<210> SEQ ID NO 158
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 158
aguugaagau guaacaguug c 21

<210> SEQ ID NO 159
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 159
aguugaagau guaacaguug c 21

<210> SEQ ID NO 160
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 160
aguugaagau guaacaguug c 21

<210> SEQ ID NO 161

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 161
acaccccugg uccuuauuga u 21

<210> SEQ ID NO 162
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 162
gcuuccaaga ccacaugauc a 21

<210> SEQ ID NO 163
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 163
cuuccaagac cacaugaucc a 21

<210> SEQ ID NO 164
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 164
ccguggggag aaauacugca a 21

<210> SEQ ID NO 165
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 165
ggaucacccu gagcaggaag a 21

<210> SEQ ID NO 166
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 166
accccugguc cuuauugaug a 21

<210> SEQ ID NO 167
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 167
cgucuacagu gacuacaaca a 21

<210> SEQ ID NO 168
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 168
ccuacaguga cuacaacacg a 21

<210> SEQ ID NO 169
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 169
ccuacaguga cuacaacacn a 21

<210> SEQ ID NO 170
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 170
gcuuccaaga ccacaunauc a 21

<210> SEQ ID NO 171
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 171
ggggagaaau acugcaacaa a 21

<210> SEQ ID NO 172
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 172
gggagaaaua cugcaacaac a 21

<210> SEQ ID NO 173
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 173
gcaacuguua caucuucaac u 21

<210> SEQ ID NO 174
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 174
uggggagauc aucaucnacu u 21

<210> SEQ ID NO 175
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 15
<223> OTHER INFORMATION: n = 2'-O-methylinosine-3'-phosphate

<400> SEQUENCE: 175
gggagaucau caucnacuuu u 21

<210> SEQ ID NO 176
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 176
gcaacugcua caucuucaac u 21

<210> SEQ ID NO 177
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 177
gcaacuguua caucuucaac a 21

<210> SEQ ID NO 178
<211> LENGTH: 25
<212> TYPE: RNA
<213> ORGANISM: Artificial sequence
<220> FEATURE:
<223> OTHER INFORMATION: RNAi agent sense strand modified sequence

<400> SEQUENCE: 178
gcaacuguua caucauuaca aacaa 25

<210> SEQ ID NO 179
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 179
gcnacuguua caucuucaac u 21

<210> SEQ ID NO 180
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 180
gcaacuguua caucuucaac a 21

<210> SEQ ID NO 181
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 181
gcnacuguua caucuucaac a 21

<210> SEQ ID NO 182
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 182
gcaacuguua caucuucaac ut 22

<210> SEQ ID NO 183
<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 183
gcaacuguua caucuucaac at 22

<210> SEQ ID NO 184
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 184
gcnacuguua caucuucaac u 21

<210> SEQ ID NO 185

-continued

<211> LENGTH: 22
<212> TYPE: DNA
<213> ORGANISM: Artificial sequence
<220> FEATURE:
<223> OTHER INFORMATION: RNAi agent sense strand modified sequence

<400> SEQUENCE: 185
gcaacuguua caucuucaac at 22

<210> SEQ ID NO 186
<211> LENGTH: 22
<212> TYPE: DNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 186
gcnacuguua caucuucaac ut 22

<210> SEQ ID NO 187
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 187
gcaacuguua caucuucaac a 21

<210> SEQ ID NO 188
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 188
gcnacuguua caucuucaac u 21

<210> SEQ ID NO 189
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 189
aucaauaagg accaggggug u 21

<210> SEQ ID NO 190
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 190
ugaucaugug gucuuggaag c 21

<210> SEQ ID NO 191
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 191
uggaucaugu ggucuuggaa g 21

<210> SEQ ID NO 192
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 192
uugcaguauu ucuccccacg g 21

<210> SEQ ID NO 193
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 193
ucuuccugcu cagggugauc c 21

<210> SEQ ID NO 194
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 194
aagucgauga ugaucucccc a 21

<210> SEQ ID NO 195
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 195
aguugaagau guaacaguug c 21

<210> SEQ ID NO 196
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 196
aagucgauga ugaucucccu u 21

<210> SEQ ID NO 197
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 197
ucaucaauaa ggaccagggg u 21

<210> SEQ ID NO 198
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 198
uuguuguagu cacuguagac g 21

<210> SEQ ID NO 199
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 199
ucguguugua gucacuguag g 21

<210> SEQ ID NO 200
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 200
uuuguugcag uauuucuccc c 21

<210> SEQ ID NO 201
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 201
uguuguugca guauuucucc c 21

<210> SEQ ID NO 202
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 202
aguugaagau guagcaguug c 21

<210> SEQ ID NO 203
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 203
uguugaagau guaacaguug c 21

<210> SEQ ID NO 204
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 204
aguugaagau guaacaguug c 21

<210> SEQ ID NO 205
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 205
uguugaagau guaacaguug c 21

<210> SEQ ID NO 206
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 206
uagucgauga ugaucucccc a 21

<210> SEQ ID NO 207
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 207
aagucgauga ugaucuuccc a 21

<210> SEQ ID NO 208
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 208
aaguugauga ugaucucccc a 21

<210> SEQ ID NO 209

<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 209
aagucgauga ugaucucccc a 21

<210> SEQ ID NO 210
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 210
uguugaagau guagcaguug c 21

<210> SEQ ID NO 211
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 211
acaccccugg uccuuauuga u 21

<210> SEQ ID NO 212
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 212
gcuuccaaga ccacaugauc a 21

<210> SEQ ID NO 213
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 213
cuuccaagac cacaugaucc a 21

<210> SEQ ID NO 214
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 214
ccguggggag aaauacugca a 21

<210> SEQ ID NO 215
<211> LENGTH: 21

<212> TYPE: RNA
<213> ORGANISM: Artificial sequence
<220> FEATURE:
<223> OTHER INFORMATION: RNAi agent sense strand underlying base sequence

<400> SEQUENCE: 215
ggaucacccu gagcaggaag a 21

<210> SEQ ID NO 216
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 216
accccugguc cuuauugaug a 21

<210> SEQ ID NO 217
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 217
cgucuacagu gacuacaaca a 21

<210> SEQ ID NO 218
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 218
ccuacaguga cuacaacacg a 21

<210> SEQ ID NO 219
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 20
<223> OTHER INFORMATION: n = hypoxanthine (inosine) nucleotide

<400> SEQUENCE: 219
ccuacaguga cuacaacacn a 21

<210> SEQ ID NO 220
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = hypoxanthine (inosine) nucleotide

<400> SEQUENCE: 220
gcuuccaaga ccacaunauc a 21

<210> SEQ ID NO 221
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 221
ggggagaaau acugcaacaa a 21

<210> SEQ ID NO 222
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 222
gggagaaaua cugcaacaac a 21

<210> SEQ ID NO 223
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 223
gcaacuguua caucuucaac u 21

<210> SEQ ID NO 224
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = hypoxanthine (inosine) nucleotide

<400> SEQUENCE: 224
uggggagauc aucaucnacu u 21

<210> SEQ ID NO 225
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 15
<223> OTHER INFORMATION: n = hypoxanthine (inosine) nucleotide

<400> SEQUENCE: 225
gggagaucau caucnacuuu u 21

<210> SEQ ID NO 226

-continued

<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 226
gcaacugcua caucuucaac u 21

<210> SEQ ID NO 227
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 227
gcaacuguua caucuucaac a 21

<210> SEQ ID NO 228
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 228
gcaacuguua caucuucaac a 21

<210> SEQ ID NO 229
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 3
<223> OTHER INFORMATION: n = 2-aminoadenine-containing nucleotide

<400> SEQUENCE: 229
gcnacuguua caucuucaac u 21

<210> SEQ ID NO 230
<211> LENGTH: 21
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 3
<223> OTHER INFORMATION: n = 2-aminoadenine-containing nucleotide

<400> SEQUENCE: 230
gcnacuguua caucuucaac a 21

<210> SEQ ID NO 231
<211> LENGTH: 22
<212> TYPE: DNA
<213> ORGANISM: Artificial sequence
<220> FEATURE:
<223> OTHER INFORMATION: RNAi agent sense strand underlying base
      sequence

<400> SEQUENCE: 231
gcaacuguua caucuucaac ut 22

<210> SEQ ID NO 232
<211> LENGTH: 22
<212> TYPE: DNA
<213> ORGANISM: Artificial sequence
<220> FEATURE:
<223> OTHER INFORMATION: RNAi agent sense strand underlying base sequence

<400> SEQUENCE: 232
gcaacuguua caucuucaac at 22

<210> SEQ ID NO 233
<211> LENGTH: 22
<212> TYPE: DNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 3
<223> OTHER INFORMATION: n = 2-aminoadenine-containing nucleotide

<400> SEQUENCE: 233
gcnacuguua caucuucaac ut 22

<210> SEQ ID NO 234
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 234
cgucuacagu gacuacaaca a 21

<210> SEQ ID NO 235
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 235
ccuacaguga cuacaacacn a 21

<210> SEQ ID NO 236
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 236
gggagaaaua cugcaacaac a 21

<210> SEQ ID NO 237
<211> LENGTH: 21
<212> TYPE: RNA

<213> ORGANISM: Artificial sequence
<220> FEATURE:
<223> OTHER INFORMATION: RNAi agent sense strand modified sequence

<400> SEQUENCE: 237
gcaacuguua caucuucaac u 21

<210> SEQ ID NO 238
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 238
uggggagauc aucaucnacu u 21

<210> SEQ ID NO 239
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 239
gcaacuguua caucuucaac a 21

<210> SEQ ID NO 240
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 240
gcnacuguua caucuucaac u 21

<210> SEQ ID NO 241
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 3
<223> OTHER INFORMATION: n = 2'-O-methyl-2-aminoadenosine-3'-phosphate

<400> SEQUENCE: 241
gcnacuguua caucuucaac a 21

<210> SEQ ID NO 242
<211> LENGTH: 19
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 1

-continued

```
<223> OTHER INFORMATION: n = 2-aminoadenine-containing nucleotide

<400> SEQUENCE: 242

nacuguuaca ucuucaacu                                                19


<210> SEQ ID NO 243
<211> LENGTH: 19
<212> TYPE: RNA
<213> ORGANISM: Artificial sequence
<220> FEATURE:
<223> OTHER INFORMATION: RNAi agent sense strand underlying base
      sequence
<220> FEATURE:
<221> NAME/KEY: modified_base
<222> LOCATION: 1
<223> OTHER INFORMATION: n = 2-aminoadenine-containing nucleotide

<400> SEQUENCE: 243

nacuguuaca ucuucaaca                                                19


<210> SEQ ID NO 244
<211> LENGTH: 21
<212> TYPE: RNA
<213> ORGANISM: Artificial sequence
<220> FEATURE:
<223> OTHER INFORMATION: RNAi agent antisense strand underlying base
      sequence

<400> SEQUENCE: 244

uuguuguagu cacuguagaa g                                             21


<210> SEQ ID NO 245
<211> LENGTH: 21
<212> TYPE: RNA
<213> ORGANISM: Artificial sequence
<220> FEATURE:
<223> OTHER INFORMATION: RNAi agent sense strand underlying base
      sequence

<400> SEQUENCE: 245

cuucuacagu gacuacaaca a                                             21


<210> SEQ ID NO 246
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 246

gcaacuguua caucuucaac u                                             21
```

RNAi AGENTS FOR INHIBITING EXPRESSION OF Beta-ENaC, COMPOSITIONS THEREOF, AND METHODS OF USE

CROSS REFERENCE TO RELATED APPLICATIONS

This application is a continuation of International Application No. PCT/US20/57778, filed on Oct. 28, 2020, which claims priority to U.S. Provisional Patent Application Ser. No. 63/024,722, filed on May 14, 2020, and U.S. Provisional Patent Application Ser. No. 62/927,637, filed on Oct. 29, 2019, the contents of each of which are incorporated herein by reference in their entirety.

SEQUENCE LISTING

This application contains a Sequence Listing which has been submitted in ASCII format and is hereby incorporated by reference in its entirety. The ASCII copy is named 30678-US1_SEQLIST.txt and is 65 kb in size.

FIELD OF THE INVENTION

The present disclosure relates to RNA interference (RNAi) agents, e.g., double stranded RNAi agents, for inhibition of beta-ENaC gene expression, compositions that include beta-ENaC RNAi agents, and methods of use thereof.

BACKGROUND

The vertebrate amiloride-sensitive epithelial sodium channel ("ENaC" or "amiloride-sensitive sodium channel") is a member of the degenerin/ENaC channel superfamily, characterized by two membrane-spanning domains, intracellular N- and C-termini, and a large extracellular loop which is a substrate for furin proteases. The channel is a heterotrimeric complex composed of three homologous subunits (alpha (α), beta (β), and gamma (δ)) encoded by three separate genes: SCNN1A (alpha), SCNN1B (beta), and SCNN1G (gamma). All three subunits are required for full channel activity. A fourth subunit (delta (δ)) encoded by SCNN1D is expressed in testes and ovaries and may be able to functionally substitute for the alpha (α) subunit in those tissues.

ENaC is expressed on the apical membrane of epithelial cells, particularly in the lung, renal distal convoluted tubule, gastrointestinal (GI) tract, reproductive tract, and ocular surface epithelium in the eye. In these epithelia, ENaC channels mediate influx of extracellular sodium ions which are then actively transported from the cell by the basolateral sodium/potassium ATPase, establishing an osmotic gradient and causing epithelial luminal water to be absorbed into the interstitium. In the kidney, ENaC mediates electrolyte balance and blood pressure, and is the target of systemic small molecule diuretics such as amiloride. In the lung, airway epithelial ENaC plays a key role in the regulation of lung hydration and mucociliary clearance.

Type 1 pseudohypoaldosteronism (PHA) patients that carry loss-of-function mutations in SCNN1A, SCNN1B, or SCNN1G, produce excess airway surface liquid and have significantly higher mucociliary clearance rates. Conversely, airway epithelial ENaC activity is significantly elevated in cystic fibrosis (CF) patients of all genotypes. Enhanced ENaC activity, together with reduced cystic fibrosis transmembrane conductance regulator (CFTR) chloride channel activity, is the primary pathogenic mechanism that underlies airway dehydration and mucociliary stasis in CF lung disease patients.

Inhaled small molecule ENaC inhibitors have shown initial promise in the treatment of CF, but their clinical development has been limited by short duration of action in the lung and on-target toxicity (hyperkalemia) associated with inhibition of renal ENaC. (See. e.g., O'Riordan et al., 27 J. Aerosol Med. & Pulmonary Drug Dev., 200-208 (2014)).

Certain RNAi agents capable of inhibiting the expression of a beta-ENaC gene (i.e., SCNN1B) have been previously identified, such as those disclosed in, for example, U.S. Pat. No. 8,344,127. However, other RNAi agent constructs with different sequences and certain chemical modifications may have superior therapeutic properties which can be used in more effective therapeutics. There still exists a need for beta-ENaC RNAi agents with greater potency that is sufficient for the treatment of beta-ENaC-associated diseases and disorders.

SUMMARY

There continues to exist a need for novel RNA interference (RNAi) agents (termed RNAi agents, RNAi triggers, or triggers), e.g., double stranded RNAi agents, that are able to selectively and efficiently inhibit the expression of a beta-ENaC (i.e., SCNN1B) gene. Further, there exists a need for compositions of novel beta-ENaC-specific RNAi agents for the treatment of diseases or disorders associated with enhanced ENaC activity and/or diseases or disorders that can be mediated at least in part by a reduction in ENaC activity.

The nucleotide sequences and chemical modifications of the beta-ENaC RNAi agents disclosed herein, as well as their combination with certain specific targeting ligands suitable for selectively and efficiently delivering the beta-ENaC RNAi agents in vivo, differ from those previously disclosed or known in the art. The beta-ENaC RNAi agents disclosed herein provide for highly potent and efficient inhibition of the expression of a beta-ENaC gene.

In general, the present disclosure features beta-ENaC gene-specific RNAi agents, compositions that include beta-ENaC RNAi agents, and methods for inhibiting expression of a beta-ENaC gene in vitro and/or in vivo using the beta-ENaC RNAi agents and compositions that include beta-ENaC RNAi agents described herein. The beta-ENaC RNAi agents described herein are able to selectively and efficiently decrease expression of a beta-ENaC gene, and thereby reduce ENaC levels in a subject, reduce ENaC activity in a subject, or reduce both ENaC levels and ENaC activity in a subject, e.g., a human or animal subject.

The described beta-ENaC RNAi agents can be used in methods for therapeutic treatment (including preventative or prophylactic treatment) of symptoms and diseases associated with enhanced or elevated ENaC activity levels, including, but not limited to various respiratory diseases such as cystic fibrosis, chronic bronchitis, chronic obstructive pulmonary disease (COPD), asthma, respiratory tract infections, primary ciliary dyskinesia, and lung carcinoma cystic fibrosis. For example, in subjects suffering from COPD, acquired CFTR and ENaC disfunction is known to contribute to drying mucus in the airway and a reduced ability of the lung to clear toxins and infectious agents.

The described beta-ENaC RNAi agents can also be used, for example, for the therapeutic treatment (including prophylactic or preventative treatment) of symptoms and diseases associated with enhanced or elevated ENaC activity levels in the ocular surface epithelium, such as the conjunctival epithelium, including for the treatment of ocular diseases and disorders such as dry eye syndrome.

In one aspect, the disclosure features RNAi agents for inhibiting expression of a beta-ENaC (SCNN1B) gene, wherein the RNAi agent includes a sense strand (also referred to as a passenger strand) and an antisense strand (also referred to as a guide strand). The sense strand and the antisense strand can be partially, substantially, or fully complementary to each other. The length of the RNAi agent sense and antisense strands described herein each can be 16 to 49 nucleotides in length. In some embodiments, the sense and antisense strands are independently 17 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the antisense strands are independently 18, 19, 20, 21, 22, 23, 24, 25, 26, 27, 28, 29, or 30 nucleotides in length. In some embodiments, the sense strands are independently 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. The RNAi agents described herein, upon delivery to a cell expressing beta-ENaC such as a pulmonary epithelial cell, inhibit the expression of one or more beta-ENaC genes in vivo and/or in vitro.

The beta-ENaC RNAi agents disclosed herein target a human beta-ENaC gene (see, e.g., SEQ ID NO:1). In some embodiments, the beta-ENaC RNAi agents disclosed herein target a portion of a beta-ENaC gene having the sequence of any of the sequences disclosed in Table 1.

In another aspect, the disclosure features compositions, including pharmaceutical compositions, that include one or more of the disclosed beta-ENaC RNAi agents that are able to selectively and efficiently decrease expression of a beta-ENaC gene. The compositions that include one or more beta-ENaC RNAi agents described herein can be administered to a subject, such as a human or animal subject, for the treatment (including prophylactic treatment or inhibition) of symptoms and diseases associated with enhanced or elevated ENaC activity (also referred to herein as enhanced ENaC channel activity levels or elevated ENaC channel activity levels).

Examples of beta-ENaC RNAi agent sense strands and antisense strands that can be used in a beta-ENaC RNAi agent are provided in Tables 3 and 4. Examples of beta-ENaC RNAi agent duplexes are provided in Tables 5A and 5B. Examples of 19-nucleotide core stretch sequences that may consist of or may be included in the sense strands and antisense strands of certain beta-ENaC RNAi agents disclosed herein, are provided in Table 2.

In another aspect, the disclosure features methods for delivering beta-ENaC RNAi agents to epithelial cells in a subject, such as a mammal, in vivo. Also described herein are compositions for use in such methods. In some embodiments, disclosed herein are methods for delivering beta-ENaC RNAi agents to pulmonary epithelial cells to a subject in vivo. In some embodiments, the subject is a human subject.

The methods disclosed herein include the administration of one or more beta-ENaC RNAi agents to a subject, e.g., a human or animal subject, by any suitable means known in the art. The pharmaceutical compositions disclosed herein that include one or more beta-ENaC RNAi agents can be administered in a number of ways depending upon whether local or systemic treatment is desired. Administration can be, but is not limited to, for example, intravenous, intraarterial, subcutaneous, intraperitoneal, subdermal (e.g., via an implanted device), and intraparenchymal administration. In some embodiments, the pharmaceutical compositions described herein are administered by inhalation (such as dry powder inhalation or aerosol inhalation), intranasal administration, intratracheal administration, or oropharyngeal aspiration administration.

In some embodiments, it is desired that the beta-ENaC RNAi agents described herein inhibit the expression of a beta-ENaC gene in the pulmonary epithelium, for which the administration is by inhalation (e.g., by an inhaler device, such as a metered-dose inhaler, or a nebulizer such as a jet or vibrating mesh nebulizer, or a soft mist inhaler).

The one or more beta-ENaC RNAi agents can be delivered to target cells or tissues using any oligonucleotide delivery technology known in the art. In some embodiments, a beta-ENaC RNAi agent is delivered to cells or tissues by covalently linking the RNAi agent to a targeting group. In some embodiments, the targeting group can include a cell receptor ligand, such as an integrin targeting ligand. Integrins are a family of transmembrane receptors that facilitate cell-extracellular matrix (ECM) adhesion. In particular, integrin beta-v-beta-6 (αvβ) is an epithelial-specific integrin that is known to be a receptor for ECM proteins and the TGF-beta latency-associated peptide (LAP), and is expressed in various cells and tissues. Integrin αvβ6 is known to be highly upregulated in injured pulmonary epithelium. In some embodiments, the beta-ENaC RNAi agents described herein are linked to an integrin targeting ligand that has affinity for integrin αvβ6. As referred to herein, an "αvβ6 integrin targeting ligand" is a compound that has affinity for integrin αvβ6, which can be utilized as a ligand to facilitate the targeting and delivery of an RNAi agent to which it is attached to the desired cells and/or tissues (i.e., to cells expressing integrin αvβ6). In some embodiments, multiple αvβ6 integrin targeting ligands or clusters of αvβ6 integrin targeting ligands are linked to a beta-ENaC RNAi agent. In some embodiments, the beta-ENaC RNAi agent-αvβ6 integrin targeting ligand conjugates are selectively internalized by lung epithelial cells, either through receptor-mediated endocytosis or by other means.

Examples of targeting groups useful for delivering beta-ENaC RNAi agents that include αvβ6 integrin targeting ligands are disclosed, for example, in International Patent Application Publication No. WO 2018/085415 and International Patent Application Publication No. WO 2019/089765, the contents of each of which are incorporated by reference herein in their entirety.

A targeting group can be linked to the 3' or 5' end of a sense strand or an antisense strand of a beta-ENaC RNAi agent. In some embodiments, a targeting group is linked to the 3' or 5' end of the sense strand. In some embodiments, a targeting group is linked to the 5' end of the sense strand. In some embodiments, a targeting group is linked internally to a nucleotide on the sense strand and/or the antisense strand of the RNAi agent. In some embodiments, a targeting group is linked to the RNAi agent via a linker.

In another aspect, the disclosure features compositions that include one or more beta-ENaC RNAi agents that have the duplex structures disclosed in Tables 5A and 5B.

The use of beta-ENaC RNAi agents provides methods for therapeutic (including prophylactic) treatment of diseases or disorders for which a reduction in ENaC activity can provide a therapeutic benefit. The beta-ENaC RNAi agents disclosed herein can be used to treat various respiratory diseases, including cystic fibrosis, chronic bronchitis, non-cystic fibrosis bronchiectasis, chronic obstructive pulmonary disease (COPD), asthma, respiratory tract infections, primary ciliary dyskinesia, and lung carcinoma cystic fibrosis. Beta-ENaC RNAi agents can further be used to treat, for example, various ocular diseases and disorders, such as dry eye. Such methods of treatment include administration of a beta-ENaC RNAi agent to a human being or animal having elevated or enhanced ENaC activity levels.

In some embodiments, a beta-ENaC RNAi agent disclosed herein includes an antisense strand that consists of, consists essentially of, or comprises a nucleobase sequence differing by 0 or 1 nucleobases from the nucleotide sequence (5'→3') selected from the group consisting of:

```
                                  (SEQ ID NO: 194)
AAGUCGAUGAUGAUCUCCCCA;

                                  (SEQ ID NO: 195)
AGUUGAAGAUGUAACAGUUGC;

                                  (SEQ ID NO: 198)
UUGUUGUAGUCACUGUAGACG;

                                  (SEQ ID NO: 244)
UUGUUGUAGUCACUGUAGAAG;

                                  (SEQ ID NO: 199)
UCGUGUUGUAGUCACUGUAGG;

                                  (SEQ ID NO: 201)
UGUUGUUGCAGUAUUUCUCCC;
and

                                  (SEQ ID NO: 203)
UGUUGAAGAUGUAACAGUUGC.
```

In some embodiments, a beta-ENaC RNAi agent disclosed herein includes an antisense strand that consists of, consists essentially of, or comprises a nucleotide sequence differing by no more than 1 nucleotide from the nucleotide sequence (5'→3') selected from the group consisting of:

```
                                  (SEQ ID NO: 194)
AAGUCGAUGAUGAUCUCCCCA;

                                  (SEQ ID NO: 195)
AGUUGAAGAUGUAACAGUUGC;

                                  (SEQ ID NO: 198)
UUGUUGUAGUCACUGUAGACG;

                                  (SEQ ID NO: 244)
UUGUUGUAGUCACUGUAGAAG;

                                  (SEQ ID NO: 199)
UCGUGUUGUAGUCACUGUAGG;

                                  (SEQ ID NO: 201)
UGUUGUUGCAGUAUUUCUCCC;
and

                                  (SEQ ID NO: 203)
UGUUGAAGAUGUAACAGUUGC;
```

wherein all or substantially all of the nucleotides are modified nucleotides.

In some embodiments, a beta-ENaC RNAi agent disclosed herein includes an antisense strand that consists of, consists essentially of, or comprises a nucleobase sequence differing by 0 or 1 nucleobases from the nucleotide sequence (5'→3') selected from the group consisting of:

```
                                  (SEQ ID NO: 194)
AAGUCGAUGAUGAUCUCCCCA;

                                  (SEQ ID NO: 195)
AGUUGAAGAUGUAACAGUUGC;

                                  (SEQ ID NO: 198)
UUGUUGUAGUCACUGUAGACG;

                                  (SEQ ID NO: 244)
UUGUUGUAGUCACUGUAGAAG;

                                  (SEQ ID NO: 199)
UCGUGUUGUAGUCACUGUAGG;

                                  (SEQ ID NO: 201)
UGUUGUUGCAGUAUUUCUCCC;
and

                                  (SEQ ID NO: 203)
UGUUGAAGAUGUAACAGUUGC;
```

wherein the respective sequence above is located at positions 1-21 (5'→3') of the antisense strand.

In some embodiments, a beta-ENaC RNAi agent disclosed herein includes an antisense strand that consists of, consists essentially of, or comprises a modified nucleotide sequence differing by no more than 1 nucleotide from the nucleotide sequence (5'→3') selected from the group consisting of:

```
                                  (SEQ ID NO: 126)
asAfsgsUfcGfaUfgAfuGfaUfcUfcCfcCfsa;

                                  (SEQ ID NO: 127)
asGfsusUfgAfagaugUfaAfcAfgUfuGfsc;

                                  (SEQ ID NO: 130)
usUfsgsUfuGfuAfgUfcAfcUfgUfaGfaCfsg;

                                  (SEQ ID NO: 131)
usCfsgsUfgUfuGfuAfgUfcAfcUfgUfaGfsg;

                                  (SEQ ID NO: 135)
usGfsusUfgUfuGfcAfgUfaUfuUfcUfcCfsc;
and

                                  (SEQ ID NO: 138)
cPrpusGfsusUfgAfagaugUfaAfcAfgUfuGfsc;

                                  (SEQ ID NO: 150)
cPrpuGfuUfgAfagaugUfaAfcAfgUfuGfsc;

                                  (SEQ ID NO: 153)
cPrpasGfsusUfgAfagaugUfaAfcAfgUfuGfsc;
and

                                  (SEQ ID NO: 154)
cPrpaGfuUfgAfagaugUfaAfcAfgUfuGfsc;
```

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpa and cPrpu represent a 5'-cyclopropyl phosphonate-2'-O-methyl adenosine and a 5'-cyclopropyl phosphonate-2'-O-methyl uridine, respectively, and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 21A through 21L showing all internucleoside linkages).

In some embodiments, a beta-ENaC RNAi agent disclosed herein includes:

(i) an antisense strand that consists of, consists essentially of, or comprises the modified nucleotide sequence (5'→3') usUfsgsUfuGfuAfgUfcAfcUfgUfaGfaCfsg (SEQ ID NO:130), and a sense strand that consists of, consists essentially of, or comprises the modified nucleotide sequence (5'→3') csgucuacaGfUfGfacuacaacaa (SEQ ID NO:234);

(ii) an antisense strand that consists of, consists essentially of, or comprises the modified nucleotide sequence (5'→3') usCfsgsUfgUfuGfuAfgUfcAfcUfgUfaGfsg (SEQ ID NO:131), and a sense strand that consists of, consists essentially of, or comprises the modified nucleotide sequence (5'→') cscuacaguGfAfCfuacaacacia (SEQ ID NO:235);

(iii) an antisense strand that consists of, consists essentially of, or comprises the modified nucleotide sequence (5'→3') usGfsusUfgUfuGfcAfgUfaUfuUfcUfcCfsc (SEQ ID NO:135), and a sense strand that consists of, consists essentially of, or comprises the modified nucleotide sequence (5'→3') gsggagaaaUfAfCfugcaacaaca (SEQ ID NO:236);

(iv) an antisense strand that consists of, consists essentially of, or comprises the modified nucleotide sequence (5'→3') asGfsusUfgAfagaugUfaAfcAfgUfuGfsc (SEQ ID NO:127), and a sense strand that consists of, consists essentially of, or comprises the modified nucleotide sequence (5'→3') gscaacuguUfAfCfaucuucaacu (SEQ ID NO:237);

(v) an antisense strand that consists of, consists essentially of, or comprises the modified nucleotide sequence (5'→3') asAfsgsUfcGfaUfgAfuGfaUfcUfcCfcCfsa (SEQ ID NO:126), and a sense strand that consists of, consists essentially of, or comprises the modified nucleotide sequence (5'→3') usggggagaUfCfAfucaucicacuu (SEQ ID NO:238);

(vi) an antisense strand that consists of, consists essentially of, or comprises the modified nucleotide sequence (5'→3') cPrpusGfsusUfgAfagaugUfaAfcAfgUfuGfsc (SEQ ID NO:138), and a sense strand that consists of, consists essentially of, or comprises the modified nucleotide sequence (5'→3') gscaacuguUfAfCfaucuucaaca (SEQ ID NO:239);

(vii) an antisense strand that consists of, consists essentially of, or comprises the modified nucleotide sequence (5'→3') asGfsusUfgAfagaugUfaAfcAfgUfuGfsc (SEQ ID NO:127), and a sense strand that consists of, consists essentially of, or comprises the modified nucleotide sequence (5'→') gsca_2NacuguUfAfCfaucuucaacu (SEQ ID NO:240);

(viii) an antisense strand that consists of, consists essentially of, or comprises the modified nucleotide sequence (5'→3') cPrpasGfsusUfgAfagaugUfaAfcAfgUfuGfsc (SEQ ID NO:153), and a sense strand that consists of, consists essentially of, or comprises the modified nucleotide sequence (5'→3') gscaacuguUfAfCfaucuucaacu (SEQ ID NO:237);

(ix) an antisense strand that consists of, consists essentially of, or comprises the modified nucleotide sequence (5'→3') cPrpuGfuUfgAfagaugUfaAfcAfgUfuGfsc (SEQ ID NO:150), and a sense strand that consists of, consists essentially of, or comprises the modified nucleotide sequence (5'→3') gscaacuguUfAfCfaucuucaaca (SEQ ID NO:239);

(x) an antisense strand that consists of, consists essentially of, or comprises the modified nucleotide sequence (5'→3') cPrpaGfuUfgAfagaugUfaAfcAfgUfuGfsc (SEQ ID NO:154), and a sense strand that consists of, consists essentially of, or comprises the modified nucleotide sequence (5'→') gsca_2NacuguUfAfCfaucuucaacu (SEQ ID NO:240); or (xi) an antisense strand that consists of, consists essentially of, or comprises the modified nucleotide sequence (5'→3') cPrpuGfuUfgAfagaugUfaAfcAfgUfuGfsc (SEQ ID NO:150), and a sense strand that consists of, consists essentially of, or comprises the modified nucleotide sequence (5'→') gsca_2NacuguUfAfCfaucuucaaca (SEQ ID NO:241);

wherein a, c, g, i, and u represent 2'-O-methyl adenosine, 2'-O-methyl cytidine, 2'-O-methyl guanosine, 2'-O-methyl inosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpa and cPrpu represent a 5'-cyclopropyl phosphonate-2'-O-methyl adenosine and a 5'-cyclopropyl phosphonate-2'-O-methyl uridine, respectively, and s represents a phosphorothioate linkage.

In some embodiments, a beta-ENaC RNAi agent disclosed herein includes:

(i) an antisense strand that consists of, consists essentially of, or comprises the modified nucleotide sequence (5'→3') usUfsgsUfuGfuAfgUfcAfcUfgUfaGfaCfsg (SEQ ID NO:130), and a sense strand that consists of, consists essentially of, or comprises the modified nucleotide sequence (5'→') csgucuacaGfUfGfacuacaacaa (SEQ ID NO:234);

(ii) an antisense strand that consists of, consists essentially of, or comprises the modified nucleotide sequence (5'→3') usCfsgsUfgUfuGfuAfgUfcAfcUfgUfaGfsg (SEQ ID NO:131), and a sense strand that consists of, consists essentially of, or comprises the modified nucleotide sequence (5'→') cscuacaguGfAfCfuacaacacia (SEQ ID NO:235);

(iii) an antisense strand that consists of, consists essentially of, or comprises the modified nucleotide sequence (5'→3') usGfsusUfgUfuGfcAfgUfaUfuUfcUfcCfsc (SEQ ID NO:135), and a sense strand that consists of, consists essentially of, or comprises the modified nucleotide sequence (5'→3') gsggagaaaUfAfCfugcaacaaca (SEQ ID NO:236);

(iv) an antisense strand that consists of, consists essentially of, or comprises the modified nucleotide sequence (5'→3') asGfsusUfgAfagaugUfaAfcAfgUfuGfsc (SEQ ID NO:127), and a sense strand that consists of, consists essentially of, or comprises the modified nucleotide sequence (5'→3') gscaacuguUfAfCfaucuucaacu (SEQ ID NO:237);

(v) an antisense strand that consists of, consists essentially of, or comprises the modified nucleotide sequence (5'→3') asAfsgsUfcGfaUfgAfuGfaUfcUfcCfcCfsa (SEQ ID NO:126), and a sense strand that consists of, consists essentially of, or comprises the modified nucleotide sequence (5'→3') usggggagaUfCfAfucaucicacuu (SEQ ID NO:238);

(vi) an antisense strand that consists of, consists essentially of, or comprises the modified nucleotide sequence (5'→3') cPrpusGfsusUfgAfagaugUfaAfcAfgUfuGfsc (SEQ ID NO:138), and a sense strand that consists of, consists essentially of, or comprises the modified nucleotide sequence (5'→3') gscaacuguUfAfCfaucuucaaca (SEQ ID NO:239);

(vii) an antisense strand that consists of, consists essentially of, or comprises the modified nucleotide sequence (5'→3') asGfsusUfgAfagaugUfaAfcAfgUfuGfsc (SEQ ID NO:127), and a sense strand that consists of, consists essentially of, or comprises the modified nucleotide sequence (5'→') gsca_2NacuguUfAfCfaucuucaacu (SEQ ID NO:240);

(viii) an antisense strand that consists of, consists essentially of, or comprises the modified nucleotide sequence (5'→3') cPrpasGfsusUfgAfagaugUfaAfcAfgUfuGfsc (SEQ ID NO:153), and a sense strand that consists of, consists essentially of, or comprises the modified nucleotide sequence (5'→3') gscaacuguUfAfCfaucuucaacu (SEQ ID NO:237);

(ix) an antisense strand that consists of, consists essentially of, or comprises the modified nucleotide sequence (5'→3') cPrpuGfuUfgAfagaugUfaAfcAfgUfuGfsc (SEQ ID NO:150), and a sense strand that consists of, consists essentially of, or comprises the modified nucleotide sequence (5'→3') gscaacuguUfAfCfaucuucaaca (SEQ ID NO:239);

(x) an antisense strand that consists of, consists essentially of, or comprises the modified nucleotide sequence (5'→3') cPrpaGfuUfgAfagaugUfaAfcAfgUfuGfsc (SEQ ID NO:154), and a sense strand that consists of, consists essentially of, or comprises the modified nucleotide sequence (5'→') gsca_2NacuguUfAfCfaucuucaacu (SEQ ID NO:240); or (xi) an antisense strand that consists of, consists essentially of, or comprises the modified nucleotide sequence (5'→3') cPrpuGfuUfgAfagaugUfaAfcAfgUfuGfsc (SEQ ID NO:150), and a sense strand that consists of, consists essentially of, or comprises the modified nucleotide sequence (5'→') gsca_2NacuguUfAfCfaucuucaaca (SEQ ID NO:241);

wherein a, c, g, i, and u represent 2'-O-methyl adenosine, 2'-O-methyl cytidine, 2'-O-methyl guanosine, 2'-O-methyl inosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpa and cPrpu represent a 5'-cyclopropyl phosphonate-2'-O-methyl adenosine and a 5'-cyclopropyl phosphonate-2'-O-methyl uridine, respectively, and s represents a phosphorothioate linkage, and wherein the respective sense strand further includes an inverted abasic residue at the 3' terminal end of the nucleotide sequence, and the sense strand also includes a targeting ligand that is covalently linked to the 5' terminal end, wherein the targeting ligand comprises an αvβ6 integrin targeting ligand.

In some embodiments, a beta-ENaC RNAi agent disclosed herein includes an antisense strand that consists of, consists essentially of, or comprises a nucleotide sequence that differs by 0 or 1 nucleotides from one of the following nucleotide sequences (5'→3'):

```
(SEQ ID NO: 194)
AAGUCGAUGAUGAUCUCCCCA;

(SEQ ID NO: 195)
AGUUGAAGAUGUAACAGUUGC;
```

-continued

```
(SEQ ID NO: 198)
UUGUUGUAGUCACUGUAGACG;

(SEQ ID NO: 244)
UUGUUGUAGUCACUGUAGAAG;

(SEQ ID NO: 199)
UCGUGUUGUAGUCACUGUAGG;

(SEQ ID NO: 201)
UGUUGUUGCAGUAUUUCUCCC;
or

(SEQ ID NO: 203)
UGUUGAAGAUGUAACAGUUGC;
```

wherein the beta-ENaC RNAi agent further includes a sense strand that is at least partially complementary to the antisense strand; and wherein all or substantially all of the nucleotides on both the antisense strand and the sense strand are modified nucleotides.

In some embodiments, a beta-ENaC RNAi agent disclosed herein includes an antisense strand that consists of, consists essentially of, or comprises a nucleotide sequence that differs by 0 or 1 nucleotides from one of the following nucleotide sequences (5'→3'):

```
(SEQ ID NO: 194)
AAGUCGAUGAUGAUCUCCCCA;

(SEQ ID NO: 195)
AGUUGAAGAUGUAACAGUUGC;

(SEQ ID NO: 198)
UUGUUGUAGUCACUGUAGACG;

(SEQ ID NO: 244)
UUGUUGUAGUCACUGUAGAAG;

(SEQ ID NO: 199)
UCGUGUUGUAGUCACUGUAGG;

(SEQ ID NO: 201)
UGUUGUUGCAGUAUUUCUCCC;
or

(SEQ ID NO: 203)
UGUUGAAGAUGUAACAGUUGC;
```

wherein the beta-ENaC RNAi agent further includes a sense strand that is at least partially complementary to the antisense strand; wherein all or substantially all of the nucleotides on both the antisense strand and the sense strand are modified nucleotides; and wherein the sense strand further includes an inverted abasic residue at the 3' terminal end of the nucleotide sequence, and the sense strand also includes a targeting ligand that is covalently linked to the 5' terminal end, wherein the targeting ligand comprises an αvβ6 integrin targeting ligand.

In some embodiments, a beta-ENaC RNAi agent disclosed herein includes an antisense strand that consists of, consists essentially of, or comprises a nucleotide sequence that differs by 0 or 1 nucleotides from one of the following nucleotide sequences (5'→3'):

```
(SEQ ID NO: 194)
AAGUCGAUGAUGAUCUCCCCA;

(SEQ ID NO: 195)
AGUUGAAGAUGUAACAGUUGC;
```

-continued (SEQ ID NO: 198)
UUGUUGUAGUCACUGUAGACG;

(SEQ ID NO: 244)
UUGUUGUAGUCACUGUAGAAG;

(SEQ ID NO: 199)
UCGUGUUGUAGUCACUGUAGG;

(SEQ ID NO: 201)
UGUUGUUGCAGUAUUUCUCCC;
or (SEQ ID NO: 203)
UGUUGAAGAUGUAACAGUUGC;

wherein the beta-ENaC RNAi agent further includes a sense strand that is at least partially complementary to the antisense strand; wherein all or substantially all of the nucleotides on both the antisense strand and the sense strand are modified nucleotides; and wherein the sense strand further includes an inverted abasic residue at the 3' terminal end of the nucleotide sequence, and the sense strand also includes a targeting ligand that is covalently linked to the 5' terminal end, wherein the targeting ligand comprises an αvβ6 integrin targeting ligand; and wherein the respective antisense strand sequence is located at positions 1-21 of the antisense strand.

In some embodiments, a beta-ENaC RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

(SEQ ID NO: 198)
UUGUUGUAGUCACUGUAGACG
and (SEQ ID NO: 217)
CGUCUACAGUGACUACAACAA;
or (SEQ ID NO: 199)
UCGUGUUGUAGUCACUGUAGG
and (SEQ ID NO: 219)
CCUACAGUGACUACAACACIA, wherein I represents an inosine (hypoxanthine) nucleotide; or (SEQ ID NO: 201)
UGUUGUUGCAGUAUUUCUCCC
and (SEQ ID NO: 222)
GGGAGAAAUACUGCAACAACA;
or (SEQ ID NO: 195)
AGUUGAAGAUGUAACAGUUGC
and (SEQ ID NO: 223)
GCAACUGUUACAUCUUCAACU;
or (SEQ ID NO: 194)
AAGUCGAUGAUGAUCUCCCCA
and -continued (SEQ ID NO: 224)
UGGGGAGAUCAUCAUCIACUU, wherein I represents an inosine (hypoxanthine) nucleotide; or (SEQ ID NO: 203)
UGUUGAAGAUGUAACAGUUGC
and (SEQ ID NO: 227)
GCAACUGUUACAUCUUCAACA;
or (SEQ ID NO: 244)
UUGUUGUAGUCACUGUAGAAG
and (SEQ ID NO: 245)
CUUCUACAGUGACUACAACAA;
or (SEQ ID NO: 195)
AGUUGAAGAUGUAACAGUUGC
and (SEQ ID NO: 229)
GC($A^{2N}$)ACUGUUACAUCUUCAACU, wherein $A^{2N}$ represents a 2-aminoadenine-containing nucleotide; or (SEQ ID NO: 203)
UGUUGAAGAUGUAACAGUUGC
and (SEQ ID NO: 230)
GC($A^{2N}$)ACUGUUACAUCUUCAACA, wherein $A^{2N}$ represents a 2-aminoadenine-containing nucleotide;

wherein all or substantially all of the nucleotides on both the antisense strand and the sense strand are modified nucleotides.

In some embodiments, a beta-ENaC RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:

(SEQ ID NO: 198)
UUGUUGUAGUCACUGUAGACG
and (SEQ ID NO: 217)
CGUCUACAGUGACUACAACAA;
or (SEQ ID NO: 199)
UCGUGUUGUAGUCACUGUAGG
and (SEQ ID NO: 219)
CCUACAGUGACUACAACACIA, wherein I represents an inosine (hypoxanthine) nucleotide; or (SEQ ID NO: 201)
UGUUGUUGCAGUAUUUCUCCC
and (SEQ ID NO: 222)
GGGAGAAAUACUGCAACAACA;
or (SEQ ID NO: 195)
AGUUGAAGAUGUAACAGUUGC
and (SEQ ID NO: 223)
GCAACUGUUACAUCUUCAACU;
or -continued (SEQ ID NO: 194)
AAGUCGAUGAUGAUCUCCCCA
and (SEQ ID NO: 224)
UGGGGAGAUCAUCAUCIACUU;
or (SEQ ID NO: 203)
UGUUGAAGAUGUAACAGUUGC
and (SEQ ID NO: 227)
GCAACUGUUACAUCUUCAACA;
or (SEQ ID NO: 244)
UUGUUGUAGUCACUGUAGAAG
and (SEQ ID NO: 245)
CUUCUACAGUGACUACAACAA;
or (SEQ ID NO: 195)
AGUUGAAGAUGUAACAGUUGC
and (SEQ ID NO: 229)
GC($A^{2N}$)ACUGUUACAUCUUCAACU, wherein $A^{2N}$ represents a 2-aminoadenine-containing nucleotide; or (SEQ ID NO: 203)
UGUUGAAGAUGUAACAGUUGC
and (SEQ ID NO: 230)
GC($A^{2N}$)ACUGUUACAUCUUCAACA, wherein $A^{2N}$ represents a 2-aminoadenine-containing nucleotide;

wherein all or substantially all of the nucleotides on both the antisense strand and the sense strand are modified nucleotides; and wherein the sense strand further includes inverted abasic residues at the 3' terminal end, and the sense strand also includes a targeting ligand that is covalently linked to the 5' terminal end, wherein the targeting ligand comprises an αvβ6 integrin targeting ligand.

In some embodiments, a beta-ENaC RNAi agent disclosed herein includes an antisense strand that consists of, consists essentially of, or comprises a modified nucleotide sequence that differs by 0 or 1 nucleotides from one of the following nucleotide sequences (5'→3'):

(SEQ ID NO: 126)
asAfsgsUfcGfaUfgAfuGfaUfcUfcCfcCfsa;

(SEQ ID NO: 127)
asGfsusUfgAfagaugUfaAfcAfgUfuGfsc;

(SEQ ID NO: 130)
usUfsgsUfuGfuAfgUfcAfcUfgUfaGfaCfsg;

(SEQ ID NO: 131)
usCfsgsUfgUfuGfuAfgUfcAfcUfgUfaGfsg;

(SEQ ID NO: 135)
usGfsusUfgUfuGfcAfgUfaUfuUfcUfcCfsc;
and (SEQ ID NO: 138)
cPrpusGfsusUfgAfagaugUfaAfcAfgUfuGfsc;

(SEQ ID NO: 150)
cPrpuGfuUfgAfagaugUfaAfcAfgUfuGfsc;

-continued (SEQ ID NO: 153)
cPrpasGfsusUfgAfagaugUfaAfcAfgUfuGfsc;
and (SEQ ID NO: 154)
cPrpaGfuUfgAfagaugUfaAfcAfgUfuGfsc;

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpa and cPrpu represent a 5'-cyclopropyl phosphonate-2'-O-methyl adenosine and a 5'-cyclopropyl phosphonate-2'-O-methyl uridine, respectively, and s represents a phosphorothioate linkage; and wherein the beta-ENaC RNAi agent further includes the sense strand that is at least partially complementary to the antisense strand; and wherein all or substantially all of the nucleotides on the sense strand are modified nucleotides.

In some embodiments, a beta-ENaC RNAi agent disclosed herein includes an antisense strand that consists of, consists essentially of, or comprises a modified nucleotide sequence that differs by 0 or 1 nucleotides from one of the following nucleotide sequences (5'→3'):

(SEQ ID NO: 126)
asAfsgsUfcGfaUfgAfuGfaUfcUfcCfcCfsa;

(SEQ ID NO: 127)
asGfsusUfgAfagaugUfaAfcAfgUfuGfsc;

(SEQ ID NO: 130)
usUfsgsUfuGfuAfgUfcAfcUfgUfaGfaCfsg;

(SEQ ID NO: 131)
usCfsgsUfgUfuGfuAfgUfcAfcUfgUfaGfsg;

(SEQ ID NO: 135)
usGfsusUfgUfuGfcAfgUfaUfuUfcUfcCfsc;
and (SEQ ID NO: 138)
cPrpusGfsusUfgAfagaugUfaAfcAfgUfuGfsc;

(SEQ ID NO: 150)
cPrpuGfuUfgAfagaugUfaAfcAfgUfuGfsc;

(SEQ ID NO: 153)
cPrpasGfsusUfgAfagaugUfaAfcAfgUfuGfsc;
and (SEQ ID NO: 154)
cPrpaGfuUfgAfagaugUfaAfcAfgUfuGfsc;

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpa and cPrpu represent a 5'-cyclopropyl phosphonate-2'-O-methyl adenosine and a 5'-cyclopropyl phosphonate-2'-O-methyl uridine, respectively, and s represents a phosphorothioate linkage; and wherein the beta-ENaC RNAi agent further includes the sense strand that is at least partially complementary to the antisense strand; and wherein all or substantially all of the nucleotides on the sense strand are modified nucleotides; and wherein the sense strand further includes inverted abasic residues at the 3' terminal end of the nucleotide sequence, and the sense strand also includes a targeting ligand that is covalently linked to the 5' terminal end, wherein the targeting ligand comprises an αvβ6 integrin targeting ligand.

In some embodiments, a beta-ENaC RNAi agent disclosed herein includes an antisense strand and a sense strand that consists of, consists essentially of, or comprises modified nucleotide sequences that differs by 0 or 1 nucleotides from one of the following nucleotide sequence pairs (5'→3'):

(SEQ ID NO: 130)
usUfsgsUfuGfuAfgUfcAfcUfgUfaGfaCfsg
and (SEQ ID NO: 234)
csgucuacaGfUfGfacuacaacaa;

(SEQ ID NO: 131)
usCfsgsUfgUfuGfuAfgUfcAfcUfgUfaGfsg
and (SEQ ID NO: 235)
cscuacaguGfAfCfuacaacacia;

(SEQ ID NO: 135)
usGfsusUfgUfuGfcAfgUfaUfuUfcUfcCfsc
and (SEQ ID NO: 236)
gsggagaaaUfAfCfugcaacaaca;

(SEQ ID NO: 127)
asGfsusUfgAfagaugUfaAfcAfgUfuGfsc
and (SEQ ID NO: 237)
gscaacuguUfAfCfaucuucaacu;
or (SEQ ID NO: 126)
asAfsgsUfcGfaUfgAfuGfaUfcUfcCfcCfsa
and (SEQ ID NO: 238)
usggggagaUfCfAfucauciacuu;

(SEQ ID NO: 138)
cPrpusGfsusUfgAfagaugUfaAfcAfgUfuGfsc
and (SEQ ID NO: 239)
gscaacuguUfAfCfaucuucaaca;

(SEQ ID NO: 127)
asGfsusUfgAfagaugUfaAfcAfgUfuGfsc
and (SEQ ID NO: 240)
gsca_2NacuguUfAfCfaucuucaacu;

(SEQ ID NO: 153)
cPrpasGfsusUfgAfagaugUfaAfcAfgUfuGfsc
and (SEQ ID NO: 237)
gscaacuguUfAfCfaucuucaacu;

(SEQ ID NO: 150)
cPrpuGfuUfgAfagaugUfaAfcAfgUfuGfsc
and (SEQ ID NO: 239)
gscaacuguUfAfCfaucuucaaca;

(SEQ ID NO: 154)
cPrpaGfuUfgAfagaugUfaAfcAfgUfuGfsc
and (SEQ ID NO: 240)
gsca_2NacuguUfAfCfaucuucaacu;

(SEQ ID NO: 150)
cPrpuGfuUfgAfagaugUfaAfcAfgUfuGfsc
and

-continued (SEQ ID NO: 241)
gsca_2NacuguUfAfCfaucuucaaca;

wherein a, c, g, i, and u represent 2'-methyl adenosine, 2'-methyl cytidine, 2'-O-methyl guanosine, 2'-G-methyl inosine, and 2'-O-methyl uridine, respectively; Af, Cf Gf, and Uf represent 2'-fluoro adenosine, 2'-fluoro cytidine, 2'-fluoro guanosine, and 2'-fluoro uridine, respectively; cPrpa and cPrpu represent a 5'-cyclopropyl phosphonate-2'-O-methyl adenosine and a 5'-cyclopropyl phosphonate-2'-O-methyl uridine, respectively, and s represents a phosphorothioate linkage.

In some embodiments, a beta-ENaC RNAi agent disclosed herein includes an antisense strand and a sense strand that consists of, consists essentially of, or comprises one of the following nucleotide sequence pairs (5'→3'):

(SEQ ID NO: 130)
usUfsgsUfuGfuAfgUfcAfcUfgUfaGfaCfsg
and (SEQ ID NO: 234)
csgucuacaGfUfGfacuacaacaa;

(SEQ ID NO: 131)
usCfsgsUfgUfuGfuAfgUfcAfcUfgUfaGfsg
and (SEQ ID NO: 235)
cscuacaguGfAfCfuacaacacia;

(SEQ ID NO: 135)
usGfsusUfgUfuGfcAfgUfaUfuUfcUfcCfsc
and (SEQ ID NO: 236)
gsggagaaaUfAfCfugcaacaaca;

(SEQ ID NO: 127)
asGfsusUfgAfagaugUfaAfcAfgUfuGfsc
and (SEQ ID NO: 237)
gscaacuguUfAfCfaucuucaacu;
or (SEQ ID NO: 126)
asAfsgsUfcGfaUfgAfuGfaUfcUfcCfcCfsa
and (SEQ ID NO: 238)
usggggagaUfCfAfucauciacuu;

(SEQ ID NO: 138)
cPrpusGfsusUfgAfagaugUfaAfcAfgUfuGfsc
and (SEQ ID NO: 239)
gscaacuguUfAfCfaucuucaaca;

(SEQ ID NO: 127)
asGfsusUfgAfagaugUfaAfcAfgUfuGfsc
and (SEQ ID NO: 240)
gsca_2NacuguUfAfCfaucuucaacu;

(SEQ ID NO: 153)
cPrpasGfsusUfgAfagaugUfaAfcAfgUfuGfsc
and (SEQ ID NO: 237)
gscaacuguUfAfCfaucuucaacu;

(SEQ ID NO: 150)
cPrpuGfuUfgAfagaugUfaAfcAfgUfuGfsc
and

-continued

```
                                    (SEQ ID NO: 239)
gscaacuguUfAfCfaucuucaaca;

                                    (SEQ ID NO: 154)
cPrpaGfuUfgAfagaugUfaAfcAfgUfuGfsc
and

                                    (SEQ ID NO: 240)
gsca_2NacuguUfAfCfaucuucaacu;

                                    (SEQ ID NO: 150)
cPrpuGfuUfgAfagaugUfaAfcAfgUfuGfsc
and

                                    (SEQ ID NO: 241)
gsca_2NacuguUfAfCfaucuucaaca;
```

wherein a, c, g, i, and u represent 2'-methyl adenosine, 2'-methyl cytidine, 2'-O-methyl guanosine, 2'-methyl inosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpa and cPrpu represent a 5'-cyclopropyl phosphonate-2'-O-methyl adenosine and a 5'-cyclopropyl phosphonate-2'-O-methyl uridine, respectively, and s represents a phosphorothioate linkage; and wherein the sense strand further includes an inverted abasic residue at the 3' terminal end of the nucleotide sequence, and the sense strand also includes a targeting ligand that is covalently linked to the 5' terminal end, wherein the targeting ligand comprises an αvβ6 integrin targeting ligand.

In some embodiments, a beta-ENaC RNAi agent disclosed herein includes an antisense strand that includes a nucleobase sequence that differs by 0 or 1 nucleobases from the nucleotide sequences selected from the group consisting of (5'→3'):

```
                          (SEQ ID NO: 60)
AAGUCGAUGAUGAUCUCCC;

                          (SEQ ID NO: 15)
AGUUGAAGAUGUAACAGUU;

                          (SEQ ID NO: 27)
UUGUUGUAGUCACUGUAGA;

                          (SEQ ID NO: 30)
UCGUGUUGUAGUCACUGUA;

                          (SEQ ID NO: 53)
UGUUGUUGCAGUAUUUCUC;
or

                          (SEQ ID NO: 16)
UGUUGAAGAUGUAACAGUU.
```

In some embodiments, a beta-ENaC RNAi agent disclosed herein includes an antisense strand that includes a nucleobase sequence that differs by 0 or 1 nucleobases from the nucleotide sequences selected from the group consisting of (5'→3'):

```
                          (SEQ ID NO: 60)
AAGUCGAUGAUGAUCUCCC;

                          (SEQ ID NO: 15)
AGUUGAAGAUGUAACAGUU;

                          (SEQ ID NO: 27)
UUGUUGUAGUCACUGUAGA;
```

-continued

```
                          (SEQ ID NO: 30)
UCGUGUUGUAGUCACUGUA;

                          (SEQ ID NO: 53)
UGUUGUUGCAGUAUUUCUC;
or

                          (SEQ ID NO: 16)
UGUUGAAGAUGUAACAGUU;
```

wherein all or substantially all of the nucleotides are modified nucleotides.

In some embodiments, a beta-ENaC RNAi agent disclosed herein includes an antisense strand that includes a nucleobase sequence that differs by 0 or 1 nucleobases from the nucleotide sequences selected from the group consisting of (5'→3'):

```
                          (SEQ ID NO: 60)
AAGUCGAUGAUGAUCUCCC;

                          (SEQ ID NO: 15)
AGUUGAAGAUGUAACAGUU;

                          (SEQ ID NO: 27)
UUGUUGUAGUCACUGUAGA;

                          (SEQ ID NO: 30)
UCGUGUUGUAGUCACUGUA;

                          (SEQ ID NO: 53)
UGUUGUUGCAGUAUUUCUC;
or

                          (SEQ ID NO: 16)
UGUUGAAGAUGUAACAGUU;
```

wherein all or substantially all of the nucleotides are modified nucleotides, and wherein the respective sequence is located at nucleotide positions 1-19 (5'→3') of the antisense strand.

In some embodiments, a beta-ENaC RNAi agent disclosed herein includes an antisense strand and a sense strand that each include a nucleobase sequences that differs by 0 or 1 nucleobases from the nucleotide sequence pairs selected from the group consisting of (5'→3'):

```
                                       (SEQ ID NO: 27)
UUGUUGUAGUCACUGUAGA
and

                                       (SEQ ID NO: 80)
UCUACAGUGACUACAACAA;
or

                                       (SEQ ID NO: 30)
UCGUGUUGUAGUCACUGUA
and

                                       (SEQ ID NO: 86)
UACAGUGACUACAACACIA, wherein I represents
an inosine (hypoxanthine) nucleotide; or

                                       (SEQ ID NO: 53)
UGUUGUUGCAGUAUUUCUC
and

                                      (SEQ ID NO: 106)
GAGAAAUACUGCAACAACA;
or

                                       (SEQ ID NO: 15)
AGUUGAAGAUGUAACAGUU
and
```

(SEQ ID NO: 68)
AACUGUUACAUCUUCAACU;
or (SEQ ID NO: 60)
AAGUCGAUGAUGAUCUCCC
and (SEQ ID NO: 115)
GGGAGAUCAUCAUCIACUU, wherein I represents an inosine (hypoxanthine) nucleotide; or (SEQ ID NO: 16)
UGUUGAAGAUGUAACAGUU
and (SEQ ID NO: 69)
AACUGUUACAUCUUCAACA;
or (SEQ ID NO: 15)
AGUUGAAGAUGUAACAGUU
and (SEQ ID NO: 242)
($A^{2N}$)ACUGUUACAUCUUCAACU, wherein $A^{2N}$ represents a 2-aminoadenine-containing nucleotide; or (SEQ ID NO: 16)
UGUUGAAGAUGUAACAGUU
and (SEQ ID NO: 243)
($A^{2N}$)ACUGUUACAUCUUCAACA, wherein $A^{2N}$ represents a 2-aminoadenine-containing nucleotide.

In some embodiments, a beta-ENaC RNAi agent disclosed herein includes an antisense strand and a sense strand that each include a nucleobase sequences that differs by 0 or 1 nucleobases from the nucleotide sequence pairs selected from the group consisting of (5'→3'):

(SEQ ID NO: 27)
UUGUUGUAGUCACUGUAGA
and (SEQ ID NO: 80)
UCUACAGUGACUACAACAA;
or (SEQ ID NO: 30)
UCGUGUUGUAGUCACUGUA
and (SEQ ID NO: 86)
UACAGUGACUACAACACIA, wherein I represents an inosine (hypoxanthine) nucleotide; or (SEQ ID NO: 53)
UGUUGUUGCAGUAUUUCUC
and (SEQ ID NO: 106)
GAGAAAUACUGCAACAACA;
or (SEQ ID NO: 15)
AGUUGAAGAUGUAACAGUU
and (SEQ ID NO: 68)
AACUGUUACAUCUUCAACU;
or (SEQ ID NO: 60)
AAGUCGAUGAUGAUCUCCC
and (SEQ ID NO: 115)
GGGAGAUCAUCAUCIACUU, wherein I represents an inosine (hypoxanthine) nucleotide; or (SEQ ID NO: 16)
UGUUGAAGAUGUAACAGUU
and (SEQ ID NO: 69)
AACUGUUACAUCUUCAACA;
or (SEQ ID NO: 15)
AGUUGAAGAUGUAACAGUU
and (SEQ ID NO: 242)
($A^{2N}$)ACUGUUACAUCUUCAACU, wherein $A^{2N}$ represents a 2-aminoadenine-containing nucleotide; or (SEQ ID NO: 16)
UGUUGAAGAUGUAACAGUU
and (SEQ ID NO: 243)
($A^{2N}$)ACUGUUACAUCUUCAACA, wherein $A^{2N}$ represents a 2-aminoadenine-containing nucleotide; and wherein all or substantially all of the nucleotides are modified nucleotides.

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. beta-ENaC mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See. e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or otherwise suitable in vivo or in vitro conditions)) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of a beta-ENaC mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol  as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art. Correspondingly, compounds described herein with labile protons or basic atoms should also be understood to represent salt forms of the corresponding compound. Compounds described herein may be in a free acid, free base, or salt form. Pharmaceutically acceptable salts of the compounds described herein should be understood to be within the scope of the invention.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects, features, aspects, and advantages of the invention will be apparent from the following detailed description, accompanying figures, and from the claims.

The following abbreviations are used in FIGS. 21A to 21L: a, c, g, and u are 2'-O-methyl modified nucleotides; Af, Cf, Gf, and Uf are 2'-fluoro modified nucleotides; o is a phosphodiester linkage; s is a phosphorothioate linkage; invAb is an inverted abasic residue (see Table 6); a_2N is a 2'-O-methyl-2-aminoadenosine modified nucleotide (see Table 6); cPrpa is a 5'-cyclopropyl phosphonate-2'-O-methyladenosine modified nucleotide (see Table 6), and cPrpu is a 5'-cyclopropyl phosphonate-2'-O-methyluridine modified nucleotide.

Figure 21A:
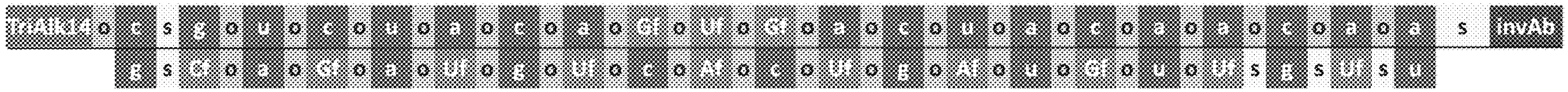
FIG. 21A. Schematic diagram of the modified sense and antisense strands of beta-ENaC RNAi agent AD06495 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.
Figure 21B:
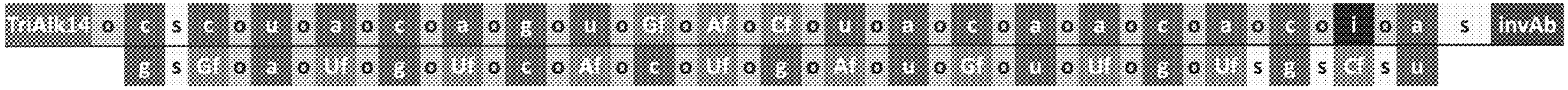

FIG. 21B. Schematic diagram of the modified sense and antisense strands of beta-ENaC RNAi agent AD06497 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 21C:
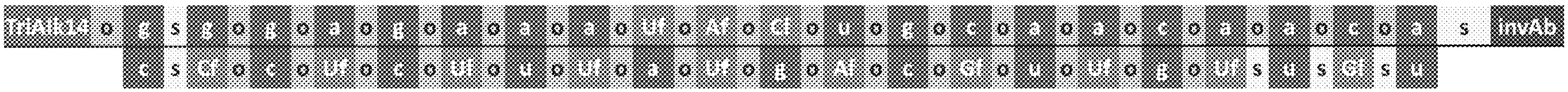

FIG. 21C. Schematic diagram of the modified sense and antisense strands of beta-ENaC RNAi agent AD06501 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 21D:
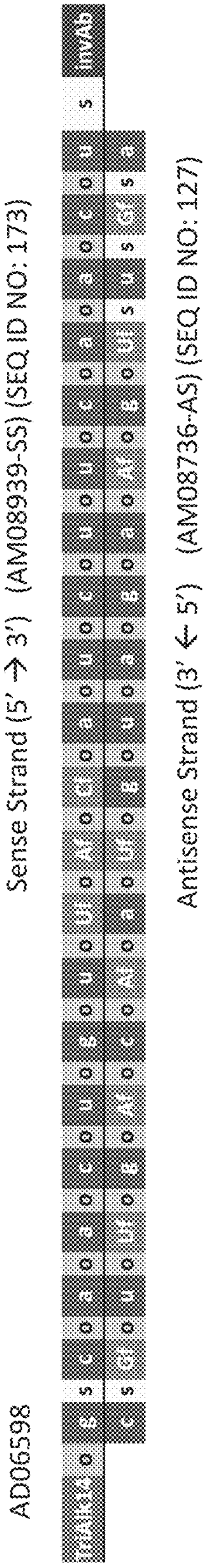

FIG. 21D. Schematic diagram of the modified sense and antisense strands of beta-ENaC RNAi agent AD06598 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 21E:
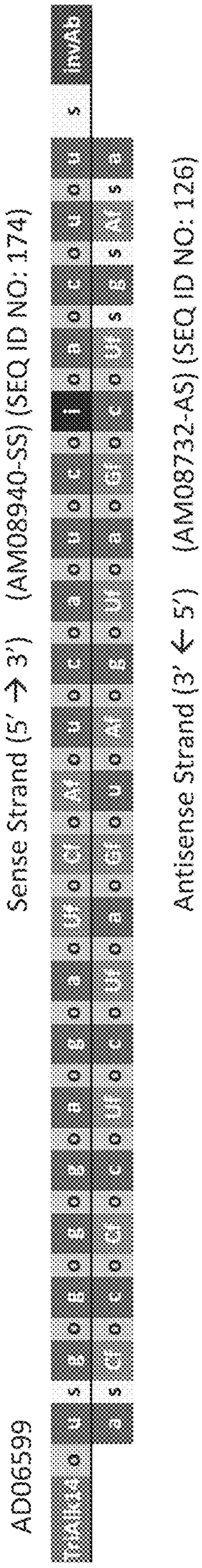

FIG. 21E. Schematic diagram of the modified sense and antisense strands of beta-ENaC RNAi agent AD06599 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 21F:
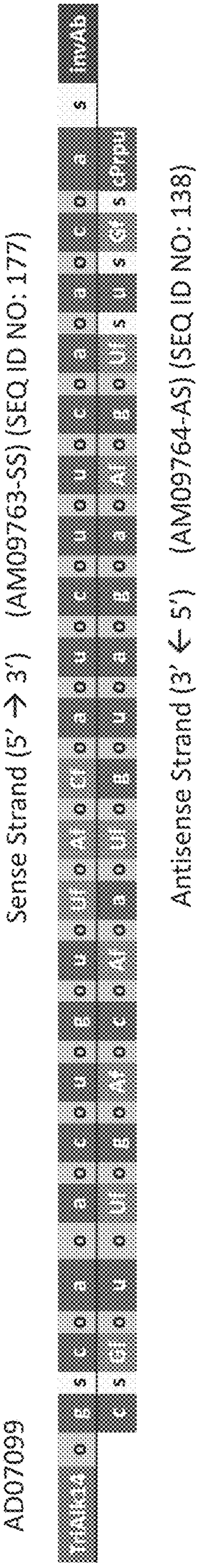

FIG. 21F. Schematic diagram of the modified sense and antisense strands of beta-ENaC RNAi agent AD07099 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 21G:
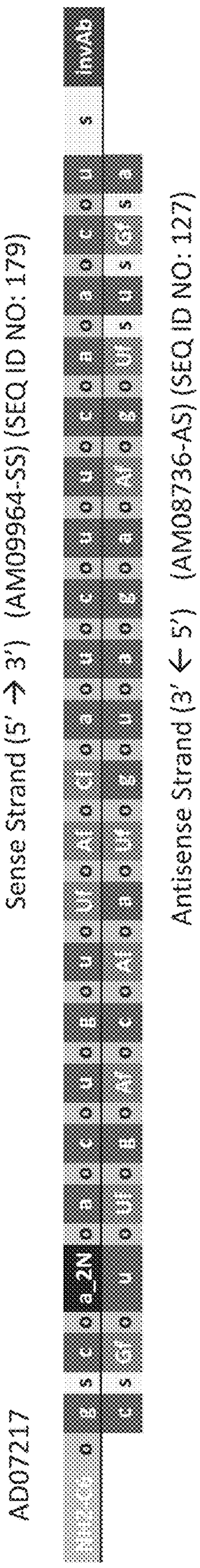

FIG. 21G. Schematic diagram of the modified sense and antisense strands of beta-ENaC RNAi agent AD07217 (see Tables 3, 4, 5A and 5B), with a (NH2-C6) linking group (see Table 6 for chemical structure) positioned at the 5' terminal end of the sense strand to facilitate the linkage to one or more targeting ligands, such as, for example, those depicted in FIGS. 1 through 8 herein.

Figure 21H:
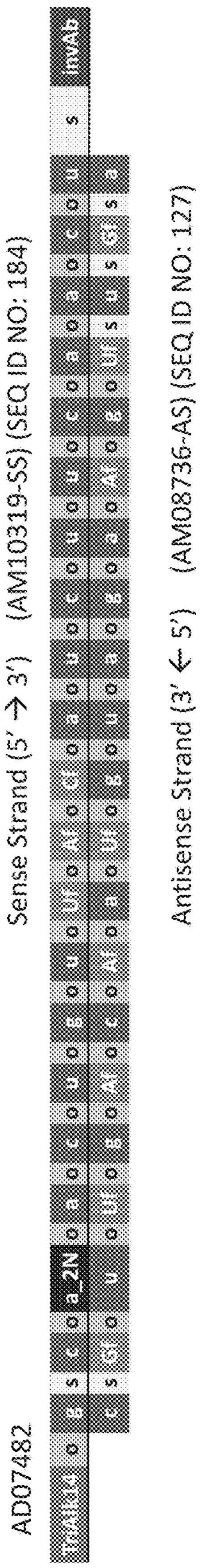

FIG. 21H. Schematic diagram of the modified sense and antisense strands of beta-ENaC RNAi agent AD07482 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 21I:
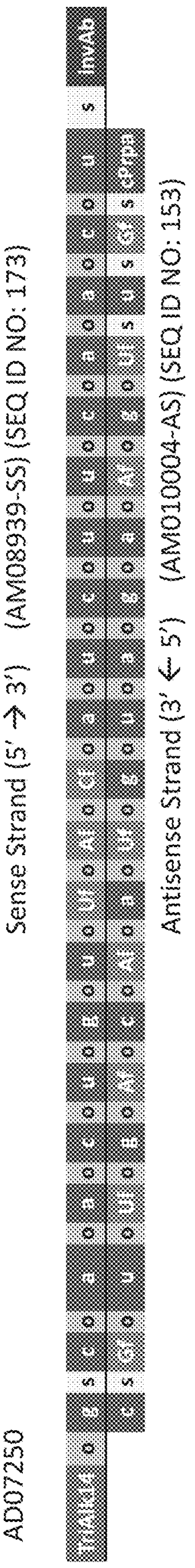

FIG. 21I. Schematic diagram of the modified sense and antisense strands of beta-ENaC RNAi agent AD07250 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 21J:
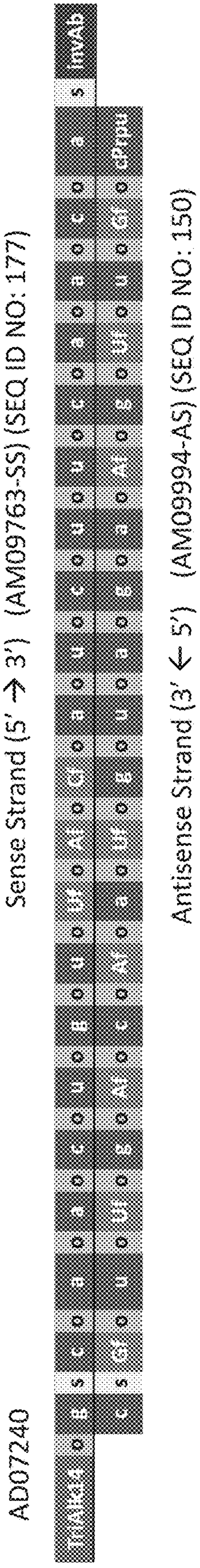

FIG. 21J. Schematic diagram of the modified sense and antisense strands of beta-ENaC RNAi agent AD07240 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 21K:
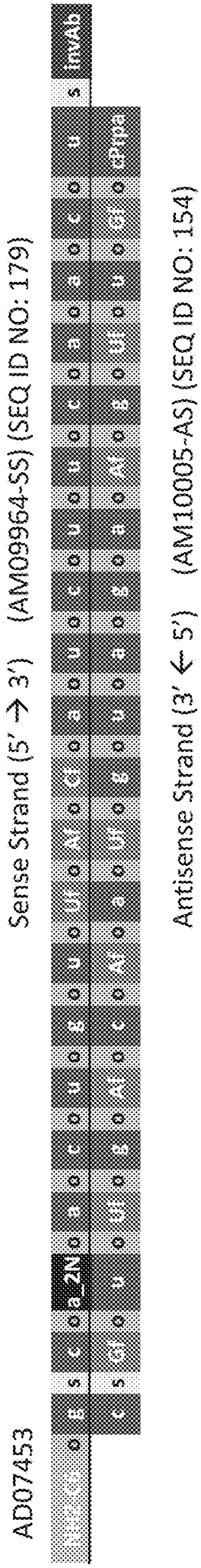

FIG. 21K. Schematic diagram of the modified sense and antisense strands of beta-ENaC RNAi agent AD07453 (see Tables 3, 4, 5A and 5B), with a (NH2-C6) linking group (see Table 6 for chemical structure) positioned at the 5' terminal end of the sense strand to facilitate the linkage to one or more targeting ligands, such as, for example, those depicted in FIGS. 1 through 8 herein.

Figure 21L:
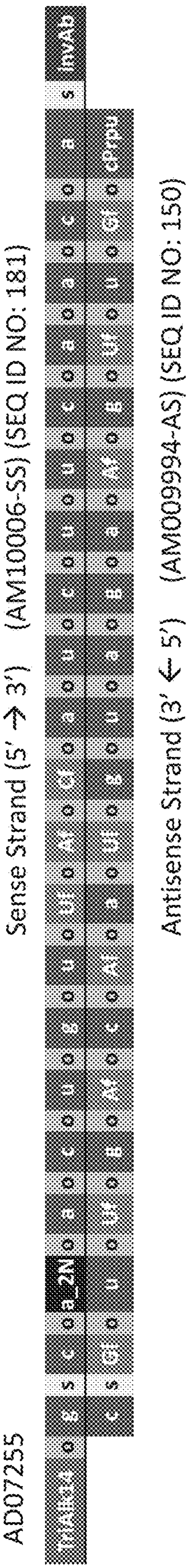

FIG. 21L. Schematic diagram of the modified sense and antisense strands of beta-ENaC RNAi agent AD07255 (see Tables 3, 4, 5A and 5B), with a (TriAlk14) linking group (see Table 6 for chemical structure) positioned at the 5' terminal end of the sense strand to facilitate the linkage to one or more targeting ligands, such as, for example, those depicted in FIGS. 1 through 8 herein.

Figure 22:
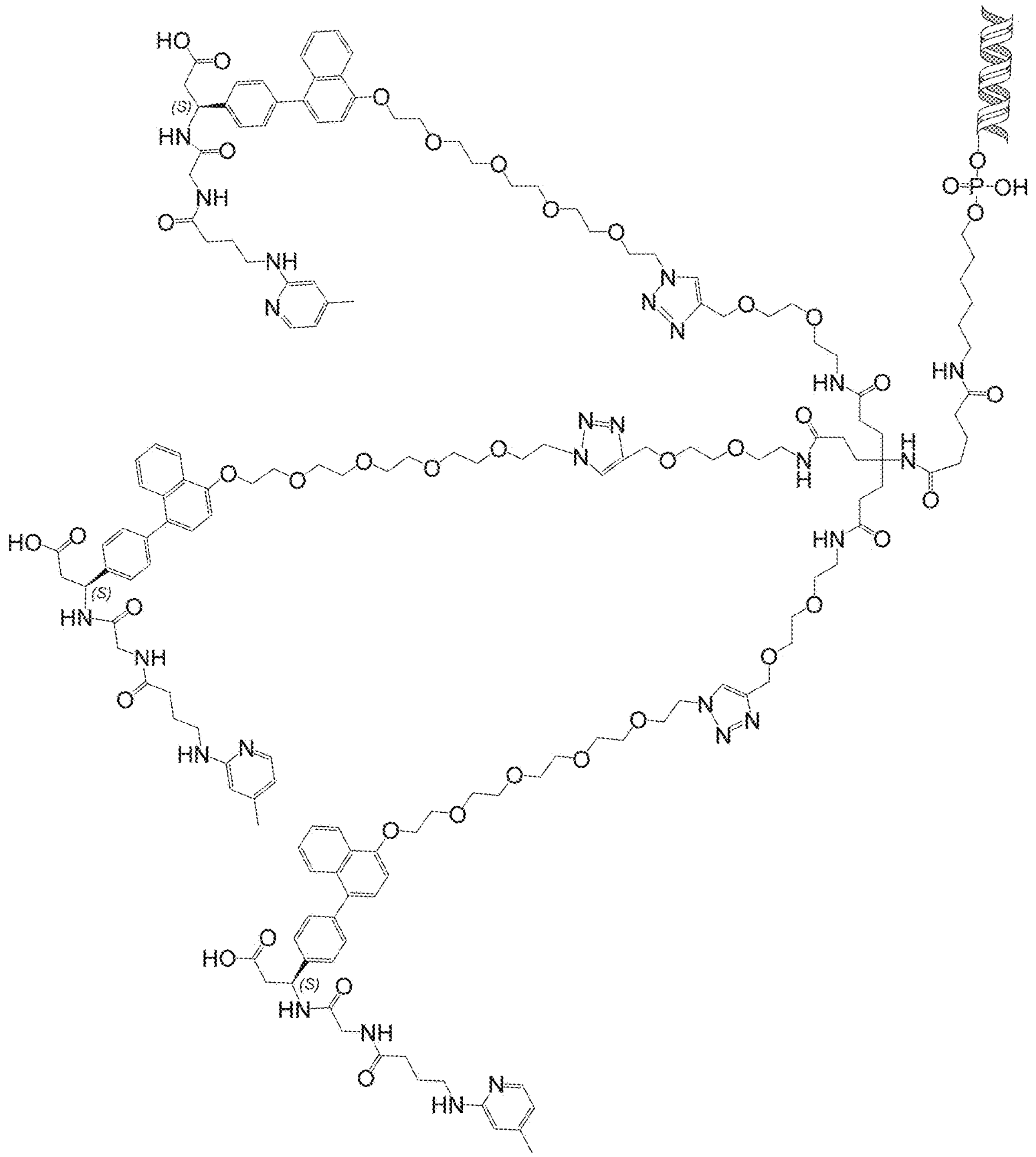

FIG. 22. Chemical structure representation of the tridentate αvβ6 epithelial cell targeting ligand referred to herein as Tri-SM6.1 linked to a TriAlk14 scaffold linking group (described herein as (TriSM6.1-avb6-TA14)), in free acid form, wherein 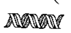 comprises the beta-ENaC RNAi agent.

Figure 23:
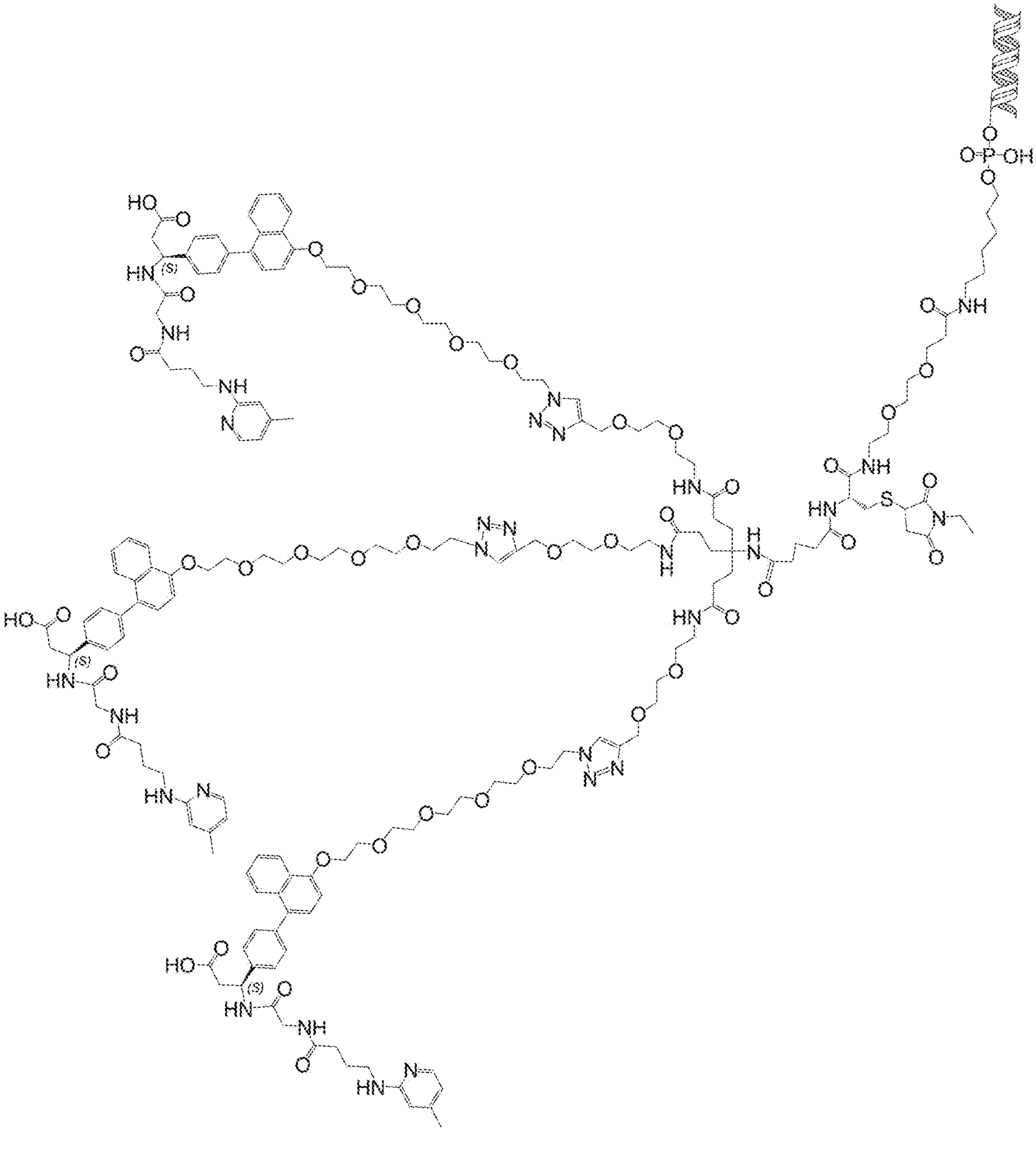

FIG. 23. Chemical structure representation of the tridentate αvβ6 epithelial cell targeting ligand referred to herein as Tri-SM6.1 linked to a TriAlk14 scaffold linking group that further includes a cysteine-maleimide linker, in free acid form, wherein  comprises the beta-ENaC RNAi agent.

Figure 24:
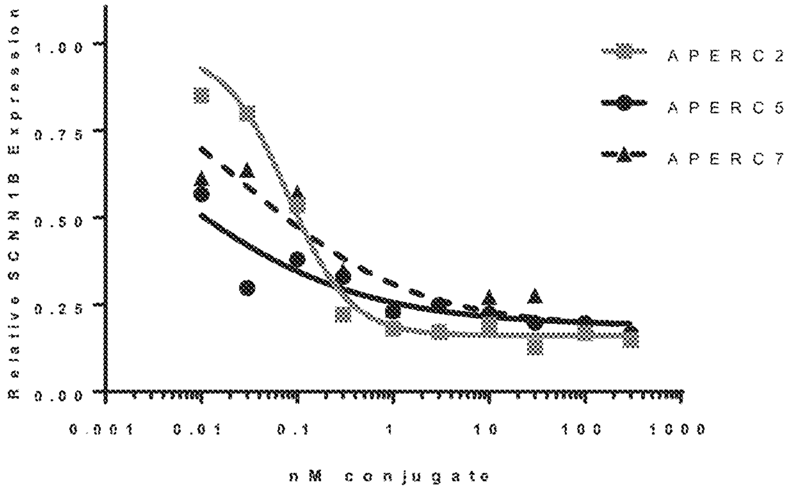
Figure 25A:
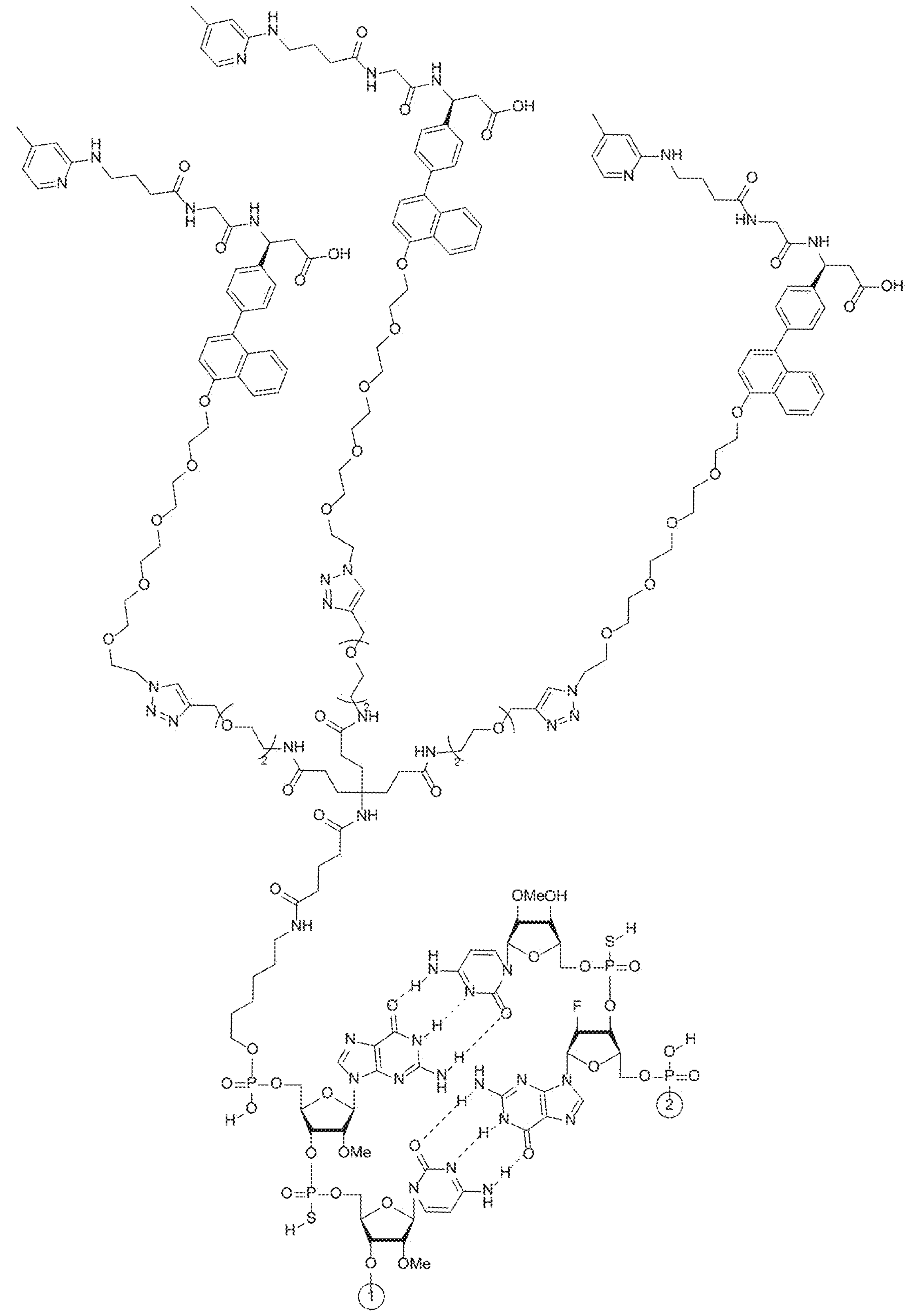
Figure 25B:
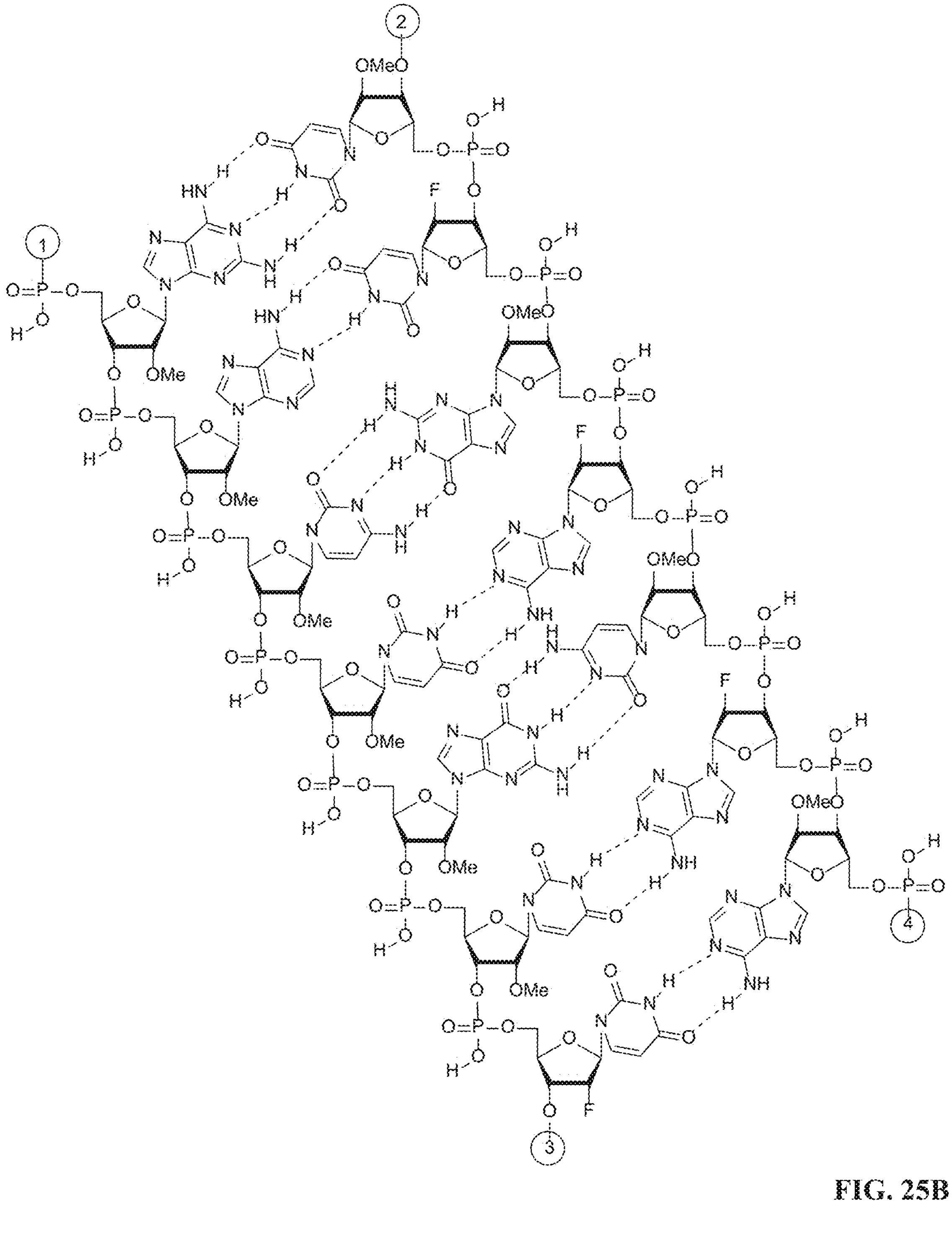
Figure 25C:
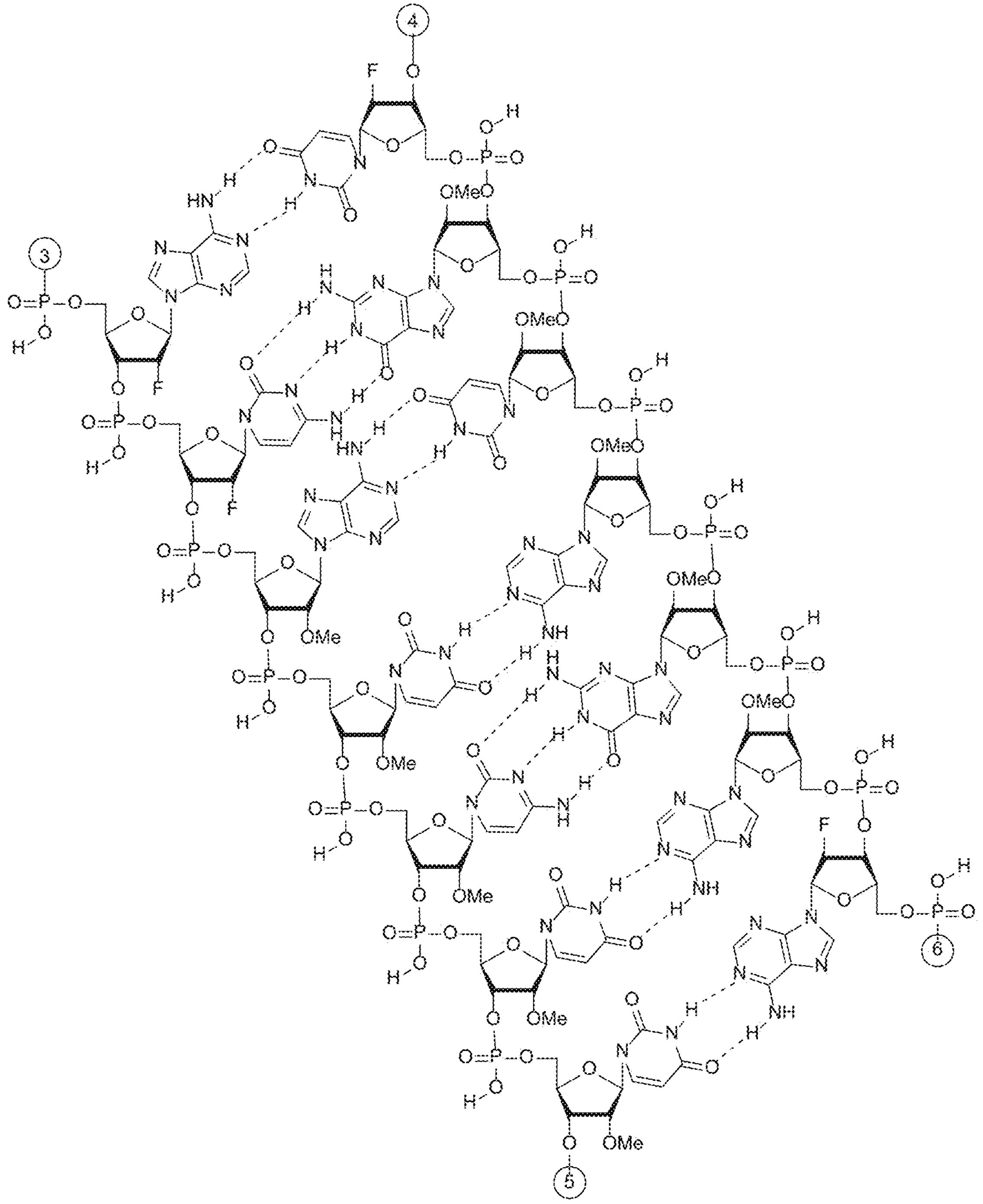
Figure 25D:
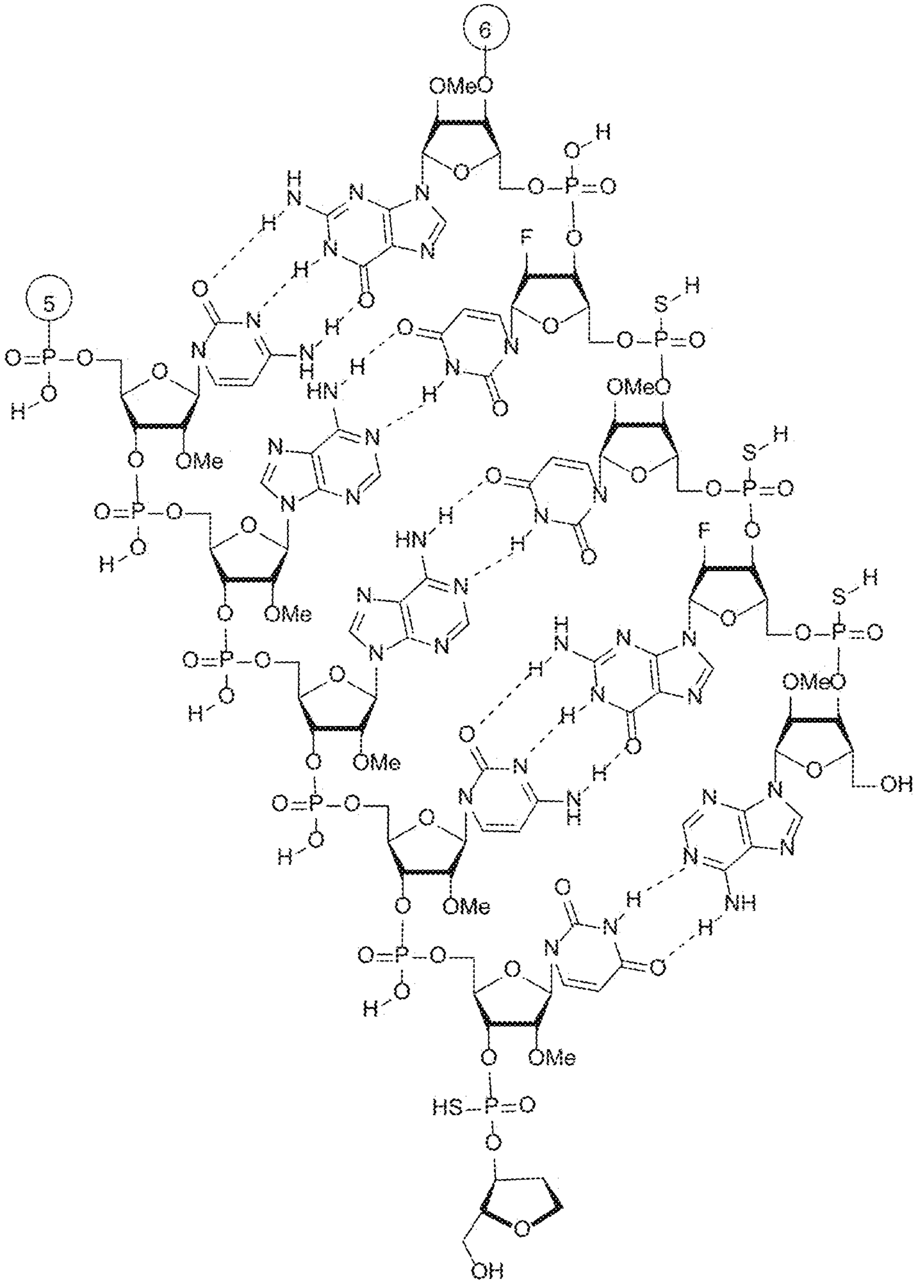
Figure 26A:
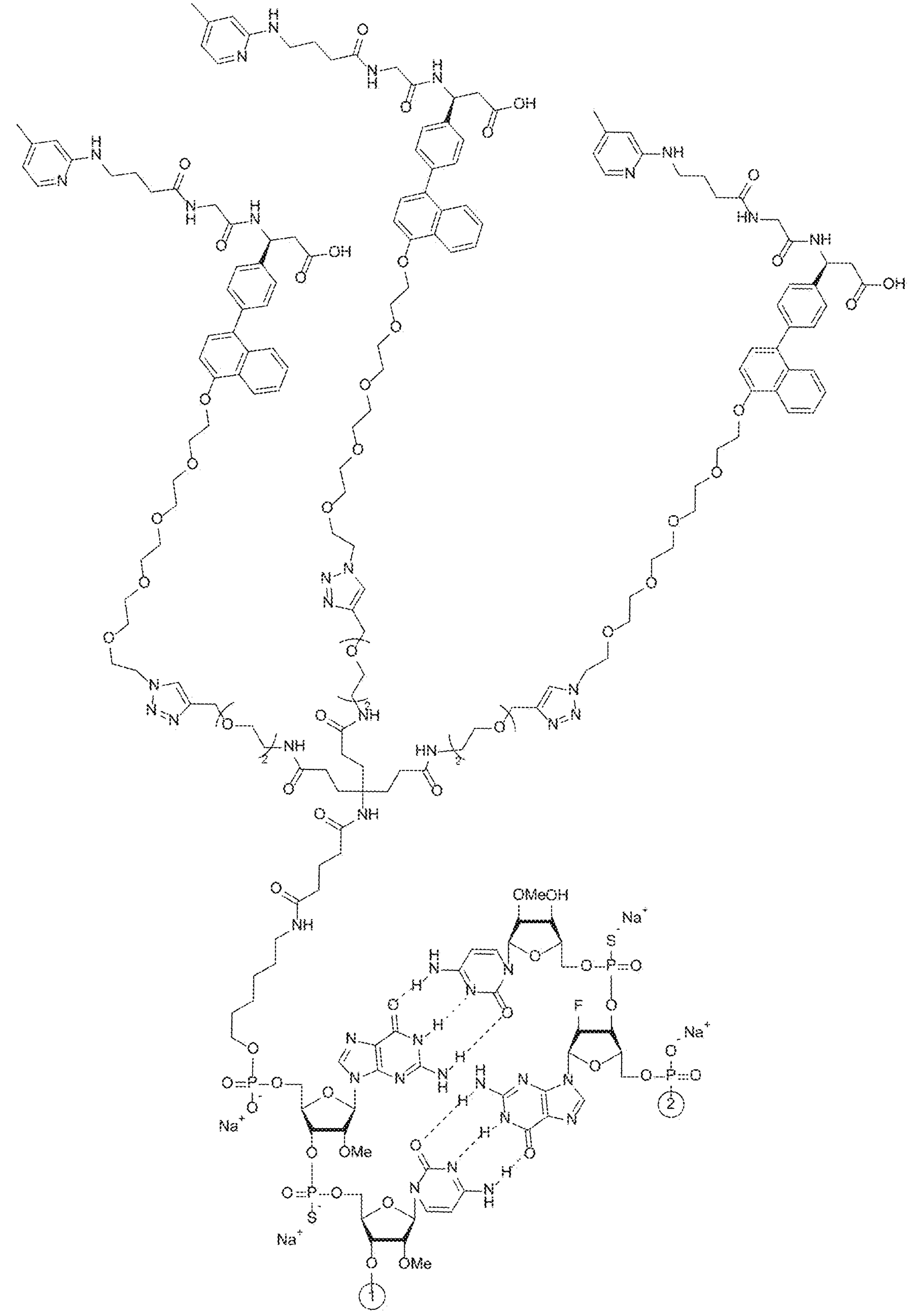
Figure 26B:
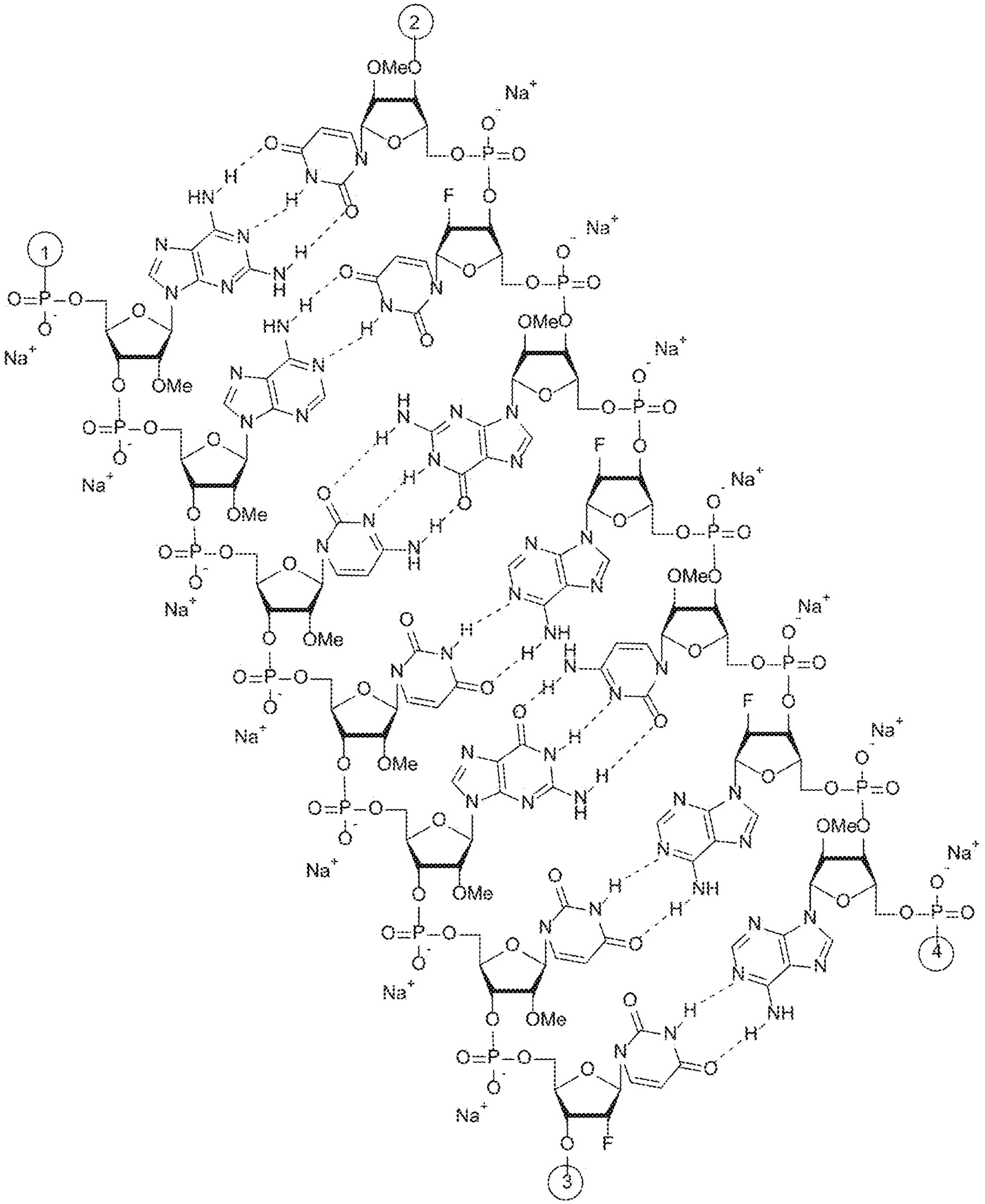
Figure 26C:
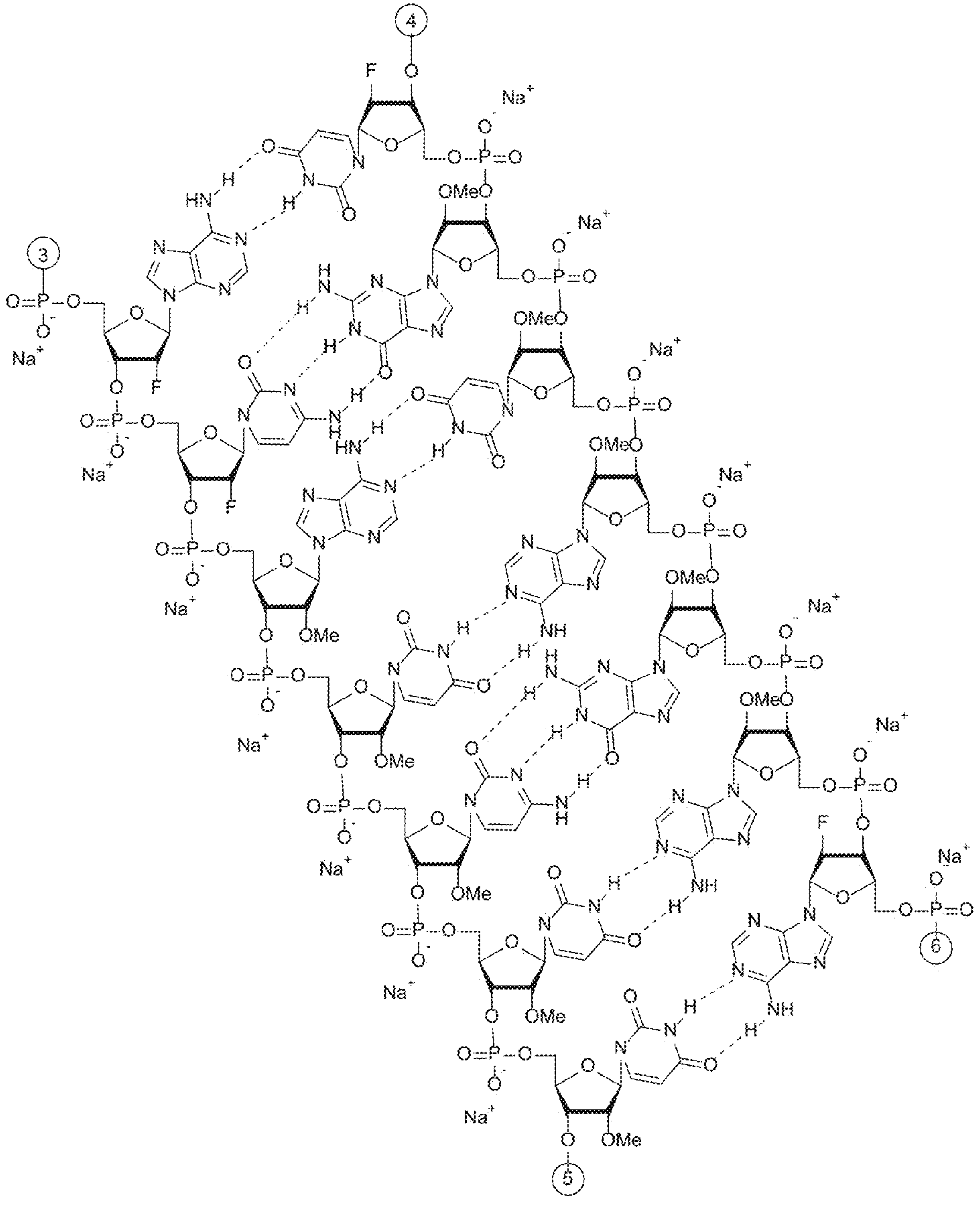
Figure 26D:
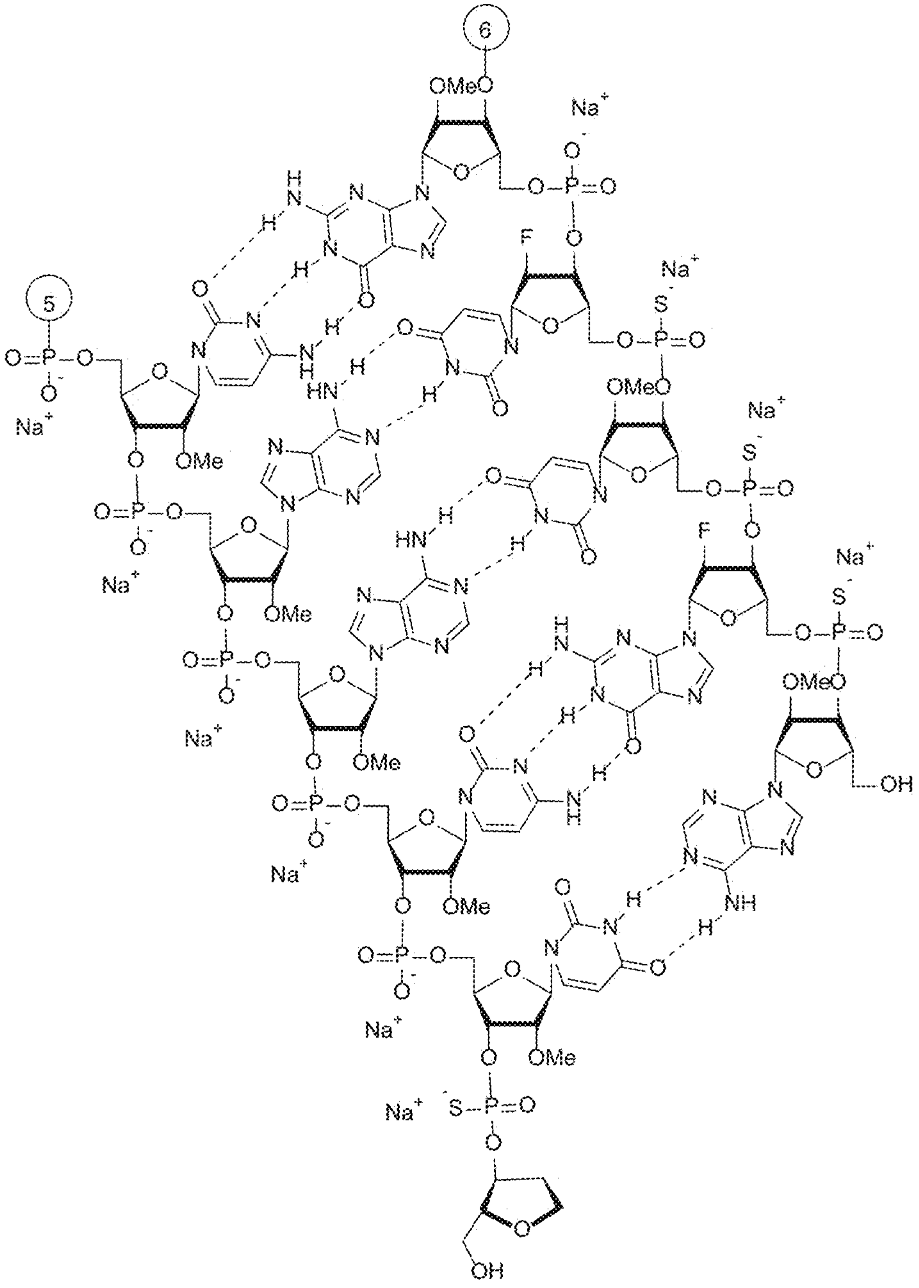
Figure 27A:
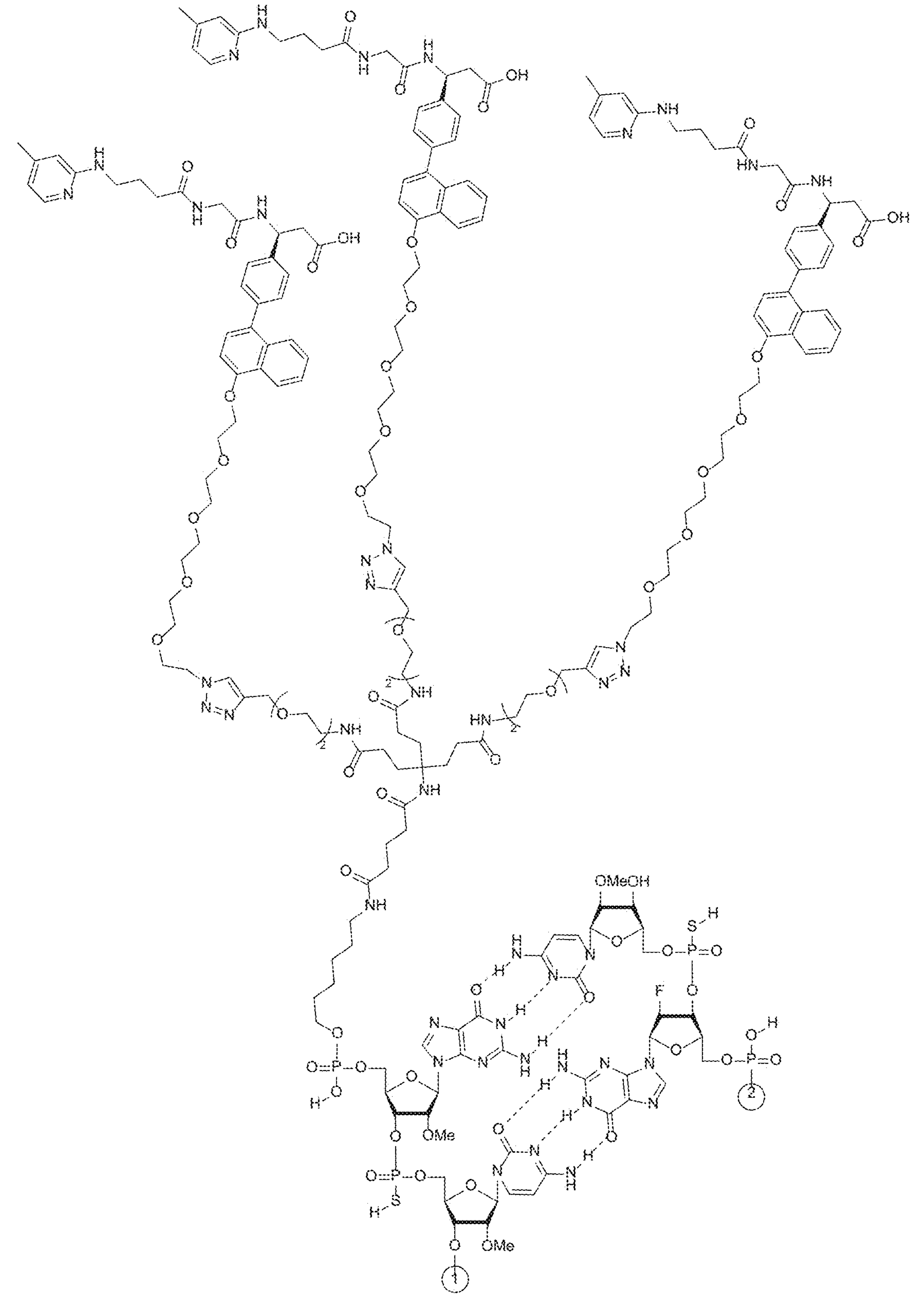
Figure 27B:
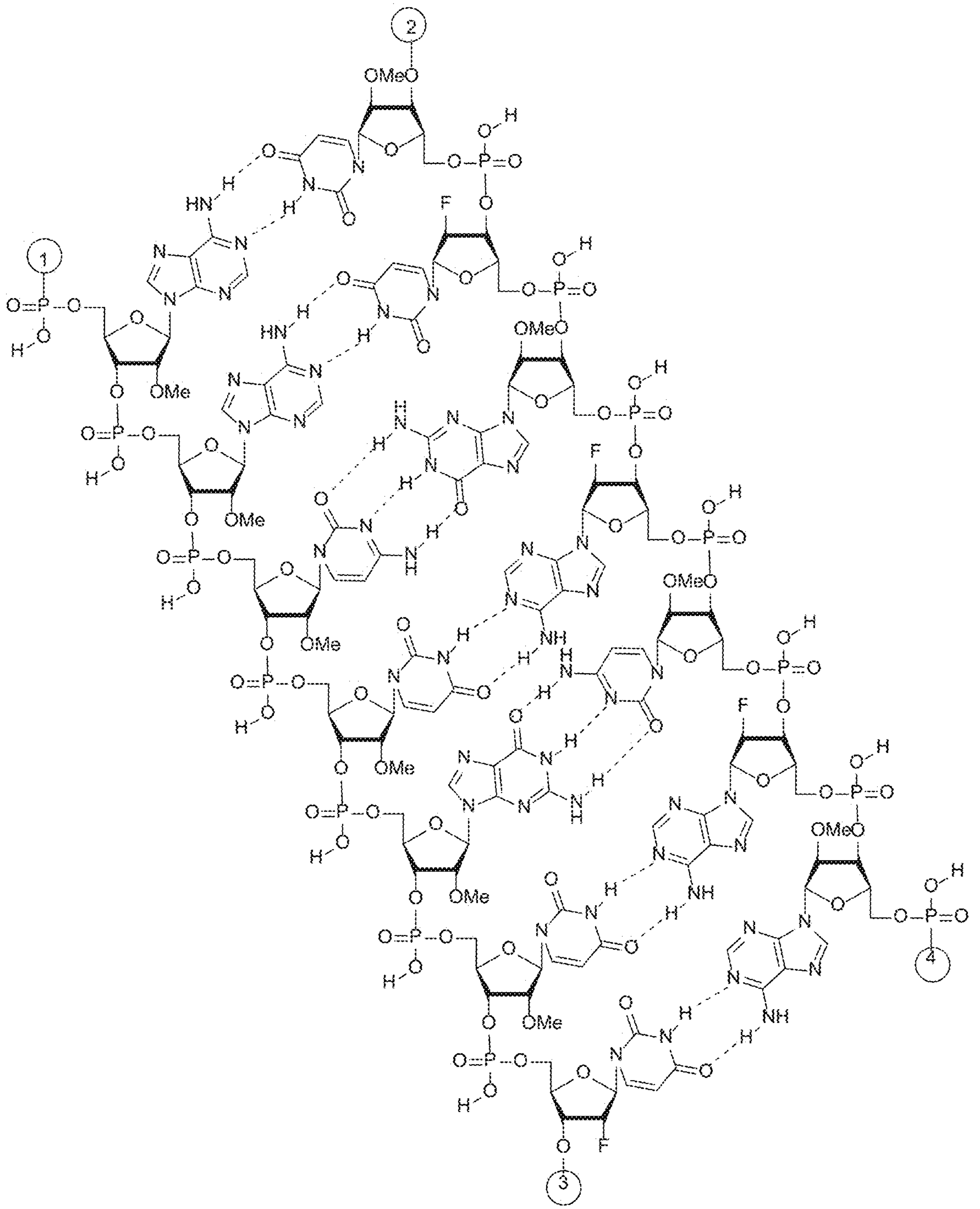
Figure 27C:
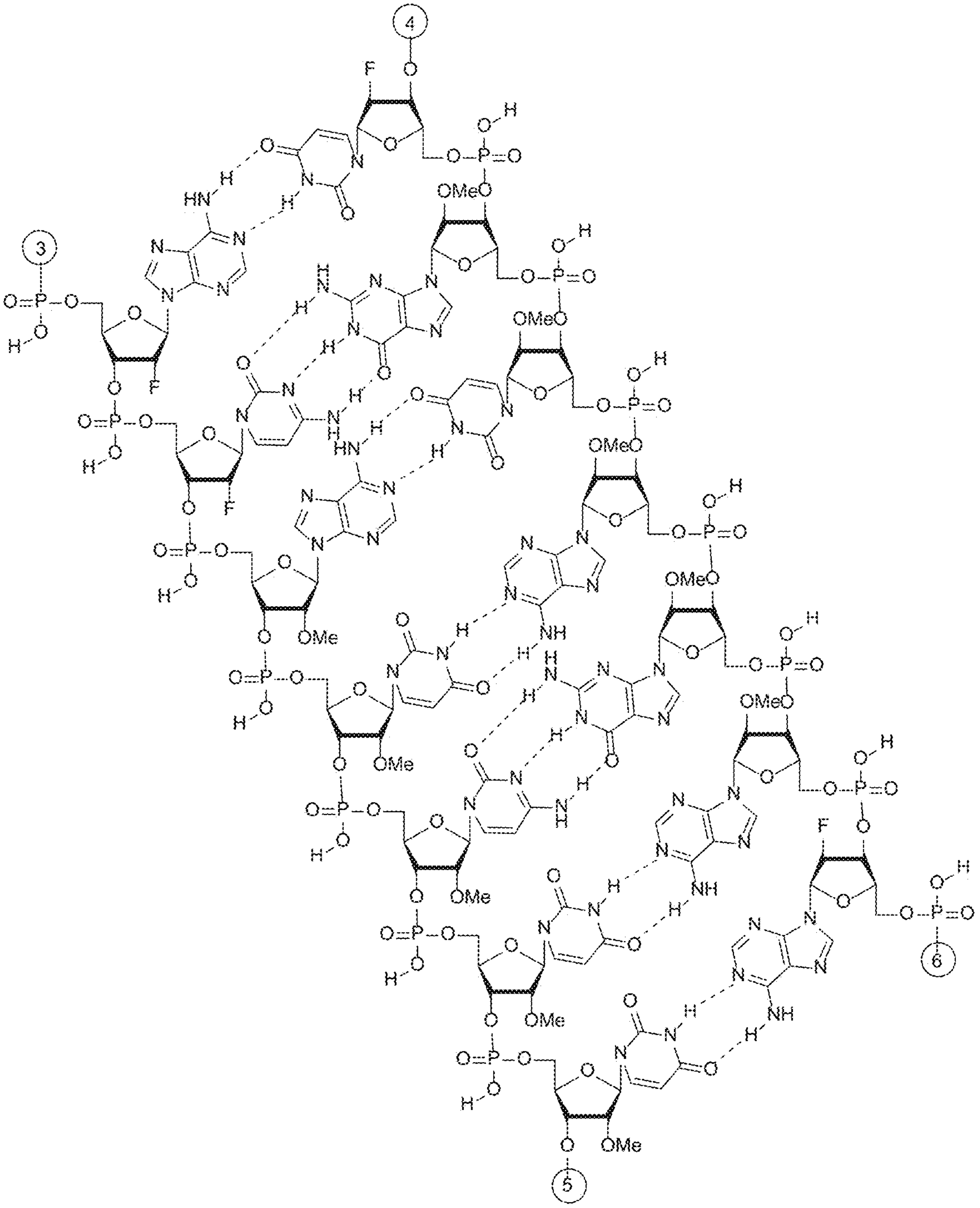
Figure 27D:
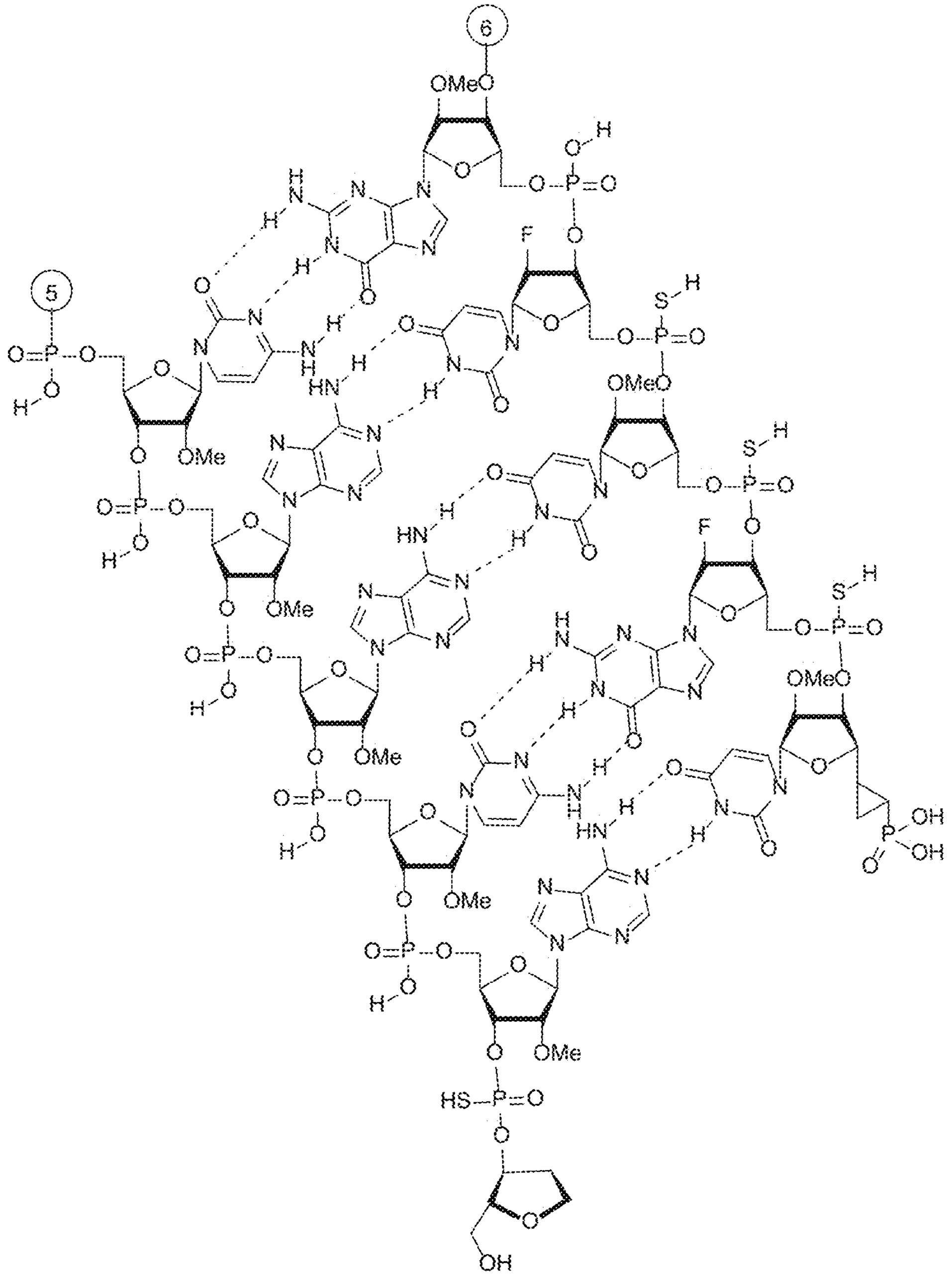
Figure 28A:
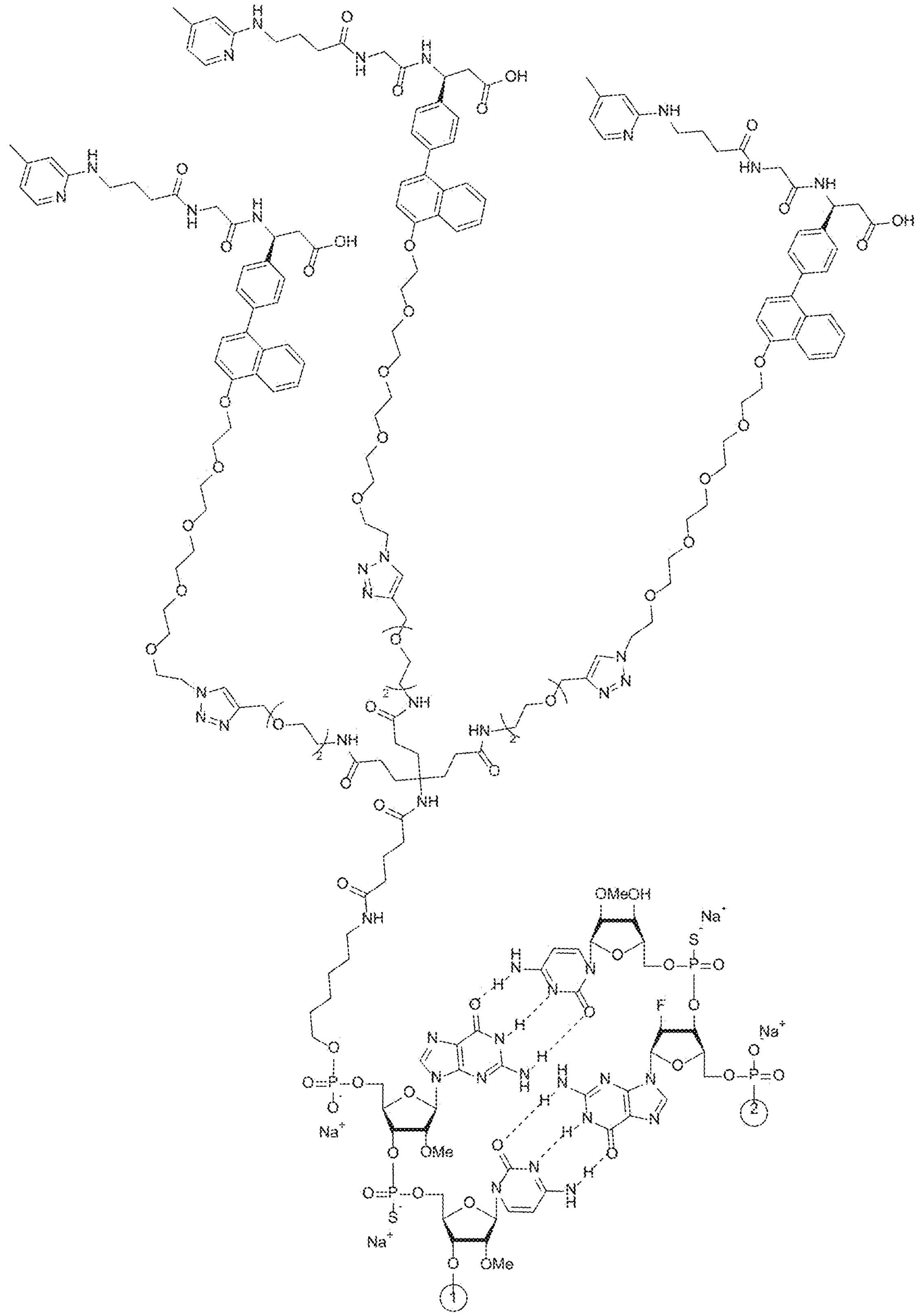
Figure 28B:
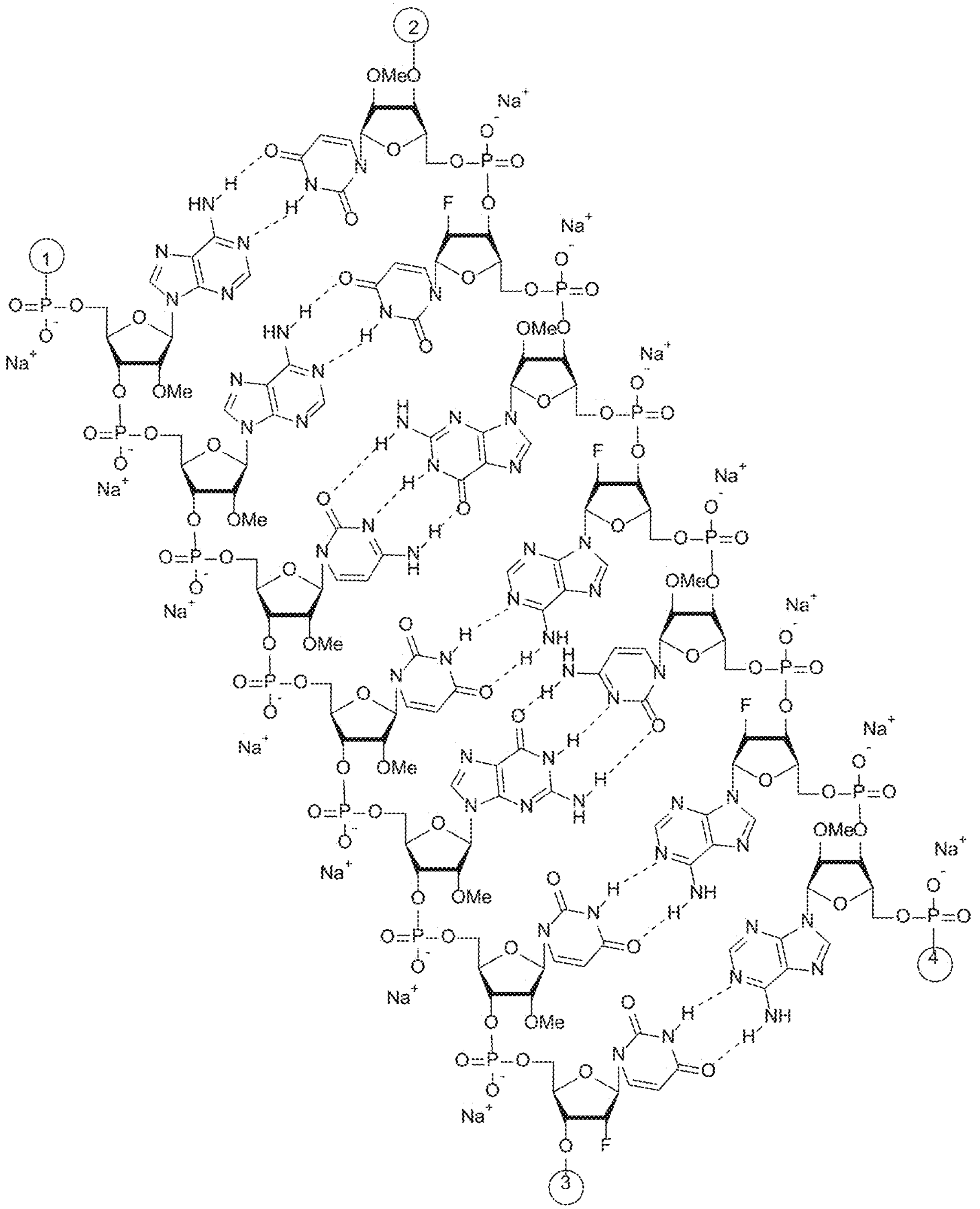
Figure 28C:
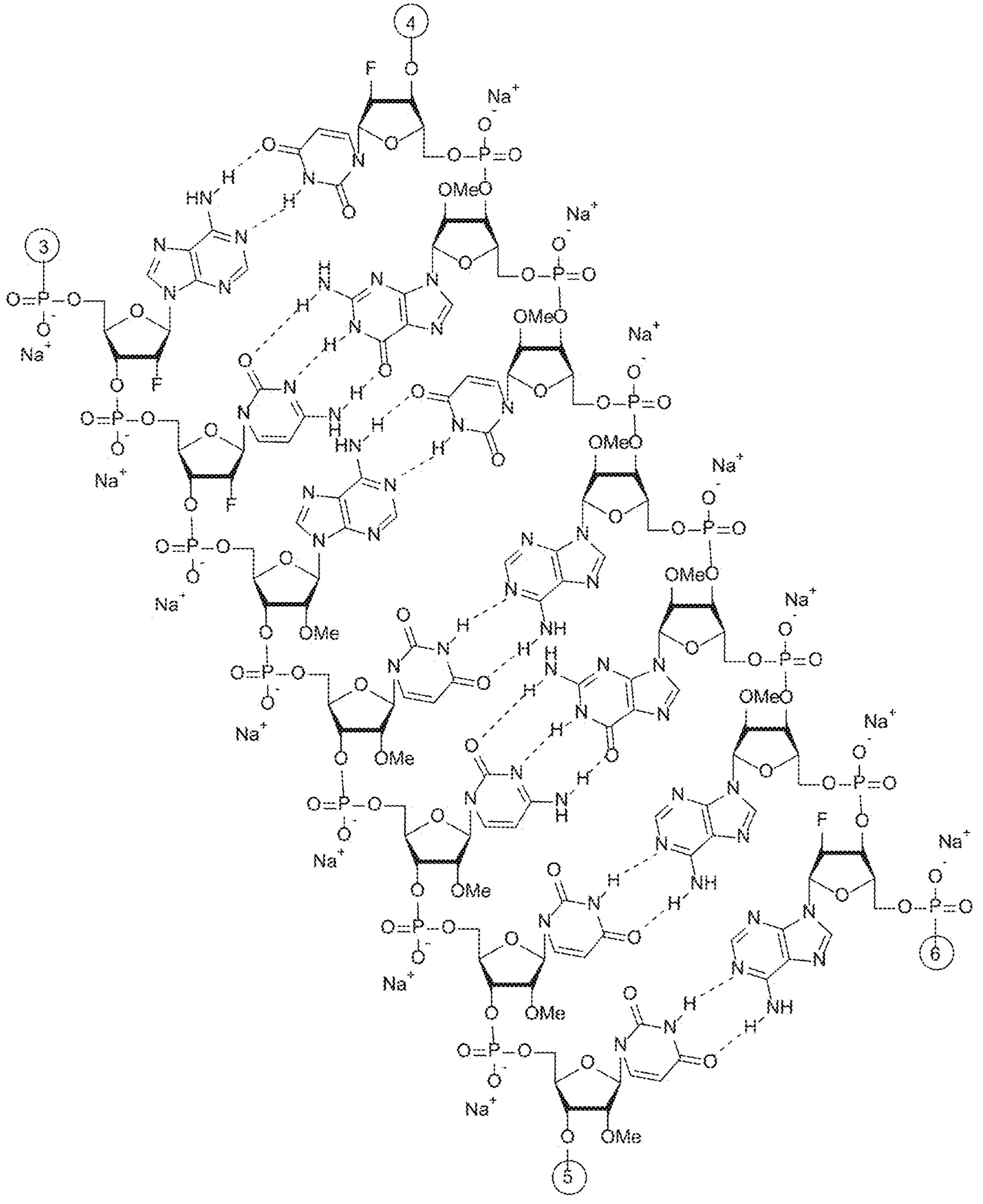
Figure 28D:
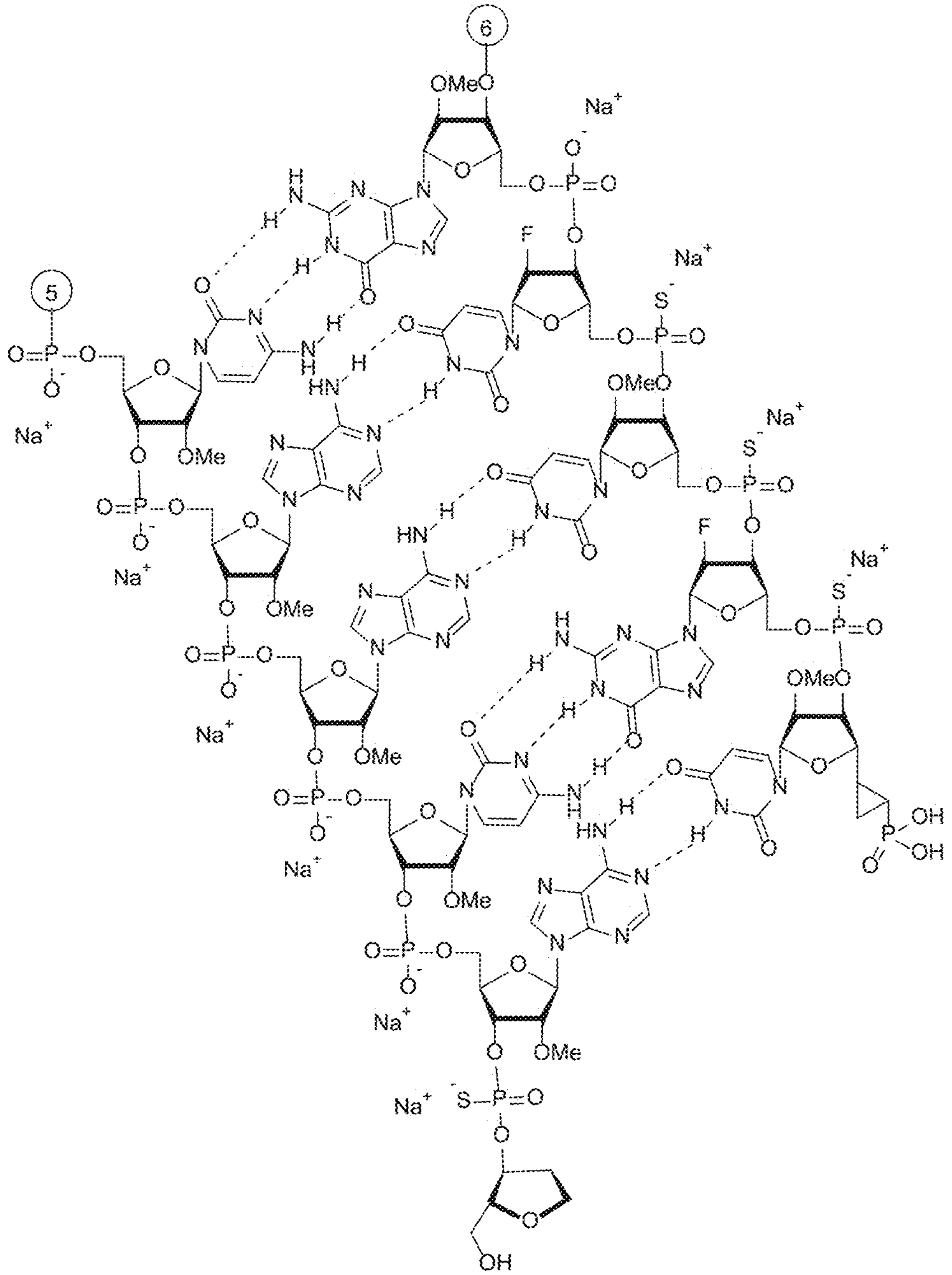
Figure 29A:
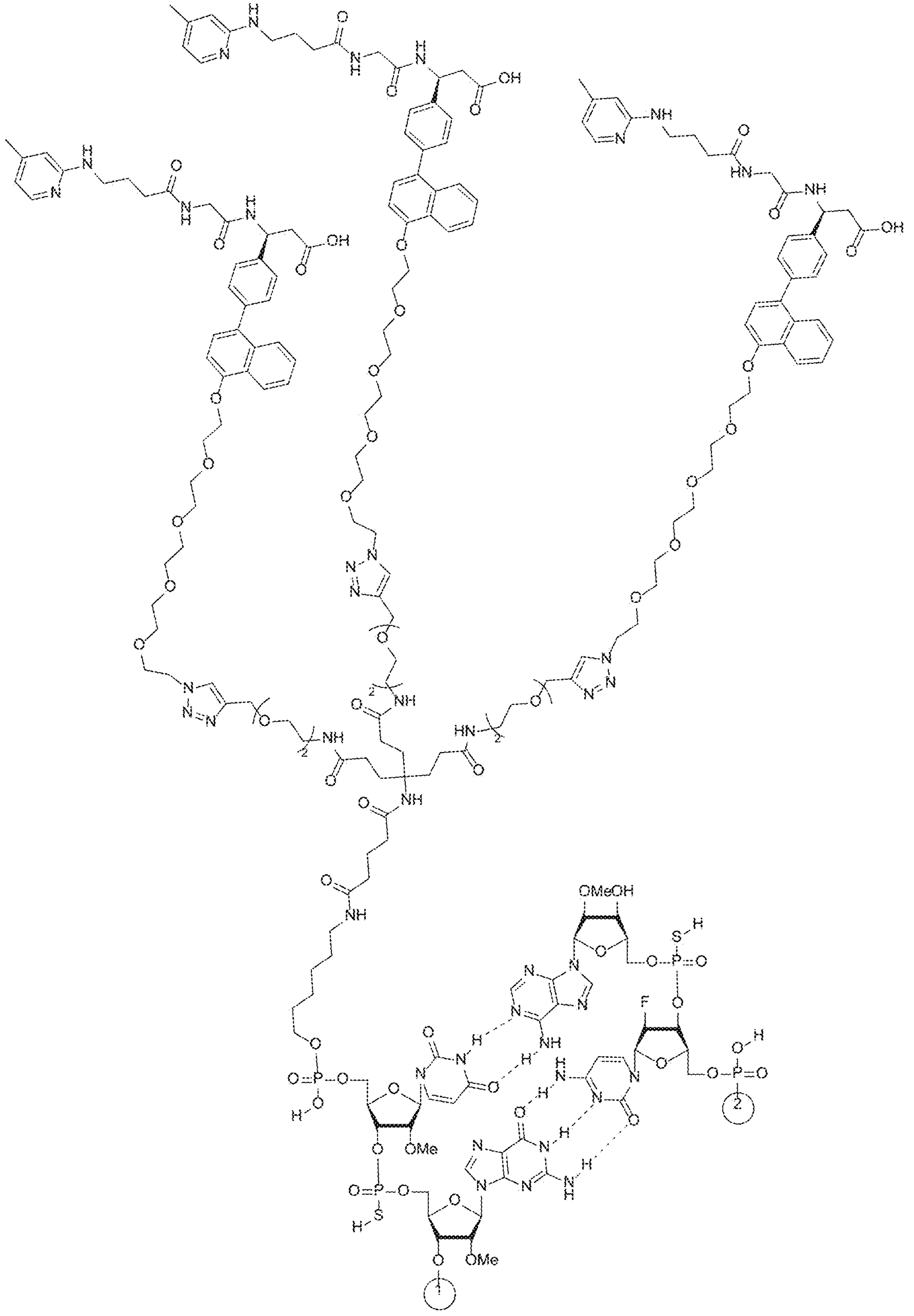
Figure 29B:
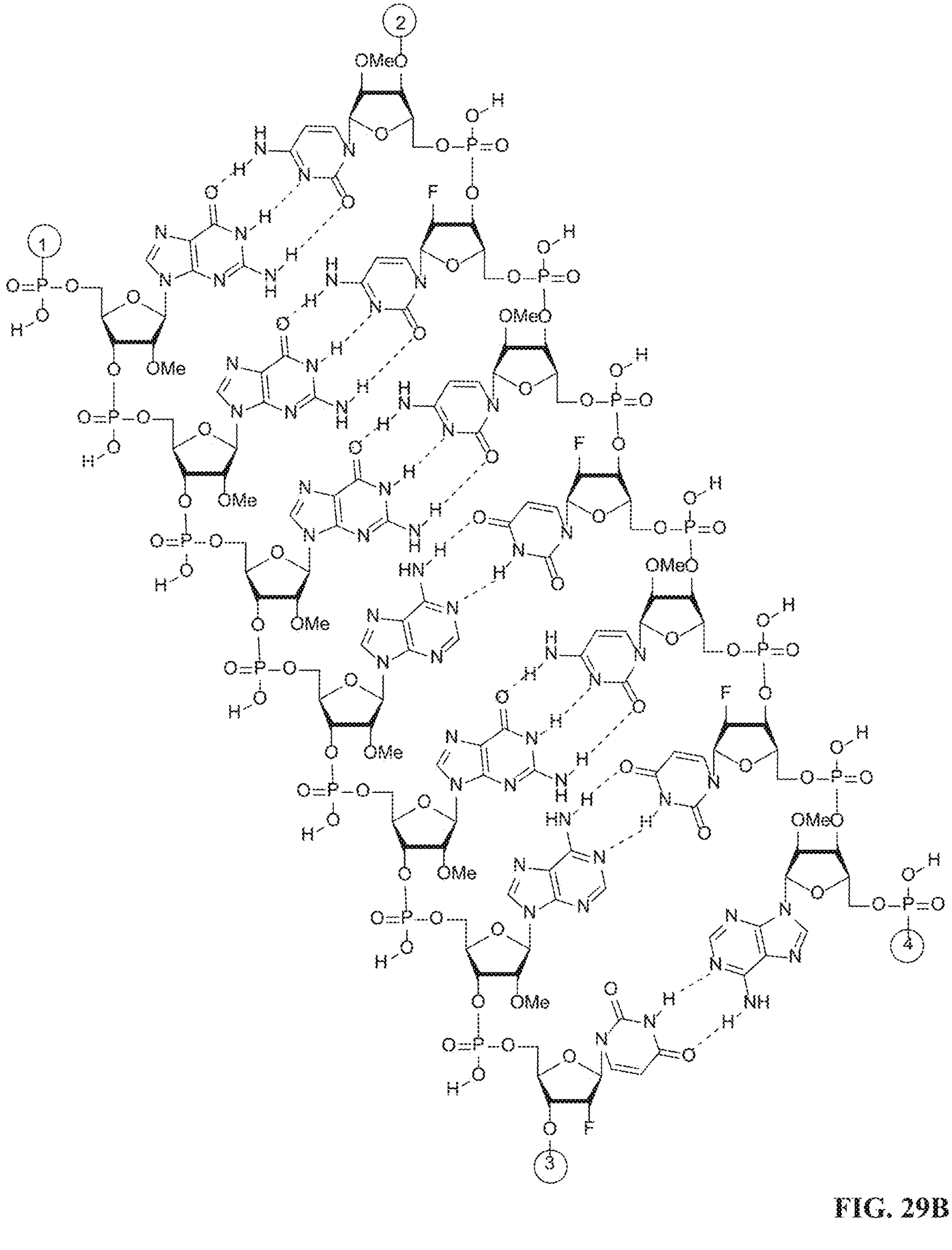
Figure 29C:
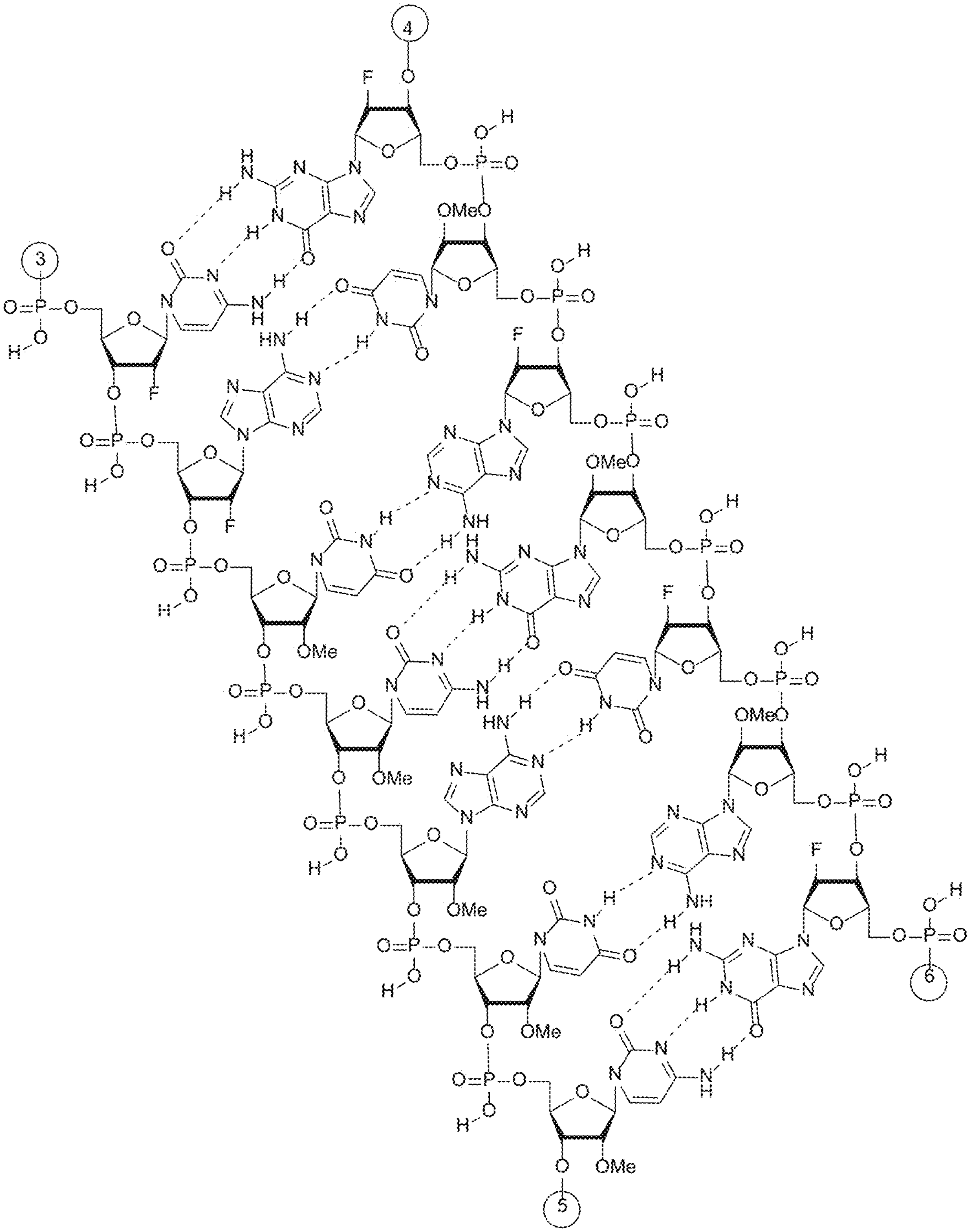
Figure 29D:
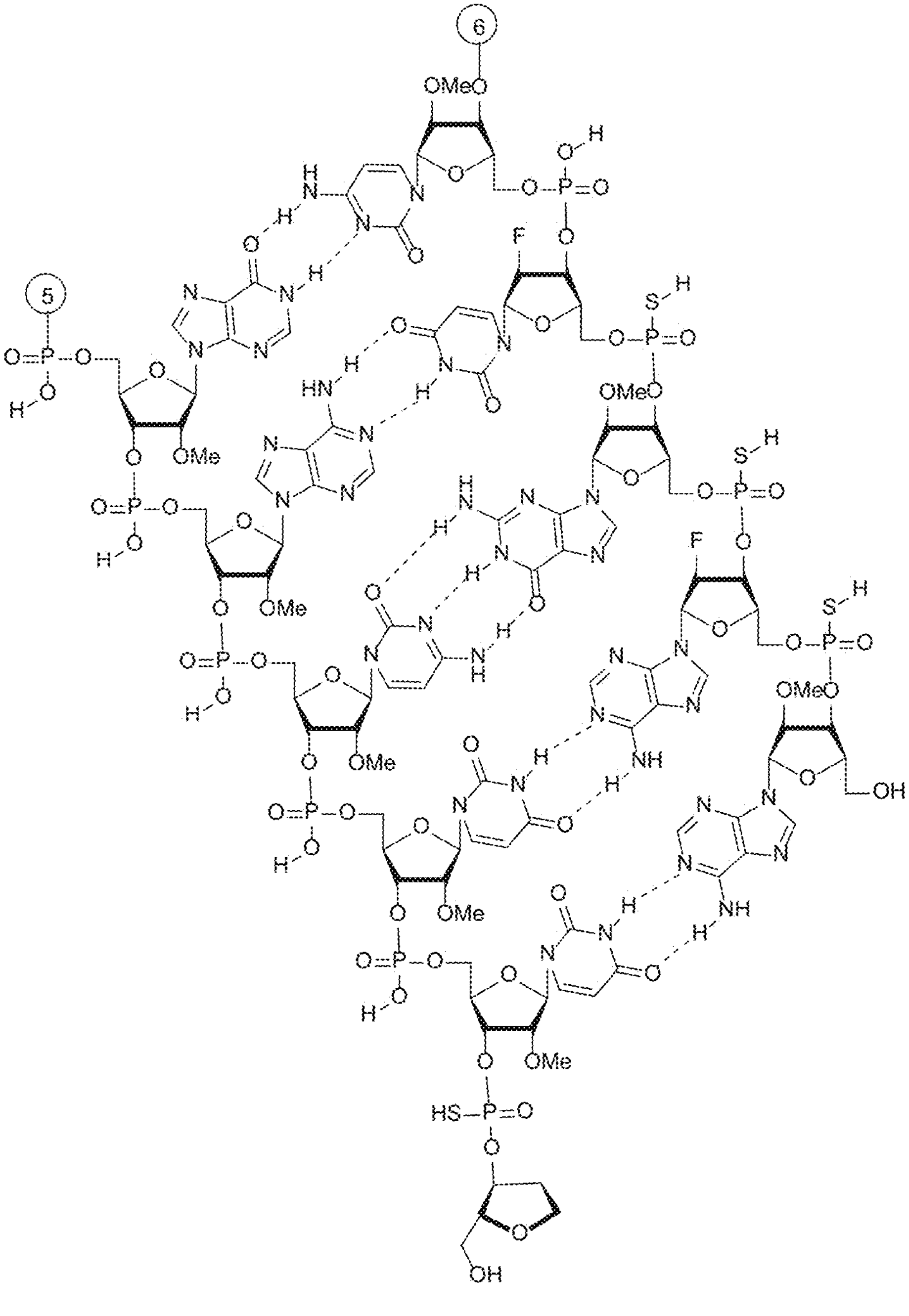
Figure 30A:
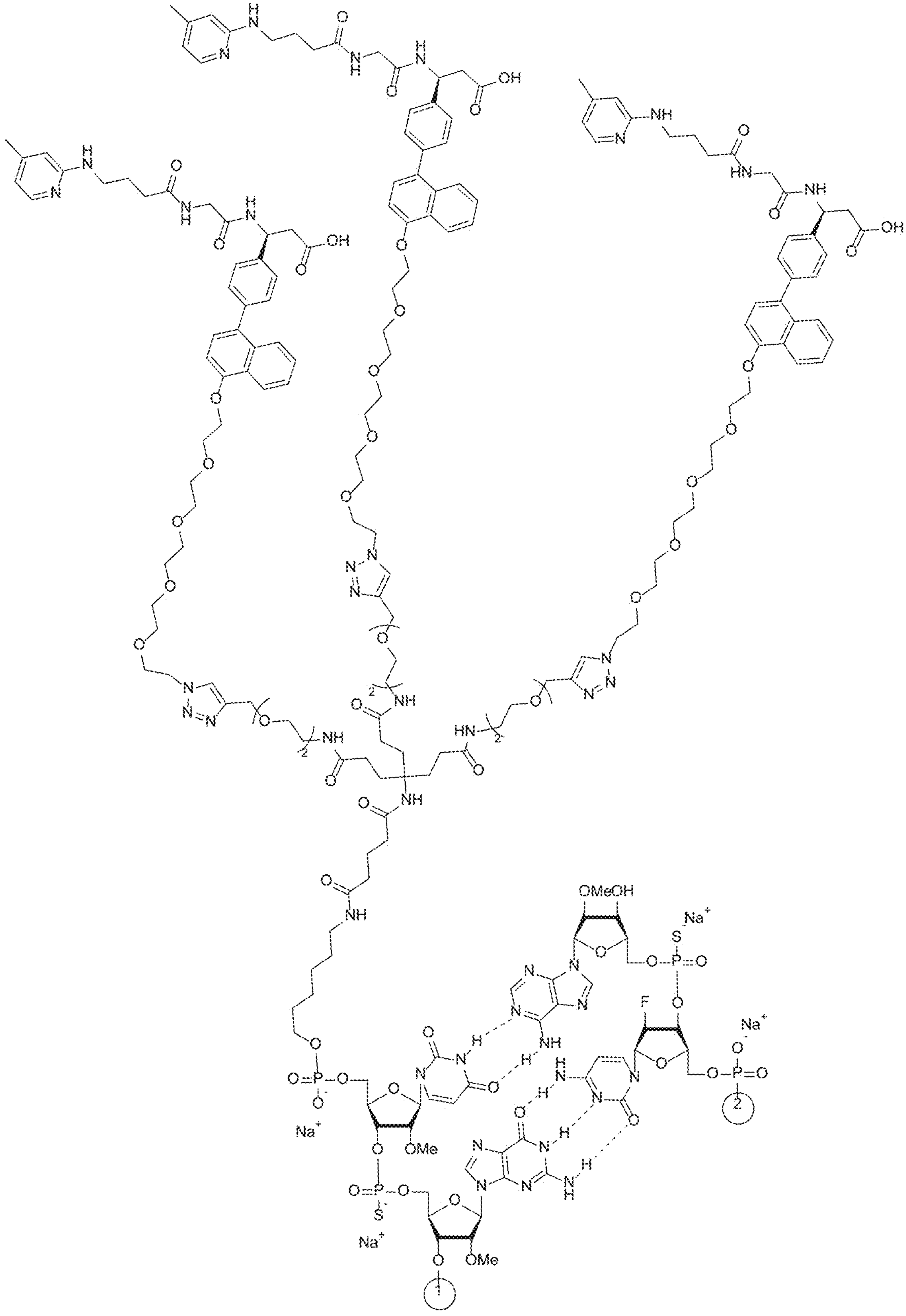
Figure 30B:
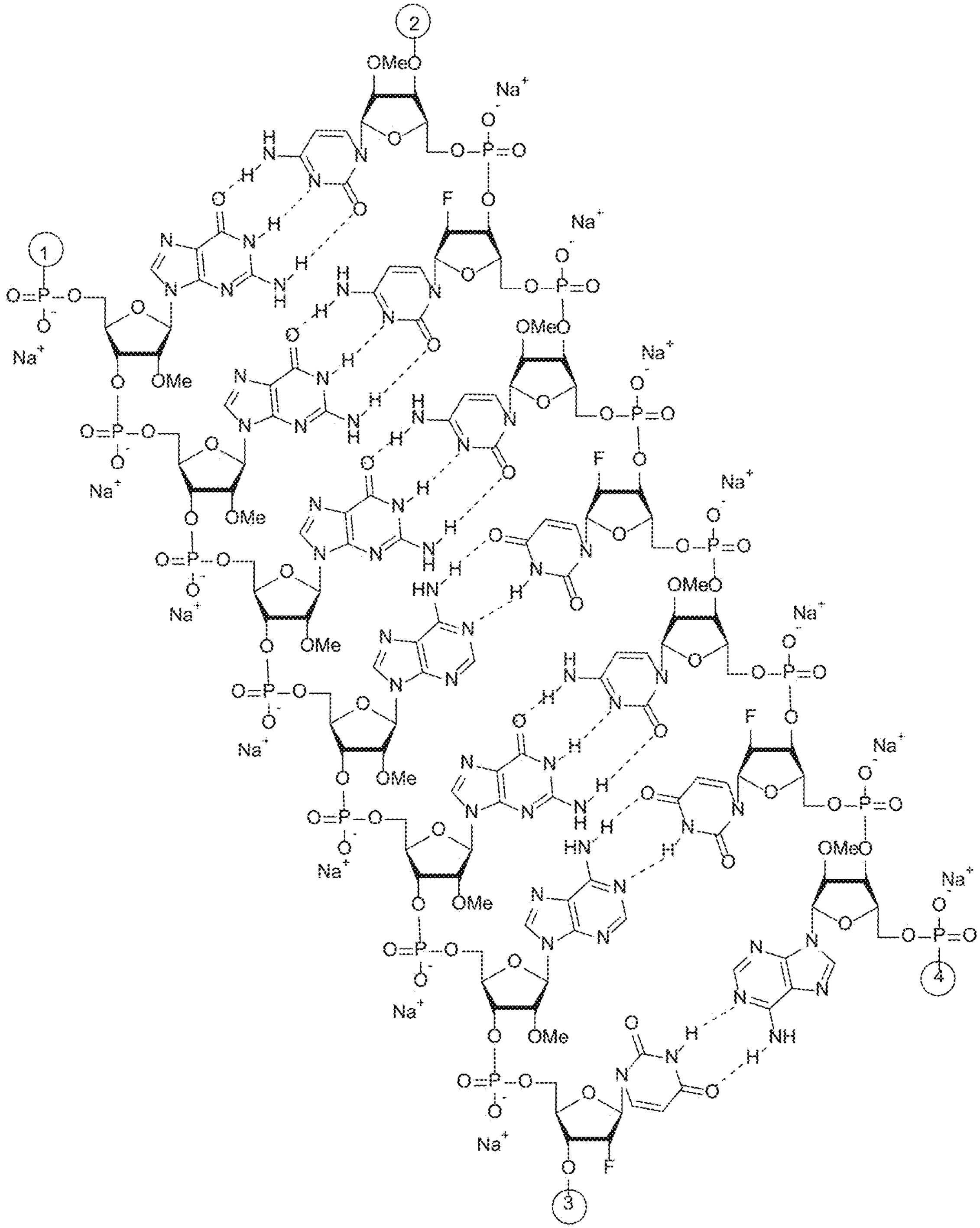
Figure 30C:
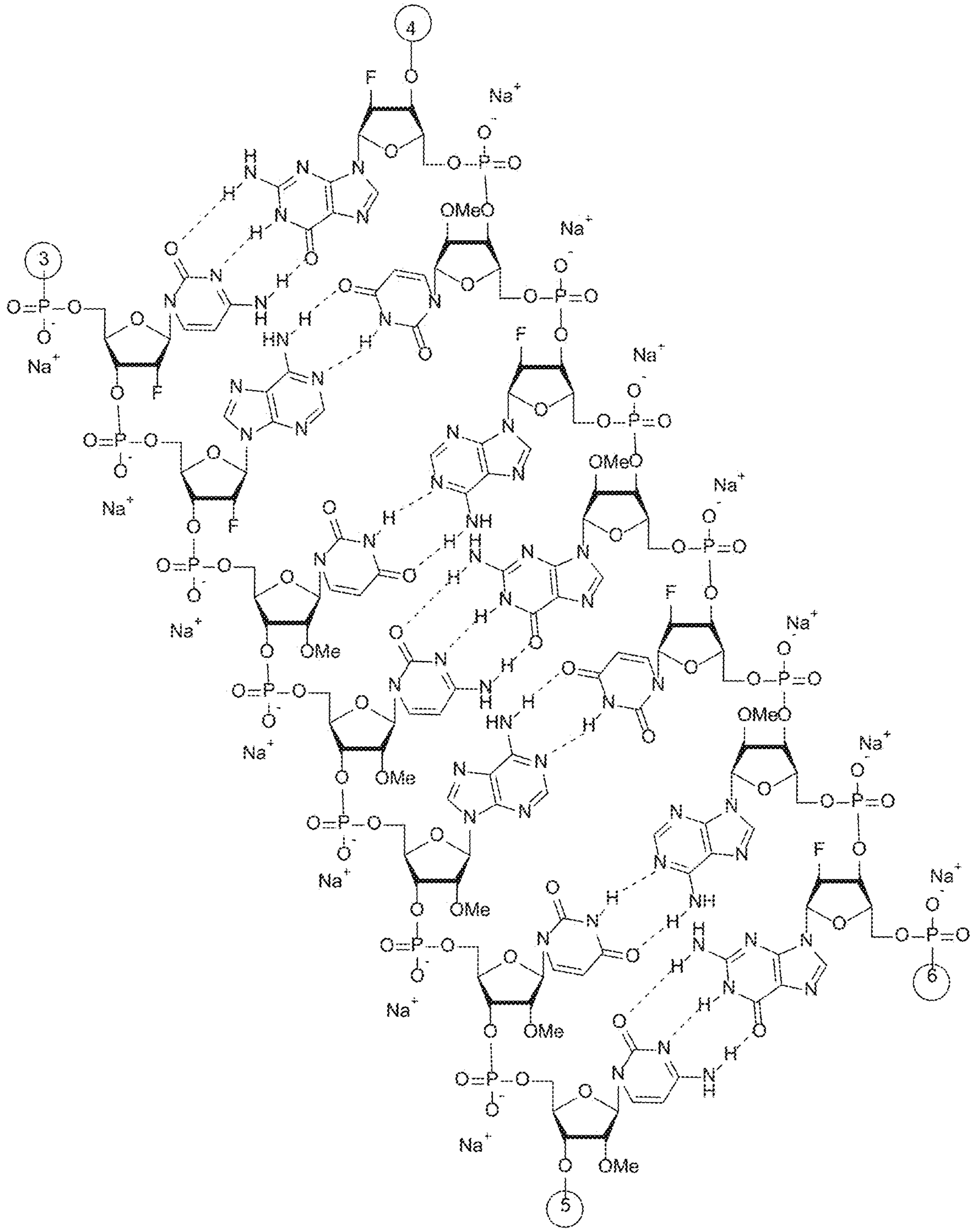
Figure 30D:
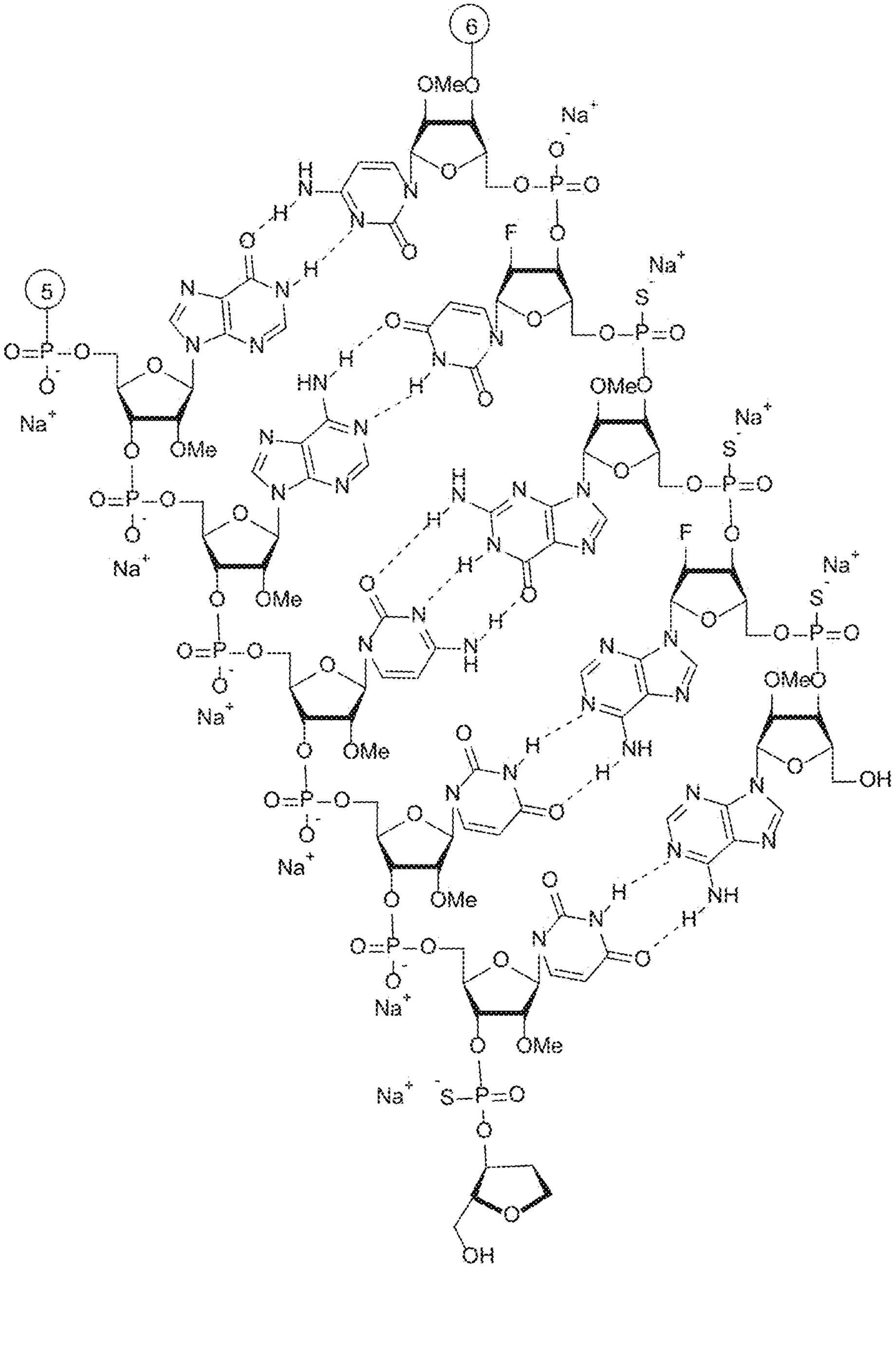

FIG. 24. Human beta-ENaC (SCNN1B) relative mRNA expression in cultured primary normal human bronchial epithelial cells transfected with beta-ENaC RNAi agents as more fully described in Example 12 (error bars not shown).

FIG. 25A through 25D. Chemical structure representation of beta-ENaC RNAi agent AD07482 conjugated to a tridentate small molecule αvβ6 epithelial cell targeting ligand (Tri-SM6.1) at the 5' terminal end of the sense strand (referred to as "APERC-7"), shown in a free acid form.

FIG. 26A through 26D. Chemical structure representation of beta-ENaC RNAi agent AD07482 conjugated to a tridentate small molecule αvβ6 epithelial cell targeting ligand (Tri-SM6.1) at the 5' terminal end of the sense strand (referred to as "APERC-7"), shown in a sodium salt form.

FIG. 27A through 27D. Chemical structure representation of beta-ENaC RNAi agent AD07099 conjugated to a tridentate small molecule αvβ6 epithelial cell targeting ligand (Tri-SM6.1) at the 5' terminal end of the sense strand (referred to as "APERC-5"), shown in a free acid form.

FIG. 28A through 28D. Chemical structure representation of beta-ENaC RNAi agent AD07099 conjugated to a tridentate small molecule αvβ6 epithelial cell targeting ligand (Tri-SM6.1) at the 5' terminal end of the sense strand (referred to as "APERC-5"), shown in a sodium salt form.

FIG. 29A through 29D. Chemical structure representation of beta-ENaC RNAi agent AD06599 conjugated to a tridentate small molecule αvβ6 epithelial cell targeting ligand (Tri-SM6.1) at the 5' terminal end of the sense strand (referred to as "APERC-9"), shown in a free acid form.

FIG. 30A through 30D. Chemical structure representation of beta-ENaC RNAi agent AD06599 conjugated to a tridentate small molecule αvβ6 epithelial cell targeting ligand (Tri-SM6.1) at the 5' terminal end of the sense strand (referred to as "APERC-9"), shown in a sodium salt form.

DETAILED DESCRIPTION

RNAi Agents

Described herein are RNAi agents for inhibiting expression of the beta-ENaC (i.e., SCNN1B) gene (referred to herein as beta-ENaC RNAi agents or beta-ENaC RNAi triggers). Each beta-ENaC RNAi agent disclosed herein comprises a sense strand and an antisense strand. The sense strand and the antisense strand each can be 16 to 49 nucleotides in length. The sense and antisense strands can be either the same length or they can be different lengths. In some embodiments, the sense and antisense strands are each independently 18 to 27 nucleotides in length. In some embodiments, both the sense and antisense strands are each 21-26 nucleotides in length. In some embodiments, the sense and antisense strands are each 21-24 nucleotides in length. In some embodiments, the sense and antisense strands are each independently 19-21 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent sense and antisense strands are each independently 16, 17, 18, 19, 20, 21, 22, 23, 24, 25, 26, 27, 28, 29, 30, 31, 32, 33, 34, 35, 36, 37, 38, or 39 nucleotides in length. In some embodiments, a double-stranded RNAi agent has a duplex length of about 16, 17, 18, 19, 20, 21, 22, 23 or 24 nucleotides.

Examples of nucleotide sequences used in forming beta-ENaC RNAi agents are provided in Tables 2, 3, and 4. Examples of RNAi agent duplexes, that include the sense strand and antisense strand sequences in Tables 2, 3, and 4, are shown in Tables 5A and 5B.

In some embodiments, the region of perfect, substantial, or partial complementarity between the sense strand and the antisense strand is 16-26 (e.g., 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

A sense strand of the beta-ENaC RNAi agents described herein includes at least 16 consecutive nucleotides that have at least 85% identity to a core stretch sequence (also referred to herein as a "core stretch" or "core sequence") of the same number of nucleotides in a beta-ENaC mRNA. In some embodiments, a sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence of the same length (sometimes referred to, e.g., as a target sequence) present in the beta-ENaC mRNA target. In some embodiments, this sense strand core stretch is 16, 17, 18, 19, 20, 21, 22, or 23 nucleotides in length. In some embodiments, this sense strand core stretch is 17 nucleotides in length. In some embodiments, this sense strand core stretch is 19 nucleotides in length.

An antisense strand of a beta-ENaC RNAi agent described herein includes at least 16 consecutive nucleotides that have at least 85% complementarity to a core stretch of the same number of nucleotides in a beta-ENaC mRNA and to a core stretch of the same number of nucleotides in the corresponding sense strand. In some embodiments, an antisense strand core stretch is 100% (perfectly) complementary or at least about 85% (substantially) complementary to a nucleotide sequence (e.g., target sequence) of the same length present in the beta-ENaC mRNA target. In some embodiments, this antisense strand core stretch is 16, 17, 18, 19, 20, 21, 22, or 23 nucleotides in length. In some embodiments, this antisense strand core stretch is 19 nucleotides in length. In some embodiments, this antisense strand core stretch is 17 nucleotides in length. A sense strand core stretch sequence can be the same length as a corresponding antisense core sequence or it can be a different length.

The beta-ENaC RNAi agent sense and antisense strands anneal to form a duplex. A sense strand and an antisense strand of a beta-ENaC RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of a beta-ENaC RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of a beta-ENaC RNAi agent disclosed herein differs by 0, 1, 2, or 3 nucleotides from any of the antisense strand sequences in Table 2 or Table 3. In some embodiments, the sense strand of a beta-ENaC RNAi agent disclosed herein differs by 0, 1, 2, or 3 nucleotides from any of the sense strand sequences in Table 2 or Table 4.

In some embodiments, the sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the beta-ENaC mRNA. The sense strand additional nucleotides, if present, may or may not be identical to the corresponding sequence in the beta-ENaC mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, a beta-ENaC RNAi agent has an antisense strand having a 3' extension and a sense strand having a 5' extension. In some embodiments, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some embodiments, a beta-ENaC RNAi agent comprises an antisense strand having a 3' extension of 1, 2, 3, 4, 5, or 6 nucleotides in length. In other embodiments, a beta-ENaC RNAi agent comprises an antisense strand having a 3' extension of 1, 2, or 3 nucleotides in length. In some embodiments, one or more of the antisense strand extension nucleotides comprise nucleotides that are complementary to the corresponding beta-ENaC mRNA sequence. In some embodiments, one or more of the antisense strand extension nucleotides comprise nucleotides that are not complementary to the corresponding beta-ENaC mRNA sequence.

In some embodiments, a beta-ENaC RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to or are the identical to nucleotides in the beta-ENaC mRNA sequence. In some embodiments, the 3' sense strand extension includes or consists of one of the following sequences, but is not limited to: T, UT, TT, UU, UUT, TTT, or TTTT (each listed 5' to 3').

A sense strand can have a 3' extension and/or a 5' extension. In some embodiments, a beta-ENaC RNAi agent comprises a sense strand having a 5' extension of 1, 2, 3, 4, 5, or 6 nucleotides in length. In some embodiments, one or more of the sense strand extension nucleotides comprise nucleotides that correspond to or are identical to nucleotides in the beta-ENaC mRNA sequence.

Examples of sequences used in forming beta-ENaC RNAi agents are provided in Tables 2, 3, and 4. In some embodiments, a beta-ENaC RNAi agent antisense strand includes a sequence of any of the sequences in Tables 2 or 3. In certain embodiments, a beta-ENaC RNAi agent antisense strand comprises or consists of any one of the modified sequences in Table 3. In some embodiments, a beta-ENaC RNAi agent antisense strand includes the sequence of nucleotides (from 5' end→3' end) 1-17, 2-15, 2-17, 1-18, 2-18, 1-19, 2-19, 1-20, 2-20, 1-21, or 2-21, of any of the sequences in Tables 2 or 3. In some embodiments, a beta-ENaC RNAi agent sense strand includes the sequence of any of the sequences in Tables 2 or 4. In some embodiments, a beta-ENaC RNAi agent sense strand includes the sequence of nucleotides (from 5' end→3' end) 1-18, 1-19, 1-20, 1-21, 2-19, 2-20, 2-21, 3-20, 3-21, or 4-21 of any of the sequences in Tables 2 or 4. In certain embodiments, a beta-ENaC RNAi agent sense strand comprises or consists of a modified sequence of any one of the modified sequences in Table 4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

The beta-ENaC RNAi agents disclosed herein may also be comprised of one or more modified nucleotides. In some embodiments, substantially all of the nucleotides of the sense strand and substantially all of the nucleotides of the antisense strand of the beta-ENaC RNAi agent are modified nucleotides. The beta-ENaC RNAi agents disclosed herein may further be comprised of one or more modified internucleoside linkages, e.g., one or more phosphorothioate linkages. In some embodiments, a beta-ENaC RNAi agent contains one or more modified nucleotides and one or more modified internucleoside linkages. In some embodiments, a 2'-modified nucleotide is combined with modified internucleoside linkage.

In some embodiments, a beta-ENaC RNAi agent is prepared or provided as a salt, mixed salt, or a free-acid. In some embodiments, a beta-ENaC RNAi agent is prepared as a sodium salt. Such forms that are well known in the art are within the scope of the inventions disclosed herein.

Modified Nucleotides

Modified nucleotides, when used in various oligonucleotide constructs, can preserve activity of the compound in cells while at the same time increasing the serum stability of these compounds, and can also minimize the possibility of activating interferon activity in humans upon administration of the oligonucleotide construct.

In some embodiments, a beta-ENaC RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e., a nucleotide with a group other than a hydroxyl group at the 2' position of the five-membered sugar ring) include, but are not limited to, 2'-O-methyl nucleotides (also referred to as 2'-methoxy nucleotides), 2'-fluoro nucleotides (also referred to herein as 2'-deoxy-2'-fluoro nucleotides), 2'-deoxy nucleotides, 2'-methoxyethyl (2'-O-2-methoxylethyl) nucleotides (also referred to as 2'-MOE), 2'-amino nucleotides, and 2'-alkyl nucleotides. It is not necessary for all positions in a given compound to be uniformly modified. Conversely, more than one modification can be incorporated in a single beta-ENaC RNAi agent or even in a single nucleotide thereof. The beta-ENaC RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, the 5' and/or 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. (See. e.g., U.S. Pat. No. 5,998,203). In some embodiments, an abasic residue can be placed internally in a nucleotide sequence. In some embodiments, Ab or AbAb can be added to the 3' end of the antisense strand. In some embodiments, the 5' end of the sense strand can include one or more additional abasic residues (e.g., (Ab) or (AbAb)). In some embodiments, UUAb, UAb, or Ab are added to the 3' end of the sense strand. In some embodiments, an abasic (deoxyribose) residue can be replaced with a ribitol (abasic ribose) residue.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense strand wherein substantially all of the nucleotides present are modified nucleotides is an antisense strand having two or fewer (i.e., 0, 1, or 2) nucleotides in the antisense strand being unmodified ribonucleotides. In some embodiments, one or more nucleotides of an RNAi agent is an unmodified ribonucleotide. Chemical structures for certain modified nucleotides are set forth in Table 6 herein.

Modified Internucleoside Linkages

In some embodiments, one or more nucleotides of a beta-ENaC RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of a beta-ENaC RNAi agent can contain 1, 2, 3, 4, 5, or 6 phosphorothioate linkages, an antisense strand of a beta-ENaC RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of a beta-ENaC RNAi agent can contain 1, 2, 3, or 4 phosphorothioate linkages, an antisense strand of a beta-ENaC RNAi agent can contain 1, 2, 3, or 4 phosphorothioate linkages, or both the sense strand and the antisense strand independently can contain 1, 2, 3, or 4 phosphorothioate linkages.

In some embodiments, a beta-ENaC RNAi agent sense strand contains at least two phosphorothioate internucleoside linkages. In some embodiments, the phosphorothioate internucleoside linkages are between the nucleotides at positions 1-3 from the 3' end of the sense strand. In some embodiments, one phosphorothioate internucleoside linkage is at the 5' end of the sense strand nucleotide sequence, and another phosphorothioate linkage is at the 3' end of the sense strand nucleotide sequence. In some embodiments, two phosphorothioate internucleoside linkage are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, a beta-ENaC RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, a beta-ENaC RNAi agent contains at least three or four phosphorothioate internucleoside linkages in the antisense strand.

Capping Residues or Moieties

In some embodiments, the sense strand may include one or more capping residues or moieties, sometimes referred to in the art as a "cap," a "terminal cap," or a "capping residue." As used herein, a "capping residue" is a non-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some embodiments, inverted abasic residues (invAb) (also referred to in the art as "inverted abasic sites") are added as capping residues (see Table A). (See, e.g., F. Czauderna, Nucleic Acids Res., 2003, 31(11), 2705-16). Capping residues are generally known in the art, and include, for example, inverted abasic residues as well as carbon chains such as a terminal $C_3H_7$ (propyl), $C_6H_{13}$ (hexyl), or $C_{12}H_{25}$ (dodecyl) groups. In some embodiments, a capping residue is present at either the 5' terminal end, the 3' terminal end, or both the 5' and 3' terminal ends of the sense strand. In some embodiments, the 5' end and/or the 3' end of the sense strand may include more than one inverted abasic deoxyribose moiety as a capping residue.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s)), or other internucleoside linkages. In some embodiments, the inclusion of one or more inverted abasic residues at or near the terminal end or terminal ends of the sense strand of an RNAi agent may allow for enhanced activity or other desired properties of an RNAi agent. In some embodiments, an inverted abasic (deoxyribose) residue can be replaced with an inverted ribitol (abasic ribose) residue. In some embodiments, the 3' end of the antisense strand core stretch sequence, or the 3' end of the antisense strand sequence, may include an inverted abasic residue. The chemical structures for inverted abasic deoxyribose residues are shown in Table 6 below.

Beta-ENaC RNAi Agents

The beta-ENaC RNAi agents disclosed herein are designed to target specific positions on a beta-ENaC gene (e.g., SEQ ID NO:1 (GenBank NM_000336.2), SEQ ID NO:2 (GenBank NM_000336.3)). As defined herein, an antisense strand sequence is designed to target a beta-ENaC gene at a given position on the gene when the 5' terminal nucleobase of the antisense strand is aligned with a position that is 19 nucleotides downstream (towards the 3' end) from the position on the gene when base pairing to the gene. For example, as illustrated in Tables 1 and 2 herein, an antisense strand sequence designed to target a beta-ENaC gene at position 987 requires that when base pairing to the gene, the 5' terminal nucleobase of the antisense strand is aligned with position 1005 of a beta-ENaC gene.

As provided herein, a beta-ENaC RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for a beta-ENaC RNAi agent disclosed herein that is designed to target position 987 of a beta-ENaC gene, the 5' terminal nucleobase of the antisense strand of the of the beta-ENaC RNAi agent must be aligned with position 1005 of the gene; however, the 5' terminal nucleobase of the antisense strand may be, but is not required to be, complementary to position 1005 of a beta-ENaC gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the beta-ENaC RNAi agent (e.g., whether the beta-ENaC RNAi agent is designed to target a beta-ENaC gene at position 987, at position 1296, at position 1798, or at some other position) is an important factor to the level of inhibition achieved by the beta-ENaC RNAi agent.

In some embodiments, the beta-ENaC RNAi agents disclosed herein target a beta-ENaC gene at or near the positions of the beta-ENaC sequence shown in Table 1. In some embodiments, the antisense strand of a beta-ENaC RNAi agent disclosed herein includes a core stretch sequence that is fully, substantially, or at least partially complementary to a target beta-ENaC 19-mer sequence disclosed in Table 1.

TABLE 1

Beta-ENaC 19-mer mRNA Target Sequences (taken from *homo sapiens* sodium channel epithelial 1 beta subunit (SCNN1B), GenBank NM_000336.2 (SEQ ID NO: 1)) (Gene positions herein are referenced according to GenBank NM_000336.2 as the reference gene for human SCNN1B. On or about Feb. 3, 2020, the gene sequence was updated as NM_000336.3 (SEQ ID NO: 2). While referencing the updated gene may change the number identified as the referenced "Targeted Gene Position" in Tables 1 and 2 herein, this has no impact on the nucleotide sequences described in the RNAi agents disclosed).

| SEQ ID No. | beta-ENaC 19-mer Target Sequences (5'→3') | Corresponding Positions of Sequence on SEQ ID NO: 1 | Targeted Gene Position (as referred to herein) |
|---|---|---|---|
| 3 | ACCCCUGGUCCUUAUUGAU | 620-638 | 620 |
| 4 | CCCUGGUCCUUAUUGAUGA | 622-640 | 622 |
| 5 | AACUGUUACAUCUUCAACU | 987-1005 | 987 |
| 6 | UCUACAGUGACUACAACAC | 1294-1312 | 1294 |
| 7 | UACAGUGACUACAACACGA | 1296-1314 | 1296 |
| 8 | UUCCAAGACCACAUGAUCC | 1347-1365 | 1347 |
| 9 | UCCAAGACCACAUGAUCCG | 1348-1366 | 1348 |
| 10 | GUGGGGAGAAAUACUGCAA | 1405-1423 | 1405 |
| 11 | GGAGAAAUACUGCAACAAC | 1409-1427 | 1409 |
| 12 | GAGAAAUACUGCAACAACC | 1410-1428 | 1410 |
| 13 | AUCACCCUGAGCAGGAAGG | 1629-1647 | 1629 |
| 14 | GGGAGAUCAUCAUCGACUU | 1798-1816 | 1798 |

In some embodiments, a beta-ENaC RNAi agent includes an antisense strand wherein position 19 of the antisense strand (5'→3') is capable of forming a base pair with position 1 of a 19-mer target sequence disclosed in Table 1. In some embodiments, a beta-ENaC agent includes an antisense strand wherein position 1 of the antisense strand (5'→3') is capable of forming a base pair with position 19 of a 19-mer target sequence disclosed in Table 1.

In some embodiments, a beta-ENaC agent includes an antisense strand wherein position 2 of the antisense strand (5'→3') is capable of forming a base pair with position 18 of a 19-mer target sequence disclosed in Table 1. In some embodiments, a beta-ENaC agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to a beta-ENaC gene, or can be non-complementary to a beta-ENaC gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, a beta-ENaC RNAi agent antisense strand comprises the sequence of nucleotides (from 5' end→3' end) 2-18 or 2-19 of any of the antisense strand sequences in Table 2 or Table 3. In some embodiments, a beta-ENaC RNAi sense strand comprises the sequence of nucleotides (from 5' end→3' end) 1-17, 1-18, or 2-18 of any of the sense strand sequences in Table 2 or Table 4.

In some embodiments, a beta-ENaC RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4.

In some embodiments, the beta-ENaC RNAi agents include core 19-mer nucleotide sequences shown in the following Table 2.

TABLE 2

Beta-ENaC RNAi Agent Antisense Strand and Sense Strand Core Stretch Base Sequences
(N = any nucleobase; I = inosine nucleotide)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corresponding Positions of Identified Sequence on SEQ ID NO: 1 | Targeted Gene Position |
|---|---|---|---|---|---|
| 15 | AGUUGAAGAUGUAACAGUU | 68 | AACUGUUACAUCUUCAACU | 987-1005 | 987 |
| 16 | UGUUGAAGAUGUAACAGUU | 69 | AACUGUUACAUCUUCAACA | 987-1005 | 987 |
| 17 | NGUUGAAGAUGUAACAGUU | 70 | AACUGUUACAUCUUCAACN | 987-1005 | 987 |
| 18 | NGUUGAAGAUGUAACAGUN | 71 | NACUGUUACAUCUUCAACN | 987-1005 | 987 |
| 19 | AUCAAUAAGGACCAGGGGU | 72 | ACCCCUGGUCCUUAUUGAU | 620-638 | 620 |
| 20 | UUCAAUAAGGACCAGGGGU | 73 | ACCCCUGGUCCUUAUUGAA | 620-638 | 620 |
| 21 | NUCAAUAAGGACCAGGGGU | 74 | ACCCCUGGUCCUUAUUGAN | 620-638 | 620 |
| 22 | NUCAAUAAGGACCAGGGGN | 75 | NCCCCUGGUCCUUAUUGAN | 620-638 | 620 |
| 23 | UCAUCAAUAAGGACCAGGG | 76 | CCCUGGUCCUUAUUGAUGA | 622-640 | 622 |
| 24 | NCAUCAAUAAGGACCAGGG | 77 | CCCUGGUCCUUAUUGAUGN | 622-640 | 622 |
| 25 | NCAUCAAUAAGGACCAGGN | 78 | NCCUGGUCCUUAUUGAUGN | 622-640 | 622 |
| 26 | GUGUUGUAGUCACUGUAGA | 79 | UCUACAGUGACUACAACAC | 1294-1312 | 1294 |
| 27 | UUGUUGUAGUCACUGUAGA | 80 | UCUACAGUGACUACAACAA | 1294-1312 | 1294 |
| 28 | NUGUUGUAGUCACUGUAGA | 81 | UCUACAGUGACUACAACAN | 1294-1312 | 1294 |
| 29 | NUGUUGUAGUCACUGUAGN | 82 | NCUACAGUGACUACAACAN | 1294-1312 | 1294 |
| 30 | UCGUGUUGUAGUCACUGUA | 83 | UACAGUGACUACAACACGA | 1296-1314 | 1296 |
| 31 | NCGUGUUGUAGUCACUGUA | 84 | UACAGUGACUACAACACGN | 1296-1314 | 1296 |
| 32 | NCGUGUUGUAGUCACUGUN | 85 | NACAGUGACUACAACACGN | 1296-1314 | 1296 |
| 33 | UCGUGUUGUAGUCACUGUA | 86 | UACAGUGACUACAACACIA | 1296-1314 | 1296 |
| 34 | NCGUGUUGUAGUCACUGUA | 87 | UACAGUGACUACAACACIN | 1296-1314 | 1296 |
| 35 | NCGUGUUGUAGUCACUGUN | 88 | NACAGUGACUACAACACIN | 1296-1314 | 1296 |
| 36 | GGAUCAUGUGGUCUUGGAA | 89 | UUCCAAGACCACAUGAUCC | 1347-1365 | 1347 |
| 37 | UGAUCAUGUGGUCUUGGAA | 90 | UUCCAAGACCACAUGAUCA | 1347-1365 | 1347 |
| 38 | UGAUCAUGUGGUCUUGGAA | 91 | UUCCAAGACCACAUIAUCA | 1347-1365 | 1347 |
| 39 | NGAUCAUGUGGUCUUGGAA | 92 | UUCCAAGACCACAUGAUCN | 1347-1365 | 1347 |
| 40 | NGAUCAUGUGGUCUUGGAN | 93 | NUCCAAGACCACAUGAUCN | 1347-1365 | 1347 |
| 41 | CGGAUCAUGUGGUCUUGGA | 94 | UCCAAGACCACAUGAUCCG | 1348-1366 | 1348 |
| 42 | UGGAUCAUGUGGUCUUGGA | 95 | UCCAAGACCACAUGAUCCA | 1348-1366 | 1348 |
| 43 | NGGAUCAUGUGGUCUUGGA | 96 | UCCAAGACCACAUGAUCCN | 1348-1366 | 1348 |
| 44 | NGGAUCAUGUGGUCUUGGN | 97 | NCCAAGACCACAUGAUCCN | 1348-1366 | 1348 |
| 45 | UUGCAGUAUUUCUCCCCAC | 98 | GUGGGGAGAAAUACUGCAA | 1405-1423 | 1405 |
| 46 | NUGCAGUAUUUCUCCCCAC | 99 | GUGGGGAGAAAUACUGCAN | 1405-1423 | 1405 |
| 47 | NUGCAGUAUUUCUCCCCAN | 100 | NUGGGGAGAAAUACUGCAN | 1405-1423 | 1405 |
| 48 | GUUGUUGCAGUAUUUCUCC | 101 | GGAGAAAUACUGCAACAAC | 1409-1427 | 1409 |
| 49 | UUUGUUGCAGUAUUUCUCC | 102 | GGAGAAAUACUGCAACAAA | 1409-1427 | 1409 |
| 50 | NUUGUUGCAGUAUUUCUCC | 103 | GGAGAAAUACUGCAACAAN | 1409-1427 | 1409 |

TABLE 2-continued

Beta-ENaC RNAi Agent Antisense Strand and Sense Strand Core Stretch Base Sequences (N = any nucleobase; I = inosine nucleotide)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corresponding Positions of Identified Sequence on SEQ ID NO: 1 | Targeted Gene Position |
|---|---|---|---|---|---|
| 51 | NUUGUUGCAGUAUUUCUCN | 104 | NGAGAAAUACUGCAACAAN | 1409-1427 | 1409 |
| 52 | GGUUGUUGCAGUAUUUCUC | 105 | GAGAAAUACUGCAACAACC | 1410-1428 | 1410 |
| 53 | UGUUGUUGCAGUAUUUCUC | 106 | GAGAAAUACUGCAACAACA | 1410-1428 | 1410 |
| 54 | NGUUGUUGCAGUAUUUCUC | 107 | GAGAAAUACUGCAACAACN | 1410-1428 | 1410 |
| 55 | NGUUGUUGCAGUAUUUCUN | 108 | NAGAAAUACUGCAACAACN | 1410-1428 | 1410 |
| 56 | CCUUCCUGCUCAGGGUGAU | 109 | AUCACCCUGAGCAGGAAGG | 1629-1647 | 1629 |
| 57 | UCUUCCUGCUCAGGGUGAU | 110 | AUCACCCUGAGCAGGAAGA | 1629-1647 | 1629 |
| 58 | NCUUCCUGCUCAGGGUGAU | 111 | AUCACCCUGAGCAGGAAGN | 1629-1647 | 1629 |
| 59 | NCUUCCUGCUCAGGGUGAN | 112 | NUCACCCUGAGCAGGAAGN | 1629-1647 | 1629 |
| 60 | AAGUCGAUGAUGAUCUCCC | 113 | GGGAGAUCAUCAUCGACUU | 1798-1816 | 1798 |
| 61 | UAGUCGAUGAUGAUCUCCC | 114 | GGGAGAUCAUCAUCGACUA | 1798-1816 | 1798 |
| 62 | AAGUCGAUGAUGAUCUCCC | 115 | GGGAGAUCAUCAUCIACUU | 1798-1816 | 1798 |
| 63 | UAGUCGAUGAUGAUCUCCC | 116 | GGGAGAUCAUCAUCIACUA | 1798-1816 | 1798 |
| 64 | NAGUCGAUGAUGAUCUCCC | 117 | GGGAGAUCAUCAUCGACUN | 1798-1816 | 1798 |
| 65 | NAGUCGAUGAUGAUCUCCC | 118 | GGGAGAUCAUCAUCIACUN | 1798-1816 | 1798 |
| 66 | NAGUCGAUGAUGAUCUCCN | 119 | NGGAGAUCAUCAUCGACUN | 1798-1816 | 1798 |
| 67 | NAGUCGAUGAUGAUCUCCN | 120 | NGGAGAUCAUCAUCIACUN | 1798-1816 | 1798 |

The beta-ENaC RNAi agent sense strands and antisense strands that comprise or consist of the nucleotide sequences in Table 2 can be modified nucleotides or unmodified nucleotides. In some embodiments, the beta-ENaC RNAi agents having the sense and antisense strand sequences that comprise or consist of any of the nucleotide sequences in Table 2 are all or substantially all modified nucleotides.

In some embodiments, the antisense strand of a beta-ENaC RNAi agent disclosed herein differs by 0, 1, 2, or 3 nucleotides from any of the antisense strand sequences in Table 2. In some embodiments, the sense strand of a beta-ENaC RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified beta-ENaC RNAi agent sense and antisense strands are provided in Table 3 and Table 4. Modified beta-ENaC RNAi agent antisense strands, as well as their underlying unmodified nucleobase sequences, are provided in Table 3. Modified beta-ENaC RNAi agent sense strands, as well as their underlying unmodified nucleobase sequences, are provided in Table 4. In forming beta-ENaC RNAi agents, each of the nucleotides in each of the underlying base sequences listed in Tables 3 and 4, as well as in Table 2, above, can be a modified nucleotide.

The beta-ENaC RNAi agents described herein are formed by annealing an antisense strand with a sense strand. A sense strand containing a sequence listed in Table 2, or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, a beta-ENaC RNAi agent antisense strand comprises a nucleotide sequence of any of the sequences in Table 2 or Table 3.

In some embodiments, a beta-ENaC RNAi agent comprises or consists of a duplex having the nucleobase sequences of the sense strand and the antisense strand of any of the sequences in Table 2, Table 3, or Table 4.

Examples of antisense strands containing modified nucleotides are provided in Table 3. Examples of sense strands containing modified nucleotides are provided in Table 4.

As used in Tables 3 and 4, the following notations are used to indicate modified nucleotides, targeting groups, and linking groups:

A=adenosine-3'-phosphate
C=cytidine-3'-phosphate
G=guanosine-3'-phosphate
U=uridine-3'-phosphate
I=inosine-3'-phosphate
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
i=2'-O-methylinosine-3'-phosphate
is =2'-O-methylinosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dT=2'-deoxythymidine-3'-phosphate
$A_{UNA}$=2',3'-seco-adenosine-3'-phosphate
$A_{UNA}$S=2',3'-seco-adenosine-3'-phosphorothioate
$C_{UNA}$=2',3'-seco-cytidine-3'-phosphate
$C_{UNA}$S=2',3'-seco-cytidine-3'-phosphorothioate
$G_{UNA}$=2',3'-seco-guanosine-3'-phosphate
$G_{UNA}$S=2',3'-seco-guanosine-3'-phosphorothioate
$U_{UNA}$=2',3'-seco-uridine-3'-phosphate
$U_{UNA}$S=2',3'-seco-uridine-3'-phosphorothioate
a_2N=see Table 6
a_2Ns=see Table 6
(invAb)=inverted abasic deoxyribonucleotide-5'-phosphate, see Table 6
(invAb)s=inverted abasic deoxyribonucleotide-5'-phosphorothioate, see Table 6
s=phosphorothioate linkage
p=terminal phosphate (as synthesized)
vpdN=vinyl phosphonate deoxyribonucleotide
cPrpa=5'-cyclopropyl phosphonate-2'-O-methyladenosine-3'-phosphate (see Table 6)
cPrpas=5'-cyclopropyl phosphonate-2'-O-methyladenosine-3'-phosphorothioate (see Table 6)
cPrpu=5'-cyclopropyl phosphonate-2'-O-methyluridine-3'-phosphate (see Table 6)
cPrpus=5'-cyclopropyl phosphonate-2'-O-methyluridine-3'-phosphorothioate (see Table 6)
aAlk=2'-O-propargyladenosine-3'-phosphate, see Table 6
aAlks=2'-O-propargyladenosine-3'-phosphorothioate, see Table 6
cAlk=2'-O-propargylcytidine-3'-phosphate, see Table 6
cAlks=2'-O-propargylcytidine-3'-phosphorothioate, see Table 6
gAlk=2'-O-propargylguanosine-3'-phosphate, see Table 6
gAlks=2'-O-propargylguanosine-3'-phosphorothioate, see Table 6
tAlk=2'-O-propargyl-5-methyluridine-3'-phosphate, see Table 6
tAlks=2'-O-propargyl-5-methyluridine-3'-phosphorothioate, see Table 6
uAlk=2'-O-propargyluridine-3'-phosphate, see Table 6
uAlks=2'-O-propargyluridine-3'-phosphorothioate, see Table 6
(Alk-SS-C6)=see Table 6
(C6-SS-Alk)=see Table 6
(C6-SS-C6)=see Table 6
(6-SS-6)=see Table 6
(C6-SS-Alk-Me)=see Table 6
(NH2-C6)=see Table 6
(TriAlk #)=see Table 6
(TriAlk #)s=see Table 6

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the embodiments disclosed herein, when viewing the respective strand 5'→3', the inverted abasic residues are inserted such that the 3' position of the deoxyribose is linked at the 3' end of the preceding monomer on the respective strand (see. e.g., Table 6). Moreover, as the person of ordinary skill would readily understand and appreciate, while the phosphorothioate chemical structures depicted herein typically show the anion on the sulfur atom, the inventions disclosed herein encompass all phosphorothioate tautomers (e.g., where the sulfur atom has a double-bond and the anion is on an oxygen atom). Unless expressly indicated otherwise herein, such understandings of the person of ordinary skill in the art are used when describing the beta-ENaC RNAi agents and compositions of beta-ENaC RNAi agents disclosed herein.

Certain examples of targeting groups and linking groups used with the beta-ENaC RNAi agents disclosed herein are included in the chemical structures provided below in Table 6. Each sense strand and/or antisense strand can have any targeting groups or linking groups listed herein, as well as other targeting or linking groups, conjugated to the 5' and/or 3' end of the sequence.

TABLE 3

Beta-ENaC RNAi Agent Antisense Strand Sequences

| AS Strand ID | Modified Antisense Strand (5'→3') | SEQ ID NO. | Underlying Base Sequence (5'→3') (Shown as an Un-modified Nucleotide Sequence) | SEQ ID NO. |
|---|---|---|---|---|
| AM08374-AS | asUfscsAfaUfaaggaCfcAfgGfgGfuGfsu | 121 | AUCAAUAAGGACCAGGGGUGU | 189 |
| AM08376-AS | usGfsasUfcAfuguggUfcUfuGfgAfaGfsc | 122 | UGAUCAUGUGGUCUUGGAAGC | 190 |
| AM08378-AS | usGfsgsAfuCfaugugGfuCfuUfgGfaAfsg | 123 | UGGAUCAUGUGGUCUUGGAAG | 191 |
| AM08380-AS | usUfsgsCfaGfuauuuCfuCfcCfcAfcGfsg | 124 | UUGCAGUAUUUCUCCCCACGG | 192 |
| AM08382-AS | usCfsusUfcCfugcucAfgGfgUfgAfuCfsc | 125 | UCUUCCUGCUCAGGGUGAUCC | 193 |
| AM08732-AS | asAfsgsUfcGfaUfgAfuGfaUfcUfcCfcCfsa | 126 | AAGUCGAUGAUGAUCUCCCCA | 194 |
| AM08736-AS | asGfsusUfgAfagaugUfaAfcAfgUfuGfsc | 127 | AGUUGAAGAUGUAACAGUUGC | 195 |
| AM08747-AS | asAfsgsUfcGfaUfgAfuGfaUfcUfcCfcusu | 128 | AAGUCGAUGAUGAUCUCCCUU | 196 |
| AM08757-AS | usCfsasUfcAfaUfaAfgGfaCfcAfgGfgGfsu | 129 | UCAUCAAUAAGGACCAGGGGU | 197 |
| AM08759-AS | usUfsgsUfuGfuAfgUfcAfcUfgUfaGfaCfsg | 130 | UUGUUGUAGUCACUGUAGACG | 198 |
| AM08761-AS | usCfsgsUfgUfuGfuAfgUfcAfcUfgUfaGfsg | 131 | UCGUGUUGUAGUCACUGUAGG | 199 |
| AM08763-AS | usCfsgsUfgUfU$_{UNA}$GfuAfgUfcAfcUfgUfaGfsg | 132 | UCGUGUUGUAGUCACUGUAGG | 199 |
| AM08765-AS | usGfsasUfcAfuGfuGfgUfcUfuGfgAfaGfsc | 133 | UGAUCAUGUGGUCUUGGAAGC | 190 |
| AM08767-AS | usUfsusGfuUfgCfaGfuAfuUfuCfuCfcCfsc | 134 | UUUGUUGCAGUAUUUCUCCCC | 200 |
| AM08769-AS | usGfsusUfgUfuGfcAfgUfaUfuUfcUfcCfsc | 135 | UGUUGUUGCAGUAUUUCUCCC | 201 |
| AM09703-AS | asGfsusUfgAfagaugUfaGfcAfgUfuGfsc | 136 | AGUUGAAGAUGUAGCAGUUGC | 202 |
| AM09758-AS | cPrpusCfsgsUfgUfuGfuAfgUfcAfcUfgUfaGfsg | 137 | UCGUGUUGUAGUCACUGUAGG | 199 |
| AM09764-AS | cPrpusGfsusUfgAfagaugUfaAfcAfgUfuGfsc | 138 | UGUUGAAGAUGUAACAGUUGC | 203 |
| AM09691-AS | asGfsusugAfaGfAfuguaAfcAfguugsc | 139 | AGUUGAAGAUGUAACAGUUGC | 195 |
| AM09692-AS | asGfsusugAfagauguaAfcAfguugsc | 140 | AGUUGAAGAUGUAACAGUUGC | 195 |
| AM09693-AS | asGfsusugAfagaugUfaAfcAfgUfuGfsc | 141 | AGUUGAAGAUGUAACAGUUGC | 195 |
| AM09695-AS | asGfsusUfgAfA$_{UNA}$gaugUfaAfcAfgUfuGfsc | 142 | AGUUGAAGAUGUAACAGUUGC | 195 |
| AM09927-AS | cPrpusGfsusUfgAfA$_{UNA}$gaugUfaAfcAfgUfuGfsc | 143 | UGUUGAAGAUGUAACAGUUGC | 203 |
| AM09984-AS | usAfsgsUfcGfaUfgAfuGfaUfcUfcCfcCfsa | 144 | UAGUCGAUGAUGAUCUCCCCA | 206 |
| AM09985-AS | cPrpusAfsgsUfcGfaUfgAfuGfaUfcUfcCfcCfsa | 145 | UAGUCGAUGAUGAUCUCCCCA | 206 |
| AM09986-AS | asAfsgsUfcGfaUfgAfuGfaUfcUfuCfcCfsa | 146 | AAGUCGAUGAUGAUCUUCCCA | 207 |
| AM09988-AS | asAfsgsUfuGfaUfgAfuGfaUfcUfcCfcCfsa | 147 | AAGUUGAUGAUGAUCUCCCCA | 208 |
| AM09990-AS | asAfsgsUfcGfA$_{UNA}$UfgAfuGfaUfcUfcCfcCfsa | 148 | AAGUCGAUGAUGAUCUCCCCA | 209 |
| AM09992-AS | asAfsgsucgaUfgAfuGfaUfcUfcCfcCfsa | 149 | AAGUCGAUGAUGAUCUCCCCA | 194 |
| AM09994-AS | cPrpuGfuUfgAfagaugUfaAfcAfgUfuGfsc | 150 | UGUUGAAGAUGUAACAGUUGC | 203 |
| AM09996-AS | cPrpusGfsusUfgAfagaugUfaGfcAfgUfuGfsc | 151 | UGUUGAAGAUGUAGCAGUUGC | 210 |
| AM09997-AS | cPrpuGfuUfgAfagaugUfaGfcAfgUfuGfsc | 152 | UGUUGAAGAUGUAGCAGUUGC | 210 |
| AM10004-AS | cPrpasGfsusUfgAfagaugUfaAfcAfgUfuGfsc | 153 | AGUUGAAGAUGUAACAGUUGC | 195 |
| AM10005-AS | cPrpaGfuUfgAfagaugUfaAfcAfgUfuGfsc | 154 | AGUUGAAGAUGUAACAGUUGC | 195 |
| AM10150-AS | usGfsusUfgAfagaugUfaGfcAfgUfuGfsc | 155 | UGUUGAAGAUGUAGCAGUUGC | 210 |
| AM10170-AS | asGfsusUfgaagaugUfaAfcAfgUfuGfsc | 156 | AGUUGAAGAUGUAACAGUUGC | 195 |
| AM10171-AS | asGfsusugaagaugUfaAfcAfgUfuGfsc | 157 | AGUUGAAGAUGUAACAGUUGC | 195 |

TABLE 3-continued

| Beta-ENaC RNAi Agent Antisense Strand Sequences | | | | |
|---|---|---|---|---|
| AS Strand ID | Modified Antisense Strand (5'→3') | SEQ ID NO. | Underlying Base Sequence (5'→3') (Shown as an Un-modified Nucleotide Sequence) | SEQ ID NO. |
| AM10172-AS | asGfsusugaagaugUfaAfcAfgUfugsc | 158 | AGUUGAAGAUGUAACAGUUGC | 195 |
| AM10173-AS | asGfsusugaagaugUfaAfcAfguugsc | 159 | AGUUGAAGAUGUAACAGUUGC | 195 |
| AM10174-AS | asGfsusugaagauguaAfcAfguugsc | 160 | AGUUGAAGAUGUAACAGUUGC | 195 |

TABLE 4

| Beta-ENaC Agent Sense Strand Sequences | | | | |
|---|---|---|---|---|
| Strand ID | Sense Strand (5'→3') Modified | SEQ ID NO. | Underlying Base Sequence (5'→3') (Shown as an Un-modified Nucleotide Sequence) | SEQ ID NO. |
| AM08373-SS | (NH2—C6)s(invAb)sacaccccuGfGfUfccuuauugaus (invAb) | 161 | ACACCCCUGGUCCUUAUUGAU | 211 |
| AM08375-SS | (NH2—C6)s(invAb)sgcuuccaaGfAfCfcacaugaucas (invAb) | 162 | GCUUCCAAGACCACAUGAUCA | 212 |
| AM08377-SS | (NH2—C6)s(invAb)scuuccaagAfCfCfacaugauccas (invAb) | 163 | CUUCCAAGACCACAUGAUCCA | 213 |
| AM08379-SS | (NH2—C6)s(invAb)sccguggggAfGfAfaauacugcaas (invAb) | 164 | CCGUGGGGAGAAAUACUGCAA | 214 |
| AM08381-SS | (NH2—C6)s(invAb)sgGfaucaccCfUfGfagcaggaagas (invAb) | 165 | GGAUCACCCUGAGCAGGAAGA | 215 |
| AM08756-SS | (TriAlk14)asccccuggUfCfCfuuauugaugas(invAb) | 166 | ACCCCUGGUCCUUAUUGAUGA | 216 |
| AM08758-SS | (TriAlk14)csgucuacaGfUfGfacuacaacaas(invAb) | 167 | CGUCUACAGUGACUACAACAA | 217 |
| AM08760-SS | (TriAlk14)cscuacaguGfAfCfuacaacacgas(invAb) | 168 | CCUACAGUGACUACAACACGA | 218 |
| AM08762-SS | (TriAlk14)cscuacaguGfAfCfuacaacacias(invAb) | 169 | CCUACAGUGACUACAACACIA | 219 |
| AM08764-SS | (TriAlk14)gscuuccaaGfAfCfcacauiaucas(invAb) | 170 | GCUUCCAAGACCACAUIAUCA | 220 |
| AM08766-SS | (TriAlk14)gsgggagaaAfUfAfcugcaacaaas(invAb) | 171 | GGGGAGAAAUACUGCAACAAA | 221 |
| AM08768-SS | (TriAlk14)gsggagaaaUfAfCfugcaacaacas(invAb) | 172 | GGGAGAAAUACUGCAACAACA | 222 |
| AM08939-SS | (TriAik14)gscaacuguUfAfCfaucuucaacus(invAb) | 173 | GCAACUGUUACAUCUUCAACU | 223 |
| AM08940-SS | (TriAlk14)usggggagaUfCfAfucauciacuus(invAb) | 174 | UGGGGAGAUCAUCAUCIACUU | 224 |
| AM08941-SS | (TriAlk14)gsggagaUfCfAfucauciacuuuus(invAb) | 175 | GGGAGAUCAUCAUCIACUUUU | 225 |
| AM09705-SS | (TriAlk14)gscaacugcUfAfCfaucuucaacus(invAb) | 176 | GCAACUGCUACAUCUUCAACU | 226 |
| AM09763-SS | (TriAlk14)gscaacuguUfAfCfaucuucaacas(invAb) | 177 | GCAACUGUUACAUCUUCAACA | 227 |
| AM09765-SS | (NH2—C6)gscaacuguUfAfCfaucAlkuuAlkcaAlkac Alkas(invAb) | 178 | GCAACUGUUACAUCUUCAACA | 227 |
| AM09964-SS | (NH2—C6)gsca_2NacuguUfAfCfaucuucaacus(invAb) | 179 | GC($A^{2N}$)ACUGUUACAUCUUCAACU | 229 |
| AM09995-SS | (TriAlk14)gcaacuguUfAfCfaucuucaaca(invAb) | 180 | GCAACUGUUACAUCUUCAACA | 227 |
| AM10006-SS | (TriAlk14)gsca_2NacuguUfAfCfaucuucaacas(invAb) | 181 | GC($A^{2N}$)ACUGUUACAUCUUCAACA | 230 |
| AM10033-SS | (NH2—C6)s(invAb)sgcaacuguUfAfCfaucuucaacus (invAb)(C6-SS-C6)dT | 182 | GCAACUGUUACAUCUUCAACUT | 231 |
| AM10293-SS | (NH2—C6)s(invAb)sgcaacuguUfAfCfaucuucaacas (invAb)(C6-SS-C6)dT | 183 | GCAACUGUUACAUCUUCAACAT | 232 |

TABLE 4-continued

Beta-ENaC Agent Sense Strand Sequences

| Strand ID | Sense Strand (5'→3') Modified | SEQ ID NO. | Underlying Base Sequence (5'→3') (Shown as an Un-modified Nucleotide Sequence) | SEQ ID NO. |
|---|---|---|---|---|
| AM10319-SS | (TriAik14)gsca_2NacuguUfAfCfaucuucaacus(invAb) | 184 | GC($A^{2N}$)ACUGUUACAUCUUCAACU | 229 |
| AM10364-SS | (NH2—C6)s(invAb)sgscaacuguUfAfCfaucuucaacas (invAb)(C6-SS-C6)dT | 185 | GCAACUGUUACAUCUUCAACAT | 232 |
| AM10365-SS | (NH2—C6)s (invAb)sgsca_2NacuguUfAfCfaucuucaacus(invAb) (C6-SS-C6)dT | 186 | GC($A^{2N}$)ACUGUUACAUCUUCAACUT | 233 |

($A^{2N}$) = 2-aminoadenine-containing nucleotide; I = hypoxanthine (inosine) nucleotide The beta-ENaC RNAi agents disclosed herein are formed by annealing an antisense strand with a sense strand. A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence.

As shown in Table 4, above, certain of the example beta-ENaC RNAi agent nucleotide sequences are shown to further include reactive linking groups at one or both of the 5' terminal end and the 3' terminal end of the sense strand. For example, many of the beta-ENaC RNAi agent sense strand sequences shown in Table 4 above have an (NH2-C6) linking group or a (TriAlk14) linking group at the 5' end of the nucleotide sequence. Similarly, a few example beta-ENaC RNAi agent sense strand nucleotide sequences shown in Table 4 above have a (6-SS-6) or (C6-SS-C6) linking group at the 3' end of the nucleotide sequence. Such reactive linking groups are positioned to facilitate the linking of targeting ligands, targeting groups, and/or PK/PD modulators to the beta-ENaC RNAi agents disclosed herein. Linking or conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction, inverse-demand Diels-Alder cycloaddition reaction, oxime ligation, and Copper (I)-catalyzed or strain-promoted azide-alkyne cycloaddition reaction cycloaddition reaction.

In some embodiments, targeting ligands, such as the integrin targeting ligands shown in the examples and figures disclosed herein, can be synthesized as activated esters, such as tetrafluorophenyl (TFP) esters, which can be displaced by a reactive amino group (e.g., NH2-C6) to attach the targeting ligand to the beta-ENaC RNAi agents disclosed herein. In some embodiments, targeting ligands are synthesized as azides, which can be conjugated to a propargyl (e.g., TriAlk14) or DBCO group, for example, via Copper (I)-catalyzed or strain-promoted azide-alkyne cycloaddition reaction.

Additionally, certain of the nucleotide sequences shown in Table 4 above were synthesized with a dT nucleotide at the 3' terminal end of the sense strand, followed by (3' →5') a linker (e.g., C6-SS-C6) (See. e.g., AM10033-SS, AM10293-SS, AM10364-SS, and AM10365-SS). The linker can, in some embodiments, facilitate the linkage to additional components, such as, for example, a PK/PD modulator or one or more targeting ligands. As described herein, the disulfide bond of C6-SS-C6 is first reduced, removing the dT from the molecule, which can then facilitate the conjugation of the desired PK/PD modulator. The terminal dT nucleotide therefore is not a part of the fully conjugated construct.

In some embodiments, the antisense strand of a beta-ENaC RNAi agent disclosed herein differs by 0, 1, 2, or 3 nucleotides from any of the antisense strand sequences in Table 3. In some embodiments, the sense strand of a beta-ENaC RNAi agent disclosed herein differs by 0, 1, 2, or 3 nucleotides from any of the sense strand sequences in Table 4.

In some embodiments, a beta-ENaC RNAi agent antisense strand comprises a nucleotide sequence of any of the sequences in Table 2 or Table 3. In some embodiments, a beta-ENaC RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24 of any of the sequences in Table 2 or Table 3. In certain embodiments, a beta-ENaC RNAi agent antisense strand comprises or consists of a modified sequence of any one of the modified sequences in Table 3.

In some embodiments, a beta-ENaC RNAi agent sense strand comprises the nucleotide sequence of any of the sequences in Table 2 or Table 4. In some embodiments, a beta-ENaC RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, or 4-24, of any of the sequences in Table 2 or Table 4. In certain embodiments, a beta-ENaC RNAi agent sense strand comprises or consists of a modified sequence of any one of the modified sequences in Table 3.

For the RNAi agents disclosed herein, the nucleotide at position 1 of the antisense strand (from 5' end→3' end) can be perfectly complementary to a beta-ENaC gene, or can be non-complementary to a beta-ENaC gene. In some embodiments, the nucleotide at position 1 of the antisense strand (from 5' end→3' end) is a U, A, or dT (or a modified version of U, A or dT). In some embodiments, the nucleotide at position 1 of the antisense strand (from 5' end→3' end) forms an A:U or U:A base pair with the sense strand.

In some embodiments, a beta-ENaC RNAi agent antisense strand comprises the sequence of nucleotides (from 5' end→3' end) 2-18 or 2-19 of any of the antisense strand sequences in Table 2 or Table 3. In some embodiments, a beta-ENaC RNAi sense strand comprises the sequence of nucleotides (from 5' end→3' end) 1-17 or 1-18 of any of the sense strand sequences in Table 2 or Table 4.

In some embodiments, a beta-ENaC RNAi agent includes (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4.

A sense strand containing a sequence listed in Table 2 or Table 4 can be hybridized to any antisense strand containing a sequence listed in Table 2 or Table 3 provided the two sequences have a region of at least 85% complementarity over a contiguous 16, 17, 18, 19, 20, or 21 nucleotide sequence. In some embodiments, the beta-ENaC RNAi agent has a sense strand consisting of the modified sequence of any of the modified sequences in Table 4, and an antisense strand consisting of the modified sequence of any of the modified sequences in Table 3. Certain representative sequence pairings are exemplified by the Duplex ID Nos. shown in Tables 5A and 5B.

In some embodiments, a beta-ENaC RNAi agent comprises, consists of, or consists essentially of a duplex represented by any one of the Duplex ID Nos. presented herein. In some embodiments, a beta-ENaC RNAi agent consists of any of the Duplex ID Nos. presented herein. In some embodiments, a beta-ENaC RNAi agent comprises the sense strand and antisense strand nucleotide sequences of any of the Duplex ID Nos. presented herein. In some embodiments, a beta-ENaC RNAi agent comprises the sense strand and antisense strand nucleotide sequences of any of the Duplex ID Nos. presented herein and a targeting group, linking group, and/or other non-nucleotide group wherein the targeting group, linking group, and/or other non-nucleotide group is covalently linked (i.e., conjugated) to the sense strand or the antisense strand. In some embodiments, a beta-ENaC RNAi agent includes the sense strand and antisense strand modified nucleotide sequences of any of the Duplex ID Nos. presented herein. In some embodiments, a beta-ENaC RNAi agent comprises the sense strand and antisense strand modified nucleotide sequences of any of the Duplex ID Nos. presented herein and a targeting group, linking group, and/or other non-nucleotide group, wherein the targeting group, linking group, and/or other non-nucleotide group is covalently linked to the sense strand or the antisense strand.

In some embodiments, a beta-ENaC RNAi agent comprises an antisense strand and a sense strand having the nucleotide sequences of any of the antisense strand/sense strand duplexes of Table 2 or Tables 5A and 5B, and further comprises a targeting group. In some embodiments, a beta-ENaC RNAi agent comprises an antisense strand and a sense strand having the nucleotide sequences of any of the antisense strand/sense strand duplexes of Table 2 or Tables 5A and 5B, and further comprises one or more αvβ6 integrin targeting ligands.

In some embodiments, a beta-ENaC RNAi agent comprises an antisense strand and a sense strand having the nucleotide sequences of any of the antisense strand/sense strand duplexes of Table 2 or Tables 5A and 5B, and further comprises a targeting group that is an integrin targeting ligand. In some embodiments, a beta-ENaC RNAi agent comprises an antisense strand and a sense strand having the nucleotide sequences of any of the antisense strand/sense strand duplexes of Table 2 or Tables 5A and 5B, and further comprises one or more αvβ6 integrin targeting ligands or clusters of αvβ6 integrin targeting ligands (e.g., a tridentate αvβ6 integrin targeting ligand).

In some embodiments, a beta-ENaC RNAi agent comprises an antisense strand and a sense strand having the modified nucleotide sequences of any of the antisense strand/sense strand duplexes of Tables 5A and 5B.

In some embodiments, a beta-ENaC RNAi agent comprises an antisense strand and a sense strand having the modified nucleotide sequences of any of the antisense strand/sense strand duplexes of Tables 5A and 5B, and further comprises an integrin targeting ligand.

In some embodiments, a beta-ENaC RNAi agent comprises, consists of, or consists essentially of any of the duplexes of Tables 5A and 5B.

TABLE 5A

Beta-ENaC RNAi Agent Duplexes with Corresponding Sense and Antisense Strand ID Numbers

| Duplex ID | Antisense Strand ID | Sense Strand ID |
|---|---|---|
| AD06283 | AM08374-AS | AM08373-SS |
| AD06284 | AM08376-AS | AM08375-SS |
| AD06285 | AM08378-AS | AM08377-SS |
| AD06286 | AM08380-AS | AM08379-SS |
| AD06287 | AM08382-AS | AM08381-SS |
| AD06494 | AM08757-AS | AM08756-SS |
| AD06495 | AM08759-AS | AM08758-SS |
| AD06496 | AM08761-AS | AM08760-SS |
| AD06497 | AM08761-AS | AM08762-SS |
| AD06498 | AM08763-AS | AM08760-SS |
| AD06499 | AM08765-AS | AM08764-SS |
| AD06500 | AM08767-AS | AM08766-SS |
| AD06501 | AM08769-AS | AM08768-SS |
| AD06598 | AM08736-AS | AM08939-SS |
| AD06599 | AM08732-AS | AM08940-SS |
| AD06600 | AM08747-AS | AM08941-SS |
| AD07054 | AM09703-AS | AM08939-SS |
| AD07055 | AM09703-AS | AM09705-SS |
| AD07095 | AM09758-AS | AM08762-SS |
| AD07099 | AM09764-AS | AM09763-SS |
| AD07100 | AM09764-AS | AM09765-SS |
| AD07217 | AM08736-AS | AM09964-SS |
| AD07240 | AM09994-AS | AM09763-SS |
| AD07241 | AM09994-AS | AM09995-SS |
| AD07242 | AM09996-AS | AM09763-SS |
| AD07243 | AM09997-AS | AM09763-SS |
| AD07244 | AM09997-AS | AM09995-SS |
| AD07250 | AM10004-AS | AM08939-SS |
| AD07251 | AM10005-AS | AM08939-SS |
| AD07252 | AM10004-AS | AM09964-SS |
| AD07253 | AM10005-AS | AM09964-SS |
| AD07254 | AM09764-AS | AM10006-SS |
| AD07255 | AM09994-AS | AM10006-SS |
| AD07280 | AM08736-AS | AM10033-SS |
| AD07281 | AM10004-AS | AM10033-SS |
| AD07351 | AM10150-AS | AM09763-SS |
| AD07473 | AM09764-AS | AM10293-SS |
| AD07482 | AM08736-AS | AM10319-SS |
| AD07506 | AM09764-AS | AM10364-SS |
| AD07507 | AM08736-AS | AM10365-SS |

TABLE 5B

Beta-ENaC RNAi Agent Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD06283 | AM08374-AS | 121 | 189 | AM08373-SS | 161 | 211 |
| AD06284 | AM08376-AS | 122 | 190 | AM08375-SS | 162 | 212 |
| AD06285 | AM08378-AS | 123 | 191 | AM08377-SS | 163 | 213 |
| AD06286 | AM08380-AS | 124 | 192 | AM08379-SS | 164 | 214 |
| AD06287 | AM08382-AS | 125 | 193 | AM08381-SS | 165 | 215 |
| AD06494 | AM08757-AS | 129 | 197 | AM08756-SS | 166 | 216 |
| AD06495 | AM08759-AS | 130 | 198 | AM08758-SS | 167 | 217 |
| AD06496 | AM08761-AS | 131 | 199 | AM08760-SS | 168 | 218 |
| AD06497 | AM08761-AS | 131 | 199 | AM08762-SS | 169 | 219 |
| AD06498 | AM08763-AS | 132 | 199 | AM08760-SS | 168 | 218 |
| AD06499 | AM08765-AS | 133 | 190 | AM08764-SS | 170 | 220 |
| AD06500 | AM08767-AS | 134 | 200 | AM08766-SS | 171 | 221 |
| AD06501 | AM08769-AS | 135 | 201 | AM08768-SS | 172 | 222 |
| AD06598 | AM08736-AS | 127 | 195 | AM08939-SS | 173 | 223 |
| AD06599 | AM08732-AS | 126 | 194 | AM08940-SS | 174 | 224 |
| AD06600 | AM08747-AS | 128 | 196 | AM08941-SS | 175 | 225 |
| AD07054 | AM09703-AS | 136 | 202 | AM08939-SS | 173 | 223 |
| AD07055 | AM09703-AS | 136 | 202 | AM09705-SS | 176 | 226 |
| AD07095 | AM09758-AS | 137 | 199 | AM08762-SS | 169 | 219 |
| AD07099 | AM09764-AS | 138 | 203 | AM09763-SS | 177 | 227 |
| AD07100 | AM09764-AS | 138 | 203 | AM09765-SS | 178 | 227 |
| AD07217 | AM08736-AS | 127 | 195 | AM09964-SS | 179 | 229 |
| AD07240 | AM09994-AS | 150 | 203 | AM09763-SS | 177 | 227 |
| AD07241 | AM09994-AS | 150 | 203 | AM09995-SS | 180 | 227 |
| AD07242 | AM09996-AS | 151 | 210 | AM09763-SS | 177 | 227 |
| AD07243 | AM09997-AS | 152 | 210 | AM09763-SS | 177 | 227 |
| AD07244 | AM09997-AS | 152 | 210 | AM09995-SS | 180 | 227 |
| AD07250 | AM10004-AS | 153 | 195 | AM08939-SS | 173 | 223 |
| AD07251 | AM10005-AS | 154 | 195 | AM08939-SS | 173 | 223 |
| AD07252 | AM10004-AS | 153 | 195 | AM09964-SS | 179 | 229 |
| AD07253 | AM10005-AS | 154 | 195 | AM09964-SS | 179 | 229 |
| AD07254 | AM09764-AS | 138 | 203 | AM10006-SS | 181 | 230 |
| AD07255 | AM09994-AS | 150 | 203 | AM10006-SS | 181 | 230 |
| AD07280 | AM08736-AS | 127 | 195 | AM10033-SS | 182 | 231 |
| AD07281 | AM10004-AS | 153 | 195 | AM10033-SS | 182 | 231 |
| AD07351 | AM10150-AS | 155 | 210 | AM09763-SS | 177 | 227 |
| AD07473 | AM09764-AS | 138 | 203 | AM10293-SS | 183 | 232 |
| AD07482 | AM08736-AS | 127 | 195 | AM10319-SS | 184 | 229 |
| AD07506 | AM09764-AS | 138 | 203 | AM10364-SS | 185 | 232 |
| AD07507 | AM08736-AS | 127 | 195 | AM10365-SS | 186 | 233 |

In some embodiments, a beta-ENaC RNAi agent is prepared or provided as a salt, mixed salt, or a free-acid. The RNAi agents described herein, upon delivery to a cell expressing a beta-ENaC gene, inhibit or knockdown expression of one or more beta-ENaC genes in vivo and/or in vitro.

Targeting Groups, Linking Groups, Pharmacokinetic/Pharmacodynamic (PK/PD) Modulators, and Delivery Vehicles In some embodiments, a beta-ENaC RNAi agent contains or is conjugated to one or more non-nucleotide groups including, but not limited to, a targeting group, a linking group, a pharmacokinetic/pharmacodynamic (PK/PD) modulator, a delivery polymer, or a delivery vehicle. The non-nucleotide group can enhance targeting, delivery, or attachment of the RNAi agent. The non-nucleotide group can be covalently linked to the 3' and/or 5' end of either the sense strand and/or the antisense strand. In some embodiments, a beta-ENaC RNAi agent contains a non-nucleotide group linked to the 3' and/or 5' end of the sense strand. In some embodiments, a non-nucleotide group is linked to the 5' end of a beta-ENaC RNAi agent sense strand. A non-nucleotide group can be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecule, cell receptor ligands, hapten, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which in some instances can serve as linkers.

A targeting group, with or without a linker, can be attached to the 5' or 3' end of any of the sense and/or antisense strands disclosed in Tables 2, 3, and 4. A linker, with or without a targeting group, can be attached to the 5' or 3' end of any of the sense and/or antisense strands disclosed in Tables 2, 3, and 4.

The beta-ENaC RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

For example, in some embodiments, the beta-ENaC RNAi agents disclosed herein are synthesized having an NH2-C6 group at the 5'-terminus of the sense strand of the RNAi agent. The terminal amino group subsequently can be reacted to form a conjugate with, for example, a group that includes an αvβ6 integrin targeting ligand. In some embodiments, the beta-ENaC RNAi agents disclosed herein are synthesized having one or more alkyne groups at the 5'-terminus of the sense strand of the RNAi agent. The terminal alkyne group(s) can subsequently be reacted to form a conjugate with, for example, a group that includes an αvβ6 integrin targeting ligand.

In some embodiments, a targeting group comprises an integrin targeting ligand. In some embodiments, an integrin targeting ligand is an αvβ6 integrin targeting ligand. The use of an αvβ6 integrin targeting ligand facilitates cell-specific targeting to cells having αvβ6 on its respective surface, and binding of the integrin targeting ligand can facilitate entry of the therapeutic agent, such as an RNAi agent, to which it is linked, into cells such as epithelial cells, including pulmonary epithelial cells and renal epithelial cells. Integrin targeting ligands can be monomeric or monovalent (e.g., having a single integrin targeting moiety) or multimeric or multivalent (e.g., having multiple integrin targeting moieties). The targeting group can be attached to the 3' and/or 5' end of the RNAi oligonucleotide using methods known in the art. The preparation of targeting groups, such as αvβ6 integrin targeting ligands, is described, for example, in International Patent Application Publication No. WO 2018/085415 and in International Patent Application Publication No. WO 2019/089765, the contents of each of which are incorporated herein in its entirety.

In some embodiments, targeting groups are linked to the beta-ENaC RNAi agents without the use of an additional linker. In some embodiments, the targeting group is designed having a linker readily present to facilitate the linkage to a beta-ENaC RNAi agent. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

In some embodiments, a linking group is conjugated to the RNAi agent. The linking group facilitates covalent linkage of the agent to a targeting group, pharmacokinetic modulator, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5'end of an RNAi agent sense strand. Examples of linking groups, include but are not limited to: C6-SS-C6, 6-SS-6, reactive groups such a primary amines (e.g., NH2-C6) and alkynes, alkyl groups, abasic residues/nucleotides, amino acids, tri-alkyne functionalized groups, ribitol, and/or PEG groups. Examples of certain linking groups are provided in Table 6.

A linker or linking group is a connection between two atoms that links one chemical group (such as an RNAi agent) or segment of interest to another chemical group (such as a targeting group, pharmacokinetic modulator, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description. In some embodiments, a beta-ENaC RNAi agent is conjugated to a polyethylene glycol (PEG) moiety, or to a hydrophobic group having 12 or more carbon atoms, such as a cholesterol or palmitoyl group.

In some embodiments, a beta-ENaC RNAi agent is linked to one or more pharmacokinetic/pharmacodynamic (PK/PD) modulators. PK/PD modulators can increase circulation time of the conjugated drug and/or increase the activity of the RNAi agent through improved cell receptor binding, improved cellular uptake, and/or other means. Various PK/PD modulators suitable for use with RNAi agents are known in the art. In some embodiments, the PK/PD modulatory can be cholesterol or cholesteryl derivatives, or in some circumstances a PK/PD modulator can be comprised of alkyl groups, alkenyl groups, alkynyl groups, aryl groups, aralkyl groups, aralkenyl groups, or aralkynyl groups, each of which may be linear, branched, cyclic, and/or substituted or unsubstituted. In some embodiments, the location of attachment for these moieties is at the 5' or 3' end of the sense strand, at the 2' position of the ribose ring of any given nucleotide of the sense strand, and/or attached to the phosphate or phosphorothioate backbone at any position of the sense strand.

Any of the beta-ENaC RNAi agent nucleotide sequences listed in Tables 2, 3, and 4, whether modified or unmodified, can contain 3' and/or 5' targeting group(s), linking group(s), and/or PK/PD modulator(s). Any of the beta-ENaC RNAi agent sequences listed in Tables 3 and 4, or are otherwise described herein, which contain a 3' or 5' targeting group, linking group, and/or PK/PD modulator can alternatively contain no 3' or 5' targeting group, linking group, or PK/PD modulator, or can contain a different 3' or 5' targeting group, linking group, or pharmacokinetic modulator including, but not limited to, those depicted in Table 6. Any of the beta-ENaC RNAi agent duplexes listed in Tables 5A and 5B, whether modified or unmodified, can further comprise a targeting group or linking group, including, but not limited to, those depicted in Table 6, and the targeting group or linking group can be attached to the 3' or 5' terminus of either the sense strand or the antisense strand of the beta-ENaC RNAi agent duplex.

Examples of certain modified nucleotides, capping moieties, and linking groups are provided in Table 6.

TABLE 6
| Structures Representing Various Modified Nucleotides, Capping Moieties, and Linking Groups |
| --- |
| 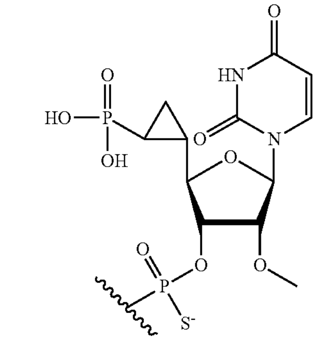 |
| cPrpus |
| 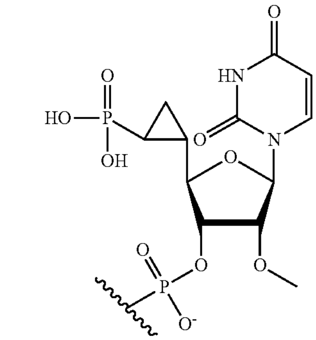 |
| cPrpu |
| 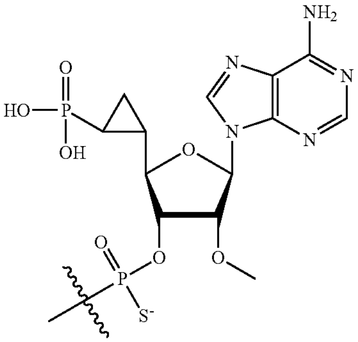 |
| cPrpas |
| 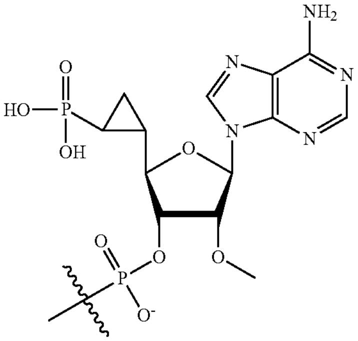 |
| cPrpa |

TABLE 6-continued
| Structures Representing Various Modified Nucleotides, Capping Moieties, and Linking Groups |
|---|
| 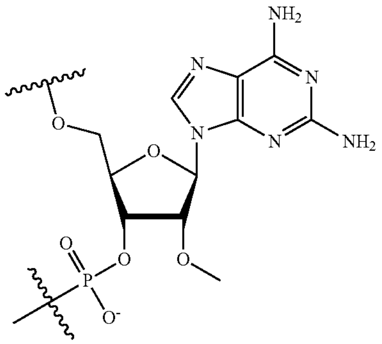 |
| a_2N |
| 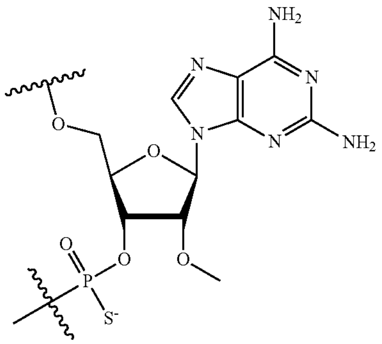 |
| a_2Ns |
| 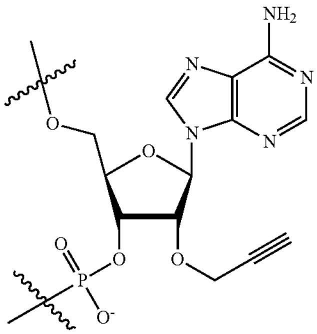 |
| aAlk |
| 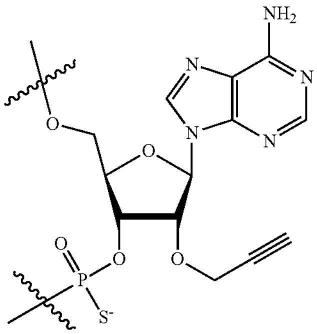 |
| aAlks |

TABLE 6-continued
| Structures Representing Various Modified Nucleotides, Capping Moieties, and Linking Groups |
|---|
| 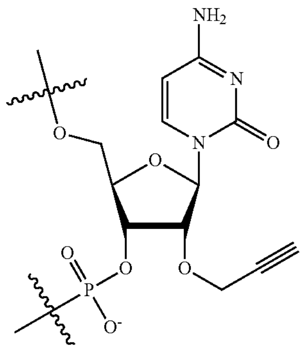 |
| cAlk |
| 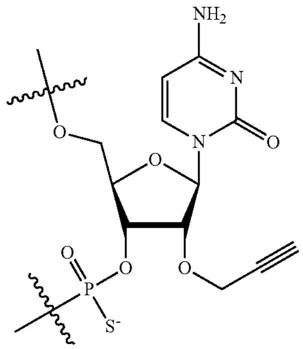 |
| cAlks |
| 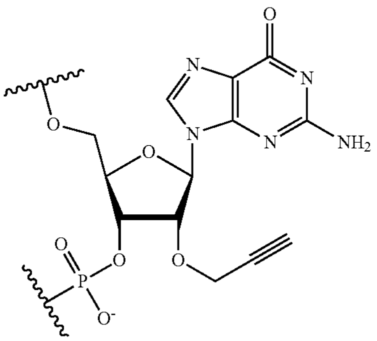 |
| gAlk |
| 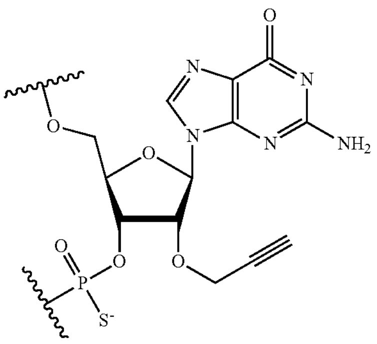 |
| gAlks |

TABLE 6-continued

Structures Representing Various Modified Nucleotides, Capping Moieties, and Linking Groups

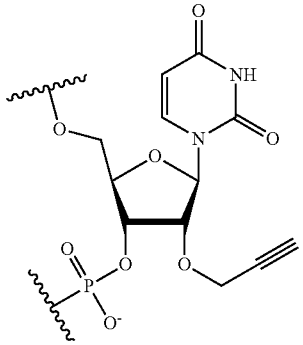

uAlk

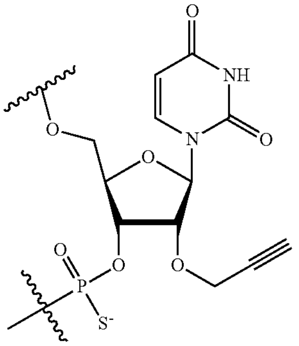

uAlks

When positioned internally:

linkage towards 5′ end of oligonucleotide

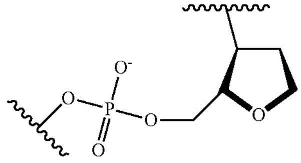

linkage towards 3′ end of oligonucleotide (invAb)

When positioned internally:

linkage towards 5′ end of oligonucleotide

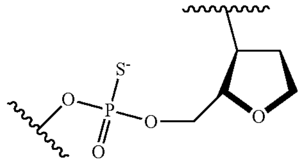

linkage towards 3′ end of oligonucleotide (invAb)s

TABLE 6-continued

| Structures Representing Various Modified Nucleotides, Capping Moieties, and Linking Groups |
|---|

When positioned at the 3' terminal end:

linkage towards 5′ end of oligonucleotide

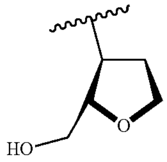

(invAb)

When positioned at the 3' terminal end of oligonucleotide:

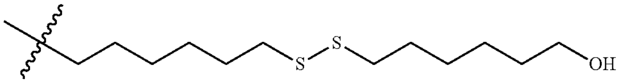

linkage towards 5′ end of oligonucleotide (C6-SS-C6)

When positioned internally:

linkage towards 5′ end of oligonucleotide linkage towards 3′ end of oligonucleotide

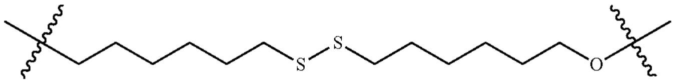

(C6-SS-C6)

When positioned at the 3' terminal end:

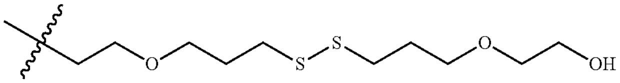

linkage towards 5′ end of oligonucleotide (6-SS-6)

When positioned internally in oligonucleotide:

linkage towards 5′ end of oligonucleotide linkage towards 3′ end of oligonucleotide

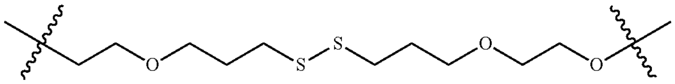

(C-SS-6)

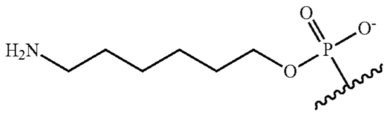

(NH2-C6)

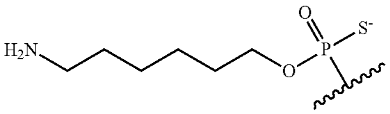

(NH2-C6)s

TABLE 6-continued
| Structures Representing Various Modified Nucleotides, Capping Moieties, and Linking Groups |
| --- |
| 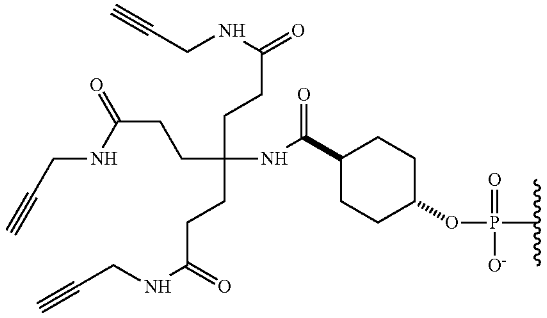 |
| (TriAlk1) |
| 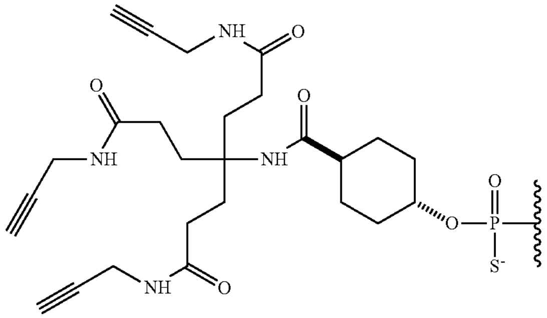 |
| (TriAlk1)s |
| 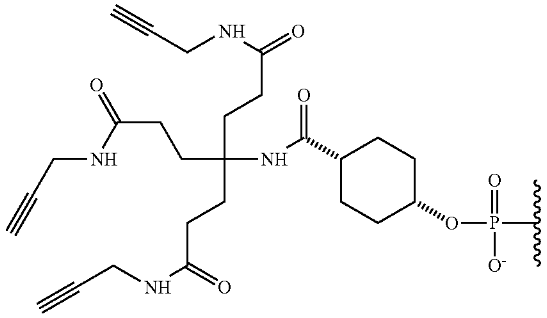 |
| (TriAlk2) |
| 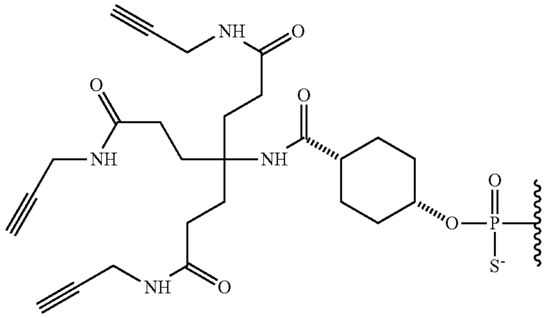 |
| (TriAlk2)s |

TABLE 6-continued
Structures Representing Various Modified Nucleotides, Capping Moieties, and Linking Groups
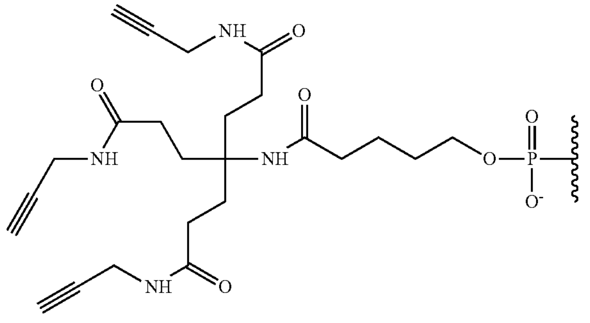
(TriAlk3)
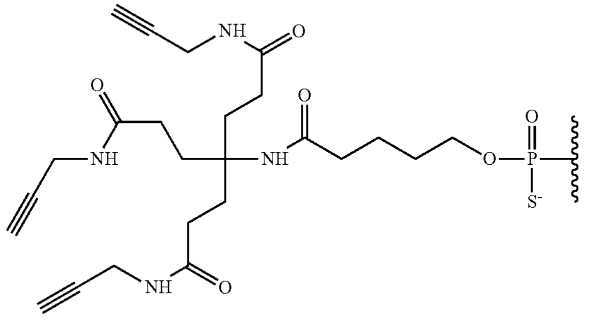
(TriAlk3)s
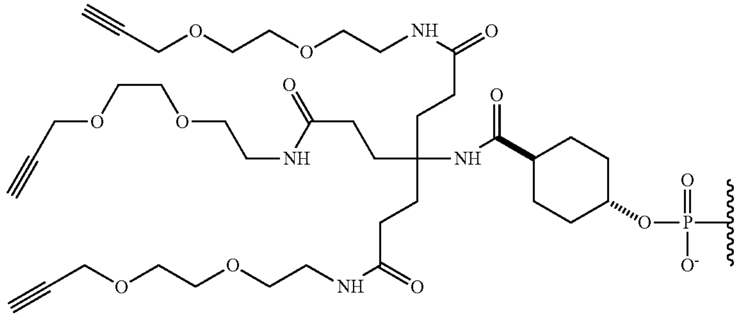
(TriAlk4)
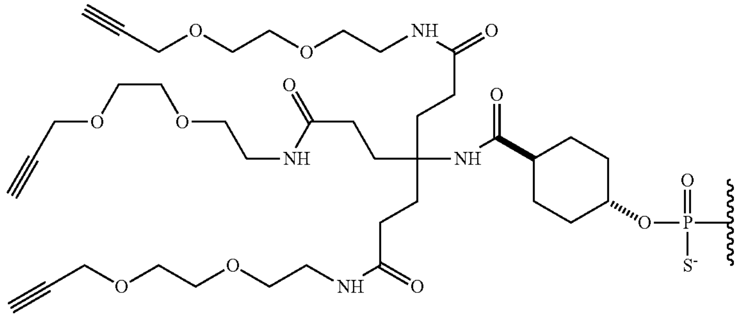
(TriAlk4)s TABLE 6-continued
| Structures Representing Various Modified Nucleotides, Capping Moieties, and Linking Groups |
| --- |
| 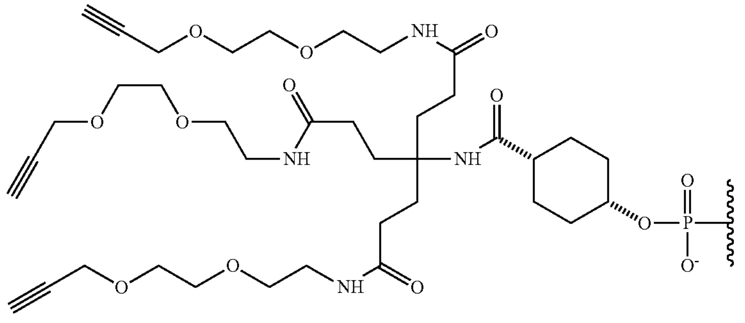 |
| (TriAlk5) |
| 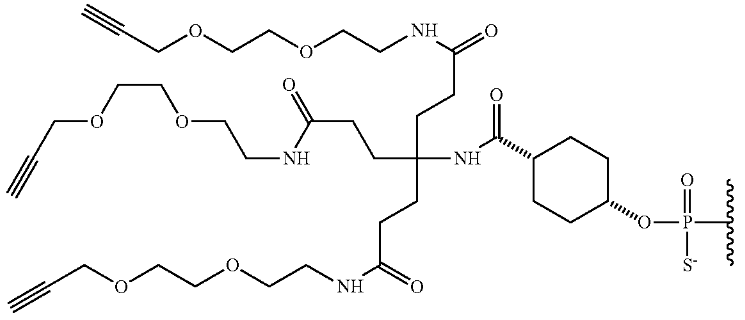 |
| (TriAlk5)s |
| 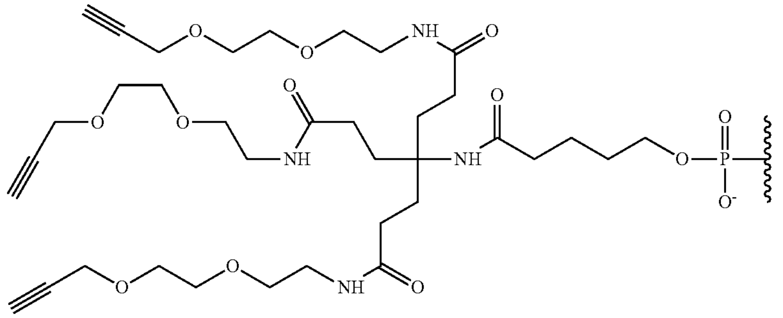 |
| (TriAlk6) |
| 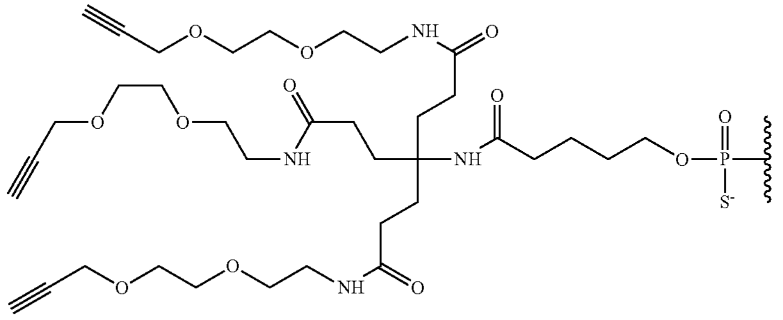 |
| (TriAlk6)s |

TABLE 6-continued
Structures Representing Various Modified Nucleotides, Capping Moieties, and Linking Groups
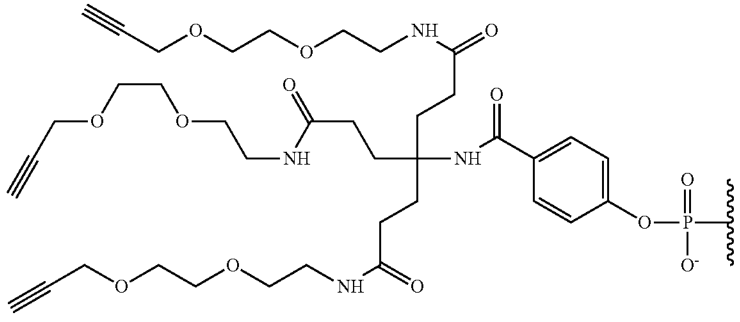
(TriAlk7)
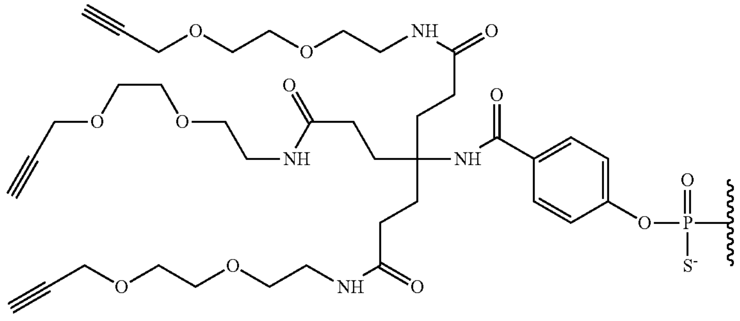
(TriAlk7)s
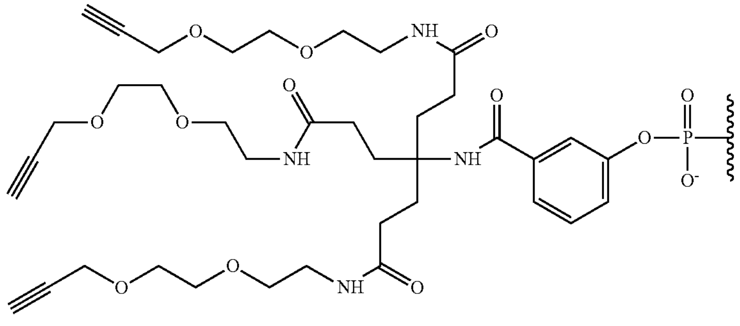
(TriAlk8)
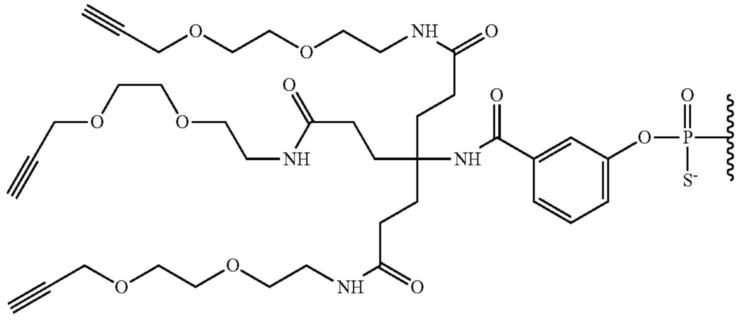
(TriAlk8)s TABLE 6-continued
| Structures Representing Various Modified Nucleotides, Capping Moieties, and Linking Groups |
| --- |
| 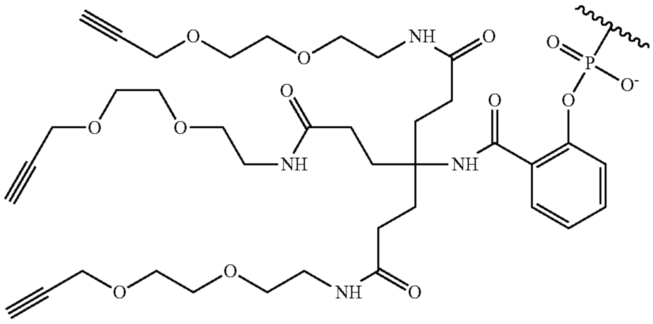 |
| (TriAlk9) |
| 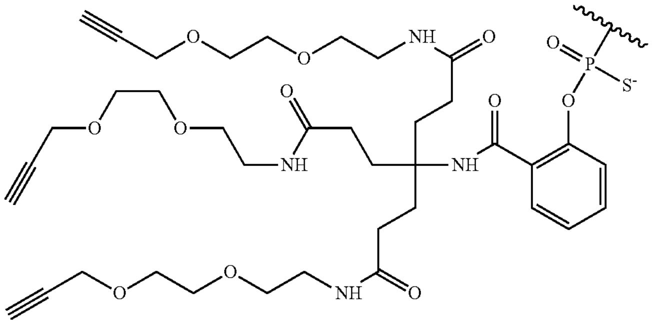 |
| (TriAlk9)s |
| 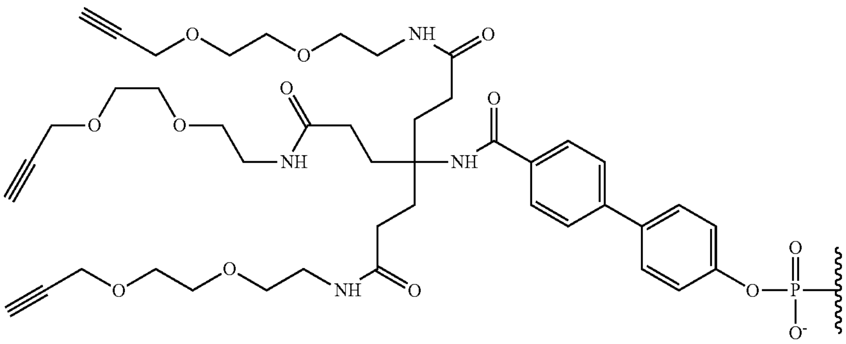 |
| (TriAlk10) |
| 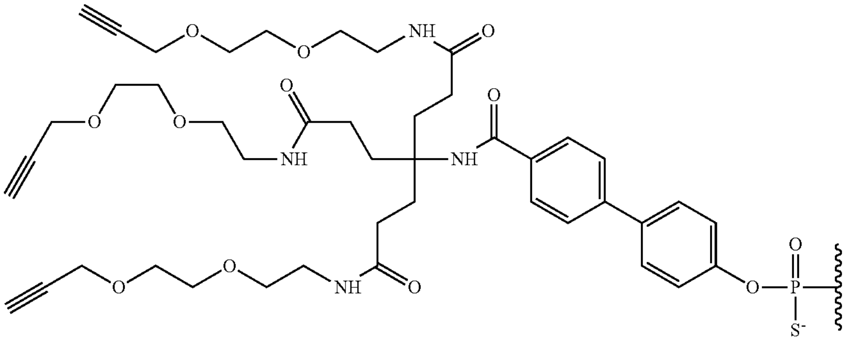 |
| (TriAlk10)s |

TABLE 6-continued
Structures Representing Various Modified Nucleotides, Capping Moieties, and Linking Groups
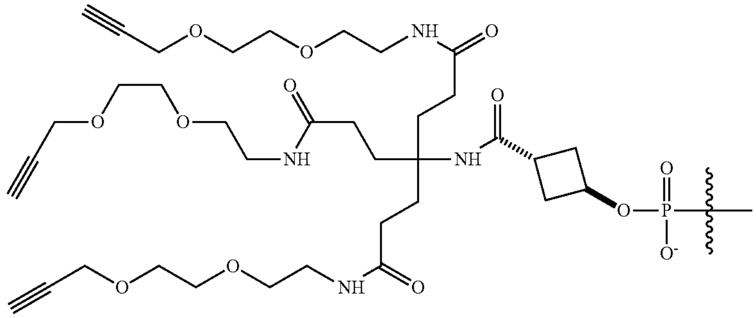
(TriAlk11)
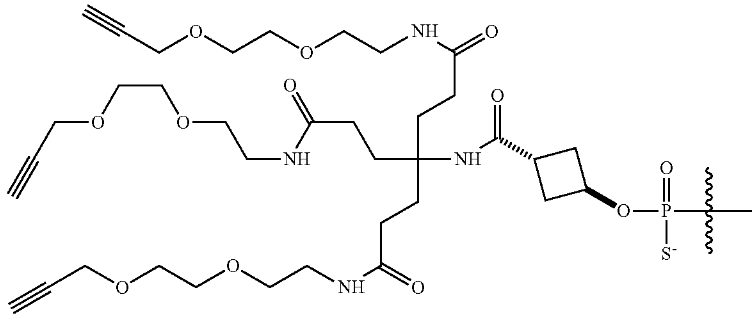
(TriAlk11)s
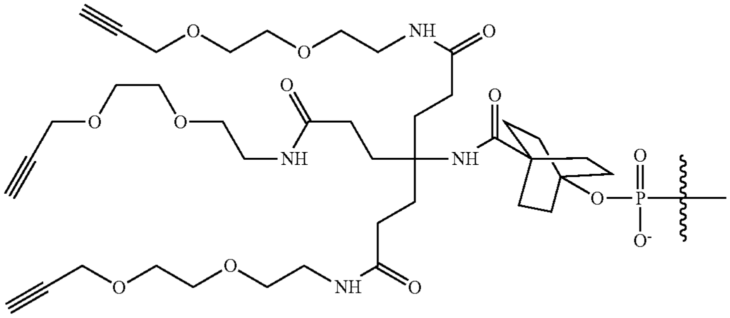
(TriAlk12)
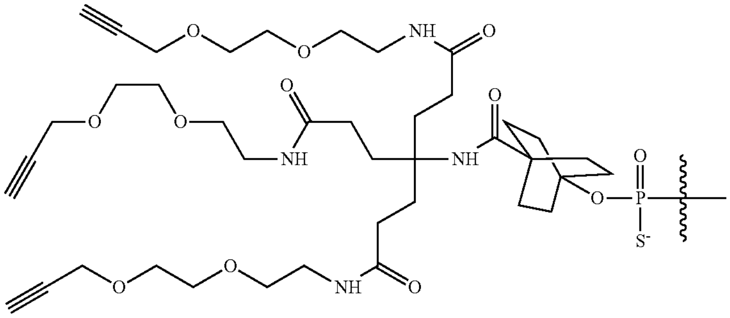
(TriAlk12)s TABLE 6-continued
Structures Representing Various Modified Nucleotides, Capping Moieties, and Linking Groups
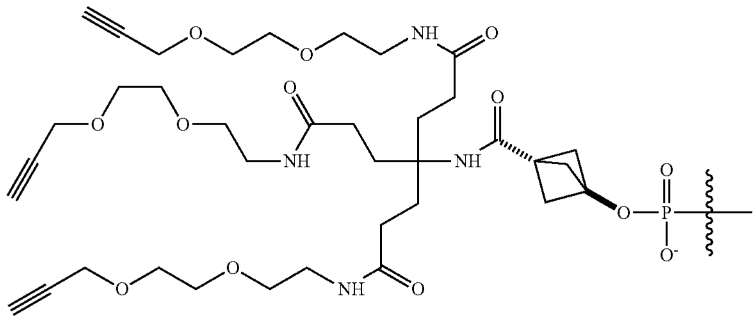
(TriAlk13)
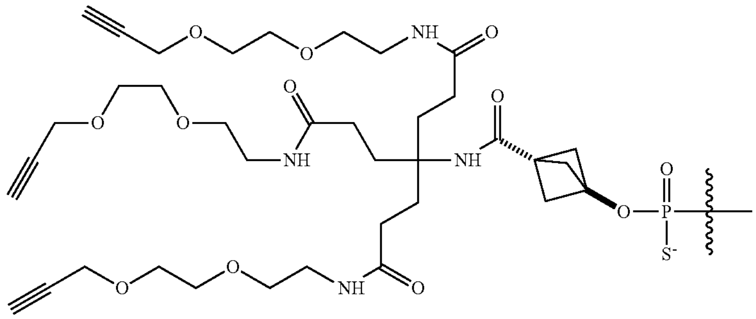
(TriAlk13)s
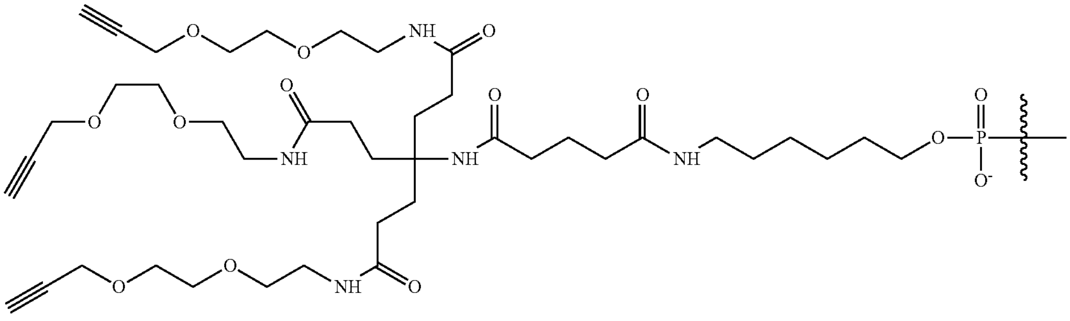
(TriAlk14)
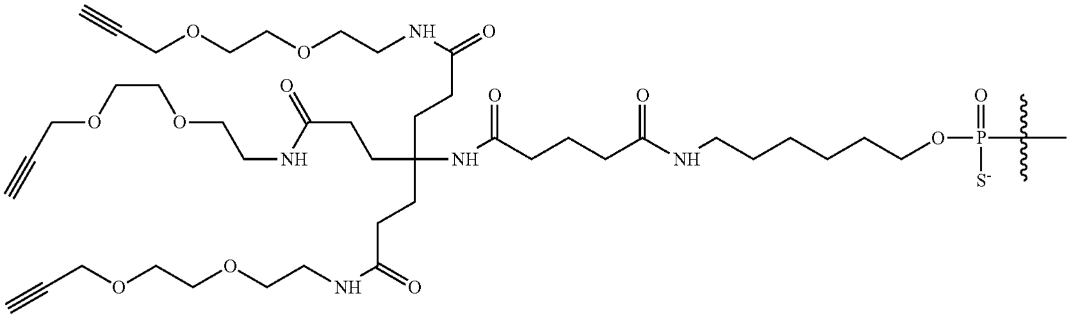
(TriAlk14)s Alternatively, other linking groups known in the art may be used. In many instances, linking groups can be commercially acquired or alternatively, are incorporated into commercially available nucleotide phosphoramidites. (See. e.g., International Patent Application Publication No. WO 2019/161213, which is incorporated herein by reference in its entirety).

In some embodiments, a beta-ENaC RNAi agent is delivered without being conjugated to a targeting ligand or pharmacokinetic/pharmacodynamic (PK/PD) modulator (referred to as being "naked" or a "naked RNAi agent").

In some embodiments, a beta-ENaC RNAi agent is conjugated to a targeting group, a linking group, a PK modulator, and/or another non-nucleotide group to facilitate delivery of the beta-ENaC RNAi agent to the cell or tissue of choice, for example, to an epithelial cell in vivo. In some embodiments, a beta-ENaC RNAi agent is conjugated to a targeting group wherein the targeting group includes an integrin targeting ligand. In some embodiments, the integrin targeting ligand is an αvβ6 integrin targeting ligand. In some embodiments, a targeting group includes one or more αvβ6 integrin targeting ligands.

In some embodiments, a delivery vehicle may be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art for nucleic acid delivery. The RNAi agents can also be chemically conjugated to targeting groups, lipids (including, but not limited to cholesteryl and cholesteryl derivatives), encapsulating in nanoparticles, liposomes, micelles, conjugating to polymers or DPCs (see, for example WO 2000/053722, WO 2008/022309, WO 2011/104169, and WO 2012/083185, WO 2013/032829, WO 2013/158141, each of which is incorporated herein by reference), by iontophoresis, or by incorporation into other delivery vehicles or systems available in the art such as hydrogels, cyclodextrins, biodegradable nanocapsules, bioadhesive microspheres, or proteinaceous vectors. In some embodiments the RNAi agents can be conjugated to antibodies having affinity for pulmonary epithelial cells. In some embodiments, the RNAi agents can be linked to targeting ligands that have affinity for pulmonary epithelial cells or receptors present on pulmonary epithelial cells.

Pharmaceutical Compositions and Formulations

The beta-ENaC RNAi agents disclosed herein can be prepared as pharmaceutical compositions or formulations (also referred to herein as "medicaments"). In some embodiments, pharmaceutical compositions include at least one beta-ENaC RNAi agent. These pharmaceutical compositions are particularly useful in the inhibition of the expression of beta-ENaC mRNA in a target cell, a group of cells, a tissue, or an organism. The pharmaceutical compositions can be used to treat a subject having a disease, disorder, or condition that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering a beta-ENaC RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include a beta-ENaC RNAi agent, thereby forming a pharmaceutical formulation or medicament suitable for in vivo delivery to a subject, including a human.

The pharmaceutical compositions that include a beta-ENaC RNAi agent and methods disclosed herein decrease the level of the target mRNA in a cell, group of cells, group of cells, tissue, organ, or subject, including by administering to the subject a therapeutically effective amount of a herein described beta-ENaC RNAi agent, thereby inhibiting the expression of beta-ENaC mRNA in the subject. In some embodiments, the subject has been previously identified or diagnosed as having a disease or disorder that is mediated at least in part by ENaC expression. In some embodiments, the subject has been previously identified or diagnosed as having enhanced ENaC activity in one or more cells or tissues. In some embodiments, the subject has been previously diagnosed with having one or more respiratory diseases such as cystic fibrosis, chronic bronchitis, non-cystic fibrosis bronchiectasis, chronic obstructive pulmonary disease (COPD), asthma, respiratory tract infections, primary ciliary dyskinesia, and lung carcinoma cystic fibrosis. In some embodiments, the subject has been previously diagnosed with having one or more ocular diseases such as dry eye. In some embodiments, the subject has been suffering from symptoms associated with one or more respiratory diseases that is associated with or caused by enhanced ENaC activity.

Embodiments of the present disclosure include pharmaceutical compositions for delivering a beta-ENaC RNAi agent to a pulmonary epithelial cell in vivo. Such pharmaceutical compositions can include, for example, a beta-ENaC RNAi agent conjugated to a targeting group that comprises an integrin targeting ligand. In some embodiments, the integrin targeting ligand is comprised of an αvβ6 integrin ligand.

In some embodiments, the described pharmaceutical compositions including a beta-ENaC RNAi agent are used for treating or managing clinical presentations in a subject that would benefit from the inhibition of expression of ENaC. In some embodiments, a therapeutically or prophylactically effective amount of one or more of pharmaceutical compositions is administered to a subject in need of such treatment. In some embodiments, administration of any of the disclosed beta-ENaC RNAi agents can be used to decrease the number, severity, and/or frequency of symptoms of a disease in a subject.

In some embodiments, the described beta-ENaC RNAi agents are optionally combined with one or more additional (i.e., second, third, etc.) therapeutics. A second therapeutic can be another beta-ENaC RNAi agent (e.g., a beta-ENaC RNAi agent that targets a different sequence within a beta-ENaC gene). In some embodiments, a second therapeutic can be an RNAi agent that targets the alpha-ENaC gene. An additional therapeutic can also be a small molecule drug, antibody, antibody fragment, and/or aptamer. The beta-ENaC RNAi agents, with or without the one or more additional therapeutics, can be combined with one or more excipients to form pharmaceutical compositions.

The described pharmaceutical compositions that include a beta-ENaC RNAi agent can be used to treat at least one symptom in a subject having a disease or disorder that would benefit from reduction or inhibition in expression of beta- ENaC mRNA. In some embodiments, the subject is administered a therapeutically effective amount of one or more pharmaceutical compositions that include a beta-ENaC RNAi agent thereby treating the symptom. In other embodiments, the subject is administered a prophylactically effective amount of one or more beta-ENaC RNAi agents, thereby preventing or inhibiting the at least one symptom.

In some embodiments, one or more of the described beta-ENaC RNAi agents are administered to a mammal in a pharmaceutically acceptable carrier or diluent. In some embodiments, the mammal is a human.

The route of administration is the path by which a beta-ENaC RNAi agent is brought into contact with the body. In general, methods of administering drugs, oligonucleotides, and nucleic acids, for treatment of a mammal are well known in the art and can be applied to administration of the compositions described herein. The beta-ENaC RNAi agents disclosed herein can be administered via any suitable route in a preparation appropriately tailored to the particular route. Thus, in some embodiments, the herein described pharmaceutical compositions are administered via inhalation, intranasal administration, intratracheal administration, or oropharyngeal aspiration administration. In some embodiments, the pharmaceutical compositions can be administered by injection, for example, intravenously, intramuscularly, intracutaneously, subcutaneously, intraarticularly, or intraperitoneally, or topically.

The pharmaceutical compositions including a beta-ENaC RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In some embodiments, the compositions are administered via inhalation, intranasal administration, oropharyngeal aspiration administration, or intratracheal administration. For example, in some embodiments, it is desired that the beta-ENaC RNAi agents described herein inhibit the expression of a beta-ENaC gene in the pulmonary epithelium, for which administration via inhalation (e.g., by an inhaler device, such as a metered-dose inhaler, or a nebulizer such as a jet or vibrating mesh nebulizer, or a soft mist inhaler) is particularly suitable and advantageous In some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., beta-ENaC RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® EL™ (BASF, Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for inhalation administration can be prepared by incorporating the active compound in the desired amount in an appropriate solvent, followed by sterile filtration. In general, formulations for inhalation administration are sterile solutions at physiological pH and have low viscosity (<5 cP). Salts may be added to the formulation to balance tonicity. In some cases, surfactants or co-solvents can be added to increase active compound solubility and improve aerosol characteristics. In some cases, excipients can be added to control viscosity in order to ensure size and distribution of nebulized droplets.

In some embodiments, pharmaceutical formulations that include the beta-ENaC RNAi agents disclosed herein suitable for inhalation administration can be prepared in an aqueous sodium phosphate buffer (e.g., the beta-ENaC RNAi agent formulated in 0.5 mM sodium phosphate monobasic, 0.5 mM sodium phosphate dibasic, in water).

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The beta-ENaC RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another beta-ENaC RNAi agent (e.g., a beta-ENaC RNAi agent that targets a different sequence within the beta-ENaC target). In other embodiments, the second therapeutic can be a small molecule drug, an antibody, an antibody fragment, and/or an aptamer.

In some embodiments, described herein are compositions that include a combination or cocktail of at least two beta-ENaC RNAi agents having different sequences. In some embodiments, the two or more beta-ENaC RNAi agents are each separately and independently linked to targeting groups. In some embodiments, the two or more beta-ENaC RNAi agents are each linked to targeting groups that include or consist of integrin targeting ligands. In some embodiments, the two or more beta-ENaC RNAi agents are each linked to targeting groups that include or consist of αvβ6 integrin targeting ligands.

Described herein are compositions for delivery of beta-ENaC RNAi agents to pulmonary epithelial cells. Furthermore, compositions for delivery of beta-ENaC RNAi agents to cells, including renal epithelial cells and/or epithelial cells in the GI or reproductive tract and/or and ocular surface epithelial cells in the eye, in vivo, are generally described herein.

Generally, an effective amount of a beta-ENaC RNAi agent disclosed herein will be in the range of from about 0.0001 to about 20 mg/kg of body weight/deposited dose, e.g., from about 0.001 to about 5 mg/kg of body weight/deposited dose. In some embodiments, an effective amount of a beta-ENaC RNAi agent will be in the range of from about 0.01 mg/kg to about 3.0 mg/kg of body weight per deposited dose. In some embodiments, an effective amount of a beta-ENaC RNAi agent will be in the range of from about 0.03 mg/kg to about 2.0 mg/kg of body weight per deposited dose. In some embodiments, an effective amount of a beta-ENaC RNAi agent will be in the range of from about 0.01 to about 1.0 mg/kg of deposited dose per body weight. In some embodiments, an effective amount of a beta-ENaC RNAi agent will be in the range of from about 0.50 to about 1.0 mg/kg of deposited dose per body weight. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum. In some embodiments, a dose is administered daily. In some embodiments, a dose is administered weekly. In further embodiments, a dose is administered bi-weekly, tri-weekly, once monthly, or once quarterly (i.e., once every three months).

For treatment of disease or for formation of a medicament or composition for treatment of a disease, the pharmaceutical compositions described herein including a beta-ENaC RNAi agent can be combined with an excipient or with a second therapeutic agent or treatment including, but not limited to: a second or other RNAi agent, a small molecule drug, an antibody, an antibody fragment, peptide, and/or an aptamer.

The described beta-ENaC RNAi agents, when added to pharmaceutically acceptable excipients or adjuvants, can be packaged into kits, containers, packs, or dispensers. The pharmaceutical compositions described herein can be packaged in dry powder or aerosol inhalers, other metered-dose inhalers, nebulizers, pre-filled syringes, or vials.

Methods of Treatment and Inhibition of Expression

The beta-ENaC RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from a reduction and/or inhibition in expression of beta-ENaC mRNA.

In some embodiments, the RNAi agents disclosed herein can be used to treat a subject (e.g., a human) having a disease or disorder for which the subject would benefit from reduction in ENaC channel activity, including but not limited to, for example, cystic fibrosis, chronic bronchitis, non-cystic fibrosis bronchiectasis, chronic obstructive pulmonary disease (COPD), asthma, respiratory tract infections, primary ciliary dyskinesia, and/or lung carcinoma cystic fibrosis and/or dry eye. Treatment of a subject can include therapeutic and/or prophylactic treatment. The subject is administered a therapeutically effective amount of any one or more beta-ENaC RNAi agents described herein. The subject can be a human, patient, or human patient. The subject may be an adult, adolescent, child, or infant. Administration of a pharmaceutical composition described herein can be to a human being or animal.

Increased ENaC activity is known to promote airway surface liquid dehydration and impair mucociliary clearance. In some embodiments, the described beta-ENaC RNAi agents are used to treat at least one symptom mediated at least in part by ENaC activity levels, in a subject. The subject is administered a therapeutically effective amount of any one or more of the described beta-ENaC RNAi agents. In some embodiments, the subject is administered a prophylactically effective amount of any one or more of the described RNAi agents, thereby treating the subject by preventing or inhibiting the at least one symptom.

In certain embodiments, the present disclosure provides methods for treatment of diseases, disorders, conditions, or pathological states mediated at least in part by beta-ENaC gene expression, in a patient in need thereof, wherein the methods include administering to the patient any of the beta-ENaC RNAi agents described herein.

In some embodiments, the beta-ENaC RNAi agents are used to treat or manage a clinical presentation or pathological state in a subject, wherein the clinical presentation or pathological state is mediated at least in part by ENaC expression. The subject is administered a therapeutically effective amount of one or more of the beta-ENaC RNAi agents or beta-ENaC RNAi agent-containing compositions described herein. In some embodiments, the method comprises administering a composition comprising a beta-ENaC RNAi agent described herein to a subject to be treated.

In a further aspect, the disclosure features methods of treatment (including prophylactic or preventative treatment) of diseases or symptoms caused by enhanced or elevated ENaC activity, the methods comprising administering to a subject in need thereof a beta-ENaC RNAi agent that includes an antisense strand comprising the sequence of any of the sequences in Table 2 or Table 3. Also described herein are compositions for use in such methods.

The described beta-ENaC RNAi agents and/or compositions that include beta-ENaC RNAi agents can be used in methods for therapeutic treatment of disease or conditions caused by enhanced or elevated ENaC activity levels. Such methods include administration of a beta-ENaC RNAi agent as described herein to a subject, e.g., a human or animal subject.

In another aspect, the disclosure provides methods for the treatment (including prophylactic treatment) of a pathological state (such as a condition or disease) mediated at least in part by beta-ENaC expression, wherein the methods include administering to a subject a therapeutically effective amount of an RNAi agent that includes an antisense strand comprising the sequence of any of the sequences in Table 2 or Table 3.

In some embodiments, methods for inhibiting expression of a beta-ENaC gene are disclosed herein, wherein the methods include administering to a cell an RNAi agent that includes an antisense strand comprising the sequence of any of the sequences in Table 2 or Table 3.

In some embodiments, methods for the treatment (including prophylactic treatment) of a pathological state mediated at least in part by beta-ENaC expression are disclosed herein, wherein the methods include administering to a subject a therapeutically effective amount of an RNAi agent that includes a sense strand comprising the sequence of any of the sequences in Table 2 or Table 4.

In some embodiments, methods for inhibiting expression of a beta-ENaC gene are disclosed herein, wherein the methods comprise administering to a cell an RNAi agent that includes a sense strand comprising the sequence of any of the sequences in Table 2 or Table 4.

In some embodiments, methods for the treatment (including prophylactic treatment) of a pathological state mediated at least in part by beta-ENaC expression are disclosed herein, wherein the methods include administering to a subject a therapeutically effective amount of an RNAi agent that includes a sense strand comprising the sequence of any of the sequences in Table 4, and an antisense strand comprising the sequence of any of the sequences in Table 3.

In some embodiments, methods for inhibiting expression of a beta-ENaC gene are disclosed herein, wherein the methods include administering to a cell an RNAi agent that includes a sense strand comprising the sequence of any of the sequences in Table 4, and an antisense strand comprising the sequence of any of the sequences in Table 3.

In some embodiments, methods of inhibiting expression of a beta-ENaC gene are disclosed herein, wherein the methods include administering to a subject a beta-ENaC RNAi agent that includes a sense strand consisting of the nucleobase sequence of any of the sequences in Table 4, and the antisense strand consisting of the nucleobase sequence of any of the sequences in Table 3. In other embodiments, disclosed herein are methods of inhibiting expression of a beta-ENaC gene, wherein the methods include administering to a subject a beta-ENaC RNAi agent that includes a sense strand consisting of the modified sequence of any of the modified sequences in Table 4, and the antisense strand consisting of the modified sequence of any of the modified sequences in Table 3.

In some embodiments, methods for inhibiting expression of a beta-ENaC gene in a cell are disclosed herein, wherein the methods include administering one or more beta-ENaC RNAi agents comprising a duplex structure of one of the duplexes set forth in Tables 5A and 5B.

In some embodiments, the gene expression level and/or mRNA level of a beta-ENaC gene in certain epithelial cells of subject to whom a described beta-ENaC RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the beta-ENaC RNAi agent or to a subject not receiving the beta-ENaC RNAi agent. In some embodiments, the ENaC levels or ENaC channel activity levels in certain epithelial cells of a subject to whom a described beta-ENaC RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the beta-ENaC RNAi agent or to a subject not receiving the beta-ENaC RNAi agent. The gene expression level, protein level, and/or mRNA level in the subject may be reduced in a cell, group of cells, and/or tissue of the subject. In some embodiments, the beta-ENaC mRNA levels in certain epithelial cells subject to whom a described beta-ENaC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the beta-ENaC RNAi agent or to a subject not receiving the beta-ENaC RNAi agent. In some embodiments, the level of the ENaC heterotrimeric protein complex in certain epithelial cells in a subject to whom a described beta-ENaC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the beta-ENaC RNAi agent or to a subject not receiving the beta-ENaC RNAi agent. The ENaC level in the subject may be reduced in a cell, group of cells, tissue, blood, and/or other fluid of the subject. For example, in some embodiments, the level of beta-ENaC mRNA and/or ENaC heterotrimeric protein complex in pulmonary epithelial cells of a subject to whom a described beta-ENaC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the beta-ENaC RNAi agent or to a subject not receiving the beta-ENaC RNAi agent. In some embodiments, the level of beta-ENaC mRNA and/or ENaC heterotrimeric protein complex and/or ENaC channel activity levels in a subset of pulmonary epithelial cells, such as airway epithelial cells, of a subject to whom a described beta-ENaC RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the beta-ENaC RNAi agent or to a subject not receiving the beta-ENaC RNAi agent.

A reduction in gene expression, mRNA, and protein levels can be assessed by any methods known in the art. Reduction or decrease in beta-ENaC mRNA level, ENaC channel activity level, and/or ENaC heterotrimeric protein complex levels, are collectively referred to herein as a reduction or decrease in beta-ENaC or inhibiting or reducing the expression of a beta-ENaC gene. The Examples set forth herein illustrate known methods for assessing inhibition of beta-ENaC gene expression.

Cells, Tissues, Organs, and Non-Human Organisms

Cells, tissues, organs, and non-human organisms that include at least one of the beta-ENaC RNAi agents described herein are contemplated. The cell, tissue, organ, or non-human organism is made by delivering the RNAi agent to the cell, tissue, organ, or non-human organism.

The above provided embodiments and items are now illustrated with the following, non-limiting examples.

EXAMPLES

Example 1. Synthesis of Beta-ENaC RNAi Agent

The Beta-ENaC RNAi agent duplexes shown in Tables 5A and 5B were synthesized in accordance with the following:

A. Synthesis

The sense and antisense strands of the beta-ENaC RNAi agents were synthesized according to phosphoramidite technology on solid phase used in oligonucleotide synthesis. Depending on the scale, a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the 2'-O-methyl phosphoramidites that were used included the following: (5'-O-dimethoxytrityl-N (benzoyl)-2'-O-methyl-adenosine-3'-2-cyanoethyl-N,N-diisopropylamino)phosphoramidite, 5'-O-dimethoxy-trityl-$N^4$-(acetyl)-2'-O-methyl-cytidine-3'-O-(2-cyanoethyl-N,N-diisopropyl-amino)phosphoramidite, (5'-O-dimethoxytrityl-$N^2$-(isobutyryl)-2'-O-methyl-guanosine-3'-O-(2-cyanoethyl-N,N-diisopropylamino)phosphoramidite, and 5'-O-dimethoxytrityl-2'-O-methyl-uridine-3'-O-(2-cyanoethyl-N,N-diisopropylamino)phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino)phosphoramidites were purchased from Glen Research (Virginia). The inverted abasic (3'-O-dimethoxytrityl-2'-deoxyribose-5'-O-(2-cyanoethyl-N,N-diisopropylamino)phosphoramidites were purchased from ChemGenes (Wilmington, MA, USA). The following UNA phosphoramidites were used: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite. TFA amino link phosphoramidites were also commercially purchased (ThermoFisher). The cyclopropyl phosphonate phosphoramidites were synthesized in accordance with International Patent Application Publication No. WO 2017/214112.

Tri-alkyne-containing phosphoramidites were dissolved in anhydrous dichloromethane or anhydrous acetonitrile (50 mM), while all other amidites were dissolved in anhydrous acetonitrile (50 mM) and molecular sieves (3A) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' O-Me), and 60 seconds (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

Alternatively, tri-alkyne moieties were introduced post-synthetically (see section E, below). For this route, the sense strand was functionalized with a 5' and/or 3' terminal nucleotide containing a primary amine. TFA amino link phosphoramidite was dissolved in anhydrous acetonitrile (50 mM) and molecular sieves (3A) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' O-Me), and 60 seconds (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

B. Cleavage and Deprotection of Support Bound Oligomer

After finalization of the solid phase synthesis, the dried solid support was treated with a 1:1 volume solution of 40 wt. % methylamine in water and 28% to 31% ammonium hydroxide solution (Aldrich) for 1.5 hours at 30° C. The solution was evaporated and the solid residue was reconstituted in water (see below).

C. Purification

Crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate, pH 6.7 and 20% Acetonitrile or filtered water. Alternatively, pooled fractions were desalted and exchanged into an appropriate buffer or solvent system via tangential flow filtration.

D. Annealing

Complementary strands were mixed by combining equimolar RNA solutions (sense and antisense) in 1× PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor (0.050 mg/(mL cm)) and the dilution factor to determine the duplex concentration.

E. Conjugation of Tri-Alkyne Linker

In some embodiments a tri-alkyne linker is conjugated to the sense strand of the RNAi agent on resin as a phosphoramidite (see Example 1G for the synthesis of an example tri-alkyne linker phosphoramidite and Example 1A for the conjugation of the phosphoramidite). In other embodiments, a tri-alkyne linker may be conjugated to the sense strand following cleavage from the resin, described as follows: either prior to or after annealing, in some embodiments, the 5' or 3' amine functionalized sense strand is conjugated to a tri-alkyne linker. An example tri-alkyne linker structure that can be used in forming the constructs disclosed herein is as follows:

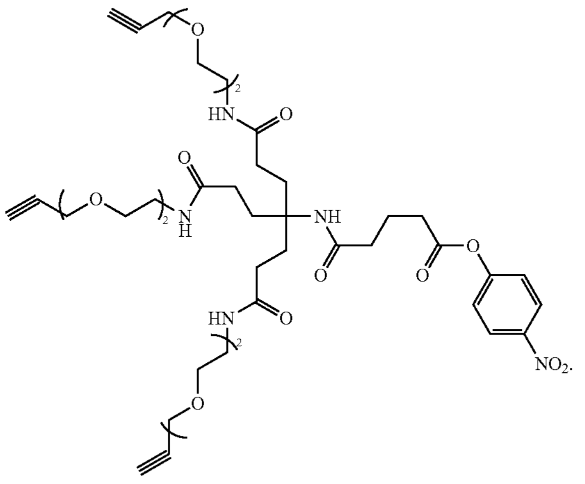

To conjugate the tri-alkyne linker to the annealed duplex, amine-functionalized duplex was dissolved in 90% DMSO/10% $H_2O$, at ~50-70 mg/mL. 40 equivalents triethylamine was added, followed by 3 equivalents tri-alkyne-PNP. Once complete, the conjugate was precipitated twice in a solvent system of 1× phosphate buffered saline/acetonitrile (1:14 ratio), and dried.

F. Synthesis of Targeting Ligand SM61

((S)-3-(4-(4-((14-azido-3.69.12-tetraoxatetradecyl)oxy)naphthalen-yl)phenyl)-3-(2-(4-((4-methylpyridin-2-yl)amino)butanamido)acetamido)propanoic acid)

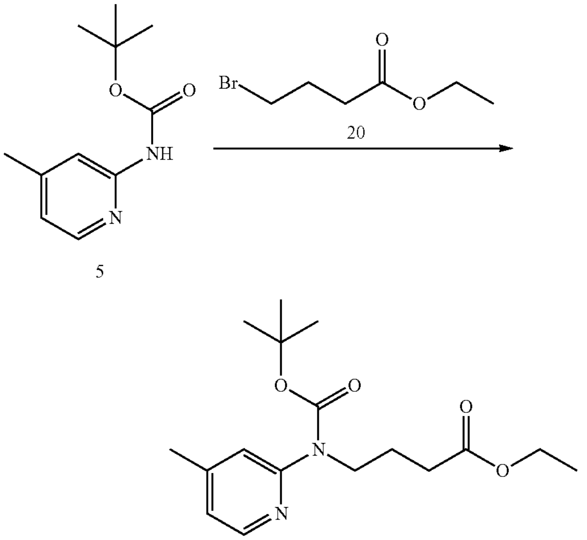

5

21

Compound 5 (tert-Butyl(4-methylpyridin-2-yl)carbamate) (0.501 g, 2.406 mmol, 1 equiv.) was dissolved in DMF (17 mL). To the mixture was added NaH (0.116 mg, 3.01 mmol, 1.25 eq, 60% dispersion in oil) The mixture stirred for 10 min before adding Compound 20 (Ethyl 4-Bromobutyrate (0.745 g, 3.82 mmol, 0.547 mL)) (Sigma 167118). After 3 hours the reaction was quenched with ethanol (18 mL) and concentrated. The concentrate was dissolved in DCM (50 mL) and washed with saturated aq. NaCl solution (1×50 mL), dried over $Na_2SO_4$, filtered and concentrated. The product was purified on silica column, gradient 0-5% Methanol in DCM.

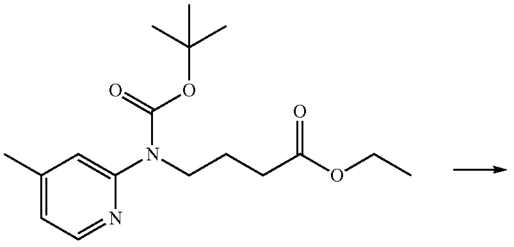

21

-continued

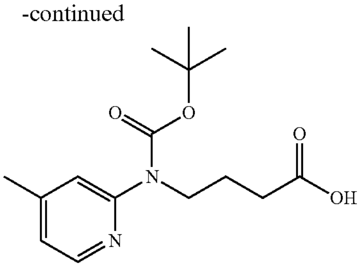

22

Compound 21 was dissolved (0.80 g, 2.378 mmol) in 100 mL of Acetone: 0.1 M NaOH [1:1]. The reaction was monitored by TLC (5% ethyl acetate in hexane). The organics were concentrated away, and the residue was acidified to pH 3-4 with 0.3 M Citric Acid (40 mL). The product was extracted with DCM (3×75 mL). The organics were pooled, dried over $Na_2SO_4$, filtered and concentrated. The product was used without further purification.

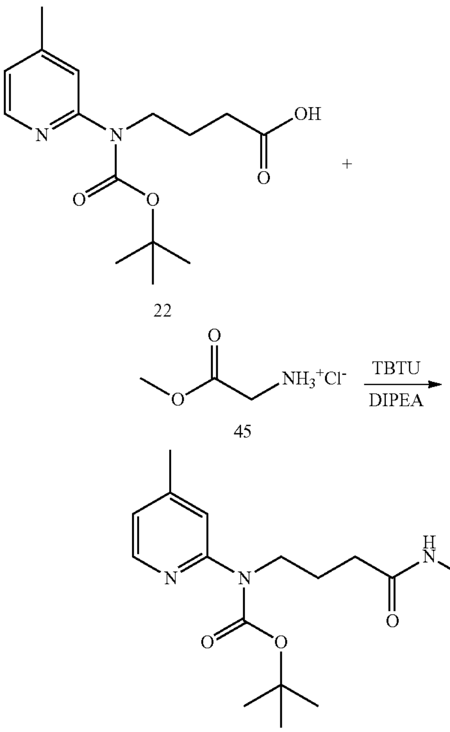

22 45 60

To a solution of Compound 22 (1.1 g, 3.95 mmol, 1 equiv.), Compound 45 (595 mg, 4.74 mmol, 1.2 equiv.), and TBTU (1.52 g, 4.74 mmol, 1.2 equiv.) in anhydrous DMF (10 mL) was added diisopropylethylamine (2.06 mL, 11.85 mmol, 3 equiv.) at 0° C. The reaction mixture was warmed to room temperature and stirred 3 hours. The reaction was quenched by saturated $NaHCO_3$ solution (10 mL). The aqueous phase was extracted with ethyl acetate (3×10 mL) and the organic phase was combined, dried over anhydrous $Na_2SO_4$, and concentrated. The product was separated by CombiFlash® using silica gel as the stationary phase. LC-MS: calculated [M+H]+366.20, found 367.

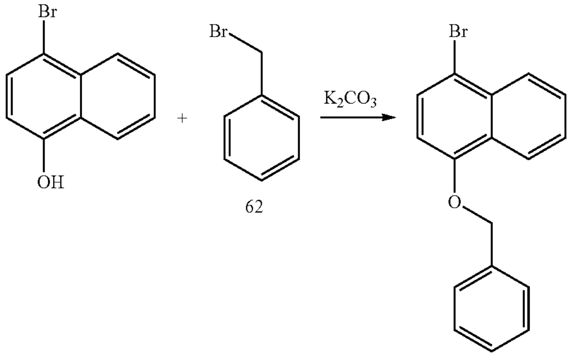

62 63

To a solution of compound 61 (2 g, 8.96 mmol, 1 equiv.), and compound 62 (2.13 mL, 17.93 mmol, 2 equiv.) in anhydrous DMF (10 mL) was added $K_2CO_3$ (2.48 g, 17.93 mmol, 2 equiv.) at 0° C. The reaction mixture was warmed to room temperature and stirred overnight. The reaction was quenched by water (10 mL). The aqueous phase was extracted with ethyl acetate (3×10 mL) and the organic phase was combined, dried over anhydrous $Na_2SO_4$, and concentrated. The product was separated by CombiFlash® using silica gel as the stationary phase.

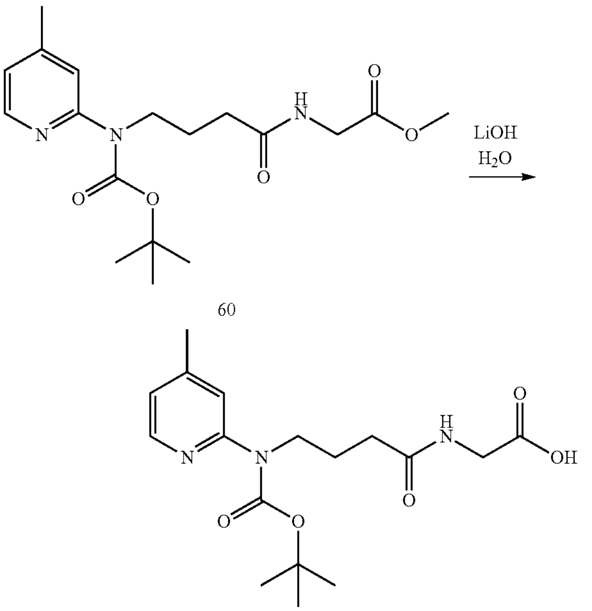

60 64

To a solution of compound 60 (1.77 g, 4.84 mmol, 1 equiv.) in THF (5 mL) and $H_2O$ (5 mL) was added lithium hydroxide monohydrate (0.61 g, 14.53 mmol, 3 equiv.) portion-wise at 0° C. The reaction mixture was warmed to room temperature. After stirring at room temperature for 3 hours, the reaction mixture was acidified by HCl (6 N) to pH 3.0. The aqueous phase was extracted with ethyl acetate (3×20 mL) and the organic layer was combined, dried over $Na_2SO_4$, and concentrated. LC-MS: calculated [M+H]+ 352.18, found 352.

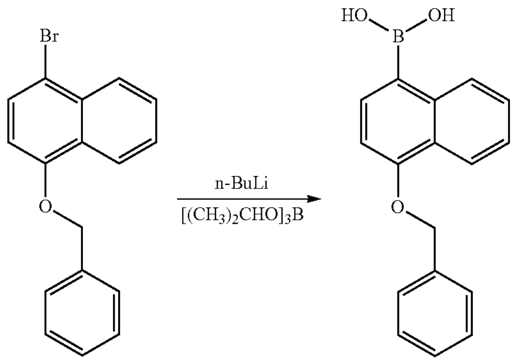

63

65

To a solution of compound 63 (1.88 g, 6.0 mmol, 1.0 equiv.) in anhydrous THF (20 mL) was added n-BuLi in hexane (3.6 mL, 9.0 mmol, 1.5 equiv.) drop-wise at −78° C. The reaction was kept at −78° C. for another 1 hour. Triisopropylborate (2.08 mL, 9.0 mmol, 1.5 equiv.) was then added into the mixture at −78° C. The reaction was then warmed up to room temperature and stirred for another 1 hour. The reaction was quenched by saturated NH4C1 solution (20 mL) and the pH was adjusted to 3. The aqueous phase was extracted with EtOAc (3×20 mL) and the organic phase was combined, dried over $Na_2SO_4$, and concentrated.

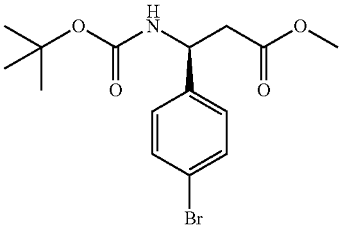

12

+

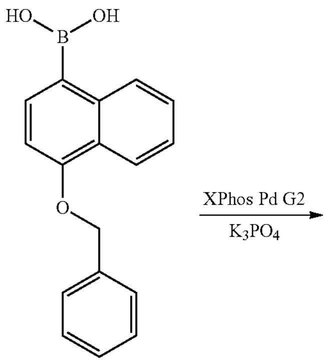

65

-continued

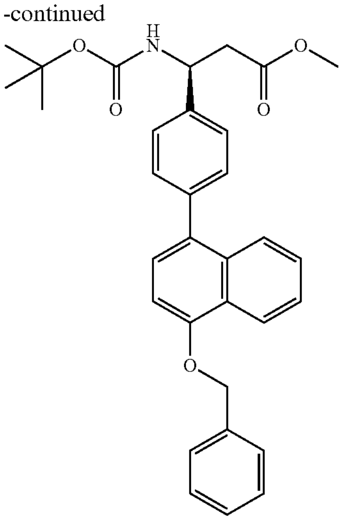

66

Compound 12 (300 mg, 0.837 mmol, 1.0 equiv.), Compound 65 (349 mg, 1.256 mmol, 1.5 equiv.), XPhos Pd G2 (13 mg, 0.0167 mmol, 0.02 equiv.), and $K_3PO_4$ (355 mg, 1.675 mmol, 2.0 equiv.) were mixed in a round-bottom flask. The flask was sealed with a screw-cap septum, and then evacuated and backfilled with nitrogen (this process was repeated a total of 3 times). Then, THF (8 mL) and water (2 mL) were added via syringe. The mixture was bubbled with nitrogen for 20 min and the reaction was kept at room temperature for overnight. The reaction was quenched with water (10 mL), and the aqueous phase was extracted with ethyl acetate (3×10 mL). The organic phase was dried over $Na_2SO_4$, concentrated, and purified via CombiFlash® using silica gel as the stationary phase and was eluted with 15% EtOAc in hexane. LC-MS: calculated [M+H]+512.24, found 512.56.

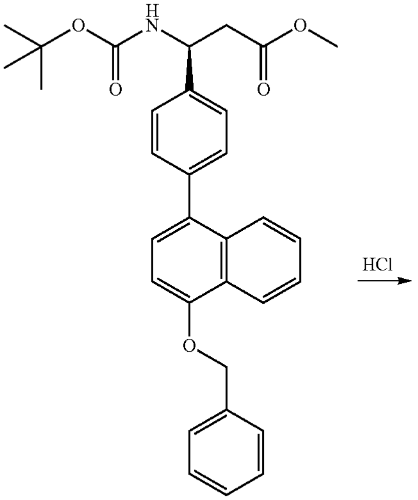

66

-continued

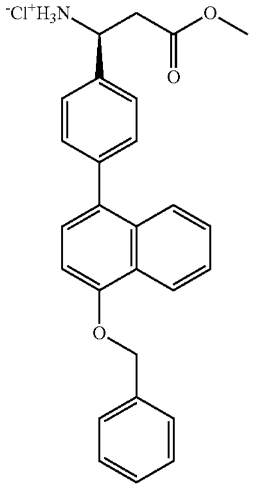

67

-continued

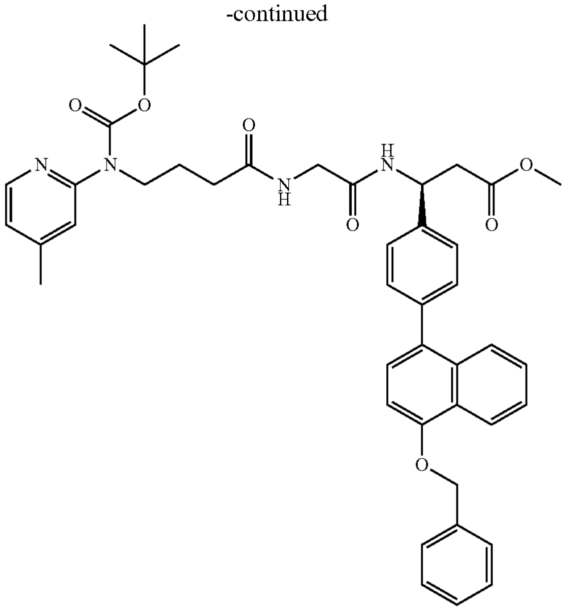

68

Compound 66 (858 mg, 1.677 mmol, 1.0 equiv.) was cooled by ice bath. HCl in dioxane (8.4 mL, 33.54 mmol, 20 equiv.) was added into the flask. The reaction was warmed to room temperature and stirred for another 1 hr. The solvent was removed by rotary evaporator and the product was directly used without further purification. LC-MS: calculated [M+H]+412.18, found 412.46.

To a solution of compound 64 (500 mg, 1.423 mmol, 1 equiv.), compound 67 (669 mg, 1.494 mmol, 1.05 equiv.), and TBTU (548 mg, 0.492 mmol, 1.2 equiv.) in anhydrous DMF (15 mL) was added diisopropylethylamine (0.744 mL, 4.268 mmol, 3 equiv.) at 0° C. The reaction mixture was warmed to room temperature and stirred for another 1 hr. The reaction was quenched by saturated $NaHCO_3$ aqueous solution (10 mL) and the product was extracted with ethyl acetate (3x20 mL). The organic phase was combined, dried over $Na_2SO_4$, and concentrated. The product was purified by CombiFlash® using silica gel as the stationary phase and was eluted with 3-4% methanol in DCM. The yield was 96.23%. LC-MS: calculated [M+H]+745.35, found 746.08.

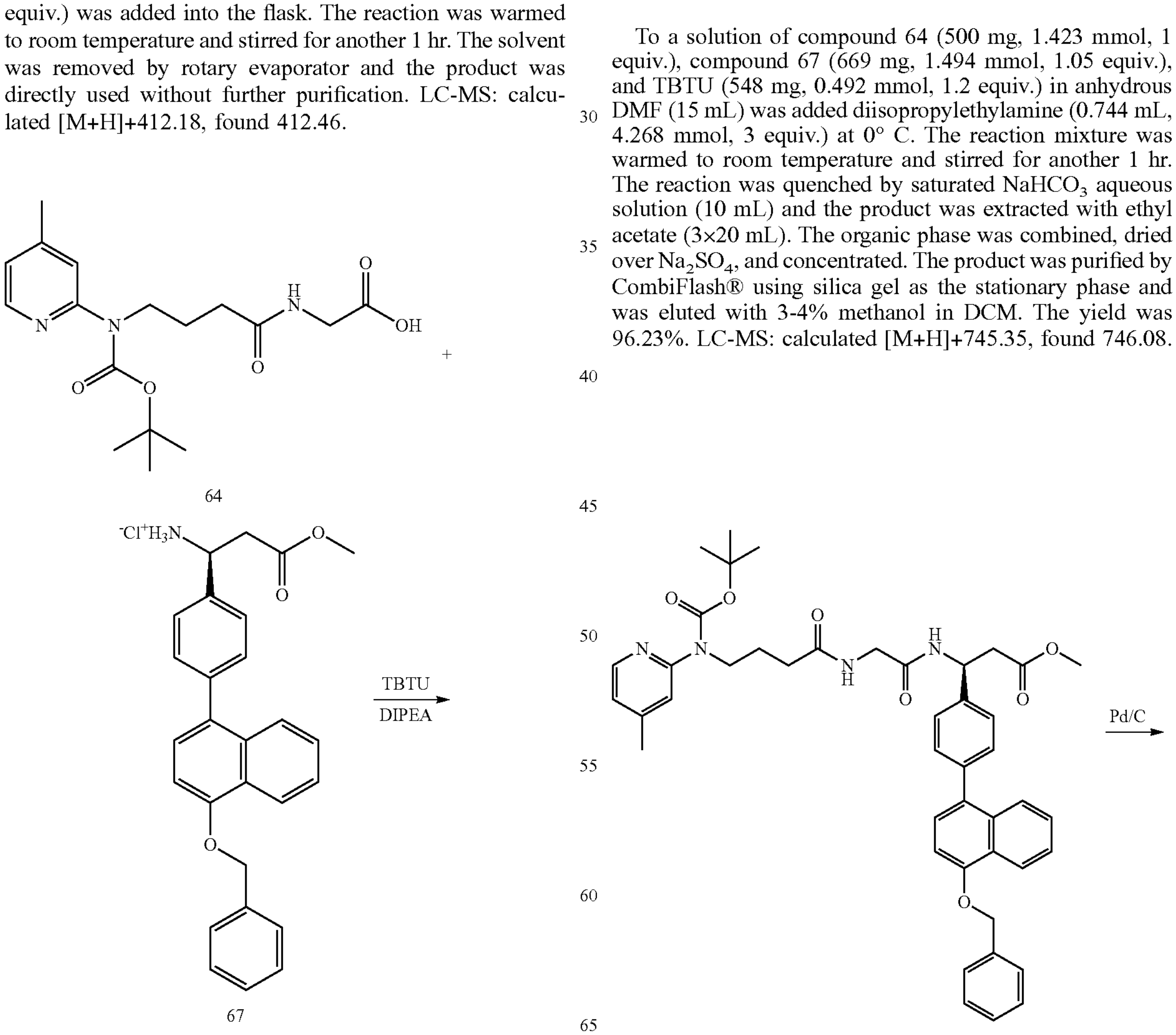

64

67

68

-continued

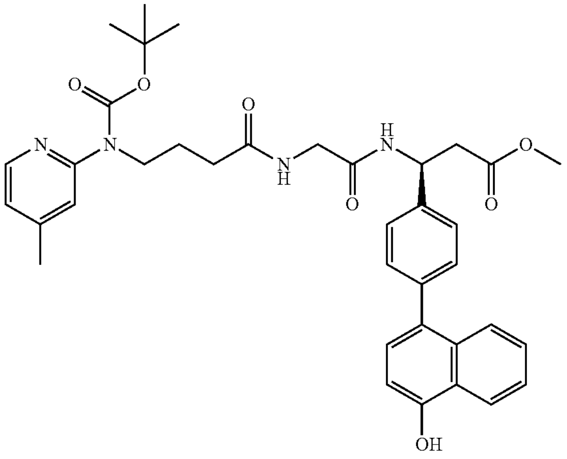

69

To a solution of compound 68 (1.02 g, 1.369 mmol, 1 equiv.) in ethyl acetate (10 mL) was added 10% Pd/C (0.15 g, 50% $H_2O$) at room temperature. The reaction mixture was warmed to room temperature and the reaction was monitored by LC-MS. The reaction was kept at room temperature overnight. The solids were filtered through Celite® and the solvent was removed by rotary evaporator. The product was directly used without further purification. LC-MS: [M+H]+ 655.31, found 655.87.

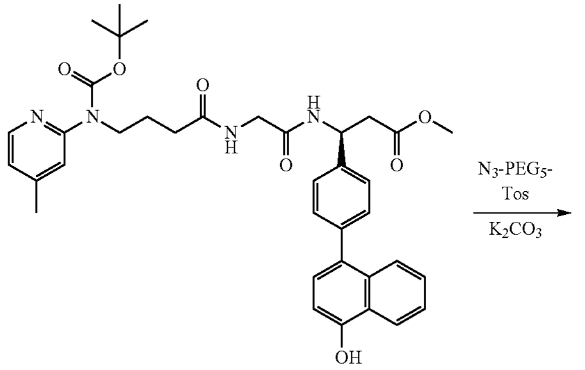

69

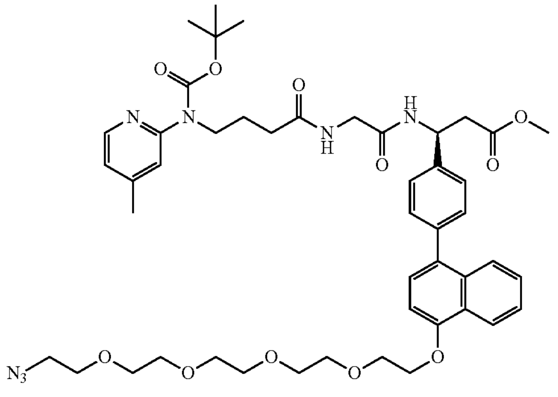

72

To a solution of compound 69 (100 mg, 0.152 mmol, 1 equiv.) and azido-$PEG_5$-OTs (128 mg, 0.305 mmol, 2 equiv.) in anhydrous DMF (2 mL) was added $K_2CO_3$ (42 mg, 0.305 mmol, 2 equiv.) at 0° C. The reaction mixture was stirred for 6 hours at 80° C. The reaction was quenched by saturated $NaHCO_3$ solution and the aqueous layer was extracted with ethyl acetate (3×10 mL). The organic phase was combined, dried over $Na_2SO_4$, and concentrated. LC-MS: calculated M+H+900.40 found 901.46.

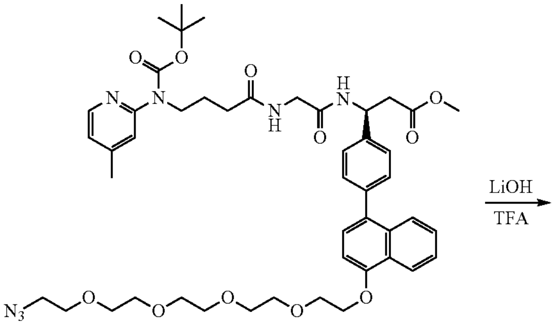

72

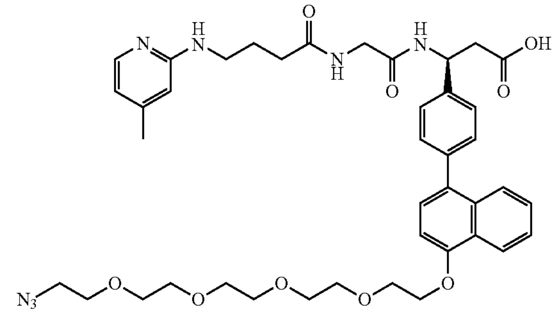

•TFA

Structure 6.1b

To a solution of compound 72 (59 mg, 0.0656 mmol, 1.0 equiv.) in THF (2 mL) and water (2 mL) was added lithium hydroxide (5 mg, 0.197 mmol, 3.0 equiv.) at room temperature. The mixture was stirred at room temperature for another 1 hr. The pH was adjusted to 3.0 by HCl (6N) and the aqueous phase was extracted with EtOAc (3×10 mL). The organic phase was combined, dried over $Na_2SO_4$, and concentrated. TFA (0.5 mL) and DCM (0.5 mL) was added into the residue and the mixture was stirred at room temperature for another 3 hr. The solvent was removed by rotary evaporator. LC-MS: calculated [M+H]+786.37, found 786.95.

G. Synthesis of TriAlk 14

TriAlk14 and (TriAlk14)s as shown in Table 6, above, may be synthesized using the synthetic route shown below. Compound 14 may be added to the sense strand as a phosphoramidite using standard oligonucleotide synthesis techniques, or compound 22 may be conjugated to the sense strand comprising an amine in an amide coupling reaction.

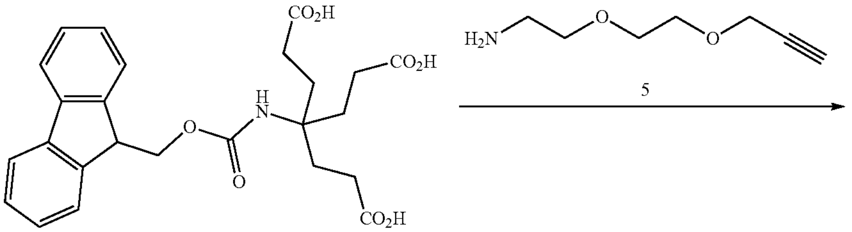

4

5

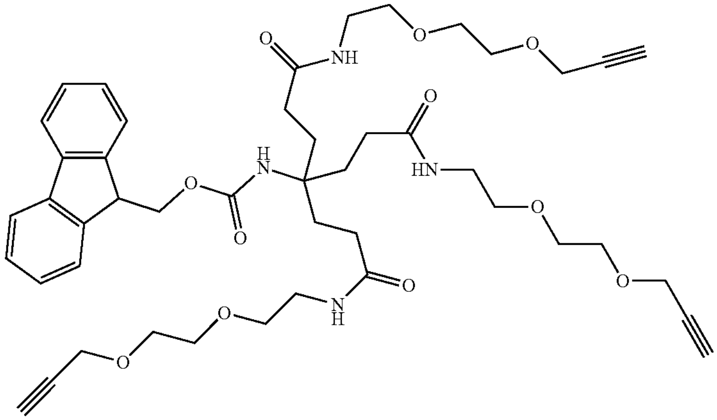

6

To a 3-L jacketed reactor was added 500 mL DCM and 4 (75.0 g, 0.16 mol). The internal temperature of the reaction was cooled to 0° C. and TBTU (170.0 g, 0.53 mol) was added. The suspension was then treated with the amine 5 (75.5 g, 0.53 mol) dropwise keeping the internal temperature less than 5° C. The reaction was then treated with DIPEA (72.3 g, 0.56 mol) slowly, keeping the internal temperature less than 5° C. After the addition was complete, the reaction was warmed up to 23° C. over 1 hour, and allowed to stir for 3 hours. A 10% kicker charge of all three reagents were added and allowed to stir an additional 3 hours. The reaction was deemed complete when <1% of 4 remained. The reaction mixture was washed with saturated ammonium chloride solution (2×500 mL) and once with saturated sodium bicarbonate solution (500 mL). The organic layer was then dried over sodium sulfate and concentrated to an oil. The mass of the crude oil was 188 g which contained 72% 6 by QNMR. The crude oil was carried to the next step. Calculated mass for $C_{46}H_{60}N_4O_{11}$=845.0 m/z. Found [M+H]=846.0.

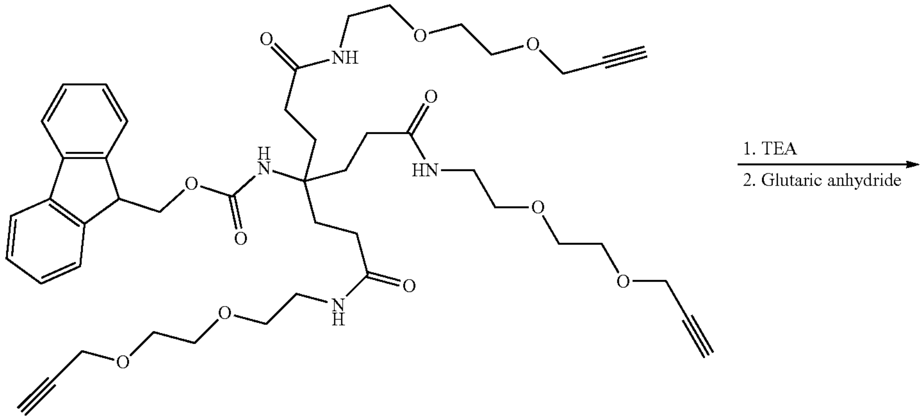

6

-continued

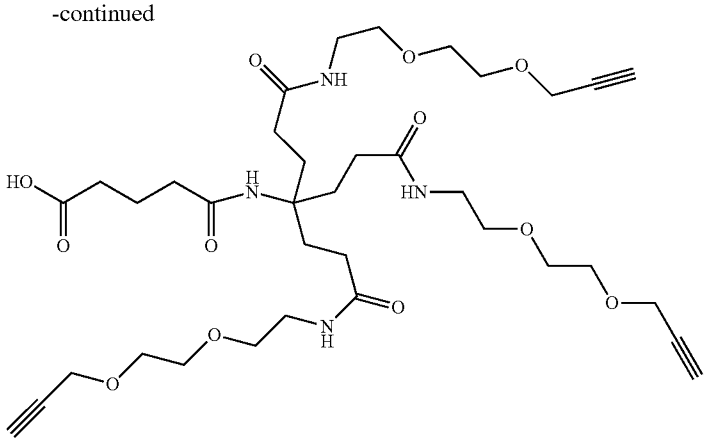

8

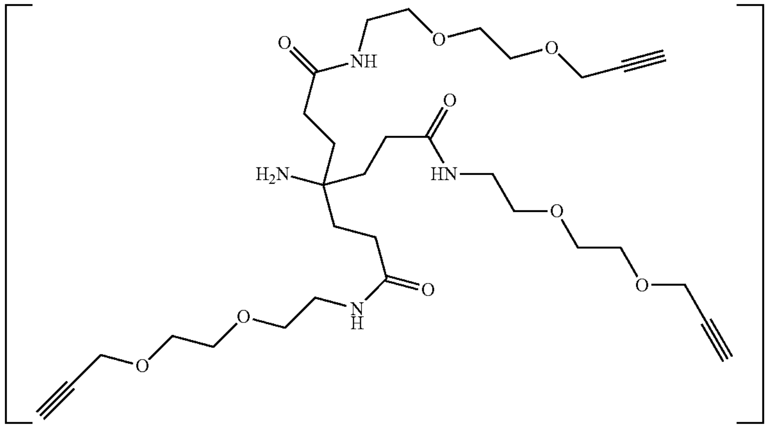

7

The 121.2 g of crude oil containing 72 wt % compound 6 (86.0 g, 0.10 mol) was dissolved in DMF (344 mL) and treated with TEA (86 mL, 20 v/v %), keeping the internal temperature below 23° C. The formation of dibenzofulvene (DBF) relative to the consumption of Fmoc-amine 6 was monitored via HPLC method 1 (FIG. 2) and the reaction was complete within 10 hours. To the solution was added glutaric anhydride (12.8 g, 0.11 mol) and the intermediate amine 7 was converted to compound 8 within 2 hours. Upon completion, the DMF and TEA were removed at 30° C. under reduced pressure resulting in 100 g of a crude oil. Due to the high solubility of compound 7 in water, an aqueous workup could not be used, and chromatography is the only way to remove DBF, TMU, and glutaric anhydride. The crude oil (75 g) was purified on a Teledyne ISCO Combi-flash® purification system in three portions. The crude oil (25 g) was loaded onto a 330 g silica column and eluted from 0-20% methanol/DCM over 30 minutes resulting in 42 g of compound 8 (54% yield over 3 steps). Calculated mass for $C_{36}H_{55}N_4O_{12}$=736.4 m/z. Found [M+H]=737.0.

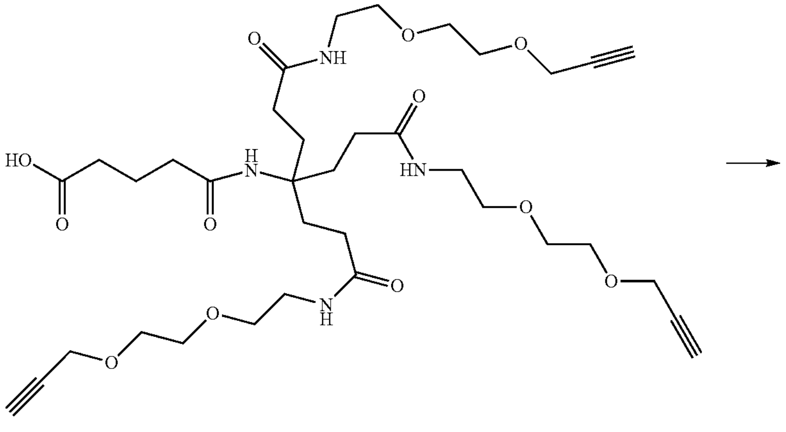

8

-continued

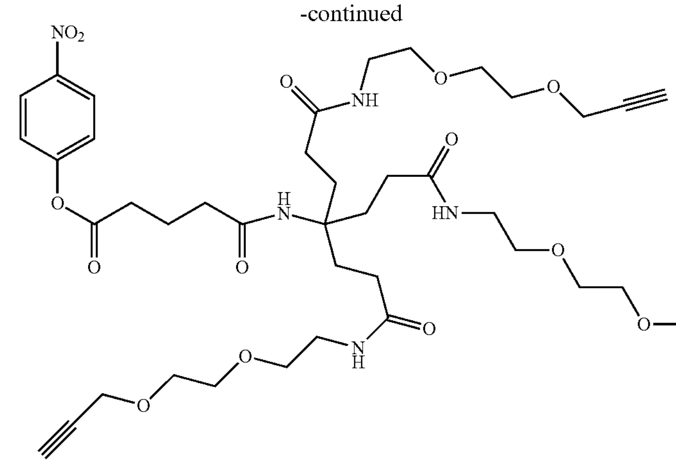

9

Compound 22

Compound 8 (42.0 g, 0.057 mol) was co-stripped with 10 volumes of acetonitrile prior to use to remove any residual methanol from chromatography solvents. The oil was redissolved in DMF (210 mL) and cooled to 0° C. The solution was treated with 4-nitrophenol (8.7 g, 0.063 moL) followed by EDC-hydrochloride (12.0 g, 0.063 mol) and found to reach completion within 10 hours. The solution was cooled to 0° C. and 10 volumes ethyl acetate was added followed by 10 volumes saturated ammonium chloride solution, keeping the internal temperature below 15° C. The layers were allowed to separate and the ethyl acetate layer was washed with brine. The combined aqueous layers were extracted twice with 5 volumes ethyl acetate. The combined organic layers were dried over sodium sulfate and concentrated to an oil. The crude oil (55 g) was purified on a Teledyne ISCO Combi-Flash® purification system in three portions. The crude oil (25 g) was loaded onto a 330 g silica column and eluted from 0-10% methanol/DCM over 30 minutes resulting in 22 g of pure 9 (Compound 22) (50% yield). Calculated mass for P $C_{42}H_{59}N_5O_{14}$=857.4 m/z. Found [M+H]=858.0.

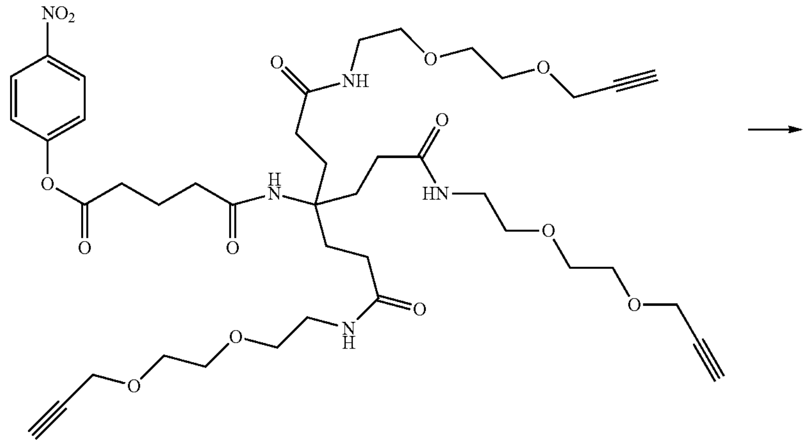

9

-continued

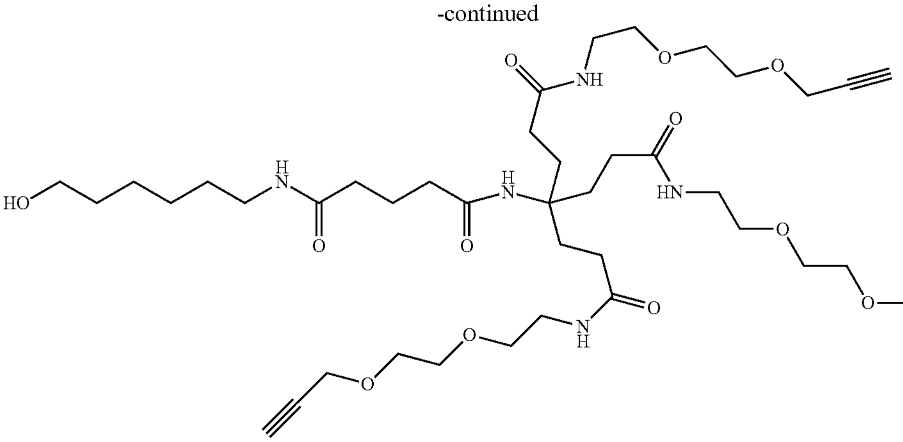

10

A solution of ester 9 (49.0 g, 57.1 mmol) and 6-amino-1-hexanol (7.36 g, 6.28 mmol) in dichloromethane (3 volumes) was treated with triethylamine (11.56 g, 111.4 mmol) dropwise. The reaction was monitored by observing the disappearance of compound 9 on HPLC Method 1 and was found to be complete in 10 minutes. The crude reaction mixture was diluted with 5 volumes dichloromethane and washed with saturated ammonium chloride (5 volumes) and brine (5 volumes). The organic layer was dried over sodium sulfate and concentrated to an oil. The crude oil was purified on a Teledyne ISCO Combi-flash® purification system using a 330 g silica column. The 4-nitrophenol was eluted with 100% ethyl acetate and 10 was flushed from the column using 20% methanol/DCM resulting in a colorless oil (39 g, 81% yield). Calculated mass for $C_{42}H_{69}N_5O_{12}$=836.0 m/z. Found [M+H]=837.0.

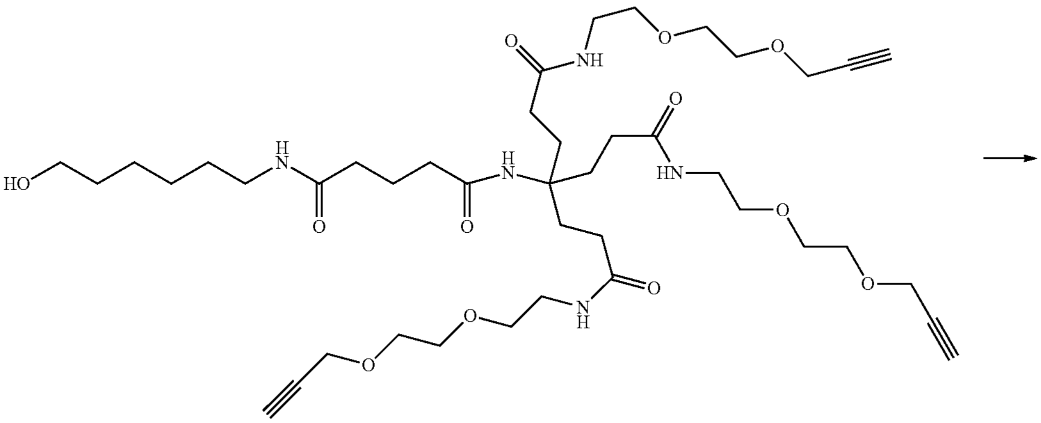

10

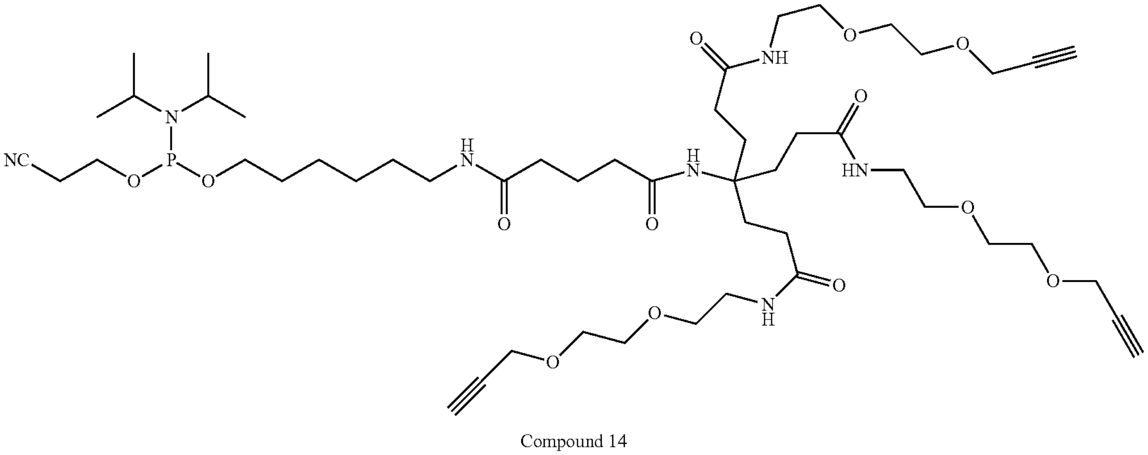

Compound 14

Alcohol 10 was co-stripped twice with 10 volumes of acetonitrile to remove any residual methanol from chromatography solvents and once more with dry dichloromethane (KF<60 ppm) to remove trace water. The alcohol 10 (2.30 g, 2.8 mmol) was dissolved in 5 volumes dry dichloromethane (KF<50 ppm) and treated with diisopropylammonium tetrazolide (188 mg, 1.1 mmol). The solution was cooled to 0° C. and treated with 2-cyanoethyl N,N,N',N'-tetraisopropylphosphoramidite (1.00 g, 3.3 mmol) dropwise. The solution was removed from ice-bath and stirred at 20° C. The reaction was found to be complete within 3-6 hours. The reaction mixture was cooled to 0° C. and treated with 10 volumes of a 1:1 solution of saturated ammonium bicarbonate/brine and then warmed to ambient over 1 minute and allowed to stir an additional 3 minutes at 20° C. The biphasic mixture was transferred to a separatory funnel and 10 volumes of dichloromethane was added. The organic layer was separated, and washed with 10 volumes of saturated sodium bicarbonate solution to hydrolyze unreacted bis-phosphorous reagent. The organic layer was dried over sodium sulfate and concentrated to an oil resulting in 3.08 g of 94 wt % Compound 14. Calculated mass for $C_{51}H_{86}N_7O_{13}P$=1035.6 m/z. Found [M+H]=1036.

H. Conjugation of Targeting Ligands

Either prior to or after annealing, the 5' or 3' tridentate alkyne functionalized sense strand is conjugated to targeting ligands. The following example describes the conjugation of targeting ligands to the annealed duplex: Stock solutions of 0.5M Tris(3-hydroxypropyltriazolylmethyl)amine (THPTA), 0.5M of Cu(II) sulfate pentahydrate (Cu(II) $SO_4 0.5H_2O$) and 2M solution of sodium ascorbate were prepared in deionized water. A 75 mg/mL solution in DMSO of targeting ligand was made. In a 1.5 mL centrifuge tube containing tri-alkyne functionalized duplex (3 mg, 75 μL, 40 mg/mL in deionized water, ~15,000 g/mol), 25 μL of 1M Hepes pH 8.5 buffer is added. After vortexing, 35 μL of DMSO was added and the solution is vortexed. Targeting ligand was added to the reaction (6 equivalents/duplex, 2 equivalents/alkyne, ~15 μL) and the solution is vortexed. Using pH paper, pH was checked and confirmed to be pH ~8. In a separate 1.5 mL centrifuge tube, 50 μL of 0.5M THPTA was mixed with 10 uL of 0.5M $Cu(II)SO_4.5H_2O$, vortexed, and incubated at room temp for 5 min. After 5 min, THPTA/Cu solution (7.2 μL, 6 equivalents 5:1 THPTA:Cu) was added to the reaction vial, and vortexed. Immediately afterwards, 2M ascorbate (5 μL, 50 equivalents per duplex, 16.7 per alkyne) was added to the reaction vial and vortexed. Once the reaction was complete (typically complete in 0.5-1 h), the reaction was immediately purified by non-denaturing anion exchange chromatography.

Example 2. In Vivo Intratrcheal Administration of Beta-ENaC RNAi Agents in Rats

On study day 1, male Sprague Dawley rats were administered 200 microliters via a microsprayer device (Penn Century, Philadelphia, PA) suitable for intratracheal (IT) administration of isotonic saline, or 0.5 mg/kg, 1.0 mg/kg, or 2 mg/kg of beta-ENaC RNAi agent AD06284 or 0.5 mg/kg, 1.0 mg/kg, or 2 mg/kg of beta-ENaC RNAi agent AD06285 (each RNAi agent without being linked to a targeting ligand and formulated in isotonic saline). Four (4) rats were dosed per group. Rats were sacrificed on study day 8, and total RNA was isolated from both lungs following collection and homogenization. Rat Beta-ENaC (SCNN1B) mRNA expression was quantitated by probe-based quantitative PCR, normalized to rat GAPDH expression, and expressed as fraction of vehicle control group (geometric mean, +/−95% confidence interval).

TABLE 7

Average Relative Rat beta-ENaC mRNA Expression at Sacrifice (Day 8) in Example 2

| Group ID | Average Relative rbeta-ENaC mRNA Expression (n = 4 for each group) | Low (error) | High (error) |
|---|---|---|---|
| Group 1 (isotonic saline) | 1.000 | 0.125 | 0.143 |
| Group 2 (0.5 mg/kg AD06284) | 0.734 | 0.039 | 0.041 |
| Group 3 (1.0 mg/kg AD06284) | 0.876 | 0.162 | 0.199 |
| Group 4 (2.0 mg/kg AD06284) | 0.641 | 0.126 | 0.156 |
| Group 5 (0.5 mg/kg AD06285) | 0.962 | 0.065 | 0.070 |
| Group 6 (1.0 mg/kg AD06285) | 0.926 | 0.118 | 0.135 |
| Group 7 (2.0 mg/kg AD06285) | 0.774 | 0.146 | 0.180 |

Example 3 In Vivo Intratracheal Administration of Bea-ENaC RNAi Agents Conjugated to Epithelial Cell Targeting Ligands in Rats On study day 1, male Sprague Dawley rats were administered 200 microliters via a microsprayer device (Penn Century, Philadelphia, PA) suitable for intratracheal (IT) administration of isotonic saline, or 0.5 mg/kg, 1.0 mg/kg, or 2.0 mg/kg of beta-ENaC RNAi agent AD06284 conjugated to a tridentate small molecule αvβ6 epithelial cell targeting ligand (Tri-SM6.1, see FIG. 3) at the 5' terminal end of the sense strand, formulated in isotonic saline. Five (5) rats were dosed per group. Rats were sacrificed on study day 8, and total RNA was isolated from both lungs following collection and homogenization. Rat Beta-ENaC (SCNN1B) mRNA expression was quantitated by probe-based quantitative PCR, normalized to rat GAPDH expression, and expressed as fraction of vehicle control group (geometric mean, +/−95% confidence interval).

TABLE 8

Average Relative rBeta-ENaC mRNA Expression at Sacrifice (Day 8) in Example 3

| Group ID | Average Relative rbeta-ENaC mRNA Expression (n = 5 for each group) | Low (error) | High (error) |
|---|---|---|---|
| Group 1 (isotonic saline) | 1.000 | 0.062 | 0.066 |
| Group 2 (0.5 mg/kg AD06284) | 0.984 | 0.339 | 0.518 |
| Group 3 (1.0 mg/kg AD06284) | 0.859 | 0.128 | 0.151 |
| Group 4 (2.0 mg/kg AD06284) | 0.901 | 0.345 | 0.560 |

Example 4. In Vivo Intratracheal Administration of Bea-ENaC RNAi Agents Conjugated to Epithelial Cell Targeting Ligands in Rats On study day 1, male Sprague Dawley rats were administered 200 microliters via a microsprayer device (Penn Century, Philadelphia, PA) suitable for intratracheal (IT) administration, of either isotonic saline vehicle for use as a control, or one of the following beta-ENaC RNAi agents according to the following dosing groups recited in Table 9:

TABLE 9

Dosing Groups of Rats in Example 4

| Group | RNAi Agent and Dose |
|---|---|
| 1 | Isotonic saline (no RNAi agent) |
| 2 | 0.5 mg/kg of AD06284 conjugated to a tridentate small molecule αvβ6 epithelial cell targeting ligand (Tri-SM6.1) at the 5' terminal end of the sense strand, formulated in isotonic saline. |
| 3 | 0.5 mg/kg of AD06499 conjugated to a tridentate small molecule αvβ6 epithelial cell targeting ligand (Tri-SM6.1) at the 5' terminal end of the sense strand, formulated in isotonic saline. |
| 4 | 0.5 mg/kg of AD06494 conjugated to a tridentate small molecule αvβ6 epithelial cell targeting ligand (Tri-SM6.1) at the 5' terminal end of the sense strand, formulated in isotonic saline. |
| 5 | 0.5 mg/kg of AD06495 conjugated to a tridentate small molecule αvβ6 epithelial cell targeting ligand (Tri-SM6.1) at the 5' terminal end of the sense strand, formulated in isotonic saline. |
| 6 | 0.5 mg/kg of AD06496 conjugated to a tridentate small molecule αvβ6 epithelial cell targeting ligand (Tri-SM6.1) at the 5' terminal end of the sense strand, formulated in isotonic saline. |
| 7 | 0.5 mg/kg of AD06497 conjugated to a tridentate small molecule αvβ6 epithelial cell targeting ligand (Tri-SM6.1) at the 5' terminal end of the sense strand, formulated in isotonic saline. |
| 8 | 0.5 mg/kg of AD06498 conjugated to a tridentate small molecule αvβ6 epithelial cell targeting ligand (Tri-SM6.1) at the 5' terminal end of the sense strand, formulated in isotonic saline. |
| 9 | 0.5 mg/kg of AD06501 conjugated to a tridentate small molecule αvβ6 epithelial cell targeting ligand (Tri-SM6.1) at the 5' terminal end of the sense strand, formulated in isotonic saline. |

Figure 1:
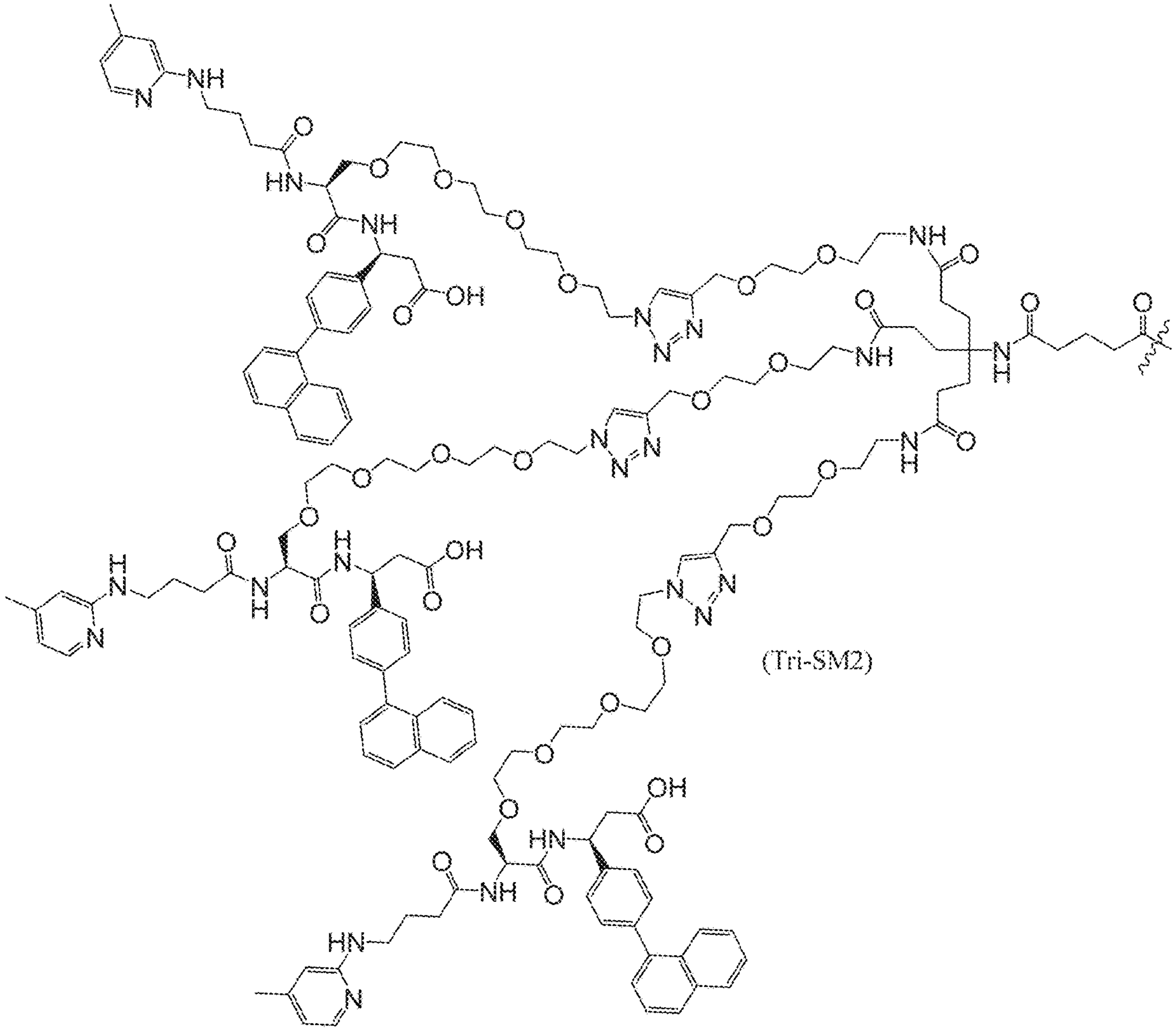
FIG. 1. Chemical structure representation of the tridentate αvβ6 epithelial cell targeting ligand referred to herein as Tri-SM2.
Figure 2:
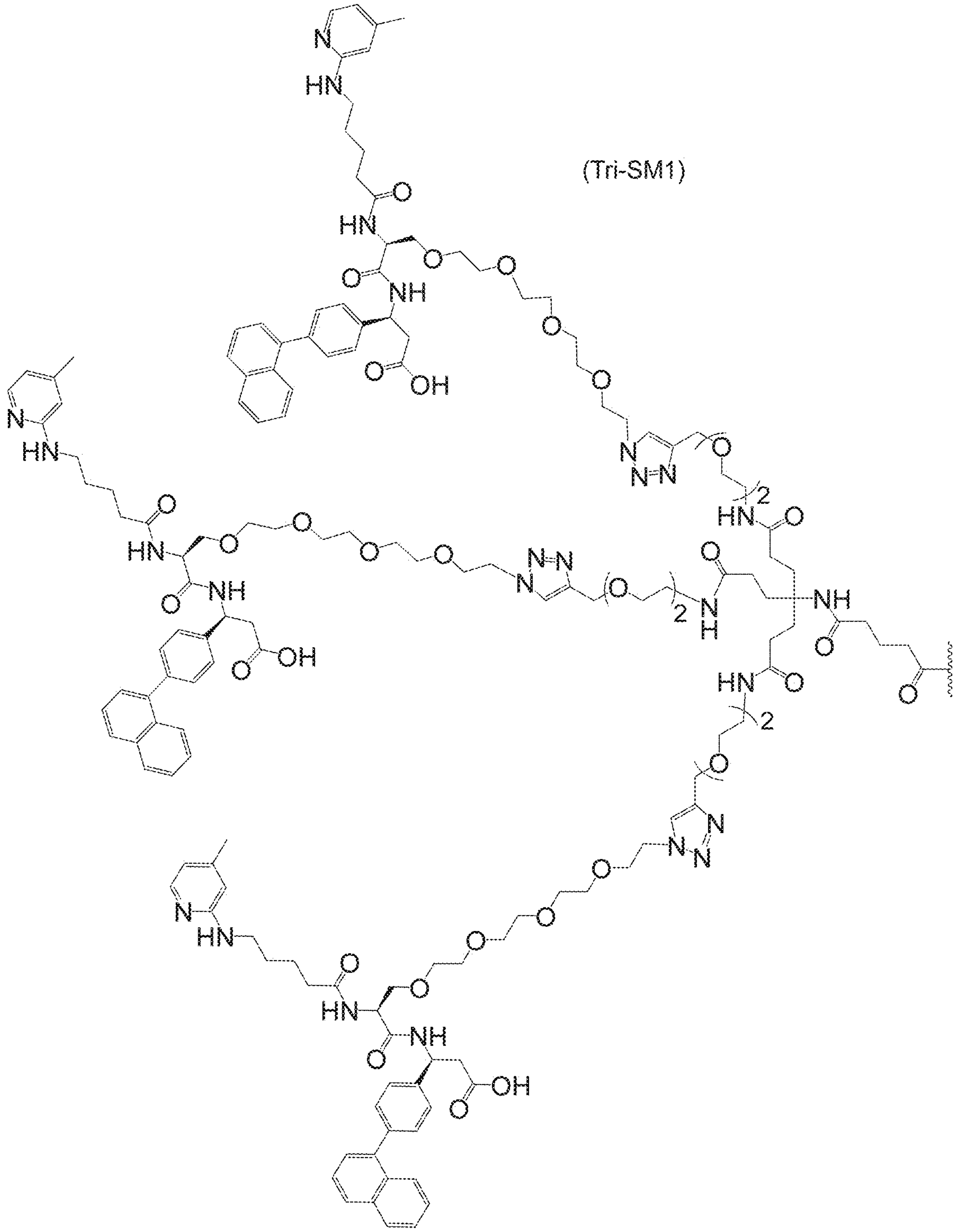
FIG. 2. Chemical structure representation of the tridentate αvβ6 epithelial cell targeting ligand referred to herein as Tri-SM1.
Figure 3:
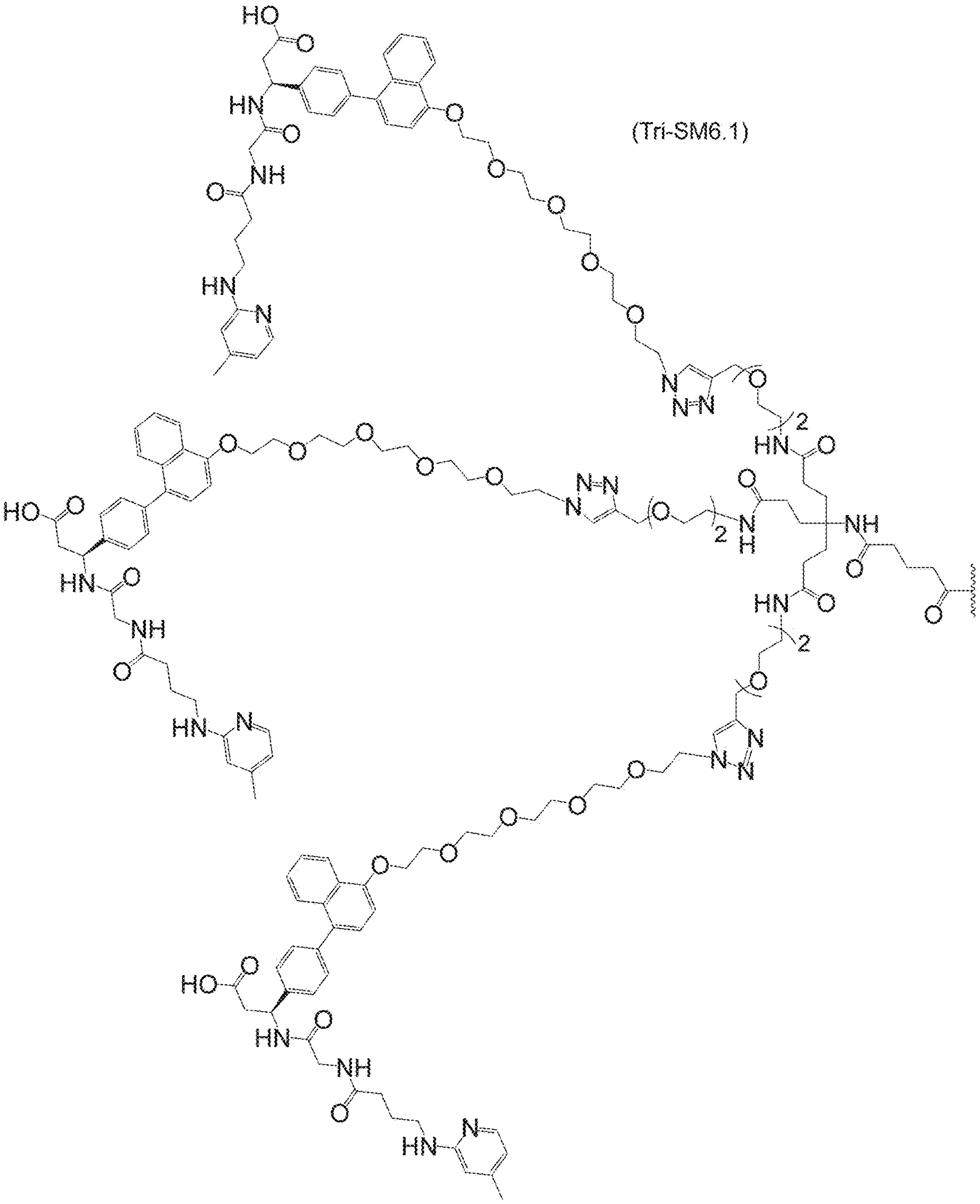
FIG. 3. Chemical structure representation of the tridentate αvβ6 epithelial cell targeting ligand referred to herein as Tri-SM6.1.
Figure 4:
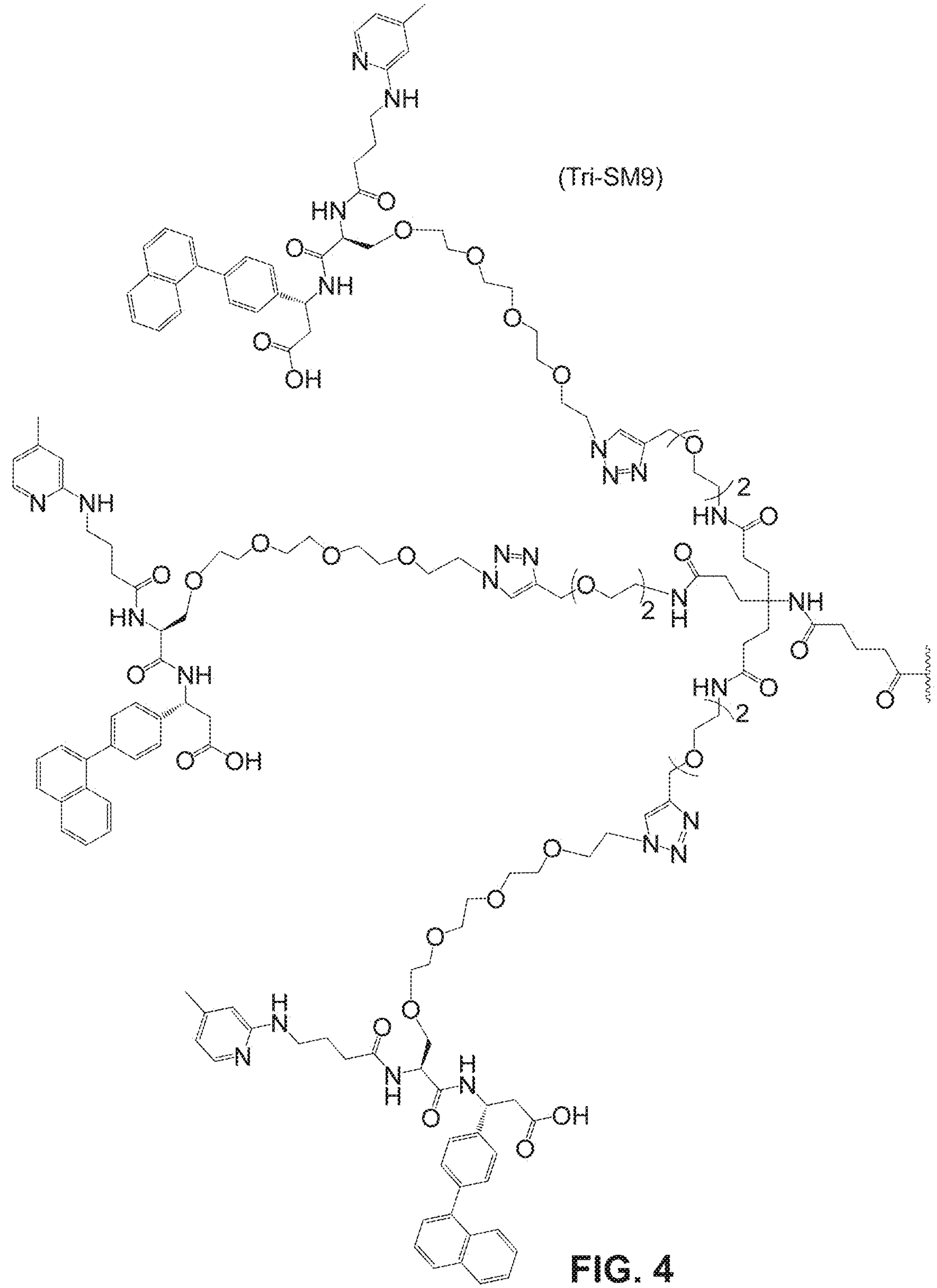
FIG. 4. Chemical structure representation of the tridentate αvβ6 epithelial cell targeting ligand referred to herein as Tri-SM9.
Figure 5:
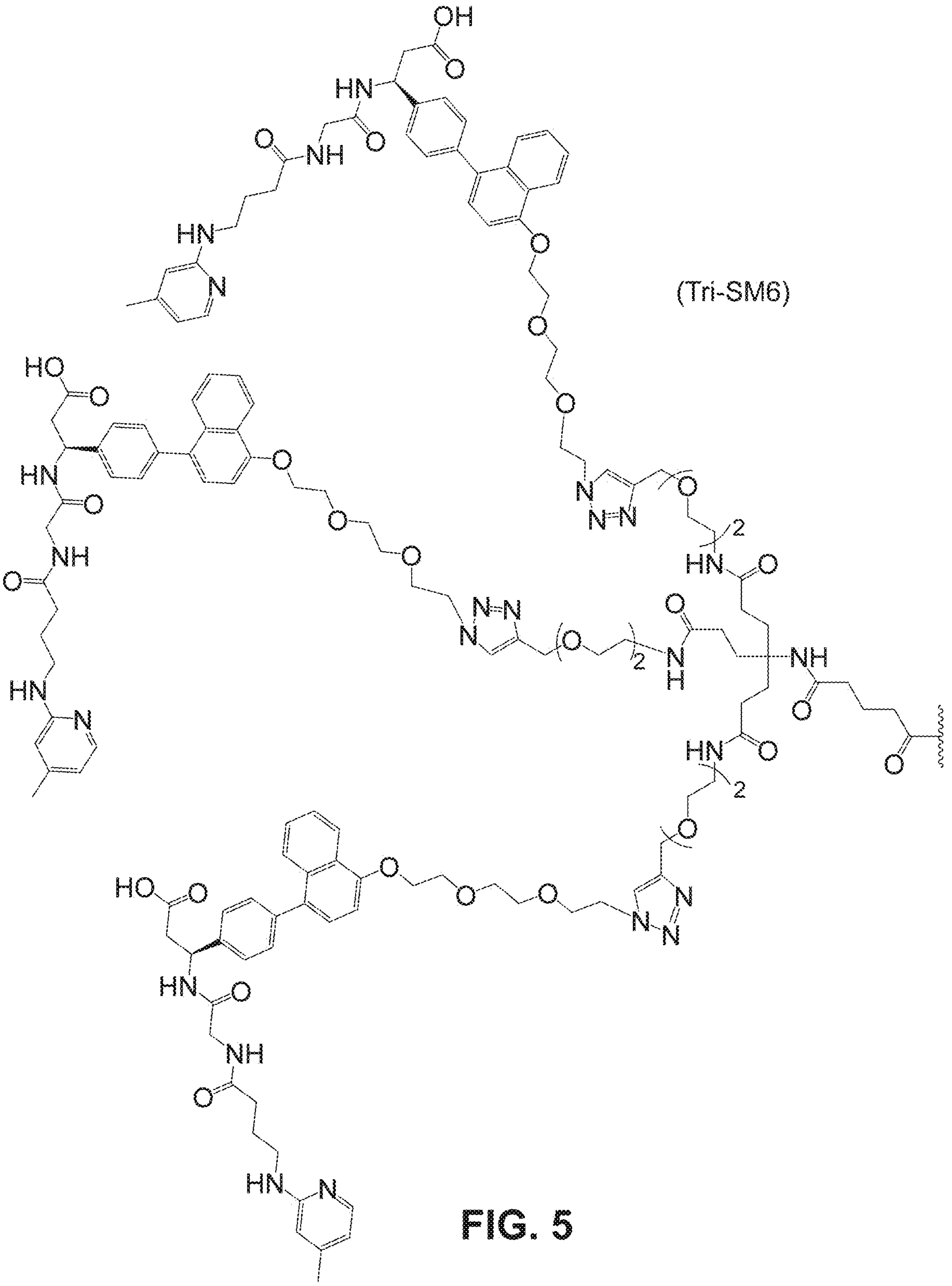
FIG. 5. Chemical structure representation of the tridentate αvβ6 epithelial cell targeting ligand referred to herein as Tri-SM6.
Figure 6:
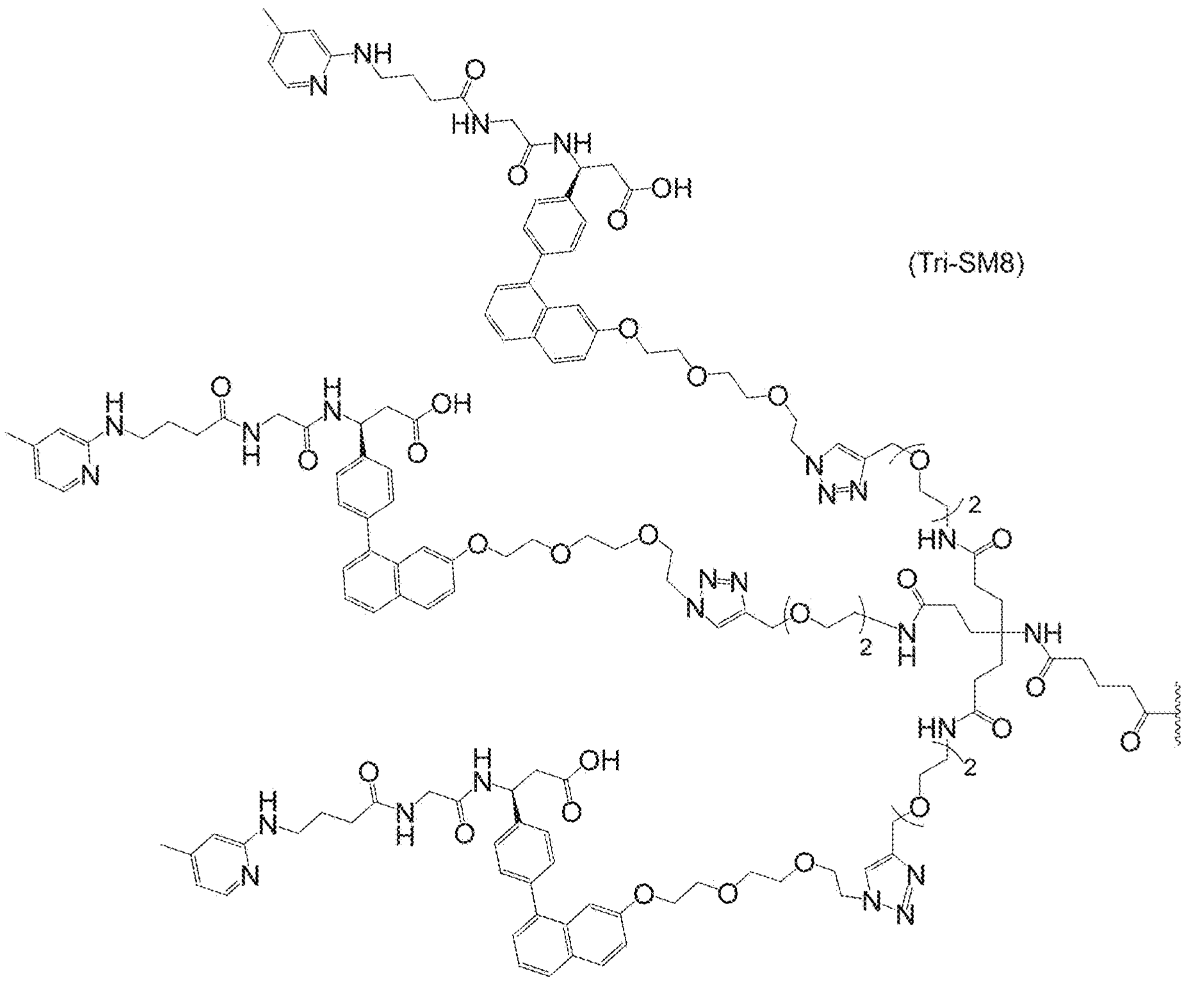
FIG. 6. Chemical structure representation of the tridentate αvβ6 epithelial cell targeting ligand referred to herein as Tri-SM8.
Figure 7:
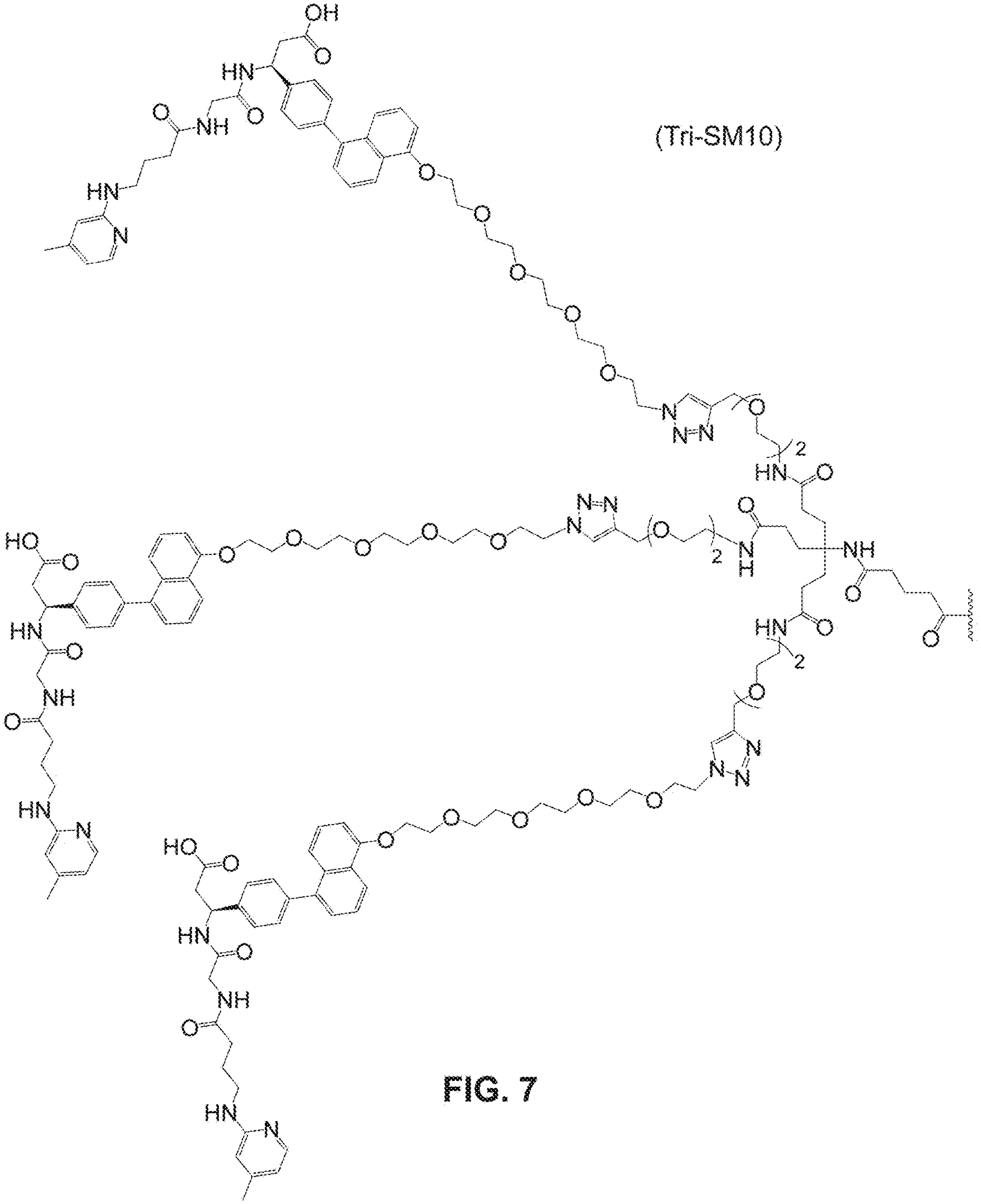
FIG. 7. Chemical structure representation of the tridentate αvβ6 epithelial cell targeting ligand referred to herein as Tri-SM10.
Figure 8:
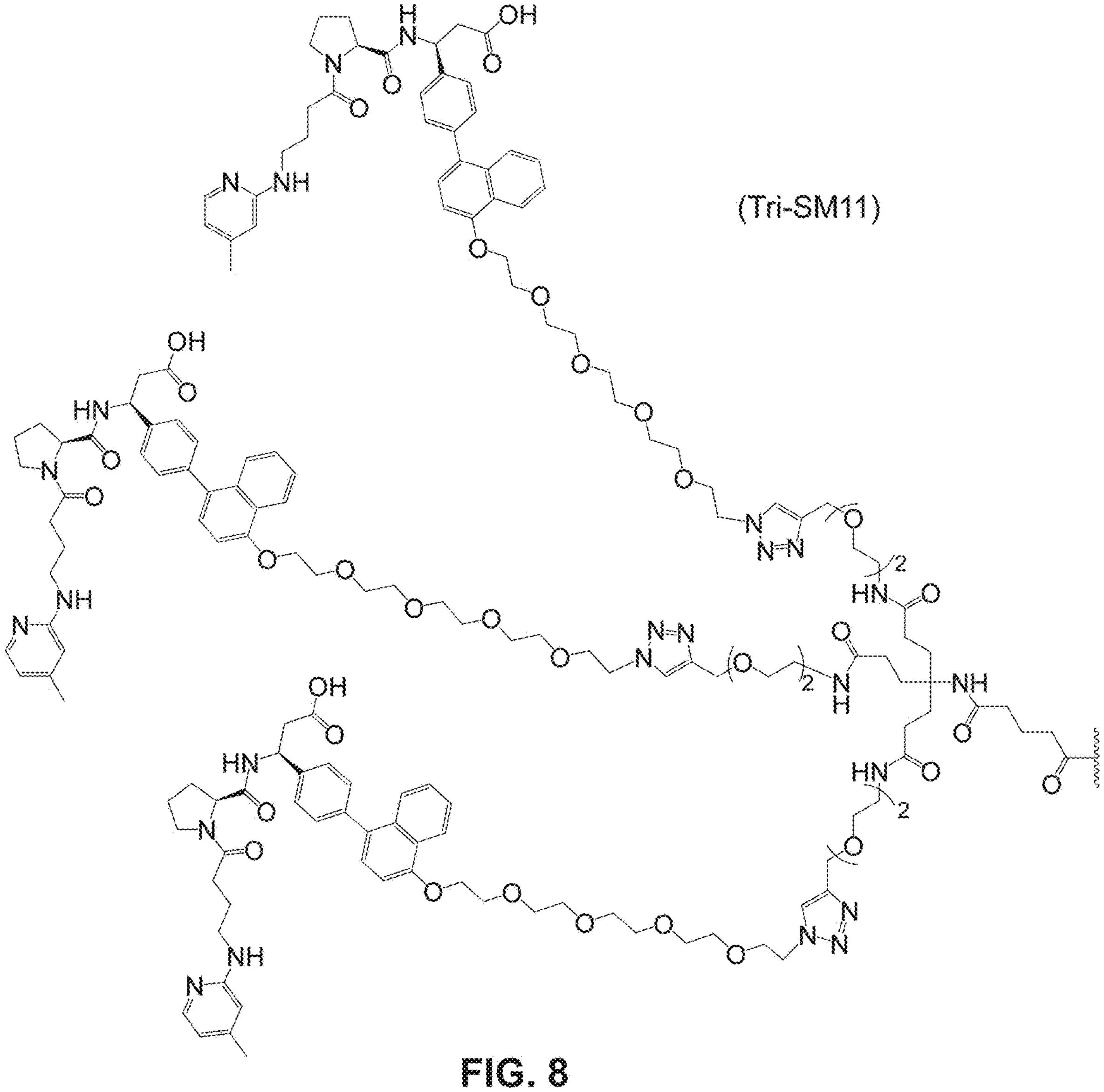
FIG. 8. Chemical structure representation of the tridentate αvβ6 epithelial cell targeting ligand referred to herein as Tri-SM11.

(See, e.g. FIG. 3 for the chemical structure of Tri-SM6.1).

Five (5) rats were dosed in each of Group were dosed (n=5). Rats were sacrificed on study day 8, and total RNA was isolated from both lungs following collection and homogenization. Rat Beta-ENaC (SCNN1B) mRNA expression was quantitated by probe-based quantitative PCR, normalized to rat GAPDH expression, and expressed as fraction of vehicle control group (geometric mean, +/−95% confidence interval).

TABLE 10

Average Relative rBeta-ENaC mRNA Expression at Sacrifice (Day 8) in Example 4

| Group ID | Average Relative rbeta-ENaC mRNA Expression | Low (error) | High (error) |
|---|---|---|---|
| Group 1 (isotonic saline) | 1.000 | 0.161 | 0.192 |
| Group 2 (0.5 mg/kg Tri-SM6.1-AD06284) | 0.877 | 0.173 | 0.216 |
| Group 3 (0.5 mg/kg Tri-SM6.1-AD06499) | 0.827 | 0.130 | 0.154 |
| Group 4 (0.5 mg/kg Tri-SM6.1-AD06494) | 0.623 | 0.072 | 0.081 |
| Group 5 (0.5 mg/kg Tri-SM6.1-AD06495) | 0.887 | 0.083 | 0.092 |
| Group 6 (0.5 mg/kg Tri-SM6.1-AD06496) | 0.775 | 0.092 | 0.104 |
| Group 7 (0.5 mg/kg Tri-SM6.1-AD06497) | 0.558 | 0.057 | 0.064 |
| Group 8 (0.5 mg/kg Tri-SM6.1-AD06498) | 0.873 | 0.070 | 0.076 |
| Group 9 (0.5 mg/kg Tri-SM6.1-AD06501) | 0.750 | 0.152 | 0.190 |

Example 5. In Vivo Administration of Beta-ENaC RNAi Agents Conjugated to Epithelial Cell Targeting Ligands in Rats On study day 1, male Sprague Dawley rats were administered 200 microliters via a microsprayer device (Penn Century, Philadelphia, PA) suitable for intratracheal (IT) administration, of either isotonic saline vehicle for use as a control, or one of the following beta-ENaC RNAi agents according to the following dosing groups recited in Table 11:

TABLE 11

Dosing Groups of Rats in Example 5

| Group | RNAi Agent and Dose | Harvest Day |
|---|---|---|
| 1 | Isotonic saline (no RNAi agent) | Day 8 |
| 2 | 1.0 mg/kg of AD06497 conjugated to a tri dentate small molecule αvβ6 epithelial cell targeting ligand (Tri-SM6.1) at the 5' terminal end of the sense strand, formulated in isotonic saline. | Day 8 |
| 3 | 1.0 mg/kg of AD06497 conjugated to a tri dentate small molecule αvβ6 epithelial cell targeting ligand (Tri-SM6.1) at the 5' terminal end of the sense strand, formulated in isotonic saline. | Day 15 |
| 4 | 1.0 mg/kg of AD06497 conjugated to a tri dentate small molecule αvβ6 epithelial cell targeting ligand (Tri-SM6.1) at the 5' terminal end of the sense strand, formulated in isotonic saline. | Day 22 |

(See, e.g. FIG. 3 for the chemical structure of Tri-SM6.1).

Five (5) rats were dosed in each Group (n=5). Rats were sacrificed on either Day 8, 15, or 22, according to the schedule in Table 11 above, and total RNA was isolated from both lungs following collection and homogenization. Beta-ENaC (SCNN1B) mRNA expression was quantitated by probe-based quantitative PCR, normalized to GAPDH expression, and expressed as fraction of vehicle control group (geometric mean, +/−95% confidence interval).

TABLE 12

Average Relative rENaC mRNA Expression at Sacrifice in Example 5

| Group ID | Average Relative rbeta-ENaC mRNA Expression | Low (error) | High (error) |
|---|---|---|---|
| Group 1 (isotonic saline, day 8 harvest) | 1.000 | 0.099 | 0.110 |
| Group 2 (1.0 mg/kg Tri-SM6.1-AD06497, day 8 harvest) | 0.491 | 0.035 | 0.037 |
| Group 3 (0.5 mg/kg Tri-SM6.1-AD06497, day 15 harvest) | 0.497 | 0.061 | 0.070 |
| Group 4 (0.5 mg/kg Tri-SM6.1-AD06497, day 22 harvest) | 0.436 | 0.062 | 0.073 |

Example 6. Aerosolized Administration of Beta-ENaC RNAi Agents Conjugated to Epithelial Cell Targeting Ligands in Sheep Mucociliary clearance (MCC) has been shown to be correlative with improved lung function ($FEV_1$) in cystic fibrosis (CF) patients. MCC was first measured in normal sheep by inhalation of aerosolized technetium-labeled sulfur colloid, followed by gamma imaging over two hours to establish baseline levels. Starting three days after establishing baseline, normal sheep received single daily inhaled deposited dose of 0.22 mg/kg or 0.5 mg/kg of aerosolized beta-ENaC RNAi agent AD06598 conjugated to a tridentate small molecule αvβ6 epithelial cell targeting ligand (Tri-SM6.1) at the 5' terminal end of the sense strand formulated in isotonic saline (referred to in FIGS. 9 and 20 as APERC-2), over three consecutive days on study days 1, 2, and 3 (i.e., three total doses). A dosing volume of 17.5 mL (0.5 mg/kg) or 8.75 mL (0.22 mg/kg) at 10 mg/mL concentration beta-ENaC RNAi agent AD06598 was aerosolized and administered to the sheep via nasal intubation. Three sheep in each Group were tested (n=3). On day 17 (two weeks after final dose), sheep were again administered inhalation of aerosolized technetium-labeled sulfur colloid, followed by gamma imaging over two hours.

Figure 9:
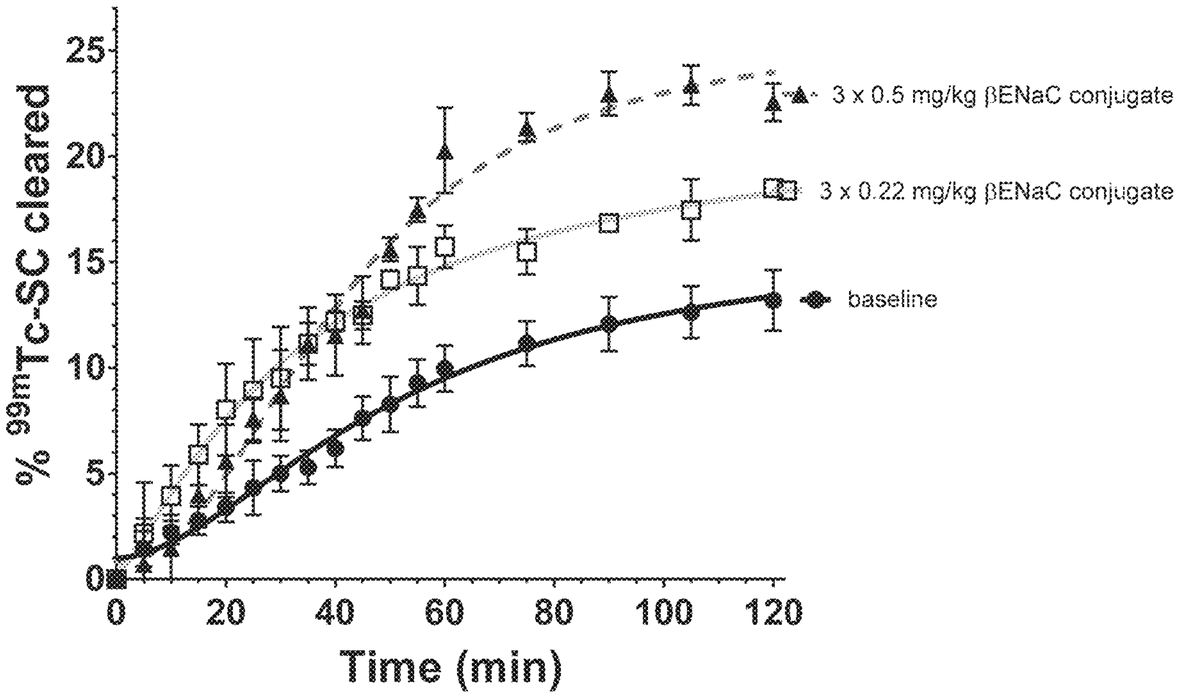
FIG. 9. Mucociliary clearance levels in sheep administered with beta-ENaC RNAi agent AD06598 conjugated to a tridentate small molecule αvβ6 epithelial cell targeting ligand (Tri-SM6.1) at the 5' terminal end of the sense strand, formulated in isotonic saline, as more fully described in Example 6.

As shown in FIG. 9, administration of the beta-ENaC RNAi agent dose-dependently showed an increase in MCC above the baseline measurement two weeks after dosing. The observed acceleration of MCC is consistent with improved airway hydration.

Example 7. Aerosolized Administration of Beta-ENaC RNAi Agents Conjugated to Epithelial Cell Targeting Ligands in Sheep Beta-ENaC RNAi agents were evaluated in the sheep Mucociliary clearance (MCC) model. MCC was first measured in normal sheep by inhalation of aerosolized technetium-labeled sulfur colloid, followed by gamma imaging over two hours to establish baseline levels. Starting three days after establishing baseline, normal sheep received a single inhaled deposited dose of 0.5 mg/kg of 1) aerosolized beta-ENaC RNAi agent AD06598 conjugated to a tridentate small molecule αvβ6 epithelial cell targeting ligand (Tri-SM6.1) at the 5' terminal end of the sense strand (referred to as APERC-2), formulated in isotonic saline; or 2) aerosolized beta-ENaC RNAi agent AD07099 conjugated to a tridentate small molecule αvβ6 epithelial cell targeting ligand (Tri-SM6.1) at the 5' terminal end of the sense strand (referred to as APERC-5), formulated in isotonic saline. A dosing volume of 17.5 mL at 10 mg/mL concentration of each respective beta-ENaC RNAi agent was aerosolized and administered to the sheep via nasal intubation. One sheep was tested (n=1) with APERC-2, and three sheep were tested in the APERC-5 group (n=3). On day 14 (two weeks after the single dose), sheep were again administered inhalation of aerosolized technetium-labeled sulfur colloid, followed by gamma imaging over two hours.

For example, when fully conjugated and annealed, APERC-2 has the following sense and antisense strand structure:

```
Modified Sense Strand (5'→3'):
                                        (SEQ ID NO: 246)
(TriSM6.1-avb6-TA14)gscaacuguUfAfCfaucuucaacus
(invAb)

Modified Antisense Strand (5'→3'):
                                        (SEQ ID NO: 127)
asGfsusUfgAfagaugUfaAfcAfgUfuGfsc
```

For the structure of (TriSM6.1-avb6-TA14), see FIG. 22.

```
Sense Strand Underlying Base Sequence (5'→3')
                                        (SEQ ID NO: 223)
GCAACUGUUACAUCUUCAACU

Antisense Strand Underlying Base Sequence (5'→3')
                                        (SEQ ID NO: 195)
AGUUGAAGAUGUAACAGUUGC
```

Further, for example, when fully conjugated and annealed, APERC-5 has the following sense and antisense strand structure:

```
Modified Sense Strand (5'→3'):
                                        (SEQ ID NO: 187)
(TriSM6.1-avb6-TA14)gscaacuguUfAfCfaucuucaacas
(invAb)

Modified Antisense Strand (5'→3'):
                                        (SEQ ID NO: 138)
cPrpusGfsusUfgAfagaugUfaAfcAfgUfuGfsc
```

For the structure of (TriSM6.1-avb6-TA14), see FIG. 22. For the full chemical structure of APERC-5 see FIGS. 27A through 27D (free acid) and 28A through 28D (sodium salt).

```
Sense Strand Underlying Base Sequence (5'→3')
                                        (SEQ ID NO: 227)
GCAACUGUUACAUCUUCAACA

Antisense Strand Underlying Base Sequence (5'→3')
                                        (SEQ ID NO: 203)
UGUUGAAGAUGUAACAGUUGC
```

Figure 20:
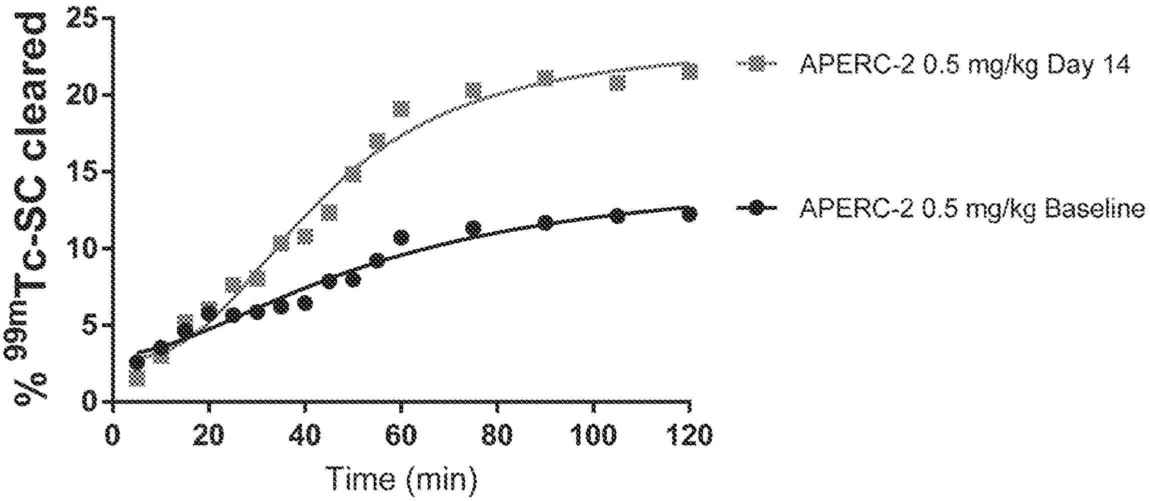
FIG. 20. Mucociliary clearance levels in sheep administered with beta-ENaC RNAi agent AD06598 conjugated to a tridentate small molecule αvβ6 epithelial cell targeting ligand (Tri-SM6.1) at the 5' terminal end of the sense strand (referred to as "APERC-2"), formulated in isotonic saline, as more fully described in Example 7.

As shown in FIG. 20, administration of the beta-ENaC RNAi agent AD06598 conjugated to a tridentate small molecule αvβ6 epithelial cell targeting ligand (Tri-SM6.1) (APERC-2) showed an increase in MCC above the baseline measurement two weeks after dosing. For example, at the 2 hour timepoint (120 minutes), a single 0.5 mg/kg dose of APERC-2 resulted in a 76% increase over baseline at day 14. (See FIG. 20).

Figure 11:
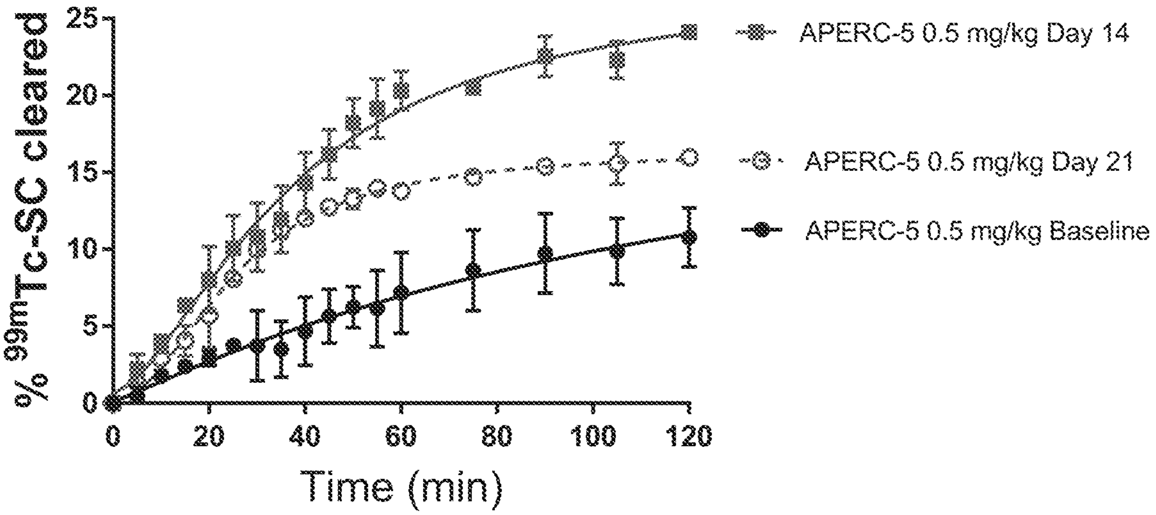
FIG. 11. Mucociliary clearance levels in sheep administered with beta-ENaC RNAi agent AD07099 conjugated to a tridentate small molecule αvβ6 epithelial cell targeting ligand (Tri-SM6.1) at the 5' terminal end of the sense strand (referred to as "APERC-5"), formulated in isotonic saline, as more fully described in Example 7 and 11.
Figure 12:
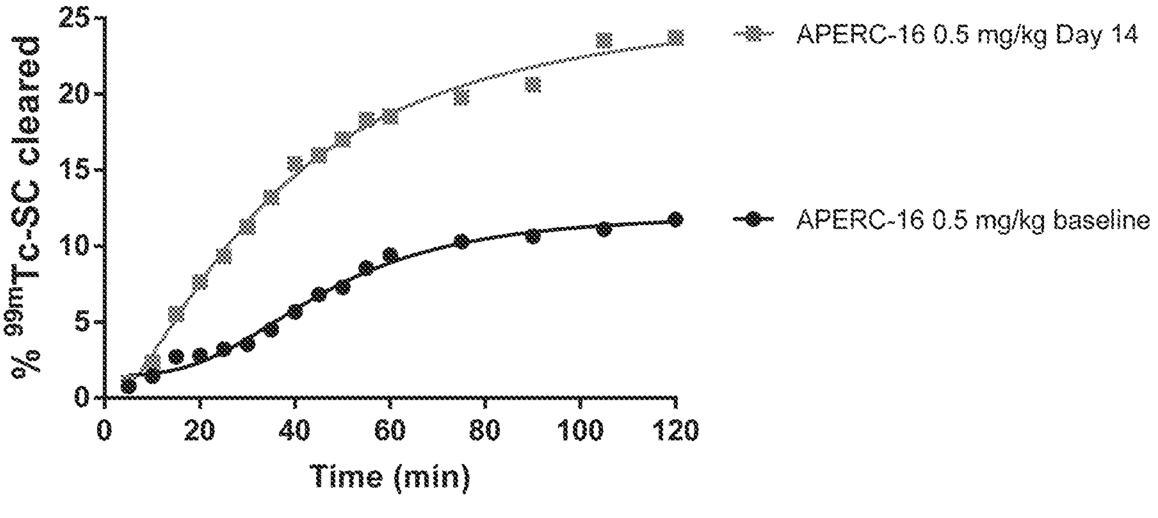
FIG. 12. Mucociliary clearance levels in sheep administered with beta-ENaC RNAi agent AD07255 conjugated to a tridentate small molecule αvβ6 epithelial cell targeting ligand (Tri-SM6.1) at the 5' terminal end of the sense strand (referred to as "APERC-16"), formulated in isotonic saline, as more fully described in Example 10.
Figure 13:
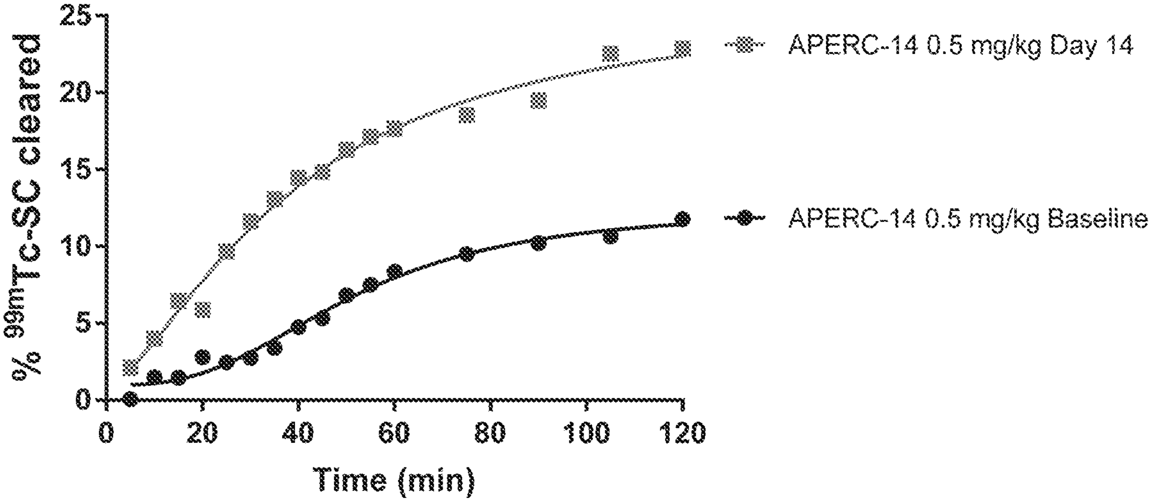
FIG. 13. Mucociliary clearance levels in sheep administered with beta-ENaC RNAi agent AD07253 conjugated to a tridentate small molecule αvβ6 epithelial cell targeting ligand (Tri-SM6.1) at the 5' terminal end of the sense strand (referred to as "APERC-14"), formulated in isotonic saline, as more fully described in Example 10.
Figure 14:
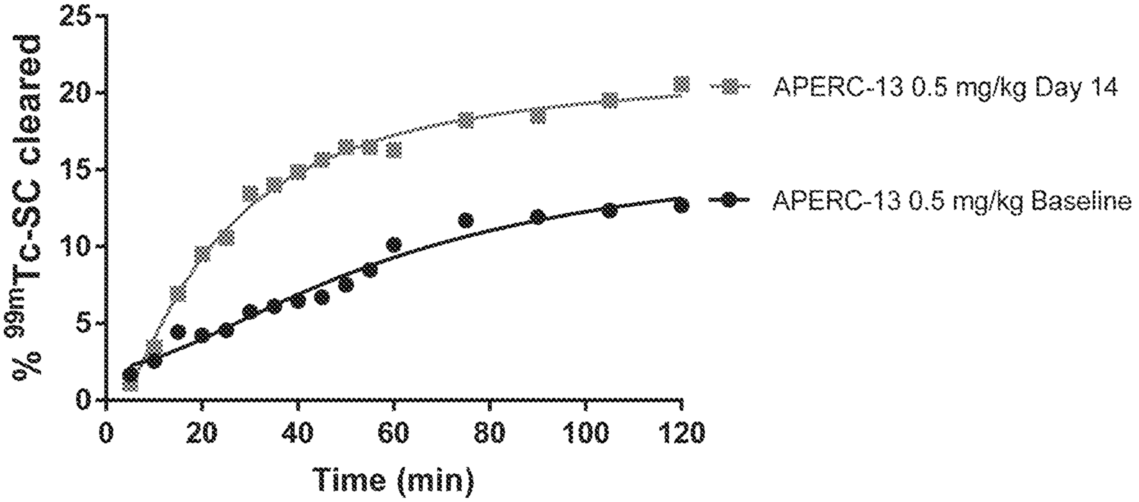
FIG. 14. Mucociliary clearance levels in sheep administered with beta-ENaC RNAi agent AD07252 conjugated to a tridentate small molecule αvβ6 epithelial cell targeting ligand (Tri-SM6.1) at the 5' terminal end of the sense strand (referred to as "APERC-13"), formulated in isotonic saline, as more fully described in Example 10.

Moreover, as shown in FIG. 11, administration of the beta-ENaC RNAi agent AD07099 conjugated to a tridentate small molecule αvβ6 epithelial cell targeting ligand (Tri-SM6.1) (APERC-5) also showed an increase in MCC above the baseline measurement two weeks after dosing. For example, at the two hour scan timepoint, a single 0.5 mg/kg dose of APERC-5 resulted in a 124% increase over baseline at day 14. (See FIG. 11).

Example 8. Aerosolized Administration of Beta-ENaC RNAi Agents Conjugated to Epithelial Cell Targeting Ligands in Sheep Beta-ENaC RNAi agents were evaluated in the sheep Mucociliary clearance (MCC) model. MCC was first measured in normal sheep by inhalation of aerosolized technetium-labeled sulfur colloid, followed by gamma imaging over two hours to establish baseline levels. Starting three days after establishing baseline, normal sheep received a single inhaled deposited dose of 0.5 mg/kg of 1) aerosolized beta-ENaC RNAi agent AD07217 conjugated to a tridentate small molecule αvβ6 epithelial cell targeting ligand (Tri-SM6.1) at the 5' terminal end of the sense strand (referred to as APERC-7), formulated in isotonic saline; or 2) aerosolized beta-ENaC RNAi agent AD07217 conjugated to a tridentate small molecule αvβ6 epithelial cell targeting ligand (Tri-SM6.1) at the 5' terminal end of the sense strand that further included a cysteine-maleimide linker (referred to as APERC-8), formulated in isotonic saline (see FIG. 23 for the chemical structure of αvβ6 epithelial cell targeting ligand Tri-SM6.1 that includes the cysteine-maleimide linker); or 3) aerosolized beta-ENaC RNAi agent AD06599 conjugated to a tridentate small molecule αvβ6 epithelial cell targeting ligand (Tri-SM6.1) at the 5' terminal end of the sense strand (referred to as APERC-9), formulated in isotonic saline. A dosing volume of 17.5 mL at 10 mg/mL concentration of the respective beta-ENaC RNAi agent was aerosolized and administered to the sheep via nasal intubation. One sheep in each Group was tested (n=1), with the exception of APERC-7, which was administered to three sheep (n=3). On day 14 (two weeks after the single dose), sheep were again administered inhalation of aerosolized technetium-labeled sulfur colloid, followed by gamma imaging over two hours.

For example, when fully conjugated and annealed, APERC-7 has the following sense and antisense strand structure:

```
Modified Sense Strand (5'→3'):
                                        (SEQ ID NO: 188)
(TriSM6.1-avb6-TA14)gsca_2NacuguUfAfCfaucuucaacus
(invAb)

Modified Antisense Strand (5'→3'):
                                        (SEQ ID NO: 127)
asGfsusUfgAfagaugUfaAfcAfgUfuGfsc
```

For the structure of (TriSM6.1-avb6-TA14), see FIG. 22. For the full chemical structure of APERC-7 see FIG. 25A through 25D (free acid) and 26A through 26D (sodium salt).

```
Sense Strand Underlying Base Sequence (5'→3')
                                        (SEQ ID NO: 229)
GC(A^2N)ACUGUUACAUCUUCAACU

Antisense Strand Underlying Base Sequence (5'→3')
                                        (SEQ ID NO: 195)
AGUUGAAGAUGUAACAGUUGC
```

The conjugated construct of APERC-7 can be synthesized using the functionalized TriAlk14 group at the 5' end of the sense strand (AD07482 in Tables 5A and 5B, above). Alternatively, the NH2-C6 group at the 5' end of the sense strand AD07217) can be coupled to compound 22 (Example 1, part e, above) to produce a structurally identical intermediate. Using either method, the same final construct can be achieved.

Figure 10:
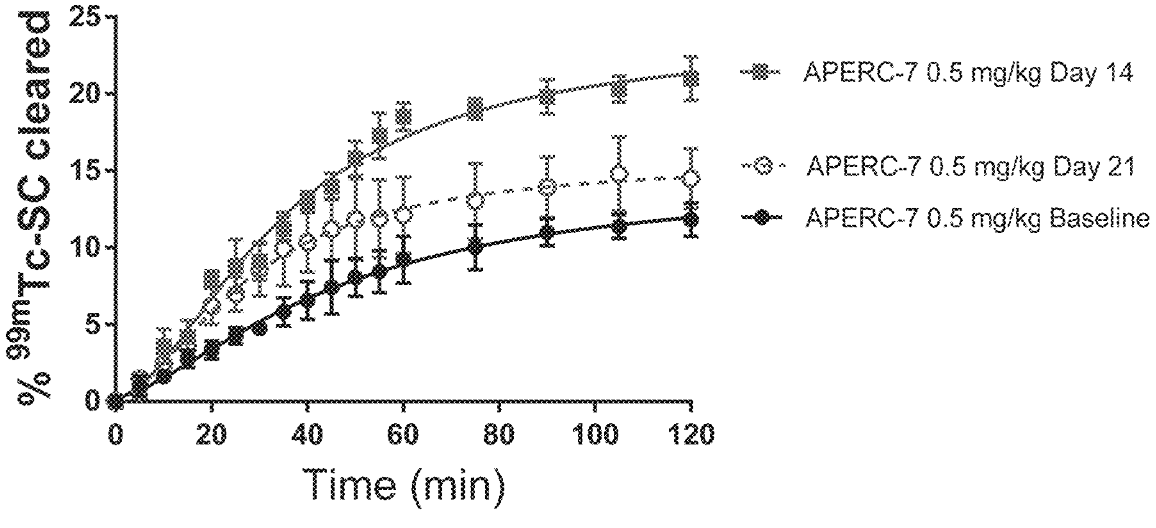
FIG. 10. Mucociliary clearance levels in sheep administered with beta-ENaC RNAi agent AD07217 conjugated to a tridentate small molecule αvβ6 epithelial cell targeting ligand (Tri-SM6.1) at the 5' terminal end of the sense strand (referred to as "APERC-7"), formulated in isotonic saline, as more fully described in Examples 8 and 11.

As shown in FIG. 10, administration of the beta-ENaC RNAi agent AD07217 conjugated to a tridentate small molecule αvβ6 epithelial cell targeting ligand (Tri-SM6.1) (APERC-7) showed an increase in MCC above the baseline measurement two weeks after dosing, with a 78% increase over baseline at day 14 at the two hour scan timepoint.

Figure 19:
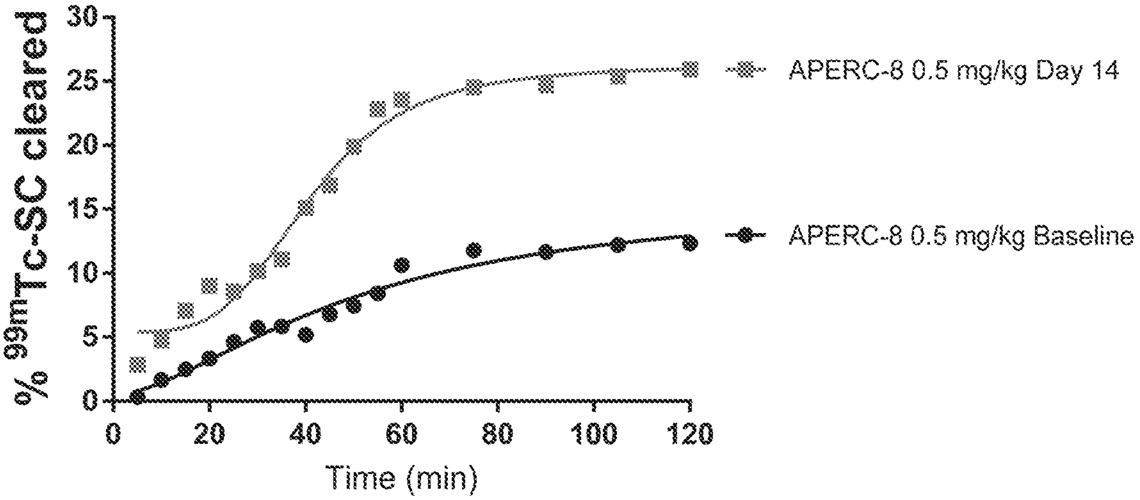
FIG. 19. Mucociliary clearance levels in sheep administered with beta-ENaC RNAi agent AD07217 conjugated to a tridentate small molecule αvβ6 epithelial cell targeting ligand (Tri-SM6.1) at the 5' terminal end of the sense strand with a cysteine-maleimide linker (referred to as "APERC-8"), formulated in isotonic saline, as more fully described in Example 8.

Similarly, as shown in FIG. 19, administration of the beta-ENaC RNAi agent AD07217 conjugated to a tridentate small molecule αvβ6 epithelial cell targeting ligand (Tri-SM6.1) with a cysteine-maleimide linker (APERC-8) showed a 110% increase over baseline at day 14 at the two hour scan timepoint.

Figure 18:
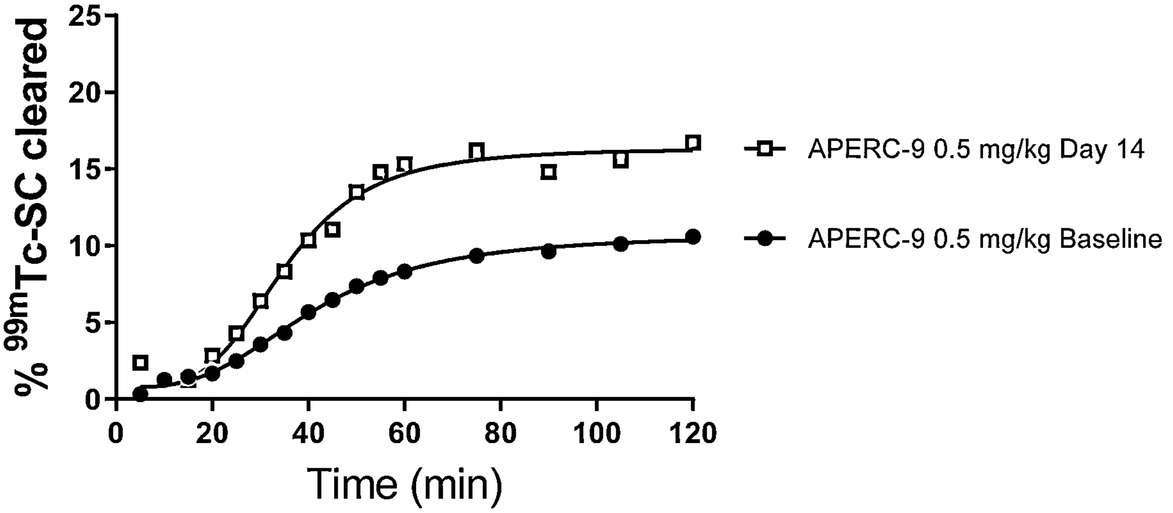
FIG. 18. Mucociliary clearance levels in sheep administered with beta-ENaC RNAi agent AD06599 conjugated to a tridentate small molecule αvβ6 epithelial cell targeting ligand (Tri-SM6.1) at the 5' terminal end of the sense strand (referred to as "APERC-9"), formulated in isotonic saline, as more fully described in Example 8.

As shown in FIG. 18, administration of the beta-ENaC RNAi agent AD06599 conjugated to a tridentate small molecule αvβ6 epithelial cell targeting ligand (Tri-SM6.1) (APERC-9) showed a 58% increase over baseline at day 14 at the two hour scan timepoint.

Example 9. Aerosolized Administration of Beta-ENaC RNAi Agents Conjugated to Epithelial Cell Targeting Ligands in Sheep Beta-ENaC RNAi agents were evaluated in the sheep Mucociliary clearance (MCC) model. MCC was first measured in normal sheep by inhalation of aerosolized technetium-labeled sulfur colloid, followed by gamma imaging over two hours to establish baseline levels. Starting three days after establishing baseline, normal sheep received a single inhaled deposited dose of 0.5 mg/kg of 1) aerosolized beta-ENaC RNAi agent AD07240 conjugated to a tridentate small molecule αvβ6 epithelial cell targeting ligand (Tri-SM6.1) at the 5' terminal end of the sense strand (referred to as APERC-10), formulated in isotonic saline; or 2) aerosolized beta-ENaC RNAi agent AD07250 conjugated to a tridentate small molecule αvβ6 epithelial cell targeting ligand (Tri-SM6.1) at the 5' terminal end of the sense strand (referred to as APERC-11), formulated in isotonic saline; or 3) aerosolized beta-ENaC RNAi agent AD07251 conjugated to a tridentate small molecule αvβ6 epithelial cell targeting ligand (Tri-SM6.1) at the 5' terminal end of the sense strand (referred to as APERC-12), formulated in isotonic saline. A dosing volume of 17.5 mL at 10 mg/mL concentration of each respective beta-ENaC RNAi agent was aerosolized and administered to the sheep via nasal intubation. One sheep in each Group was tested (n=1). On day 14 (two weeks after the single dose), sheep were again administered inhalation of aerosolized technetium-labeled sulfur colloid, followed by gamma imaging over two hours.

Figure 15:
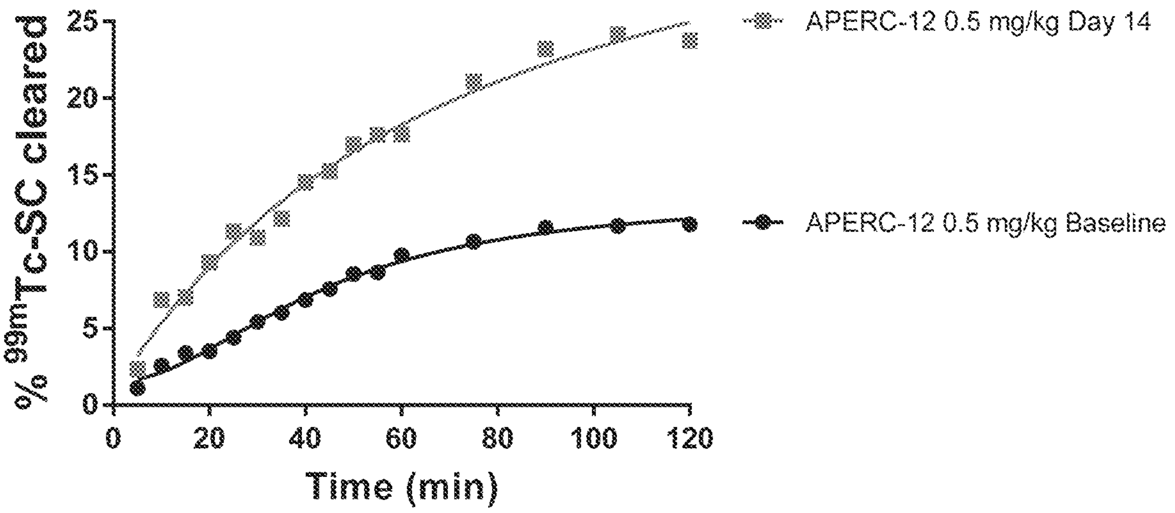
FIG. 15. Mucociliary clearance levels in sheep administered with beta-ENaC RNAi agent AD07251 conjugated to a tridentate small molecule αvβ6 epithelial cell targeting ligand (Tri-SM6.1) at the 5' terminal end of the sense strand (referred to as "APERC-12"), formulated in isotonic saline, as more fully described in Example 9.
Figure 16:
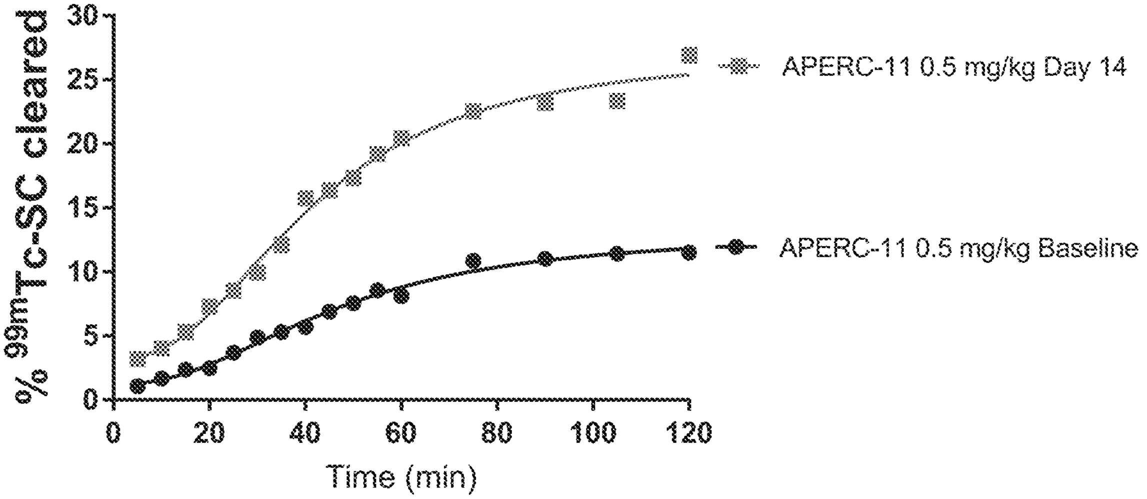
FIG. 16. Mucociliary clearance levels in sheep administered with beta-ENaC RNAi agent AD07250 conjugated to a tridentate small molecule αvβ6 epithelial cell targeting ligand (Tri-SM6.1) at the 5' terminal end of the sense strand (referred to as "APERC-11"), formulated in isotonic saline, as more fully described in Example 9.
Figure 17:
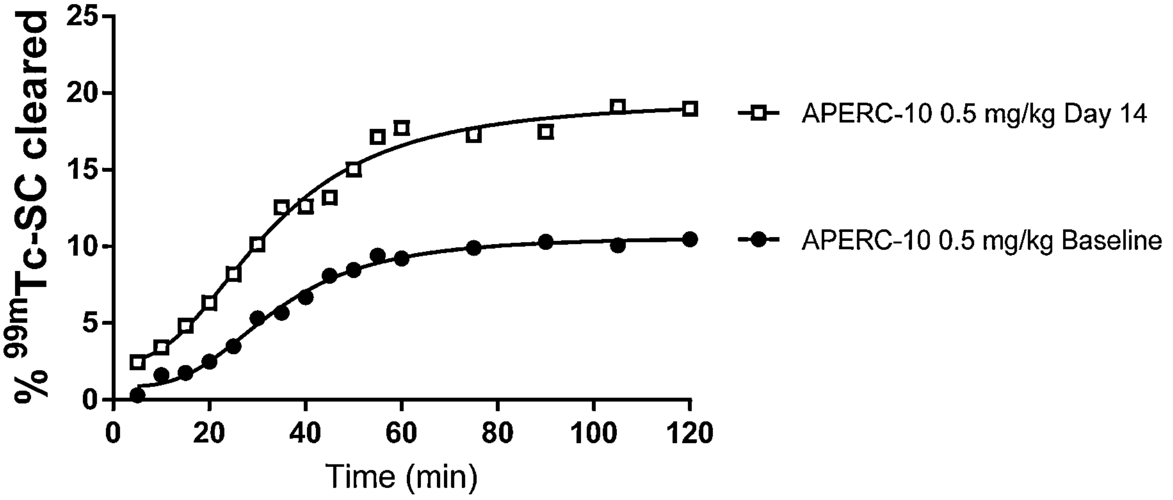
FIG. 17. Mucociliary clearance levels in sheep administered with beta-ENaC RNAi agent AD07240 conjugated to a tridentate small molecule αvβ6 epithelial cell targeting ligand (Tri-SM6.1) at the 5' terminal end of the sense strand (referred to as "APERC-10"), formulated in isotonic saline, as more fully described in Example 9.

As shown in FIG. 17, administration of the beta-ENaC RNAi agent AD07240 conjugated to a tridentate small molecule αvβ6 epithelial cell targeting ligand (Tri-SM6.1) (APERC-10) showed an 82% increase over baseline at day 14 at the two hour timepoint. As shown in FIG. 16, administration of the beta-ENaC RNAi agent AD07250 conjugated to a tridentate small molecule αvβ6 epithelial cell targeting ligand (Tri-SM6.1) (APERC-11) showed a 134% increase over baseline at day 14 at the two hour timepoint. And as shown in FIG. 15, administration of the beta-ENaC RNAi agent AD07251 conjugated to a tridentate small molecule αvβ6 epithelial cell targeting ligand (Tri-SM6.1) (APERC-12) showed a 102% increase over baseline at day 14 at the two hour timepoint.

Example 10. Aerosolized Administration of Bea-ENaC RNAi Agents Conjugated to Epithelial Cell Targeting Ligands in Sheep Beta-ENaC RNAi agents were evaluated in the sheep Mucociliary clearance (MCC) model. MCC was first measured in normal sheep by inhalation of aerosolized technetium-labeled sulfur colloid, followed by gamma imaging over two hours to establish baseline levels. Starting three days after establishing baseline, normal sheep received a single inhaled deposited dose of 0.5 mg/kg of 1) aerosolized beta-ENaC RNAi agent AD07252 conjugated to a tridentate small molecule αvβ6 epithelial cell targeting ligand (Tri-SM6.1) at the 5' terminal end of the sense strand (referred to as APERC-13), formulated in isotonic saline; or 2) aerosolized beta-ENaC RNAi agent AD07253 conjugated to a tridentate small molecule αvβ6 epithelial cell targeting ligand (Tri-SM6.1) at the 5' terminal end of the sense strand (referred to as APERC-14), formulated in isotonic saline; or 3) aerosolized beta-ENaC RNAi agent AD07255 conjugated to a tridentate small molecule αvβ6 epithelial cell targeting ligand (Tri-SM6.1) at the 5' terminal end of the sense strand (referred to as APERC-16), formulated in isotonic saline. A dosing volume of 17.5 mL at 10 mg/mL concentration of each respective beta-ENaC RNAi agent was aerosolized and administered to the sheep via nasal intubation. One sheep in each Group was tested (n=1). On day 14 (two weeks after the single dose), sheep were again administered inhalation of aerosolized technetium-labeled sulfur colloid, followed by gamma imaging over two hours.

As shown in FIG. 17, administration of the beta-ENaC RNAi agent AD07252 conjugated to a tridentate small molecule αvβ6 epithelial cell targeting ligand (Tri-SM6.1) (APERC-13) showed a 62% increase over baseline at day 14 at the two hour timepoint. As shown in FIG. 16, administration of the beta-ENaC RNAi agent AD07253 conjugated to a tridentate small molecule αvβ6 epithelial cell targeting ligand (Tri-SM6.1) (APERC-14) showed a 94% increase over baseline at day 14 at the two hour timepoint. And as shown in FIG. 15, administration of the beta-ENaC RNAi agent AD07255 conjugated to a tridentate small molecule αvβ6 epithelial cell targeting ligand (Tri-SM6.1) (APERC-16) showed a 102% increase over baseline at day 14 at the two hour timepoint.

Example 11. Aerosolized Administration of Beta-ENaC RNAi Agents Conjugated to Epithelial Cell Targeting Ligands in Sheep Beta-ENaC RNAi agents were evaluated in the sheep Mucociliary clearance (MCC) model. MCC was first measured in normal sheep by inhalation of aerosolized technetium-labeled sulfur colloid, followed by gamma imaging over two hours to establish baseline levels. Starting three days after establishing baseline, normal sheep received a single inhaled deposited dose of 0.5 mg/kg of 1) aerosolized beta-ENaC RNAi agent AD07217 conjugated to a tridentate small molecule αvβ6 epithelial cell targeting ligand (Tri-SM6.1) at the 5' terminal end of the sense strand (referred to as APERC-7), formulated in isotonic saline; or 2) aerosolized beta-ENaC RNAi agent AD07099 conjugated to a tridentate small molecule αvβ6 epithelial cell targeting ligand (Tri-SM6.1) at the 5' terminal end of the sense strand (referred to as APERC-5), formulated in isotonic saline. A dosing volume of 17.5 mL at 10 mg/mL concentration of each respective beta-ENaC RNAi agent was aerosolized and administered to the sheep via nasal intubation. Two sheep in each Group were tested (n=2). On day 21 (three weeks after the single dose), sheep were again administered inhalation of aerosolized technetium-labeled sulfur colloid, followed by gamma imaging over two hours.

As shown in FIG. 10, at day 21 administration of the beta-ENaC RNAi agent AD07217 conjugated to a tridentate small molecule αvβ6 epithelial cell targeting ligand (Tri-SM6.1) (APERC-7) continued to show a 17% increase over baseline at the two hour scan timepoint. And as shown in FIG. 11, at day 21 administration of the beta-ENaC RNAi agent AD07099 conjugated to a tridentate small molecule αvβ6 epithelial cell targeting ligand (Tri-SM6.1) (APERC-5) continued to show a 56% increase over baseline at day at the two hour scan timepoint.

Example 12 Human Beta-ENaC (SCNN1B) Relative mRNA Expression in Cultured Primary Normal Human Bronchial Epithelial Cells Transfected with Beta-ENaC RNAI Agents Primary bronchial epithelial cells from normal human lungs were cultured in 96-well tissue culture plates (10,000 cells/well). RNAiMAX transfection reagent was use to transfect cells with: beta-ENaC RNAi agent AD06598 conjugated to a tridentate small molecule αvβ6 epithelial cell targeting ligand (Tri-SM6.1) at the 5' terminal end of the sense strand (referred to as APERC-2), beta-ENaC RNAi agent AD07099 conjugated to a tridentate small molecule αvβ6 epithelial cell targeting ligand (Tri-SM6.1) at the 5' terminal end of the sense strand (referred to as APERC-5), or beta-ENaC RNAi agent AD07217 conjugated to a tridentate small molecule αvβ6 epithelial cell targeting ligand (Tri-SM6.1) at the 5' terminal end of the sense strand (referred to as APERC-7). Forty-eight hours after transfection, total RNA was isolated and cDNA generated from cells by Cells-to-CT extraction and SCNN1B mRNA expression was quantified by probe-based quantitative PCR, normalized to rat GAPDH expression, and expressed as fraction of lipofectamine only (untransfected) control group (geometric mean, +/−95% confidence interval). As shown in FIG. 24, transfection with the disclosed beta-ENaC RNAi agents resulted in potent dose-depending silencing of SCNN1B mRNA expression in cultured normal human bronchial epithelial cells.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent for inhibiting expression of a beta-ENaC gene, comprising:

an antisense strand comprising the nucleotide sequence (5'→3') cPrpusGfsusUfgAfagaugUfaAfcAfgUfuGfsc (SEQ ID NO: 138); and a sense strand comprising a nucleotide sequence that is at least partially complementary to the antisense strand;

wherein a represents 2'-O-methyl adenosine, c represents 2'-O-methyl cytidine, g represents 2'-O-methyl guanosine, and u represents 2'-O-methyl uridine; Af represents 2'-fluoro adenosine, Cf represents 2'-fluoro cytidine, Gf represents 2'-fluoro guanosine, and Uf represents 2'-fluoro uridine; cPrpu represents a 5'-cyclopropyl phosphonate-2'-O-methyl uridine; s represents a phosphorothioate linkage; and wherein all or substantially all of the nucleotides on the sense strand are modified nucleotides.

2. The RNAi agent of claim 1, wherein the sense strand comprises the nucleotide sequence (5'→3') gscaacuguU-fAfCfaucuucaaca (SEQ ID NO: 239)

wherein a represents 2'-O-methyl adenosine, c represents 2'-O-methyl cytidine, g represents 2'-O-methyl guanosine, and u represents 2'-O-methyl uridine; Af represents 2'-fluoro adenosine, Cf represents 2'-fluoro cytidine, Gf represents 2'-fluoro guanosine, and Uf represents 2'-fluoro uridine; s represents a phosphorothioate linkage.

3. The RNAi agent of claim 1, wherein the sense strand comprises one or two inverted abasic residues.

4. The RNAi agent of claim 1, wherein the RNAi agent comprises of a sense strand and an antisense strand that form a duplex having the structure of AD07099 (SEQ ID NO: 138 and SEQ ID NO: 177.

5. The RNAi agent of claim 1, wherein the RNAi agent is linked to a targeting ligand.

6. The RNAi agent of claim 5, wherein the targeting ligand comprises the structure:

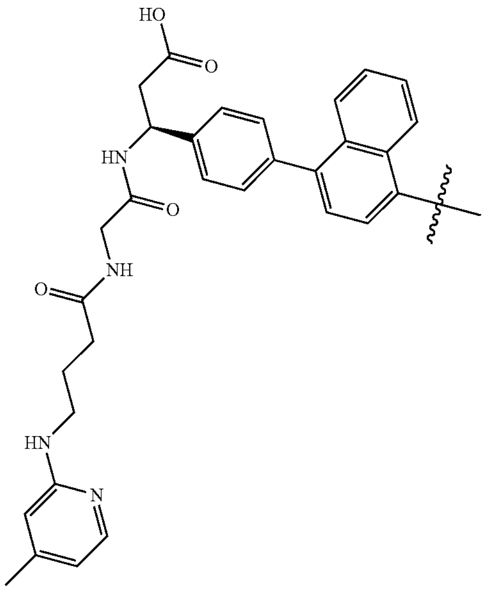 [SMILES: *c1ccc(-c2ccc([C@H](CC(=O)O)NC(=O)CNC(=O)CCCNc3cc(C)ccn3)cc2)c2ccccc12]

or a pharmaceutically acceptable salt thereof, wherein indicates the point of connection to the RNAi agent.

7. The RNAi agent of claim 5, wherein the targeting ligand has a structure selected from the group consisting of:

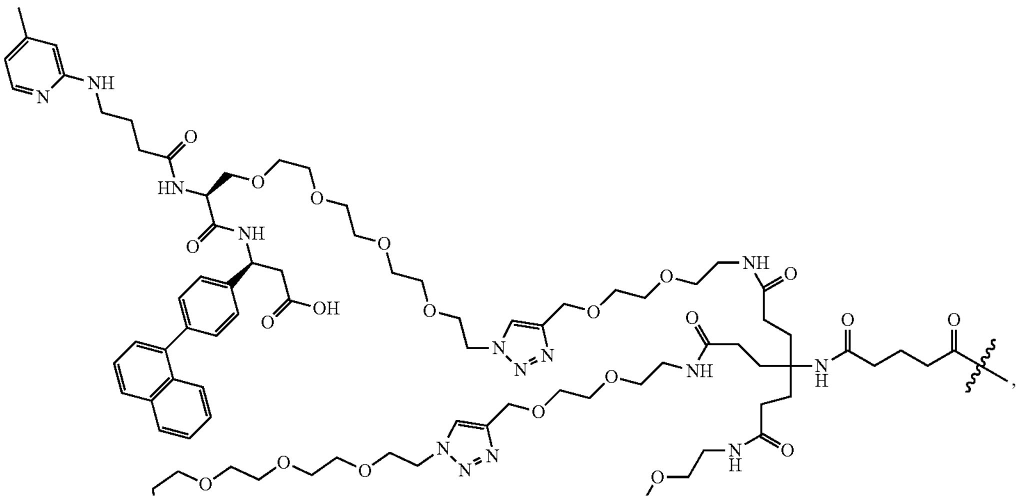
,

-continued
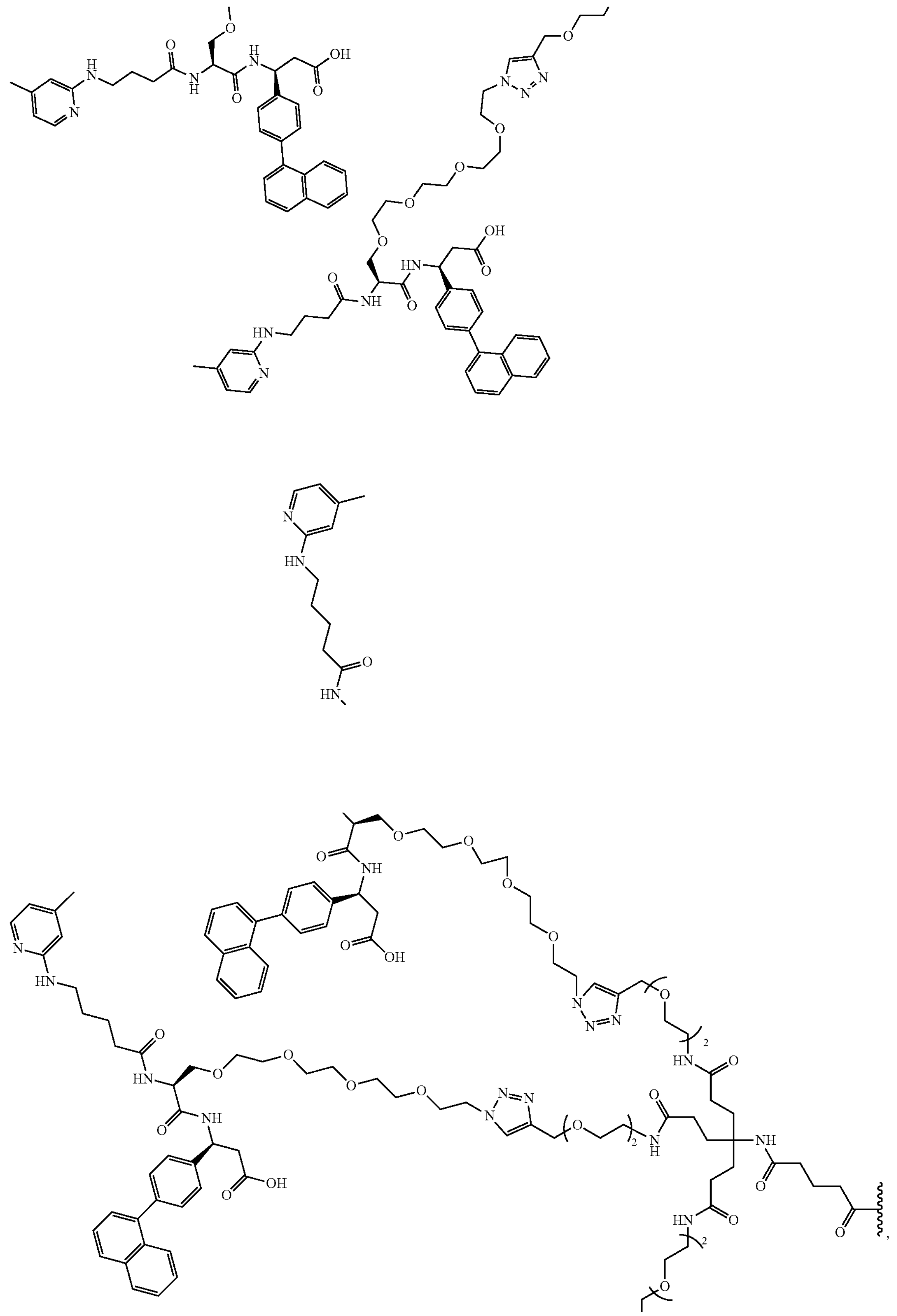

-continued
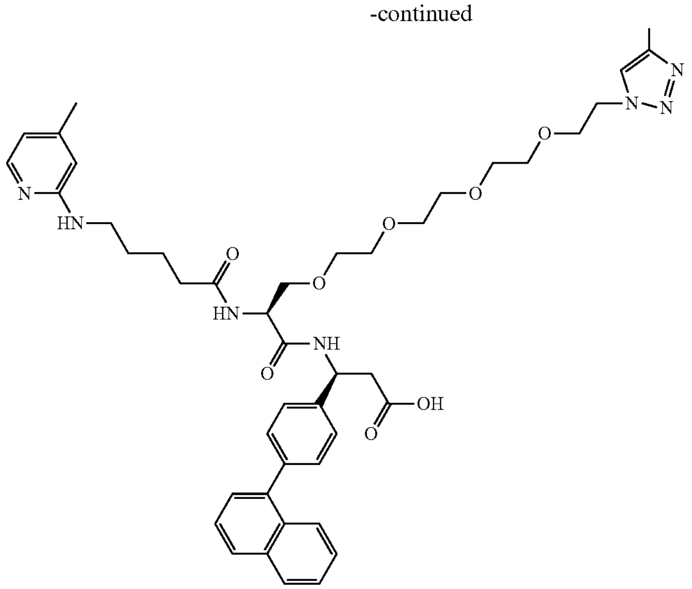
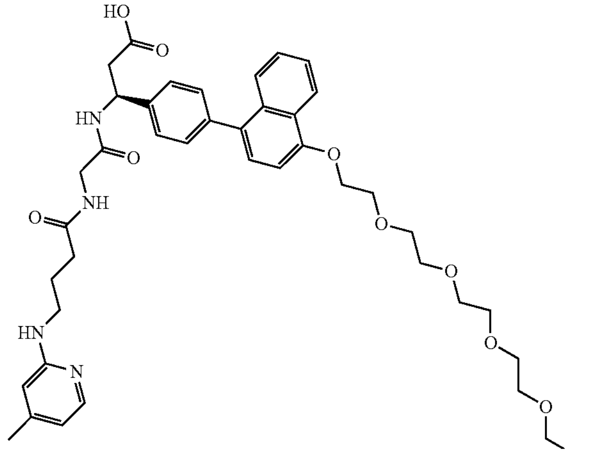
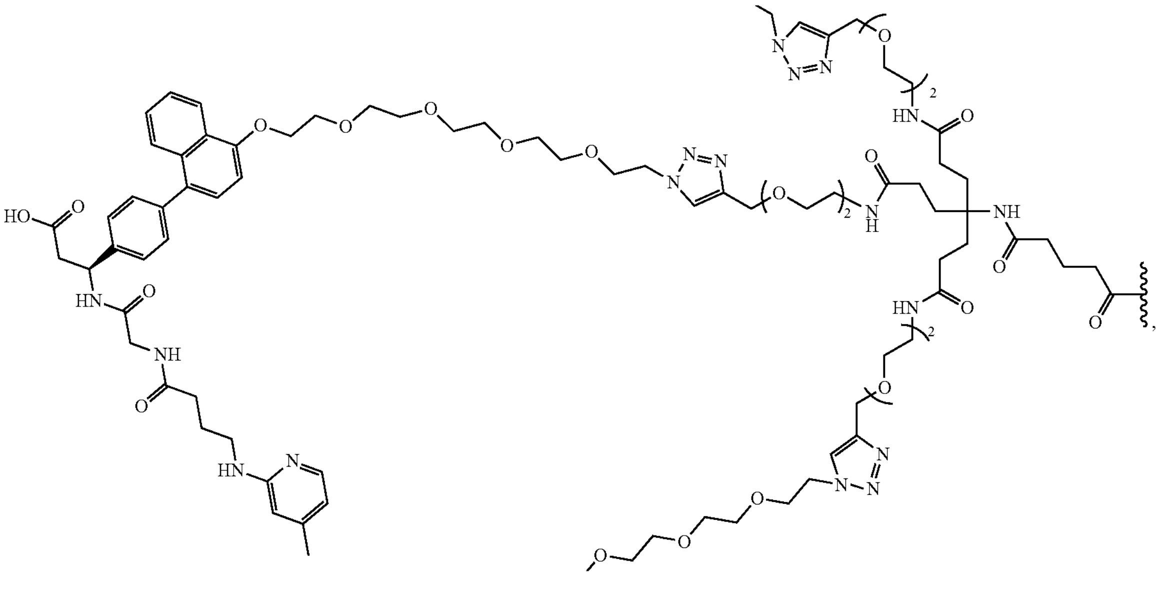
,

-continued
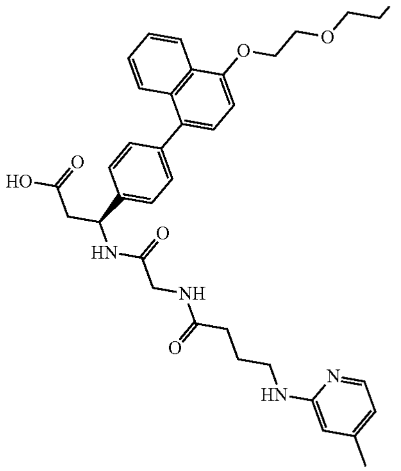
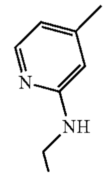
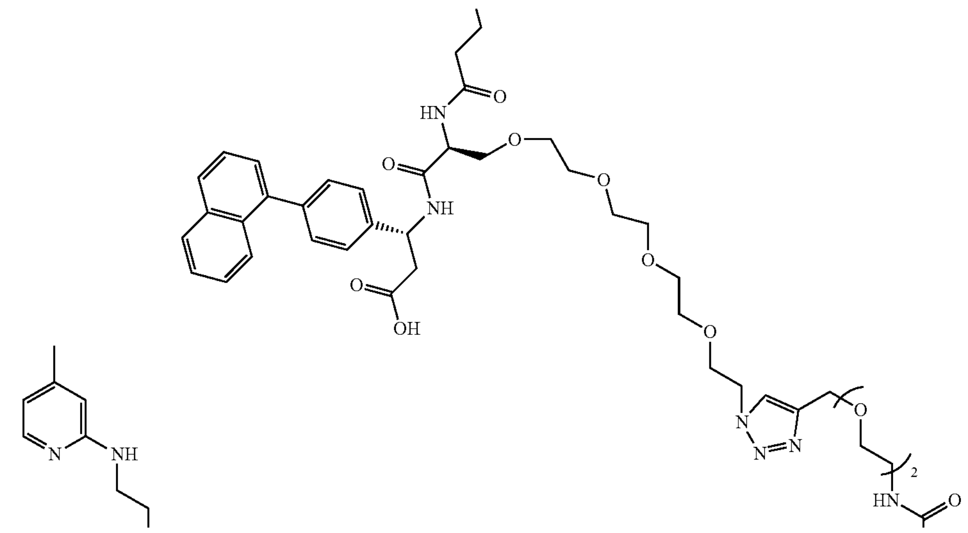

-continued
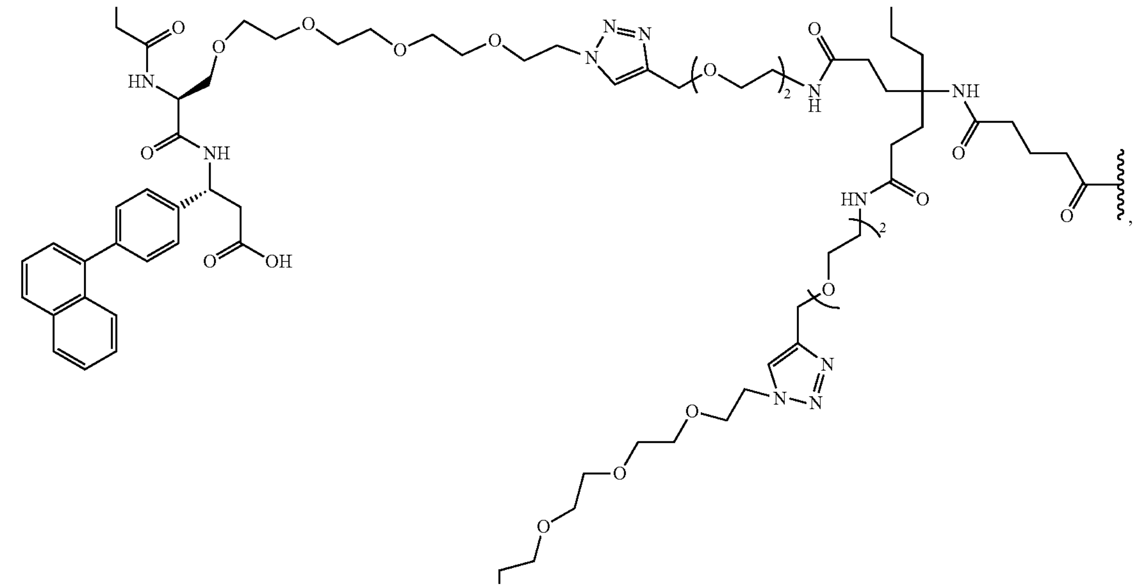
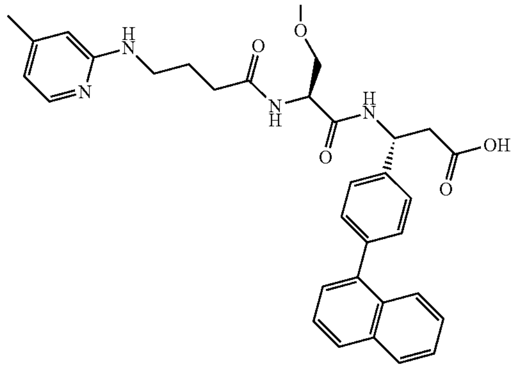
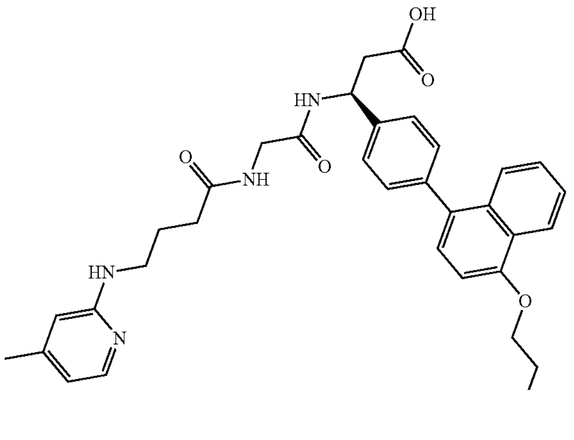

-continued
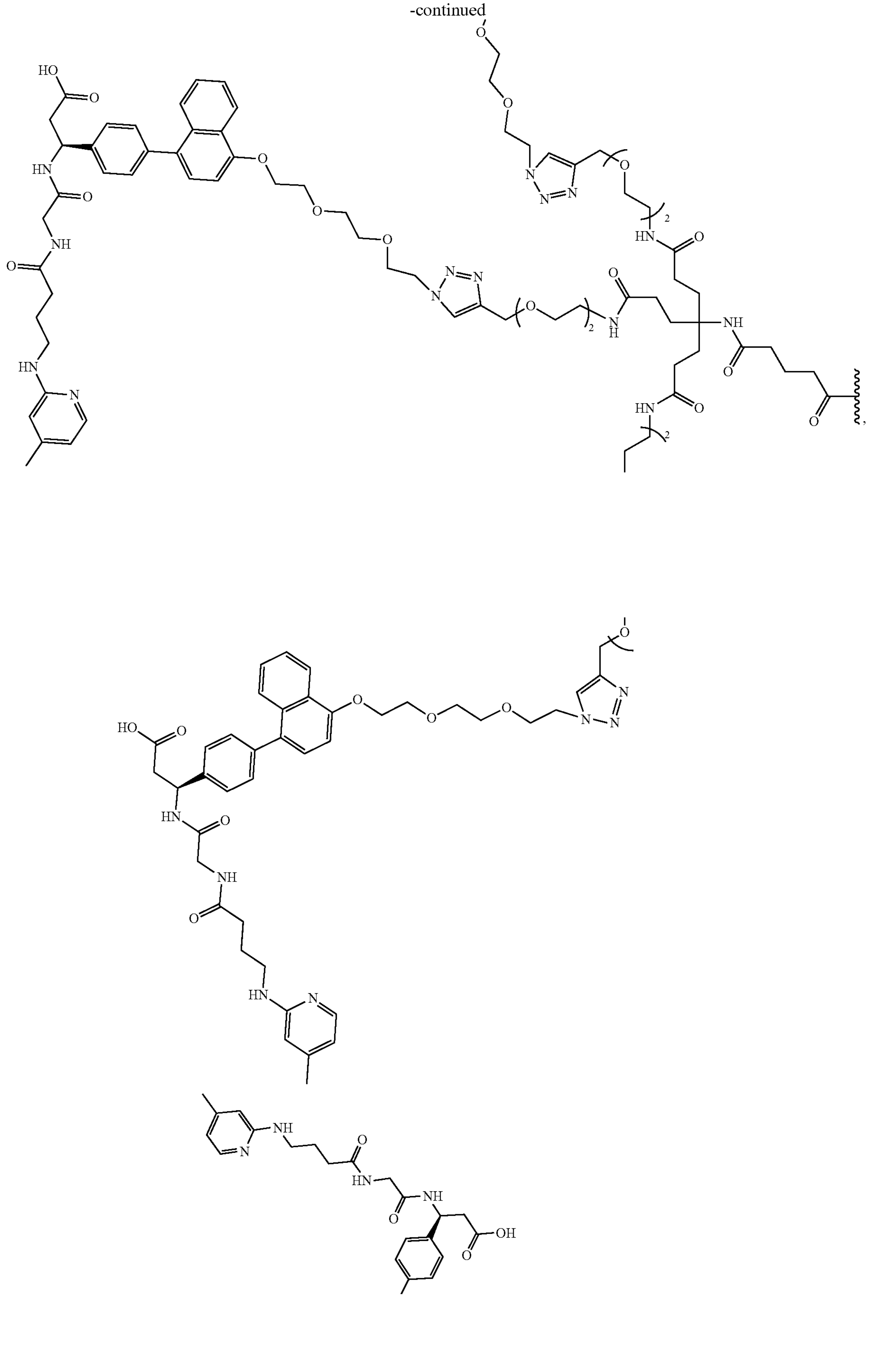

-continued
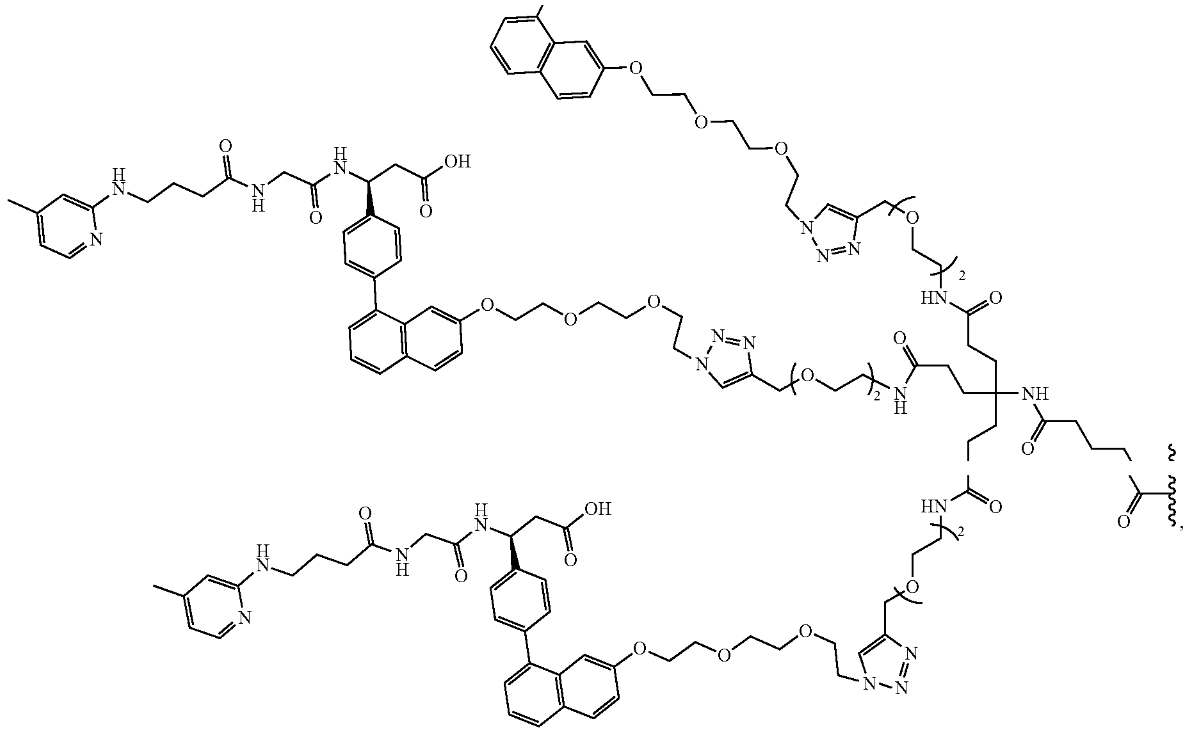
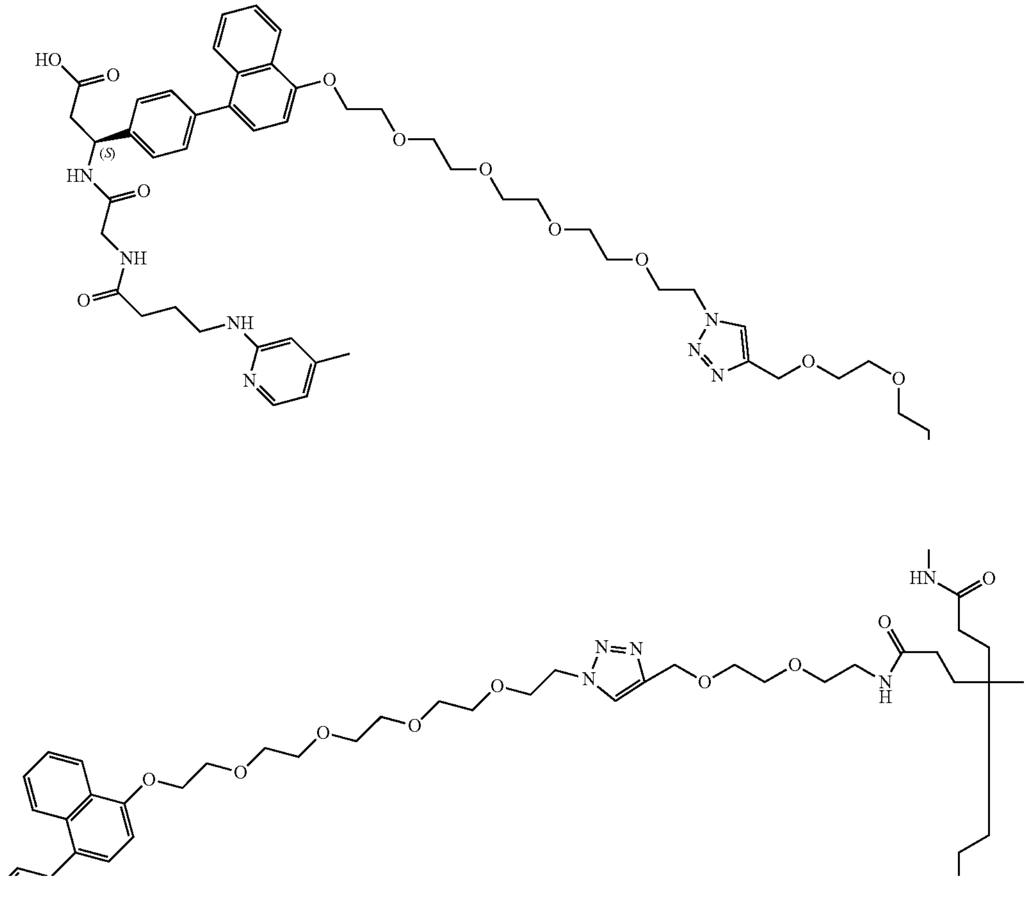

-continued
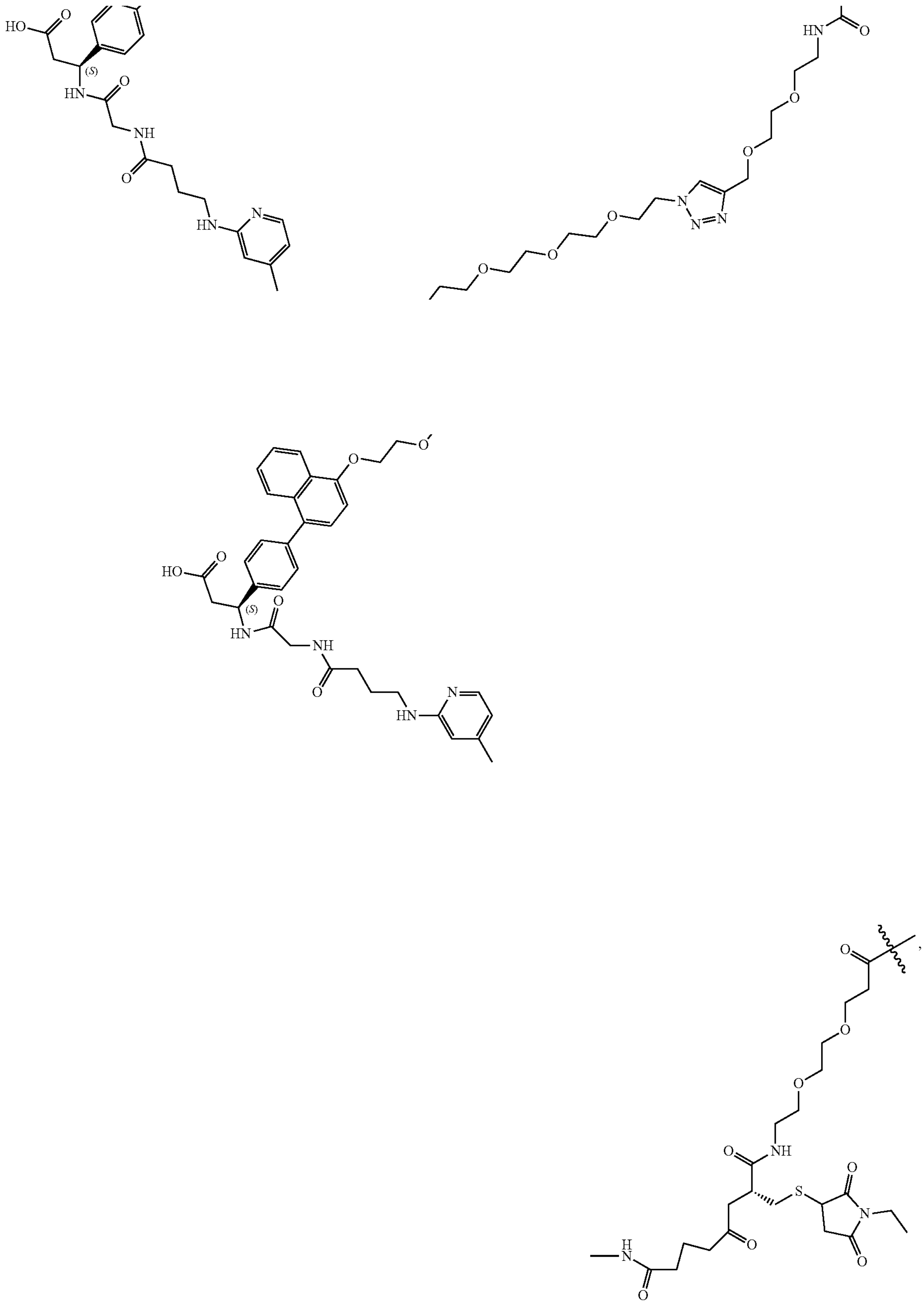
,

-continued
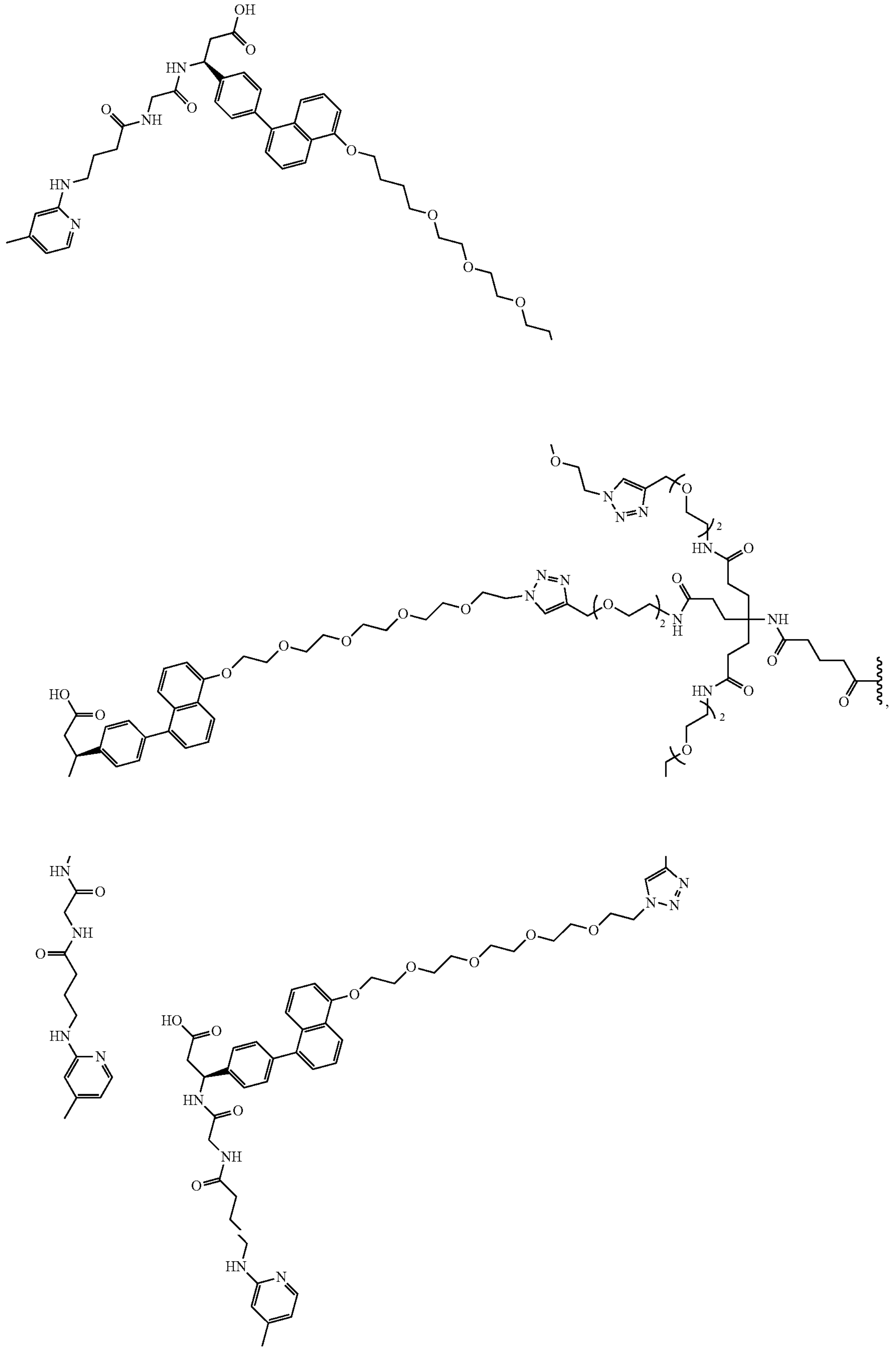
, and

-continued

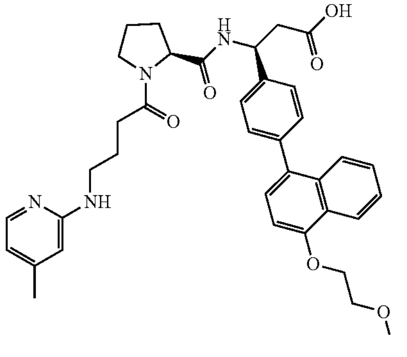

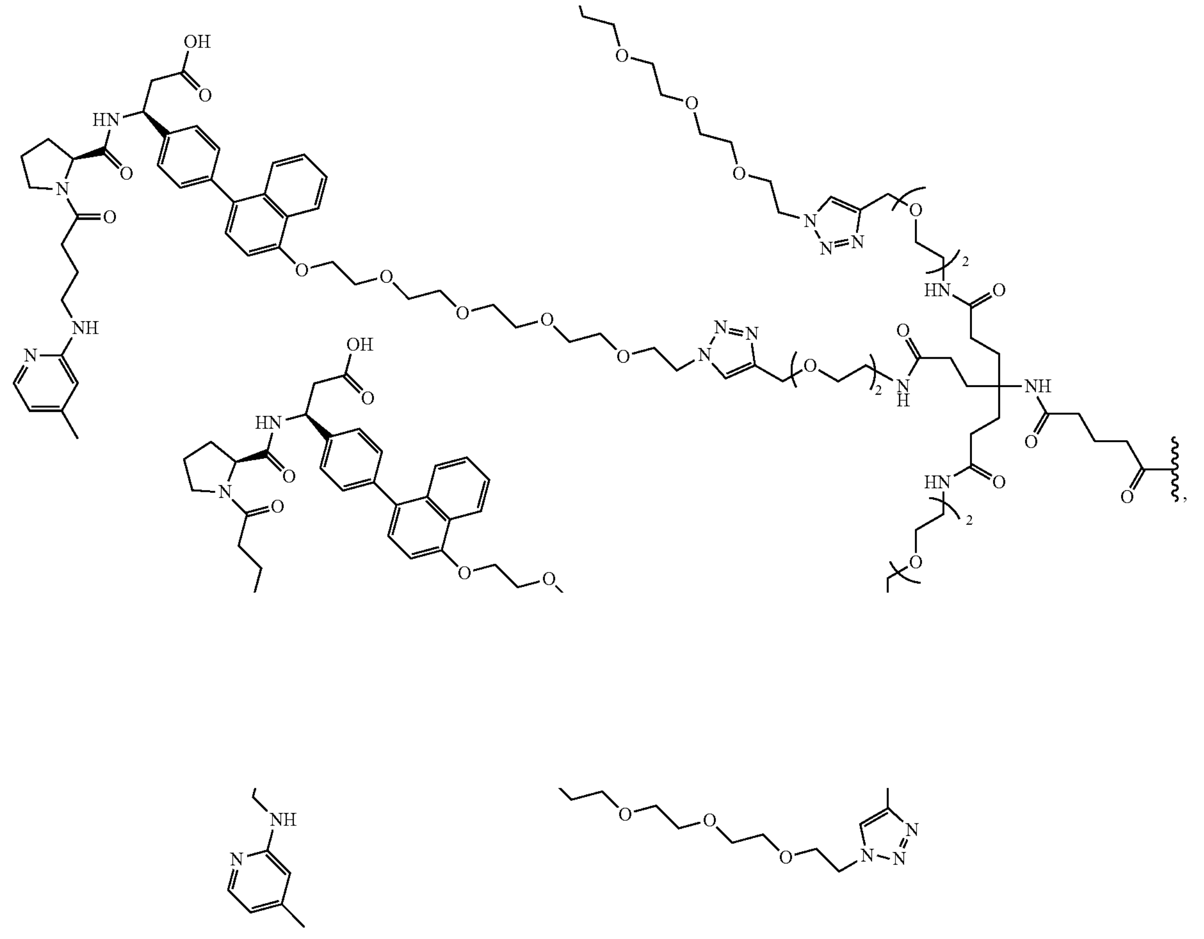

wherein ⸾ indicates the point of connection to the RNAi agent.

8. The RNAi agent of claim 1, wherein the antisense strand comprises the structure (5'→3'): cPrpusGfsusUfgAfagaugUfaAfcAfgUfuGfsc (SEQ ID NO: 138); and the sense strand comprises the structure (5'→3'): (TriSM6.1-avb6-TA14) gscaacuguUfAfCfaucuucaacas (invAb) (SEQ ID NO: 187);

wherein a represents 2'-O-methyl adenosine, c represents 2'-O-methyl cytidine, g represents 2'-O-methyl guanosine, and u represents 2'-O-methyl uridine; Af represents 2'-fluoro adenosine, Cf represents 2'-fluoro cytidine, Gf represents 2'-fluoro guanosine, and Uf represents 2'-fluoro uridine; cPrpu represents a 5'-cyclopropyl phosphonate-2'-O-methyl uridine; s represents a phosphorothioate linkage; (invAb) represents an inverted abasic residue; and (TriSM6.1-avb6-TA14) represents:

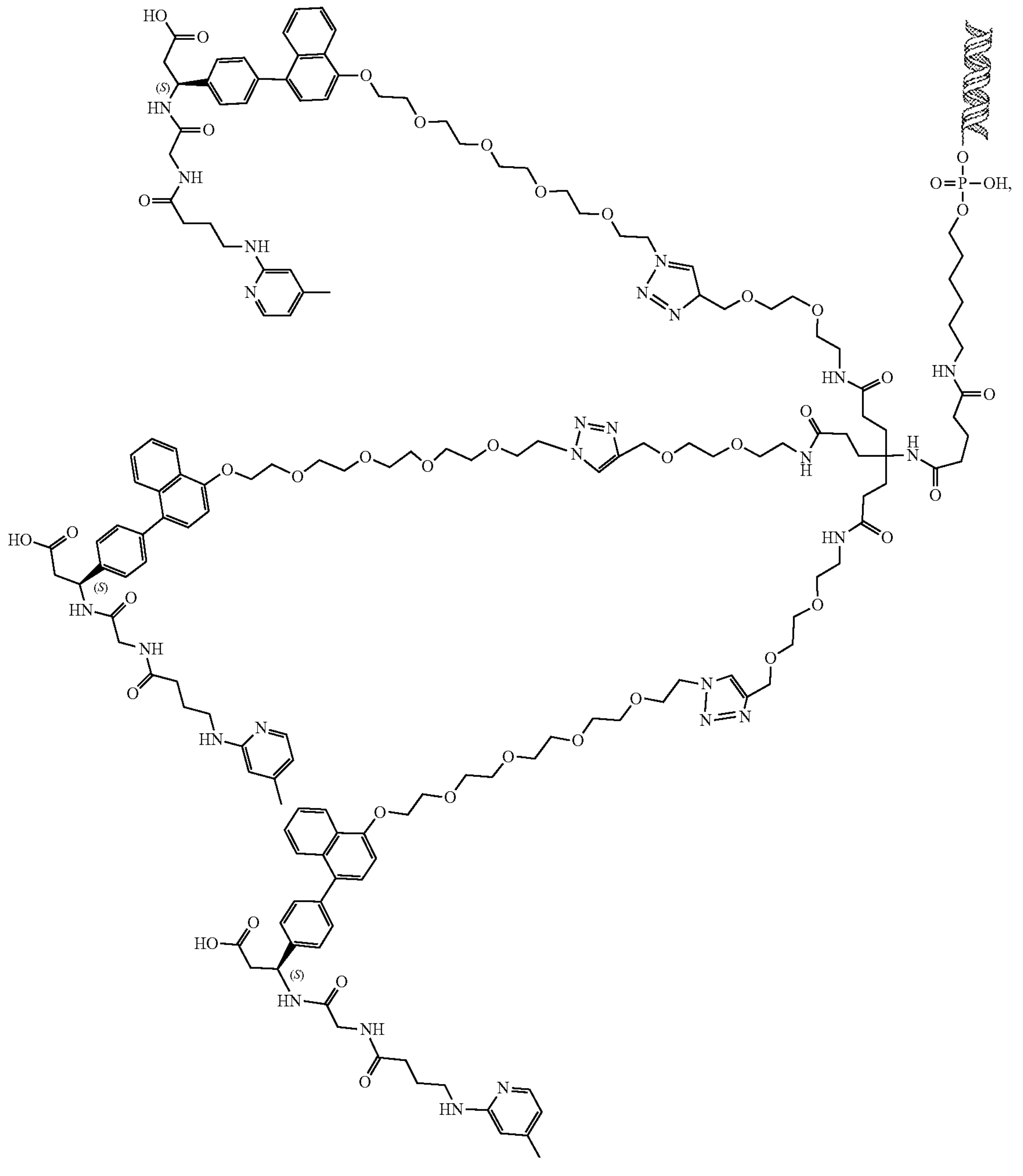

pharmaceutically acceptable salt thereof, wherein 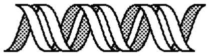 represents the remainder of the RNAi agent.

9. A method for inhibiting expression of a beta-ENaC gene in a cell, the method comprising introducing into a cell an effective amount of an RNAi agent of claim 1.

10. A method of treating one or more symptoms or diseases associated with enhanced or elevated ENaC activity levels, the method comprising administering to a human subject in need thereof a therapeutically effective amount of the RNAi agent of claim 1.

11. The method of claim 10, wherein the disease is a respiratory disease.

12. The method of claim 11, wherein the respiratory disease is cystic fibrosis, chronic bronchitis, non-cystic fibrosis bronchiectasis, chronic obstructive pulmonary disease (COPD), asthma, respiratory tract infections, primary ciliary dyskinesia, or lung carcinoma cystic fibrosis.

13. The method of claim 10, wherein the RNAi agent is administered at a deposited dose of about 0.01 mg/kg to about 5.0 mg/kg of body weight of the subject.

* * * * *